US012582655B2

(12) United States Patent
Flynn et al.

(10) Patent No.: US 12,582,655 B2
(45) Date of Patent: *Mar. 24, 2026

(54) METHODS OF TREATING DISORDERS USING CSFIR INHIBITORS

(71) Applicant: Deciphera Pharmaceuticals, LLC, Waltham, MA (US)

(72) Inventors: Daniel L. Flynn, Waltham, MA (US); Bryan D. Smith, Waltham, MA (US); Rodrigo Ruiz Soto, Waltham, MA (US); Keisuke Kuida, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/364,654

(22) Filed: Oct. 21, 2025

(65) Prior Publication Data

US 2026/0034131 A1 Feb. 5, 2026

Related U.S. Application Data

(63) Continuation of application No. 19/079,727, filed on Mar. 14, 2025, now Pat. No. 12,485,120, which is a continuation of application No. 18/140,942, filed on Apr. 28, 2023, now Pat. No. 12,285,430, which is a continuation of application No. 17/358,137, filed on Jun. 25, 2021, now Pat. No. 11,679,110, which is a continuation of application No. 16/725,282, filed on Dec. 23, 2019, now Pat. No. 11,103,507.

(60) Provisional application No. 62/933,830, filed on Nov. 11, 2019, provisional application No. 62/926,341, filed on Oct. 25, 2019, provisional application No. 62/786,105, filed on Dec. 28, 2018.

(51) Int. Cl.

| | |
|---|---|
| ***A61K 31/505*** | (2006.01) |
| ***A61K 9/00*** | (2006.01) |
| ***A61K 31/513*** | (2006.01) |
| ***A61K 45/06*** | (2006.01) |
| ***A61P 35/00*** | (2006.01) |
| ***A61P 35/02*** | (2006.01) |

(52) U.S. Cl.

CPC .......... *A61K 31/513* (2013.01); *A61K 9/0053* (2013.01); *A61K 45/06* (2013.01); *A61P 35/00* (2018.01)

(58) Field of Classification Search

CPC ......... A61K 31/505; A61P 35/00; A61P 35/02

USPC .......................................................... 514/272

See application file for complete search history.

(56) References Cited

U.S. PATENT DOCUMENTS

| | | | | |
|---|---|---|---|---|
| 7,144,911 | B2 | 12/2006 | Flynn et al. | |
| 7,202,257 | B2 | 4/2007 | Flynn et al. | |
| 7,279,576 | B2 | 10/2007 | Flynn et al. | |
| 7,342,037 | B2 | 3/2008 | Flynn et al. | |
| 7,531,566 | B2 | 5/2009 | Flynn et al. | |
| 7,666,895 | B2 | 2/2010 | Flynn et al. | |
| 7,737,283 | B2 | 6/2010 | Flynn et al. | |
| 7,790,756 | B2 | 9/2010 | Flynn et al. | |
| 7,897,762 | B2 | 3/2011 | Flynn et al. | |
| 8,143,293 | B2 | 3/2012 | Flynn et al. | |
| 8,163,756 | B2 | 4/2012 | Flynn et al. | |
| 8,188,113 | B2 | 5/2012 | Flynn et al. | |
| 8,278,331 | B2 | 10/2012 | Flynn et al. | |
| 8,461,179 | B1 | 6/2013 | Flynn et al. | |
| 8,486,951 | B2 | 7/2013 | Flynn et al. | |
| 8,569,319 | B2 | 10/2013 | Flynn et al. | |
| 8,586,565 | B2 | 11/2013 | Flynn et al. | |
| 8,637,672 | B2 | 1/2014 | Flynn et al. | |
| 8,741,911 | B2 | 6/2014 | Allgeier et al. | |
| 8,921,565 | B2 | 12/2014 | Flynn et al. | |
| 8,940,756 | B2 | 1/2015 | Flynn et al. | |
| 9,012,635 | B2 | 4/2015 | Flynn et al. | |
| 9,133,183 | B2 | 9/2015 | Flynn et al. | |
| 9,181,223 | B2 | 11/2015 | Kaufman et al. | |
| 9,187,474 | B2 | 11/2015 | Flynn et al. | |
| 9,193,719 | B2 | 11/2015 | Flynn et al. | |
| 9,309,224 | B2 | 4/2016 | Flynn et al. | |
| 9,334,267 | B2 | 5/2016 | Flynn et al. | |
| 9,382,228 | B2 | 7/2016 | Flynn et al. | |
| 9,387,202 | B2 | 7/2016 | Flynn et al. | |
| 9,457,019 | B2 | 10/2016 | Flynn et al. | |
| 11,103,507 | B2 * | 8/2021 | Flynn .................. | A61K 31/506 |
| 11,679,110 | B2 * | 6/2023 | Flynn ...................... | A61P 35/00 514/361 |
| 12,285,430 | B2 * | 4/2025 | Flynn .................. | A61K 31/437 |
| 2008/0214544 | A1 | 9/2008 | Bellon et al. | |

(Continued)

FOREIGN PATENT DOCUMENTS

| | | | |
|---|---|---|---|
| CN | 105120864 | A | 12/2015 |
| CN | 105473617 | A | 4/2016 |

(Continued)

OTHER PUBLICATIONS

U.S. Appl. No. 11/450,850, filed Jun. 9, 2006, Expired, US 2008-0299639 A1.

(Continued)

*Primary Examiner* — Raymond J Henley, III

(74) *Attorney, Agent, or Firm* — Goodwin Procter LLP

(57) ABSTRACT

Described herein are methods of treating cancers and other tumors related to the decreased proliferation, the depletion, or the repolarization of tumor-associated macrophages (TAMs) and treatment of associated disorders, including tenosynovial giant cell tumor (TGCT) and diffuse-type tenosynovial giant cell tumor (DTGCT).

29 Claims, 17 Drawing Sheets

Specification includes a Sequence Listing.

(56) References Cited

U.S. PATENT DOCUMENTS

| | | | |
|---|---|---|---|
| 2008/0255155 | A1 | 10/2008 | Raeppel et al. |
| 2010/0120806 | A1 | 5/2010 | Flynn et al. |
| 2010/0166699 | A1 | 7/2010 | Thompson et al. |
| 2011/0053906 | A1 | 3/2011 | Huck et al. |
| 2014/0145025 | A1 | 5/2014 | Fang et al. |
| 2015/0073129 | A1 | 3/2015 | Herting et al. |
| 2019/0091217 | A1 | 3/2019 | Flynn et al. |
| 2020/0129489 | A1 | 4/2020 | Flynn et al. |
| 2020/0352920 | A1 | 11/2020 | Flynn et al. |
| 2020/0354346 | A1 | 11/2020 | Flynn et al. |
| 2020/0354352 | A1 | 11/2020 | Flynn et al. |
| 2021/0015801 | A1 | 1/2021 | Flynn et al. |
| 2023/0414614 | A1 | 12/2023 | Flynn et al. |

FOREIGN PATENT DOCUMENTS

| | | | |
|---|---|---|---|
| CN | 113880812 | A | 1/2022 |
| CN | 116283919 | A | 6/2023 |
| EA | 200802129 | A1 | 4/2009 |
| EP | 3632906 | A1 | 4/2020 |
| EP | 3632907 | A1 | 4/2020 |
| EP | 3682881 | A1 | 7/2020 |
| JP | 6364472 | B2 | 7/2018 |
| RU | 2330024 | C2 | 7/2008 |
| WO | WO-2003/000660 | A1 | 1/2003 |
| WO | WO-2008/079291 | A2 | 7/2008 |
| WO | WO-2010051373 | | 5/2010 |
| WO | WO-2014145015 | | 9/2014 |
| WO | WO-2014145023 | A1 | 9/2014 |
| WO | WO-2014145025 | | 9/2014 |
| WO | WO-2014145028 | | 9/2014 |
| WO | WO-2020139828 | A1 | 7/2020 |
| WO | WO-2022247786 | A1 | 12/2022 |

OTHER PUBLICATIONS

U.S. Appl. No. 11/963,740, filed Dec. 21, 2007, Granted, U.S. Pat. No. 8,163,756.

U.S. Appl. No. 12/829,561, filed Jul. 2, 2010, Granted, U.S. Pat. No. 8,586,565.

U.S. Appl. No. 11/870,388, filed Oct. 10, 2007, Granted, U.S. Pat. No. 7,790,756.

U.S. Appl. No. 11/854,354, filed Sep. 12, 2007, Granted, U.S. Pat. No. 8,188,113.

U.S. Appl. No. 12/105,408, filed Apr. 18, 2008, Expired, US 2008-0261965 A1.

U.S. Appl. No. 13/590,955, filed Aug. 21, 2012, Expired, US 2013-0079362 A1.

U.S. Appl. No. 13/559,170, filed Jul. 26, 2012, Expired, US 2012-0322834 A1.

U.S. Appl. No. 14/214,134, filed Mar. 14, 2014, Granted, U.S. Pat. No. 9,133,183.

U.S. Appl. No. 13/785,575, filed Mar. 5, 2013, Published, US 2013-0252977 A1.

U.S. Appl. No. 14/383,803, filed Mar. 5, 2013, Granted, U.S. Pat. No. 9,187,474.

U.S. Appl. No. 13/491,394, filed Jun. 7, 2012, Granted, U.S. Pat. No. 8,461,179.

U.S. Appl. No. 13/801,753, filed Mar. 13, 2013, Granted, U.S. Pat. No. 8,940,756.

U.S. Appl. No. 16/387,315, filed Apr. 17, 2019, Granted, U.S. Pat. No. Re. 4,8731.

U.S. Appl. No. 14/214,160, filed Mar. 14, 2014, Granted, U.S. Pat. No. 9,193,719.

U.S. Appl. No. 14/214,171, filed Mar. 14, 2014, Granted, U.S. Pat. No. 9,181,223.

U.S. Appl. No. 14/214,185, filed Mar. 14, 2014, Granted, U.S. Pat. No. 9,382,228.

U.S. Appl. No. 14/214,179, filed Mar. 14, 2014, Granted, U.S. Pat. No. 9,309,224.

U.S. Appl. No. 14/535,900, filed Nov. 7, 2014, Granted, U.S. Pat. No. 9,457,019.

U.S. Appl. No. 17/845,275, filed Jun. 21, 2022, Published, US 2022-0370423 A1.

U.S. Appl. No. 17/845,278, filed Jun. 21, 2022, Pending, US 2022-0370424 A1.

U.S. Appl. No. 16/943,821, filed Jul. 30, 2020, Granted, U.S. Pat. No. 11,986,463.

U.S. Appl. No. 18/631,891, filed Apr. 10, 2024, Published, US 2024-0415818 A1.

U.S. Appl. No. 16/943,871, filed Jul. 30, 2020, Granted, U.S. Pat. No. 12,102,620.

U.S. Appl. No. 18/815,054, filed Aug. 26, 2024, Published, US 2025-0090506 A1.

U.S. Appl. No. 16/725,282, filed Dec. 23, 2019, Granted, U.S. Pat. No. 11,103,507.

U.S. Appl. No. 17/358,137, filed Jun. 25, 2021, Granted, U.S. Pat. No. 11,679,110.

U.S. Appl. No. 18/140,942, filed Apr. 28, 2023, Granted, U.S. Pat. No. 12,285,430.

U.S. Appl. No. 19/079,727, filed Mar. 14, 2025, Granted, U.S. Pat. No. 12,485,120.

U.S. Appl. No. 16/870,384, filed May 8, 2020, Granted, U.S. Pat. No. 11,530,206.

U.S. Appl. No. 17/833,272, filed Jun. 6, 2022, Granted, U.S. Pat. No. 12,071,432.

U.S. Appl. No. 18/770,318, filed Jul. 11, 2024, Published, US 2025-0084073 A1.

U.S. Appl. No. 16/870,418, filed May 8, 2020, Granted, U.S. Pat. No. 11,518,758.

U.S. Appl. No. 17/832,224, filed Jun. 3, 2022, Granted, U.S. Pat. No. 12,479,833.

U.S. Appl. No. 16/902,989, filed Jun. 16, 2020, Granted, U.S. Pat. No. 11,590,134.

U.S. Appl. No. 18/152,993, filed Jan. 11, 2023, Granted, U.S. Pat. No. 12,377,097.

U.S. Appl. No. 16/991,644, filed Aug. 12, 2020, Published, US 2023-0277522 A1.

U.S. Appl. No. 17/180,234, filed Feb. 19, 2021, Granted, U.S. Pat. No. 11,185,535.

U.S. Appl. No. 17/504,133, filed Oct. 18, 2021, Granted, U.S. Pat. No. 11,576,903.

U.S. Appl. No. 18/314,348, filed May 9, 2023, Granted, U.S. Pat. No. 11,801,237.

U.S. Appl. No. 18/463,498, filed Sep. 8, 2023, Published, US 2024-0197696 A1.

U.S. Appl. No. 17/028,640, filed Sep. 22, 2020, Granted, U.S. Pat. No. 10,966,966.

U.S. Appl. No. 17/180,218, filed Feb. 19, 2021, Granted, U.S. Pat. No. 11,266,635.

U.S. Appl. No. 17/583,977, filed Jan. 25, 2022, Granted, U.S. Pat. No. 11,426,390.

U.S. Appl. No. 17/583,985, filed Jan. 25, 2022, Granted, U.S. Pat. No. 11,344,536.

U.S. Appl. No. 17/727,307, filed Apr. 22, 2022, Granted, U.S. Pat. No. 11,534,432.

U.S. Appl. No. 17/735,678, filed May 3, 2022, Granted, U.S. Pat. No. 11,529,336.

U.S. Appl. No. 17/735,682, filed May 3, 2022, Granted, U.S. Pat. No. 11,576,904.

U.S. Appl. No. 17/735,862, filed May 3, 2022, Granted, U.S. Pat. No. 11,433,056.

U.S. Appl. No. 17/869,108, filed Jul. 20, 2022, Granted, U.S. Pat. No. 11,969,414.

U.S. Appl. No. 18/091,743, filed Dec. 30, 2022, Granted, U.S. Pat. No. 11,813,251.

U.S. Appl. No. 18/500,549, filed Nov. 2, 2023, Granted, U.S. Pat. No. 12,059,410.

U.S. Appl. No. 18/500,650, filed Nov. 2, 2023, Granted, U.S. Pat. No. 12,023,325.

U.S. Appl. No. 18/500,730, filed Nov. 2, 2023, Granted, U.S. Pat. No. 12,023,327.

(56) References Cited

OTHER PUBLICATIONS

U.S. Appl. No. 18/500,792, filed Nov. 2, 2023, Granted, U.S. Pat. No. 12,059,411.
U.S. Appl. No. 15/500,686, filed Nov. 2, 2023, Granted, U.S. Pat. No. 12,023,326.
U.S. Appl. No. 18/750,014, filed Jun. 21, 2024, Granted, U.S. Pat. No. 12,295,944.
U.S. Appl. No. 18/750,032, filed Jun. 21, 2024, Granted, U.S. Pat. No. 12,318,373.
U.S. Appl. No. 19/194,583, filed Apr. 30, 2025, Pending.
U.S. Appl. No. 17/180,241, filed Feb. 19, 2021, Granted, U.S. Pat. No. 11,395,818.
U.S. Appl. No. 17/735,820, filed May 3, 2022, Granted, U.S. Pat. No. 11,612,591.
U.S. Appl. No. 18/148,766, filed Dec. 30, 2022, Granted, U.S. Pat. No. 11,896,585.
U.S. Appl. No. 18/178,789, filed Mar. 6, 2023, Granted, U.S. Pat. No. 11,793,795.
U.S. Appl. No. 18/448,309, filed Aug. 11, 2023, Granted, U.S. Pat. No. 11,850,240.
U.S. Appl. No. 18/448,312, filed Aug. 11, 2023, Granted, U.S. Pat. No. 11,903,933.
U.S. Appl. No. 18/448,347, filed Aug. 11, 2023, Granted, U.S. Pat. No. 11,844,788.
U.S. Appl. No. 18/448,333, filed Aug. 11, 2023, Granted, U.S. Pat. No. 11,850,241.
U.S. Appl. No. 18/518,093, filed Nov. 22, 2023, Granted, U.S. Pat. No. 12,064,422.
U.S. Appl. No. 18/490,188, filed Oct. 19, 2023, Granted, U.S. Pat. No. 11,911,370.
U.S. Appl. No. 18/490,197, filed Oct. 19, 2023, Granted, U.S. Pat. No. 11,918,564.
U.S. Appl. No. 18/518,100, filed Nov. 22, 2023, Granted, U.S. Pat. No. 11,969,415.
U.S. Appl. No. 18/518,110, filed Nov. 22, 2023, Granted, U.S. Pat. No. 12,023,328.
U.S. Appl. No. 18/758,007, filed Jun. 28, 2024, Granted, U.S. Pat. No. 12,318,374.
U.S. Appl. No. 18/795,711, filed Aug. 6, 2024, Granted, U.S. Pat. No. 12,226,406.
U.S. Appl. No. 18/795,683, filed Aug. 6, 2024, Granted, U.S. Pat. No. 12,213,967.
U.S. Appl. No. 18/795,731, filed Aug. 6, 2024, Granted, U.S. Pat. No. 12,213,968.
U.S. Appl. No. 19/085,149, filed Mar. 20, 2025, Pending.
U.S. Appl. No. 17/528,478, filed Nov. 17, 2021, Granted, U.S. Pat. No. 11,912,668.
U.S. Appl. No. 18/408,956, filed Jan. 10, 2024, Published, US 2024-0376058 A1.
U.S. Appl. No. 18/512,447, filed Nov. 17, 2023, Pending.
U.S. Appl. No. 17/534,795, filed Nov. 24, 2021, Granted, U.S. Pat. No. 12,414,955.
U.S. Appl. No. 17/534,768, filed Nov. 24, 2021, Granted, U.S. Pat. No. 11,801,238.
U.S. Appl. No. 18/073,886, filed Dec. 2, 2022, Published, US 2023-0382915 A1.
U.S. Appl. No. 18/505,396, filed Nov. 9, 2023, Published, US 2024-0122906 A1.
U.S. Appl. No. 18/683,078, filed Feb. 12, 2024, Published, US 2025-0127790 A.
U.S. Appl. No. 18/078,269, filed Dec. 9, 2022, Published, US 2023-0357179 A1.
U.S. Appl. No. 18/078,271, filed Dec. 9, 2022, Granted, U.S. Pat. No. 12,319,655.
U.S. Appl. No. 19/001,282, filed Dec. 24, 2024, Published, US 2025-0250235 A1.
U.S. Appl. No. 18/073,721, filed Dec. 2, 2022, Published, US 2024-0116877 A1.
U.S. Appl. No. 18/456,381, filed Aug. 28, 2023, Published, US 2024-0150368 A1.
U.S. Appl. No. 17/938,353, filed Oct. 6, 2022, Granted, U.S. Pat. No. 11,779,572.
U.S. Appl. No. 18/464,519, filed Sep. 11, 2023, Published, US 2024-0261270 A1.
U.S. Appl. No. 18/389,888, filed Dec. 20, 2023, Published, US 2024-0245660 A1.
U.S. Appl. No. 18/985,885, filed Dec. 18, 2024, Published, US 2025-0206729 A1.
U.S. Appl. No. 15/999,530, filed Aug. 17, 2018, Granted, U.S. Pat. No. 11,077,113.
U.S. Appl. No. 17/362,763, filed Jun. 29, 2021, Granted, U.S. Pat. No. 11,633,403.
U.S. Appl. No. 18/181,046, filed Mar. 9, 2023, Published, US 2024-0050439 A1.
U.S. Appl. No. 15/999,432, filed Aug. 17, 2018, Granted, U.S. Pat. No. 11,179,399.
U.S. Appl. No. 17/501,407, filed Oct. 14, 2021, Published, US 2022-0175788 A1.
U.S. Appl. No. 16/638,727, filed Feb. 12, 2020, Granted, U.S. Pat. No. 11,498,919.
U.S. Appl. No. 18/045,605, filed Oct. 11, 2022, Published, US 2023-0322772 A1.
U.S. Appl. No. 16/639,895, filed Feb. 18, 2020, Granted, U.S. Pat. No. 11,219,618.
U.S. Appl. No. 17/644,486, filed Dec. 15, 2021, Published, US 2022-0218688 A1.
U.S. Appl. No. 16/639,900, filed Feb. 18, 2020, Granted, U.S. Pat. No. 11,208,423.
U.S. Appl. No. 17/530,119, filed Nov. 18, 2021, Granted, U.S. Pat. No. 11,780,858.
U.S. Appl. No. 18/457,682, filed Aug. 29, 2023, Pending.
U.S. Appl. No. 16/639,902, filed Feb. 18, 2020, Granted, U.S. Pat. No. 11,560,374.
U.S. Appl. No. 18/084,208, filed Dec. 19, 2022, Published, US 2023-0234949 A1.
U.S. Appl. No. 18/457,825, filed Aug. 29, 2023, Published, US 2024-0180923 A1.
U.S. Appl. No. 18/980,378, filed Dec. 13, 2024, Published, US 2025-0236609 A1.
U.S. Appl. No. 18/971,800, filed Dec. 6, 2024, Published, US 2025-0206720 A1.
U.S. Appl. No. 19/079,010, filed Mar. 13, 2025, Pending, US 2025-0243182 A1.
U.S. Appl. No. 18/971,846, filed Dec. 6, 2024, Published, US 2025-0205161 A1.
U.S. Appl. No. 19/079,070, filed Mar. 13, 2025, Published, US 2025-0205236 A1.
U.S. Appl. No. 19/235,263 filed Jun. 11, 2025, Pending.
U.S. Appl. No. 19/299,588, filed Aug. 14, 2025, Pending.
U.S. Appl. No. 19/079,965, filed Mar. 14, 2025, Pending.
U.S. Appl. No. 18/980,426, filed Dec. 13, 2024, Published, US 2025-0195487 A1.
U.S. Appl. No. 17/437,552, filed Sep. 9, 2021, Published, US 2022-0144825 A1.
U.S. Appl. No. 19/299,605, filed Aug. 14, 2025, Pending.
U.S. Appl. No. 19/364,654, filed Oct. 21, 2025, Pending.
U.S. Appl. No. 19/360,369, filed Oct. 16, 2025, Pending.
U.S. Appl. No. 19/393,975, filed Nov. 19, 2025, Pending.
U.S. Appl. No. 19/295,254, filed Aug. 8, 2025, Allowed, US 2025-0360133 A1.
"Deciphera Pharmaceuticals Announces Positive, Preliminary, Top-Line Clinical Data for the Ongoing Phase 1 Clincial Study with DCC-3014 and an Update on Future Development Plans," 2019, 1-3.
"History of Changes for Study: NCT03069469 Study of DCC-3014 in Patients with Advanced Malignancies," ClinicalTrials.gov Archive, 2018, 1-5.
Al-Muhsen et al., "The Expression of Stem Cell Factor and c-Kit Receptor in Human Asthmatic Airways," Clinical and Experimental Allergy, 2004, 34: 911-917.
Attoub et al., "The C-Kit Tyrosine Kinase Inhibitor STI571 for Colorectal Cancer Therapy," Cancer Research, 2002, 62: 4879-4883.

(56) References Cited

OTHER PUBLICATIONS

Blay, JY et al., "P63: Patient-Reported Outcomes Following Treatment with Vimseltinib for Tenosynovial Giant Cell Tumour in a Phase 2 Expansion Study", Value in Health, Elsevier, Amsterdam, NL, vol. 25, No. 12 (Dec. 1, 2022), XP087229982.
Boisson et al., "c-Kit and c-kit mutations in mastocytosis and other hematological diseases," Journal of Leukocyte Biology, 2000, 67(2):135-148.
Brahmi, M. et al., Current Systemic Treatment Options for Tenosynovial Giant Cell Tumor/Pigmented Villonodular Synovitis: Targeting the CSF1/CSF1R Axis, Curr. Treat. Options in Oncol., 17:10 (2016).
Brinkmann et al., "Fingolimod (FTY720): Discovery and Development of an Oral Drug to Treat Multiple Sclerosis," Nature Reviews | Drug Discovery, 2010, 9: 883-897.
Brunton et al., "Chemotherapy of Neoplastic Diseases," in, Goodman and Gilman's: The Pharmacological Basis of Therapeutics, 2008, 11th ed.: 853-908.
Burns et al., "C-FMS Inhibitors: A Patent Review," Expert Opinion on Therapeutic Patents, 2011, 147-165.
Caira M. R. et al. "Crystalline Polymorphism of Organic Compounds", Design of Organic Solids. Topics in Current Chemistry, vol. 198, p. 163-208 (1998).
Caldwell, T. M. et al., "Discovery of vimseltinib (DCC-3014), a highly selective CSF1R switch-control kinase inhibitor, in clinical development for the treatment of Tenosynovial Giant Cell Tumor (TGCT)," Biorg. Med. Chem. Lett. 74, (2022) 128928, 7 pages.
Carvajal et al., "KIT as a Therapeutic Target in Metastatic Melanoma," Journal of the American Medical Association, 2011, 305(22): 2327-2334.
Dewar et al., "Inhibition of c-fms by Imatinib: expanding the spectrum of treatment," Cell Cycle, 2005, 4(7):851-853.
Dewar et al., "Macrophage Colony-Stimulating Factor Receptor C-Fms is a Novel Target of Imatinib," Blood, 2005, 105(8): 3127-3132.
Di Lorenzo et al., "Expression of Proto-Oncogene C-Kit in High Risk Prostate Cancer," European Journal of Surgical Oncology, 2004, 30: 987-992.
Dorwald, "Side Reactions in Organic Synthesis," Wiley: VCH Weinhem Preface, 2005, 1-15 & 8: 279-308.
El Agamy et al., "Targeting c-Kit in the Therapy of Mast Cell Disorders: Current Update," European Journal of Pharmacology, 2012, 690: 1-3.
El-Gamal, M. I. et al., Recent Advances of Colony-Stimulating Factor-1 Receptor (CSF-1R) Kinase and Its Inhibitors, J. Med. Chem., 61:5450-5466 (2018).
Fang Z. et al. Conformational restriction: an effective tactic in 'follow-on'-based drug discovery, Fugure Med Chem. 2014, 6(8): 885-901.
Fine et al., "Neoplasms of the Central Nervous System," Cancer Principles & Practice of Oncology, 2005, 1834-1887.
Fogarty et al., "Development of Protein Kinase Activators: AMPK as a Target in Metabolic Disorders and Cancer," Biochimica et Biophysica Acta, 2010, 1804: 581-591.
Gelderblom, H. et al., " 475P: Safety and Efficacy of Vimseltinib in Tenosynovial Giant Cell Tumour (TGCT)): Long-term Phase I Update", Annals of Oncology, vol. 33, (Sep. 1, 2022), p. S757, XP093241096.
Gelderblom, H. et al., "Vimseltinib versus placebo for tenosynovial giant cell tumour (MOTION): a multicentre, randomised, double-blind, placebo-controlled, phase 3 trial", The Lancet, vol. 403, No. 10445, (Jun. 3, 2024), pp. 2709-2719, XP093241015.
Girouard et al., "Neurovascular Coupling in the Normal Brain and in Hypertension, Stroke, and Alzheimer Disease," J. Appl Physiol., 2006, 100: 328-335.
Gupta et al., "IL-3 Inhibits Human Osteoclastogenesis and Bone Resorption through Downregulation of c-Fms and Diverts the Cells to Dendritic Cell Lineage," The Journal of Immunology, 2010, 2261-2272.
Heinrich et al., "Inhibition of c-kit receptor tyrosine kinase activity by STI 571, a selective tyrosine kinase inhibitor," Blood, 2000, 96(3):925-932.
Henriksen et al., "Assessment of Osteoclast No. and Function: Application in the Development of New and Improved Treatment Modalities for Bone Diseases," Osteoporosis International, 2006, 18: 681-685.
International Search Report and Written Opinion for International Patent Application No. PCT/US2014/029661 mailed Jun. 11, 2014.
International Search Report and Written Opinion for International Patent Application No. PCT/US2014/029664 mailed Jun. 11, 2014.
International Search Report and Written Opinion for International Patent Application No. PCT/US2019/068311 mailed Jul. 2, 2020.
International Search Report and Written Opinion for International Patent Application No. PCT/US2024/053261 mailed Feb. 6, 2025.
Judge et al., "Potassium Channel Blockers in Multiple Sclerosis: Neuronal Kv Channels and Effects of Symptomatic Treatment," Pharmacology & Therapeutics, 2006, 224-259.
Khadka, P. et al., Pharmaceutical particle technologies: An approach to improve drug solubility, dissolution and bioavailability, Asian Journal of Pharmaceutical Sciences, 9(6): 304-316 (2014).
Kumari A. et al. 3D-QSAR analysis of anilinoquinoline inhibitors of colony stimulating factor-1 kinase(cFMS): implementation of field-based molecular alignment, Med Chem Res 22, 5167-5183 (2013).
Kung et al., "Structure Activity Relationships of Quinoline-Containing c-Met Inhibitors," European Journal of Medicinal Chemistry 43, 2008, 1321-1329.
Kuster et al., "Kinase Inhibitors Methods and Protocols," Methods in Molecular Biology, 2012, 1-46.
Lewitt, "Levodopa for the Treatment of Parkinson's Disease," New England Journal of Medicine, 2008, 359: 2468-2476.
Luo et al., "Principles of Cancer Therapy: Oncogene and Non-oncogene Addiction," Cell, 2009, 36: 823-837.
Minkin, "Bone Acid Phosphatase: Tartrate-Resistant Acid Phosphatase as a Marker of Osteoclast Function," Calcified Tissue International, 1982, 34: 285-290.
Mitchell et al., "Amyotrophic Lateral Sclerosis," The Lancet, 2007, 369: 2031-2041.
National Cancer Institute (http://www.cancer.gov) 2014.
O'Brien et al., "Vascular Cognitive Impairment," The Lancet Neurology, 2003, 2: 89-98.
Ohno et al., "A c-fms tyrosine kinase inhibitor, Ki20227, suppresses osteoclast differentiation and osteolytic bone destruction in a bone metastasis model," Mol Cancer Ther., 2006, 5(11):2634-2643.
PCT/US2019/068311 International Search Report and Written Opinion mailed Jul. 2, 2020.
PCT/US2024/058988 International Search Report and Written Opinion dated Mar. 24, 2025.
PCT/US2024/058998 International Search Report and Written Opinion mailed Jun. 2, 2025, 15 pages.
PCT/US2024/060067 International Search Report and Written Opinion mailed Apr. 10, 2025, 48 pages.
PCT/US2025/027041 International Search Report and Written Opinion mailed Sep. 19, 2025, 17 pages.
PCT/US2025/027042 International Search Report and Written Opinion mailed Jul. 23, 2025, 12 pages.
Pyonteck et al., "CSF-1R inhibition alters macrophage polarization and blocks glioma progression," Nature Medicine, 2013, 19(10):1264-1274.
Reber et al., "Stem Cell Factor and its Receptor c-Kit as Targets for Inflammatory Diseases," European Journal of Pharmacology, 2006, 533: 327-340.
Roberts et al., "Antiangiogenic and Antitumor Activity of a Selective PDGFR Tyrosine Kinase Inhibitor, CP-673, 451," Cancer Research, 2005, 957-966.
Rubin et al., "KIT activation is a ubiquitous feature of gastrointestinal stromal tumors," Cancer Research, 2001, 61(22):8118-8121.
Shah et al., "Current Approaches in the Treatment of Alzheimer's Disease," Biomedicine & Pharmacotherapy, 2008, 62: 199-207.
Silverman R.B. et al. Lead Discovery, The Organic Chemistry of Drug Design and Drug Action, 3rd Ed, Chapter 2, pp. 19-122, Elsevier (2014).

(56) References Cited

OTHER PUBLICATIONS

Smith, B. D. et al., "Vimseltinib: A Precision CSF1R Therapy for Tenosynovial Giant Cell Tumors and Diseases Promoted by Macrophages", Molecular Cancer Therapeutics, vol. 20, No. 11, (Aug. 25, 2021), pp. 2098-2109, XP093171464.

Tap et al., "Pexidartinib Versus Placebo for Advanced Tenosynovial Giant Cell Tumour (ENLIVEN): a Randomised Phase 3 Trial, " Lancet, 2019, 394: 478-487.

Tap et al., "Structure-Guided Blockade of CSF1R Kinase in Tenosynovial Giant-Cell Tumor," New England Journal of Medicine, 2015, 373(5):428-437.

Tap, W. D. et al., "Efficacy, safety, and patient-reported outcomes of vimseltinib in patients with tenosynovial giant cell tumor: Results from the phase 3 MOTION trial", Journal of Clinical Oncology, vol. 42, No. 16_suppl, (Jun. 1, 2024), pp. 11500-11500, XP093241007.

Tap, W. D. et al., "MOTION: A randomized, phase 3, placebo-controlled, double-blind study of vimseltinib (DCC-3014) for the treatment of tenosynovial giant cell tumour", Journal of Clinical Oncology, vol. 40, No. 16_suppl., (Jun. 2, 2022), pp. TPS11590-TPS11590, XP093241022.

Wen et al., "Osteosarcoma Cell-Intrinsic Colony Stimulating Factor-1 Receptor Functions to Promote Tumor Cell Metastasis Through JAG1 Signaling," American Journal of Cancer Research, 2017, 7(4): 801-815.

Yasuda et al., "The Stem Cell Factor/C-Kit Receptor Pathway Enhance Proliferation and Invasion of Pancreatic Cancer Cells," Molecular Cancer, 2006, 5(46): 1-10.

* cited by examiner

C, cycle; CSF1R, colony stimulating factor 1 receptor; D, day; IL-34, interleukin 34; QD, once daily.
Data are presented as mean ± standard deviation C, cycle; D, day.

C, cycle; D, day.

A)

B)

C)

CSF1=colony stimulating factor 1

BiWeekly = twice weekly; CD16+ = cluster of differentiation 16 positive monocytes; QD = daily; SD = standard deviation BiWeekly = twice weekly; CSF1 = colony-stimulating factor 1; QD = daily; SD = standard deviation

SEQUENCE LISTING

```
Sequence total quantity: 4
SEQ ID NO: 1          moltype = AA  length = 444
FEATURE               Location/Qualifiers
source                1..444
                      mol_type = protein
                      organism = synthetic construct
SEQUENCE: 1
MHHHHHHEFY KYKQKPKYQV RWKIIESYEG NSYTFIDPTQ LPYNEKWEFP RNNLQFGKTL  60
GAGAFGKVVE ATAFGLGKED AVLKVAVKML KSTAHADEKE ALMSELKIMS HLGQHENIVN  120
LLGACTHGGP VLVITEYCCY GDLLNFLRRK AEAMLGPSLS PGQDPEGGVD YKNIHLEKKY  180
VRRDSGFSSQ GVDTYVEMRP VSTSSNDSFS EQDLDKEDGR PLELRDLLHF SSQVAQGMAF  240
LASKNCIHRD VAARNVLLTN GHVAKIGDFG LARDIMNDSN YIVKGNARLP VKWMAPESIF  300
DCVYTVQSDV WSYGILLWEI FSLGLNPYPG ILVNSKFYKL VKDGYQMAQP AFAPKNIYSI  360
MQACWALEPT HRPTFQQICS FLQEQAQEDR RERDYTNLPS SSRSGGSGSS SSELEEESSS  420
EHLTCCEQGD IAQPLLQPNN YQFC                                         444

SEQ ID NO: 2          moltype = AA  length = 696
FEATURE               Location/Qualifiers
source                1..696
                      mol_type = protein
                      organism = synthetic construct
SEQUENCE: 2
MEHHHHHHHH EYMPMEMAPI LGYWKIKGLV QPTRLLLEYL EEKYEEHLYE RDEGDKWRNK  60
KFELGLEFPN LPYYIDGDVK LTQSMAIIRY IADKHNMLGG CPKERAEISM LEGAVDIRYG  120
VSRIAYSKDF ETLKVDFLSK LPEMLKMFED RLCHKTYLNG DHVTHPDFML YDALDVVLYM  180
DPMCLDAFPK LVCFKKRIEA IPQIDKYLKS SKYIWPLQGW QATFGGGDHP PKSDLVPRHN  240
QTSLYKKAGS AAAVLEENLY FQGTYKYLQK PMYEVQWKVV EEINGNNYVY IDPTQLPYDH  300
KWEFPRNRLS FGKTLGAGAF GKVVEATAYG LIKSDAAMTV AVKMLKPSAH LTEREALMSE  360
```

-continued

```
LKVLSYLGNH MNIVNLLGAC TIGGPTLVIT EYCCYGDLLN FLRRKRDSFI CSKQEDHAEA  420
ALYKNLLHSK ESSCSDSTNE YMDMKPGVSY VVPTKADKRR SVRIGSYIER DVTPAIMEDD  480
ELALDLEDLL SFSYQVAKGM AFLASKNCIH RDLAARNILL THGRITKICD FGLARDIKND  540
SNYVVKGNAR LPVKWMAPES IFNCVYTFES DVWSYGIFLW ELFSLGSSPY PGMPVDSKFY  600
KMIKEGFRML SPEHAPAEMY DIMKTCWDAD PLKRPTFKQI VQLIEKQISE STNHIYSNLA  660
NCSPNRQKPV VDHSVRINSV GSTASSSQPL LVHDDV                            696

SEQ ID NO: 3            moltype = AA  length = 792
FEATURE                 Location/Qualifiers
source                  1..792
                        mol_type = protein
                        organism = synthetic construct
SEQUENCE: 3
MEHHHHHHHH MAPILGYWKI KGLVQPTRLL LEYLEEKYEE HLYERDEGDK WRNKKFELGL  60
EFPNLPYYID GDVKLTQSMA IIRYIADKHN MLGGCPKERA EISMLEGAVL DIRYGVSRIA  120
YSKDFETLKV DFLSKLPEML KMFEDRLCHK TYLNGDHVTH PDFMLYDALD VVLYMDPMCL  180
DAFPKLVCFK KRIEAIPQID KYLKSSKYIA WPLQGWQATF GGGDHPPKSD LVPRHNQTSL  240
YKKAGFEGDR TMKQKPRYEI RWRVIESISP DGHEYIYVDP MQLPYDSRWE FPRDGLVLGR  300
VLGSGAFGKV VEGTAYGLSR SQPVMKVAVK MLKPTARSSE KQALMSELKI MTHLGPHLNI  360
VNLLGACTKS GPIYIITEYC FYGDLVNYLH KNRDSFLSHH PEKPKKELDI FGLNPADEST  420
RSYVILSFEN NGDYMDMKQA DTTQYVPMLE RKEVSKYSDI QRSLYDRPAS YKKKSMLDSE  480
VKNLLSDDNS EGLTLLDLLS FTYQVARGME FLASKNCVHR DLAARNVLLA QGKIVKICDF  540
GLARDIMHDS NYVSKGSTFL PVKWMAPESI FDNLYTTLSD VWSYGILLWE IFSLGGTPYP  600
GMMVDSTFYN KIKSGYRMAK PDHATSEVYE IMVKCWNSEP EKRPSFYHLS EIVENLLPGQ  660
YKKSYEKIHL DFLKSDHPAV ARMRVDSDNA YIGVTYKNEE DKLKDWEGGL DEQRLSADSG  720
YIIPLPDIDP VPEEEDLGKR NRHSSQTSEE SAIETGSSSS TFIKREDETI EDIDMMDDIG  780
IDSSDLVEDS FL                                                      792

SEQ ID NO: 4            moltype = AA  length = 419
FEATURE                 Location/Qualifiers
source                  1..419
                        mol_type = protein
                        organism = synthetic construct
SEQUENCE: 4
MHKYKKQFRY ESQLQMVQVT GSSDNEYFYV DFREYEYDLK WEFPRENLEF GKVLGSGAFG  60
KVMNATAYGI SKTGVSIQVA VKMLKEKADS SEREALMSEK MMTQLGSHEN IVNLLGACTL  120
SGPIYLIFEY CCYGDLLNYL RSKREKFHRT WTEIFKEHNF SFYPTFQSHP NSSMPGSREV  180
QIHPDSDQIS GLHGNSFHSE DEIEYENQKR LEEEEDLNVL TFEDLLCFAY QVAKGMEFLE  240
FKSCVHRDLA ARNVLVTHGK VVKICDFGLA RDIMSDSNYV VRGNARLPVK WMAPESLFEG  300
IYTIKSDVWS YGILLWEIFS LGVNPYPGIP VDANFYKLIQ NGFKMDQPFY ATEEIYIIMQ  360
SCWAFDSRKR PSFPNLTSFL GCQLADAEEA MYQNVKGVEA CQLGTDDYDI PTTHHHHHH   419
```

METHODS OF TREATING DISORDERS USING CSFIR INHIBITORS

CROSS-REFERENCE TO RELATED APPLICATIONS

This application is a continuation of U.S. Ser. No. 19/079,727 filed on Mar. 14, 2025, which is a continuation of U.S. Ser. No. 18/140,942 filed Apr. 28, 2023, issued as U.S. Pat. No. 12,285,430, which is a continuation of U.S. Ser. No. 17/358,137 filed Jun. 25, 2021, issued as U.S. Pat. No. 11,679,110, which is a continuation of U.S. Ser. No. 16/725,282 filed Dec. 23, 2019, issued as U.S. Pat. No. 11,103,507, which claims priority to U.S. Ser. No. 62/786,105 filed Dec. 28, 2018, U.S. Ser. No. 62/926,341 filed Oct. 25, 2019, and U.S. Ser. No. 62/933,830 filed Nov. 11, 2019, the contents of each of which are incorporated herein by reference in their entireties.

REFERENCE TO A SEQUENCE LISTING XML

This application contains a Sequence Listing which has been submitted electronically in XML format. The Sequence Listing XML is incorporated herein by reference. Said XML file, created on Oct. 20, 2025, is named DCP-078USC4_SL.xml and is 6,862 bytes in size.

BACKGROUND

Colony-stimulating factor 1 receptor (CSF1R) and its ligand, colony stimulating factor 1 (CSF1) together form a lineage dependency for normal macrophage development and differentiation from monocytes. As such, tumor-associated macrophages (TAMs) are dependent on CSF1R (also known as FMS) kinase activity for proliferation, and maintenance of their differentiated state and immunosuppressive phenotype. The role of TAMs in promoting an invasive and immunosuppressive tumor microenvironment is well established. TAMs mediate tumor growth, angiogenesis, invasiveness, metastasis, and immunosuppression through the secretion of and response to a variety of cytokines or other soluble factors. TAMs are educated by tumors to enable escape from immune surveillance by dampening a cytotoxic T cell immune response, thereby shielding the tumor from T cell eradication. For example, TAMs express PD-L1, a known immunosuppressive checkpoint that induces T cell anergy.

Several inhibitors targeting CSF1R have advanced into the clinic as direct antitumor therapies and potential immunotherapies. Many of these drugs also inhibit the closely related Type III tyrosine receptor kinases KIT, PDGFRα/β and FLT3, which may limit their utility due to off-target toxicity. Antibodies targeting CSF1R are much more specific yet result in >10,000-fold increases in plasma levels of CSF1, the ligand for CSF1R, due to blockade of CSF1 clearance, among other drawbacks.

Tenosynovial giant cell tumor (TGCT) is a proliferative and inflammatory disease that includes entities formerly known as pigmented villonodular synovitis (PVNS), and giant cell tumor of the tendon sheath (GCTTS), intraarticular or extraarticular. It is a rare neoplasm of the joint or tendon sheath, with destructive proliferation of synovial like mononuclear cells, admixed with multinucleate giant cells, foam cells, siderophages and inflammatory cells. There are two types of TGCT: the local or nodular form (where the tumor involves the tendons that support the joint, or in one area of the joint) and the diffuse form (where the entire lining of the joint is involved). Treatment is surgical excision of the tumor. However, it is often difficult to perform a marginal excision for the diffuse form of TGCT resulting in a high recurrence rate. It can be characterized by overexpression of CSF1.

There is a need for selective small-molecule CSF1R inhibitors that are useful in the treatment of disorders associated with the proliferation of TAMs including solid tumors of various cancers and treatment of mesenchymal tumors including TGCT and diffuse-type tenosynovial giant cell tumor (DTGCT).

SUMMARY

Provided herein, in part, are methods of treating disorders such as tenosynovial giant cell tumors and/or or cancers in a patient in need thereof, comprising orally administering to the patient a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof.

For example, described herein is a method of treating a cancer selected from the group consisting of solid tumors, acute myeloid leukemia, myelodysplastic syndrome, acute lymphocytic leukemia, and chronic lymphocytic leukemia, in a patient in need thereof, comprising administering to the patient a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof, wherein administering comprises: administering a loading dose of the compound daily for a first time period; and administering a maintenance dose of the compound once a week, twice a week (also described as biweekly), or three times a week for a second time period.

The disclosure also provides for a method of treating tumors, e.g., GCTTS, PVNS, TGCT or DTGCT, comprising administering to the patient a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof, wherein administering comprises: administering a loading dose of the compound daily for a first time period; and administering a maintenance dose of the compound once a week, twice a week, or three times a week for a second time period.

A method of inhibiting the proliferation of a cell known to have expression of the receptor colony-stimulating factor 1 receptor (CSF1R) or its ligands, colony-stimulating factor 1 (CSF1) or interleukin (IL)-34 in a patient in need thereof is also contemplated herein, comprising administering to the patient a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof, wherein administering comprises: administering a loading dose of the compound daily for a first time period; and administering a maintenance dose of the compound once a week, twice a week, or three times a week for a second time period.

DETAILED DESCRIPTION

Definitions

Figure 1:
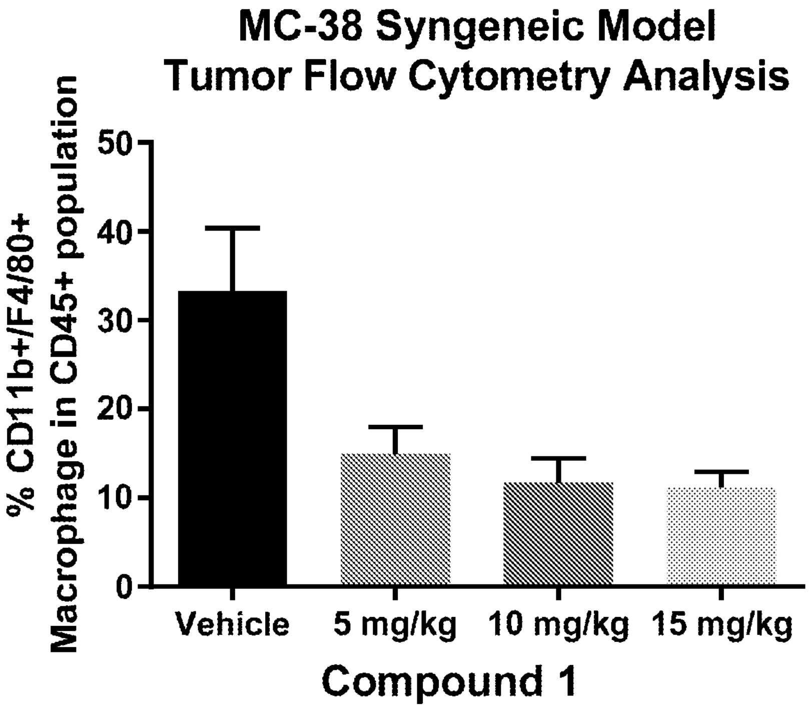
FIG. 1 depicts dose-dependent changes in the amount of CD11b+/F4/80+ intratumoral macrophages in mice that received treatment with Compound 1.

As used herein, "DTGCT" refers to diffuse-type tenosynovial giant cell tumor.

"Individual," "patient," or "subject" are used interchangeably herein and include any animal, including mammals, including mice, rats, other rodents, rabbits, dogs, cats, swine, cattle, sheep, horses, or primates, and humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods described herein is desirably a mammal in which treatment of a disorder described herein is desired, such as a human.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

As used herein, "TAM" refers to tumor-associated macrophage.

As used herein, "TGCT" refers to tenosynovial giant cell tumor.

As used herein, "DTGCT" refers to diffuse tenosynovial giant cell tumor.

As used herein, "GCTTS" refers to giant cell tumor of the tendon sheath.

As used herein, "PVNS" refers to pigmented villonodular synovitis.

As used herein, "treating" includes any effect, e.g., lessening, reducing, modulating, or eliminating, that results in the improvement of the condition, disease, disorder and the like.

Therapeutically effective amount" includes the amount of the subject compound that will elicit the biological or medical response of a tissue, system, animal or human that is being sought by the researcher, veterinarian, medical doctor or other clinician. A compound described herein, e.g., Compound 1, is administered in therapeutically effective amounts to treat a condition, e.g., TGCT or DTGCT. Alternatively, a therapeutically effective amount of a compound is the quantity required to achieve a desired therapeutic and/or prophylactic effect, such as an amount which results in the prevention of or a decrease in the symptoms associated with the condition.

A compound described herein, e.g., Compound 1, can be formulated as a pharmaceutical composition using a pharmaceutically acceptable carrier and administered by a variety of routes. In some embodiments, such compositions are for oral administration. In some embodiments, such compositions are for parenteral (by injection) administration (e.g., a composition formulated for local injection at the site of a tumor, e.g., a diffuse-type giant cell tumor). In some embodiments, such compositions are for transdermal administration. In some embodiments, such compositions are for intravenous (IV) administration. In some embodiments, such compositions are for intramuscular (IM) administration. Such pharmaceutical compositions and processes for preparing them are well known in the art. See, e.g., REMINGTON: THE SCIENCE AND PRACTICE OF PHARMACY (A. Gennaro, et al., eds., $19^{th}$ ed., Mack Publishing Co., 1995).

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

ChemDraw version 10 or 12 (CambridgeSoft Corporation, Cambridge, Mass.) was used to name the structures of intermediates and exemplified compounds.

Methods of Use

Described herein are selective inhibitors of CSF1R including 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one (i.e., Compound 1) and pharmaceutically acceptable salts thereof. Compound 1 can be represented by:

Compound 1

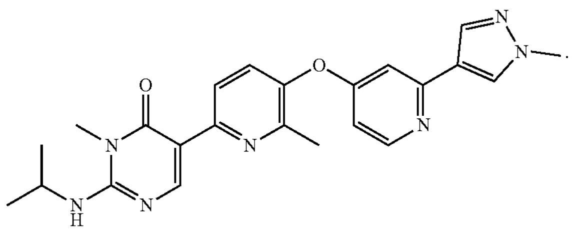

A compound described herein, e.g., Compound 1, can be useful in the inhibition of the proliferation of TAMs, the depletion of TAMs, the repolarization of protumoral M2 TAMs to antitumoral M1 type macrophages, and treatment of related disorders in patients, such as disorders disclosed herein, for example, diffuse-type tenosynovial giant cell tumor (DTGCT), wherein treatment with Compound 1 causes depletion of macrophages in this mesenchymal type tumor. In some embodiments, Compound 1, potently inhibits CSF1R signaling. In some embodiments, Compound 1 blocks macrophage-mediated tumor cell migration. In some embodiments, Compound 1 blocks osteoclast differentiation. In some embodiments, Compound 1 blocks proliferation of a CSF1R-dependent cell line. In some embodiments, Compound 1 potently inhibits CSF1R signaling in cellular assays, as well as blocks macrophage-mediated tumor cell migration, osteoclast differentiation, and proliferation of a CSF1R-dependent cell line. In some embodiments, the compound is selective in inhibiting CSF1R over one or more of the FLT3, KIT, PDGFRα, PDGFRβ and VEGFR2 kinases. In some embodiments, the compound has greater than 100-fold selectivity in inhibiting CSF1R over the FLT3, KIT, PDGFRα, PDGFRβ, and VEGFR2 kinases.

A method of treating a tenosynovial giant cell tumor in a patient in need thereof, comprising orally administering to the patient (e.g., a human patient) a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof is provided, in an embodiment. In some embodiments, such tenosynovial giant cell tumor may be localized, e.g., as a single, well-defined nodule. In some embodiments, such tenosynovial giant cell tumor may be diffuse-type tenosynovial giant cell tumor, e.g., may be benign tumors. In some embodiments, such tenosynovial giant cell tumor may be diffuse-type tenosynovial giant cell tumor, e.g., with multiple nodules that are more aggressive. The method may include administering about 2 mg to about 60 mg of the compound (e.g., Compound 1) daily, once a week, twice a week, or three times a week. For example, a disclosed method such as a method of treating tenosynovial giant cell tumor may include administering about 10 mg to about 90 mg of a disclosed compound daily, twice a week, or three times a week to the patient in need thereof. In some embodiments, a method of treating tenosynovial giant cell tumor may include administering about 5 mg to about 70 mg of a disclosed compound daily, twice a week, or three times a week to the patient in need thereof. In some embodiments, a method of treating tenosynovial giant cell tumor may include administering about 5 mg to about 50 mg of a disclosed compound daily, twice a week, or three times a week to the patient in need thereof. In some embodiments, a method of treating tenosynovial giant cell tumor may include administering about 5 mg to about 30 mg of a disclosed compound daily, twice a week, or three times a week to the patient in need thereof. In some embodiments, a method of treating tenosynovial giant cell tumor may include administering about 6 mg to about 25 mg of a disclosed compound daily, twice a week, or three times a week to the patient in need thereof. In some embodiments, a method of treating tenosynovial giant cell tumor may include administering about 6 mg to about 20 mg of a disclosed compound daily, twice a week, or three times a week to the patient in need thereof. In some embodiments, a method of treating tenosynovial giant cell tumor may include administering about 20 mg to about 50 mg of a disclosed compound daily, twice a week, or three times a week to the patient in need thereof.

Such a disclosed method may include, in an embodiment, administering a loading dose of the compound daily for a first time period; and administering a maintenance dose of the compound daily, once a week, twice a week or three times a week for a second time period. For example, a loading dose may be about 10 mg/day to about 80 mg/day, or about 20 mg/day to about 60 mg/day. In some embodiments, the loading dose is about 20 mg/day, about 30 mg/day, about 40 mg/day, about 50 mg/day or about 60 mg/day. In some embodiments, the maintenance dose of the compound is about 6 mg/day, 7 mg/day, 8 mg/day, 9 mg/day, 10 mg/day, 11 mg/day, 12 mg/day, 13 mg/day, 14 mg/day, 15 mg/day, 16 mg/day, 17 mg/day, 18 mg/day, 19 mg/day, 20 mg/day, 21 mg/day, 22 mg/day, 23 mg/day, 24 mg/day, 26 mg/day, 27 mg/day, 28 mg/day, 29 mg/day, or 30 mg/day.

Administering a maintenance dose may include administering to the patient about 10 mg to about 60 mg of the compound, e.g., about 10 mg, about 20 mg, about 25 mg, about 30 mg, about 40 mg or about 50 mg, which may be each administered once, twice or three times a week. In some embodiments, the maintenance dose may include administering to the patient about 2 mg to about 40 mg of the compound once a week. In some embodiments, the maintenance dose may include administering to the patient about 2 mg to about 30 mg of the compound once a week. In some embodiments, the maintenance dose may include administering to the patient about 2 mg to about 20 mg of the compound once a week. In some embodiments, the maintenance dose may include administering to the patient about 5 mg to about 40 mg of the compound once a week. In some embodiments, the maintenance dose may include administering to the patient about 5 mg to about 30 mg of the compound once a week. In some embodiments, the maintenance dose may include administering to the patient about 5 mg to about 20 mg of the compound once a week. In some embodiments, the maintenance dose may include administering to the patient about 6 mg to about 40 mg of the compound once a week. In some embodiments, the maintenance dose may include administering to the patient about 6 mg to about 30 mg of the compound once a week. In some embodiments, the maintenance dose may include administering to the patient about 6 mg to about 20 mg of the compound once a week. In some embodiments, the maintenance dose may include administering to the patient about 10 mg to about 40 mg of the compound once a week. In some embodiments, the maintenance dose may include administering to the patient about 10 mg to about 30 mg of the compound once a week. In some embodiments, the maintenance dose may include administering to the patient about 10 mg to about 20 mg of the compound once a week. In some embodiments, the maintenance dose may include administering to the patient about 3 mg of the compound once a week. In some embodiments, the maintenance dose may include administering to the patient about 5 mg of the compound once a week. In some embodiments, the maintenance dose may include administering to the patient about 6 mg of the compound once a week. In some embodiments, the maintenance dose may include administering to the patient about 8 mg of the compound once a week. In some embodiments, the maintenance dose may include administering to the patient about 10 mg of the compound once a week. In some embodiments, the maintenance dose may include administering to the patient about 11 mg of the compound once a week. In some embodiments, the maintenance dose may include administering to the patient about 12 mg of the compound once a week. In some embodiments, the maintenance dose may include administering to the patient about 13 mg of the compound once a week. In some embodiments, the maintenance dose may include administering to the patient about 14 mg of the compound once a week. In some embodiments, the maintenance dose may include administering to the patient about 15 mg of the compound once a week. In some embodiments, the maintenance dose may include administering to the patient about 16 mg of the compound once a week. In some embodiments, the maintenance dose may include administering to the patient about 17 mg of the compound once a week. In some embodiments, the maintenance dose may include administering to the patient about 18 mg of the compound once a week. In some embodiments, the maintenance dose may include administering to the patient about 19 mg of the compound once a week. In some embodiments, the maintenance dose may include administering to the patient about 20 mg of the compound once a week. In some embodiments, the maintenance dose may include administering to the patient about 22 mg of the compound once a week. In some embodiments, the maintenance dose may include administering to the patient about 24 mg of the compound once a week. In some embodiments, the maintenance dose may include administering to the patient about 26 mg of the compound once a week. In some embodiments, the maintenance dose may include administering to the patient about 28 mg of the compound once a week. In some embodiments, the maintenance dose may include administering to the patient about 30 mg of the compound once a week. In some embodiments, the maintenance dose may include administering to the patient about 32 mg of the compound once a week. In some embodiments, the maintenance dose may include administering to the patient about 34 mg of the compound once a week. In some embodiments, the maintenance dose may include administering to the patient about 36 mg of the compound once a week. In some embodiments, the maintenance dose may include administering to the patient about 38 mg of the compound once a week. In some embodiments, the maintenance dose may include administering to the patient about 40 mg of the compound once a week. In some embodiments, the maintenance dose may include administering to the patient about 42 mg of the compound once a week. In some embodiments, the maintenance dose may include administering to the patient about 44 mg of the compound once a week. In some embodiments, the maintenance dose may include administering to the patient about 46 mg of the compound once a week. In some embodiments, the maintenance dose may include administering to the patient about 48 mg of the compound once a week. In some embodiments, the maintenance dose may include administering to the patient about 50 mg of the compound once a week.

In some embodiments, the maintenance dose may include administering to the patient about 2 mg to about 40 mg of the compound twice a week. In some embodiments, the maintenance dose may include administering to the patient about 2 mg to about 30 mg of the compound twice a week. In some embodiments, the maintenance dose may include administering to the patient about 2 mg to about 20 mg of the compound twice a week. In some embodiments, the maintenance dose may include administering to the patient about 5 mg to about 40 mg of the compound twice a week. In some embodiments, the maintenance dose may include administering to the patient about 5 mg to about 30 mg of the compound twice a week. In some embodiments, the maintenance dose may include administering to the patient about 5 mg to about 20 mg of the compound twice a week. In some embodiments, the maintenance dose may include administering to the patient about 6 mg to about 40 mg of the compound twice a week. In some embodiments, the maintenance dose may include administering to the patient about 6 mg to about 30 mg of the compound twice a week. In some embodiments, the maintenance dose may include administering to the patient about 6 mg to about 20 mg of the compound twice a week. In some embodiments, the maintenance dose may include administering to the patient about 10 mg to about 40 mg of the compound twice a week. In some embodiments, the maintenance dose may include administering to the patient about 10 mg to about 30 mg of the compound twice a week. In some embodiments, the maintenance dose may include administering to the patient about 10 mg to about 20 mg of the compound twice a week. In some embodiments, the maintenance dose may include administering to the patient about 3 mg of the compound twice a week. In some embodiments, the maintenance dose may include administering to the patient about 5 mg of the compound twice a week. In some embodiments, the maintenance dose may include administering to the patient about 6 mg of the compound twice a week. In some embodiments, the maintenance dose may include administering to the patient about 8 mg of the compound twice a week. In some embodiments, the maintenance dose may include administering to the patient about 10 mg of the compound twice a week. In some embodiments, the maintenance dose may include administering to the patient about 11 mg of the compound twice a week. In some embodiments, the maintenance dose may include administering to the patient about 12 mg of the compound twice a week. In some embodiments, the maintenance dose may include administering to the patient about 13 mg of the compound twice a week. In some embodiments, the maintenance dose may include administering to the patient about 14 mg of the compound twice a week. In some embodiments, the maintenance dose may include administering to the patient about 15 mg of the compound twice a week. In some embodiments, the maintenance dose may include administering to the patient about 16 mg of the compound twice a week. In some embodiments, the maintenance dose may include administering to the patient about 17 mg of the compound twice a week. In some embodiments, the maintenance dose may include administering to the patient about 18 mg of the compound twice a week. In some embodiments, the maintenance dose may include administering to the patient about 19 mg of the compound twice a week. In some embodiments, the maintenance dose may include administering to the patient about 20 mg of the compound twice a week. In some embodiments, the maintenance dose may include administering to the patient about 22 mg of the compound twice a week. In some embodiments, the maintenance dose may include administering to the patient about 24 mg of the compound twice a week. In some embodiments, the maintenance dose may include administering to the patient about 26 mg of the compound twice a week. In some embodiments, the maintenance dose may include administering to the patient about 28 mg of the compound twice a week. In some embodiments, the maintenance dose may include administering to the patient about 30 mg of the compound twice a week. In some embodiments, the maintenance dose may include administering to the patient about 32 mg of the compound twice a week. In some embodiments, the maintenance dose may include administering to the patient about 34 mg of the compound twice a week. In some embodiments, the maintenance dose may include administering to the patient about 36 mg of the compound twice a week. In some embodiments, the maintenance dose may include administering to the patient about 38 mg of the compound twice a week. In some embodiments, the maintenance dose may include administering to the patient about 40 mg of the compound twice a week. In some embodiments, the maintenance dose may include administering to the patient about 42 mg of the compound twice a week. In some embodiments, the maintenance dose may include administering to the patient about 44 mg of the compound twice a week. In some embodiments, the maintenance dose may include administering to the patient about 46 mg of the compound twice a week. In some embodiments, the maintenance dose may include administering to the patient about 48 mg of the compound twice a week. In some embodiments, the maintenance dose may include administering to the patient about 50 mg of the compound twice a week.

In some embodiments, the maintenance dose may include administering to the patient about 2 mg to about 40 mg of the compound three times a week. In some embodiments, the maintenance dose may include administering to the patient about 2 mg to about 30 mg of the compound three times a week. In some embodiments, the maintenance dose may include administering to the patient about 2 mg to about 20 mg of the compound three times a week. In some embodiments, the maintenance dose may include administering to the patient about 5 mg to about 40 mg of the compound three times a week. In some embodiments, the maintenance dose may include administering to the patient about 5 mg to about 30 mg of the compound three times a week. In some embodiments, the maintenance dose may include administering to the patient about 5 mg to about 20 mg of the compound three times a week. In some embodiments, the maintenance dose may include administering to the patient about 6 mg to about 40 mg of the compound three times a week. In some embodiments, the maintenance dose may include administering to the patient about 6 mg to about 30 mg of the compound three times a week. In some embodiments, the maintenance dose may include administering to the patient about 6 mg to about 20 mg of the compound three times a week. In some embodiments, the maintenance dose may include administering to the patient about 10 mg to about 40 mg of the compound three times a week. In some embodiments, the maintenance dose may include administering to the patient about 10 mg to about 30 mg of the compound three times a week. In some embodiments, the maintenance dose may include administering to the patient about 10 mg to about 20 mg of the compound three times a week. In some embodiments, the maintenance dose may include administering to the patient about 3 mg of the compound three times a week. In some embodiments, the maintenance dose may include administering to the patient about 5 mg of the compound three times a week. In some embodiments, the maintenance dose may include administering to the patient about 6 mg of the compound three times a week. In some embodiments, the maintenance dose may include administering to the patient about 8 mg of the compound three times a week. In some embodiments, the maintenance dose may include administering to the patient about 10 mg of the compound three times a week. In some embodiments, the maintenance dose may include administering to the patient about 11 mg of the compound three times a week. In some embodiments, the maintenance dose may include administering to the patient about 12 mg of the compound three times a week. In some embodiments, the maintenance dose may include administering to the patient about 13 mg of the compound three times a week. In some embodiments, the maintenance dose may include administering to the patient about 14 mg of the compound three times a week. In some embodiments, the maintenance dose may include administering to the patient about 15 mg of the compound three times a week. In some embodiments, the maintenance dose may include administering to the patient about 16 mg of the compound three times a week. In some embodiments, the maintenance dose may include administering to the patient about 17 mg of the compound three times a week. In some embodiments, the maintenance dose may include administering to the patient about 18 mg of the compound three times a week. In some embodiments, the maintenance dose may include administering to the patient about 19 mg of the compound three times a week. In some embodiments, the maintenance dose may include administering to the patient about 20 mg of the compound three times a week. In some embodiments, the maintenance dose may include administering to the patient about 22 mg of the compound three times a week. In some embodiments, the maintenance dose may include administering to the patient about 24 mg of the compound three times a week. In some embodiments, the maintenance dose may include administering to the patient about 26 mg of the compound three times a week. In some embodiments, the maintenance dose may include administering to the patient about 28 mg of the compound three times a week. In some embodiments, the maintenance dose may include administering to the patient about 30 mg of the compound three times a week. In some embodiments, the maintenance dose may include administering to the patient about 32 mg of the compound three times a week. In some embodiments, the maintenance dose may include administering to the patient about 34 mg of the compound three times a week. In some embodiments, the maintenance dose may include administering to the patient about 36 mg of the compound three times a week. In some embodiments, the maintenance dose may include administering to the patient about 38 mg of the compound three times a week. In some embodiments, the maintenance dose may include administering to the patient about 40 mg of the compound three times a week. In some embodiments, the maintenance dose may include administering to the patient about 42 mg of the compound three times a week. In some embodiments, the maintenance dose may include administering to the patient about 44 mg of the compound three times a week. In some embodiments, the maintenance dose may include administering to the patient about 46 mg of the compound three times a week. In some embodiments, the maintenance dose may include administering to the patient about 48 mg of the compound three times a week. In some embodiments, the maintenance dose may include administering to the patient about 50 mg of the compound three times a week.

The maintenance dose may also be administered once daily. For example, the maintenance dose may include administering to the patient about 2 mg of the compound once a day. In some embodiments, the maintenance may include administering to the patient about 2 mg to about 40 mg of the compound once a day. In some embodiments, the maintenance may include administering to the patient about 2 mg to about 30 mg of the compound once a day. In some embodiments, the maintenance may include administering to the patient about 2 mg to about 20 mg of the compound once a day. In some embodiments, the maintenance may include administering to the patient about 5 mg to about 40 mg of the compound once a day. In some embodiments, the maintenance may include administering to the patient about 5 mg to about 30 mg of the compound once a day. In some embodiments, the maintenance may include administering to the patient about 5 mg to about 20 mg of the compound once a day. In some embodiments, the maintenance may include administering to the patient about 6 mg to about 40 mg of the compound once a day. In some embodiments, the maintenance may include administering to the patient about 6 mg to about 30 mg of the compound once a day. In some embodiments, the maintenance may include administering to the patient about 6 mg to about 20 mg of the compound once a day. In some embodiments, the maintenance may include administering to the patient about 10 mg to about 40 mg of the compound once a day. In some embodiments, the maintenance may include administering to the patient about 10 mg to about 30 mg of the compound once a day. In some embodiments, the maintenance may include administering to the patient about 10 mg to about 20 mg of the compound once a day. In some embodiments, the maintenance may include administering to the patient about 3 mg of the compound once a day. In some embodiments, the maintenance may include administering to the patient about 5 mg of the compound once a day. In some embodiments, the maintenance may include administering to the patient about 6 mg of the compound once a day. In some embodiments, the maintenance may include administering to the patient about 8 mg of the compound once a day. In some embodiments, the maintenance may include administering to the patient about 10 mg of the compound once a day. In some embodiments, the maintenance may include administering to the patient about 11 mg of the compound once a day. In some embodiments, the maintenance may include administering to the patient about 12 mg of the compound once a day. In some embodiments, the maintenance may include administering to the patient about 13 mg of the compound once a day. In some embodiments, the maintenance may include administering to the patient about 14 mg of the compound once a day. In some embodiments, the maintenance may include administering to the patient about 15 mg of the compound once a day. In some embodiments, the maintenance may include administering to the patient about 16 mg of the compound once a day. In some embodiments, the maintenance may include administering to the patient about 17 mg of the compound once a day. In some embodiments, the maintenance may include administering to the patient about 18 mg of the compound once a day. In some embodiments, the maintenance may include administering to the patient about 19 mg of the compound once a day. In some embodiments, the maintenance may include administering to the patient about 20 mg of the compound once a day. In some embodiments, the maintenance may include administering to the patient about 22 mg of the compound once a day. In some embodiments, the maintenance may include administering to the patient about 24 mg of the compound once a day. In some embodiments, the maintenance may include administering to the patient about 26 mg of the compound once a day. In some embodiments, the maintenance may include administering to the patient about 28 mg of the compound once a day. In some embodiments, the maintenance may include administering to the patient about 30 mg of the compound once a day. In some embodiments, the maintenance dose may include administering to the patient about 32 mg of the compound once a day. In some embodiments, the maintenance dose may include administering to the patient about 34 mg of the compound once a day. In some embodiments, the maintenance dose may include administering to the patient about 36 mg of the compound once a day. In some embodiments, the maintenance dose may include administering to the patient about 38 mg of the compound once a day. In some embodiments, the maintenance dose may include administering to the patient about 40 mg of the compound once a day. In some embodiments, the maintenance dose may include administering to the patient about 42 mg of the compound once a day. In some embodiments, the maintenance dose may include administering to the patient about 44 mg of the compound once a day. In some embodiments, the maintenance dose may include administering to the patient about 46 mg of the compound once a day. In some embodiments, the maintenance dose may include administering to the patient about 48 mg of the compound once a day. In some embodiments, the maintenance dose may include administering to the patient about 50 mg of the compound once a day.

In some embodiments, the maintenance dose may include administering to the patient about 2 mg to about 40 mg of the compound every other day. In some embodiments, the maintenance dose may include administering to the patient about 2 mg to about 30 mg of the compound every other day. In some embodiments, the maintenance dose may include administering to the patient about 2 mg to about 20 mg of the compound every other day. In some embodiments, the maintenance dose may include administering to the patient about 5 mg to about 40 mg of the compound every other day. In some embodiments, the maintenance dose may include administering to the patient about 5 mg to about 30 mg of the compound every other day. In some embodiments, the maintenance dose may include administering to the patient about 5 mg to about 20 mg of the compound every other day. In some embodiments, the maintenance dose may include administering to the patient about 6 mg to about 40 mg of the compound every other day. In some embodiments, the maintenance dose may include administering to the patient about 6 mg to about 30 mg of the compound every other day. In some embodiments, the maintenance dose may include administering to the patient about 6 mg to about 20 mg of the compound every other day. In some embodiments, the maintenance dose may include administering to the patient about 10 mg to about 40 mg of the compound every other day. In some embodiments, the maintenance dose may include administering to the patient about 10 mg to about 30 mg of the compound every other day. In some embodiments, the maintenance dose may include administering to the patient about 10 mg to about 20 mg of the compound every other day. In some embodiments, the maintenance dose may include administering to the patient about 3 mg of the compound every other day. In some embodiments, the maintenance dose may include administering to the patient about 5 mg of the compound every other day. In some embodiments, the maintenance dose may include administering to the patient about 6 mg of the compound every other day. In some embodiments, the maintenance dose may include administering to the patient about 8 mg of the compound every other day. In some embodiments, the maintenance dose may include administering to the patient about 10 mg of the compound every other day. In some embodiments, the maintenance dose may include administering to the patient about 11 mg of the compound every other day. In some embodiments, the maintenance dose may include administering to the patient about 12 mg of the compound every other day. In some embodiments, the maintenance dose may include administering to the patient about 13 mg of the compound every other day. In some embodiments, the maintenance dose may include administering to the patient about 14 mg of the compound every other day. In some embodiments, the maintenance dose may include administering to the patient about 15 mg of the compound every other day. In some embodiments, the maintenance dose may include administering to the patient about 16 mg of the compound every other day. In some embodiments, the maintenance dose may include administering to the patient about 17 mg of the compound every other day. In some embodiments, the maintenance dose may include administering to the patient about 18 mg of the compound every other day. In some embodiments, the maintenance dose may include administering to the patient about 19 mg of the compound every other day. In some embodiments, the maintenance dose may include administering to the patient about 20 mg of the compound every other day. In some embodiments, the maintenance dose may include administering to the patient about 22 mg of the compound every other day. In some embodiments, the maintenance dose may include administering to the patient about 24 mg of the compound every other day. In some embodiments, the maintenance dose may include administering to the patient about 26 mg of the compound every other day. In some embodiments, the maintenance dose may include administering to the patient about 28 mg of the compound every other day. In some embodiments, the maintenance dose may include administering to the patient about 30 mg of the compound every other day. In some embodiments, the maintenance dose may include administering to the patient about 32 mg of the compound every other day. In some embodiments, the maintenance dose may include administering to the patient about 34 mg of the compound every other day. In some embodiments, the maintenance dose may include administering to the patient about 36 mg of the compound every other day. In some embodiments, the maintenance dose may include administering to the patient about 38 mg of the compound every other day. In some embodiments, the maintenance dose may include administering to the patient about 40 mg of the compound every other day. In some embodiments, the maintenance dose may include administering to the patient about 42 mg of the compound every other day. In some embodiments, the maintenance dose may include administering to the patient about 44 mg of the compound every other day. In some embodiments, the maintenance dose may include administering to the patient about 46 mg of the compound every other day. In some embodiments, the maintenance dose may include administering to the patient about 48 mg of the compound every other day. In some embodiments, the maintenance dose may include administering to the patient about 50 mg of the compound every other day. In some embodiments, the first time period, for example during which a loading dose is administered (e.g., daily or every other day, or twice daily) is about one or two weeks, or one to three weeks, e.g., such a first time period may be about 4 days, about 5 days, about 6 days, or about 10 days. In some embodiments, the first time period is about one to six days. In some embodiments, the first time period is about one to five days. In some embodiments, the first time period is about one to four days. In some embodiments, the first time period is about one to three days. In some embodiments, the first time period is about one to two days. In some embodiments, the first time period is about one to five weeks. In some embodiments, the first time period is about one to four weeks. In some embodiments, the first time period is about one to three weeks. In some embodiments, the first time period is about one to two weeks.

In some embodiments, the loading dose is about 2 mg to about 100 mg of the compound. In some embodiments, the loading dose is about 5 mg to about 90 mg of the compound. In some embodiments, the loading dose is about 10 mg to about 80 mg of the compound. In some embodiments, the loading dose is about 10 mg to about 70 mg of the compound. In some embodiments, the loading dose is about 10 mg to about 60 mg of the compound. In some embodiments, the loading dose is about 10 mg to about 50 mg of the compound. In some embodiments, the loading dose is about 10 mg to about 40 mg of the compound. In some embodiments, the loading dose is about 10 mg to about 30 mg of the compound. In some embodiments, the loading dose is about 10 mg to about 20 mg of the compound. In some embodiments, the loading dose is about 2 mg of the compound. In some embodiments, the loading dose is about 3 mg of the compound. In some embodiments, the loading dose is about 4 mg of the compound. In some embodiments, the loading dose is about 5 mg of the compound. In some embodiments, the loading dose is about 10 mg of the compound. In some embodiments, the loading dose is about 11 mg of the compound. In some embodiments, the loading dose is about 12 mg of the compound. In some embodiments, the loading dose is about 13 mg of the compound. In some embodiments, the loading dose is about 14 mg of the compound. In some embodiments, the loading dose is about 15 mg of the compound. In some embodiments, the loading dose is about 16 mg of the compound. In some embodiments, the loading dose is about 17 mg of the compound. In some embodiments, the loading dose is about 18 mg of the compound. In some embodiments, the loading dose is about 19 mg of the compound. In some embodiments, the loading dose is about 20 mg of the compound. In some embodiments, the loading dose is about 22 mg of the compound. In some embodiments, the loading dose is about 24 mg of the compound. In some embodiments, the loading dose is about 26 mg of the compound. In some embodiments, the loading dose is about 28 mg of the compound. In some embodiments, the loading dose is about 30 mg of the compound. In some embodiments, the loading dose is about 32 mg of the compound. In some embodiments, the loading dose is about 34 mg of the compound. In some embodiments, the loading dose is about 36 mg of the compound. In some embodiments, the loading dose is about 38 mg of the compound. In some embodiments, the loading dose is about 40 mg of the compound. In some embodiments, the loading dose is about 42 mg of the compound. In some embodiments, the loading dose is about 44 mg of the compound. In some embodiments, the loading dose is about 40 mg of the compound. In some embodiments, the loading dose is about 46 mg of the compound. In some embodiments, the loading dose is about 48 mg of the compound. In some embodiments, the loading dose is about 50 mg of the compound.

In some embodiments, the loading dose is about 2 mg to about 100 mg of the compound once a day. In some embodiments, the loading dose is about 2 mg to about 100 mg of the compound once a day. In some embodiments, the loading dose is about 5 mg to about 90 mg of the compound once a day. In some embodiments, the loading dose is about 10 mg to about 80 mg of the compound once a day. In some embodiments, the loading dose is about 10 mg to about 70 mg of the compound once a day. In some embodiments, the loading dose is about 10 mg to about 60 mg of the compound once a day. In some embodiments, the loading dose is about 10 mg to about 50 mg of the compound once a day. In some embodiments, the loading dose is about 10 mg to about 40 mg of the compound once a day. In some embodiments, the loading dose is about 10 mg to about 30 mg of the compound once a day. In some embodiments, the loading dose is about 10 mg to about 20 mg of the compound once a day. In some embodiments, the loading dose is about 2 mg of the compound once a day. In some embodiments, the loading dose is about 3 mg of the compound once a day. In some embodiments, the loading dose is about 4 mg of the compound once a day. In some embodiments, the loading dose is about 5 mg of the compound once a day. In some embodiments, the loading dose is about 10 mg of the compound once a day. In some embodiments, the loading dose is about 11 mg of the compound once a day. In some embodiments, the loading dose is about 12 mg of the compound once a day. In some embodiments, the loading dose is about 13 mg of the compound once a day. In some embodiments, the loading dose is about 14 mg of the compound once a day. In some embodiments, the loading dose is about 15 mg of the compound once a day. In some embodiments, the loading dose is about 16 mg of the compound once a day. In some embodiments, the loading dose is about 17 mg of the compound once a day. In some embodiments, the loading dose is about 18 mg of the compound once a day. In some embodiments, the loading dose is about 19 mg of the compound once a day. In some embodiments, the loading dose is about 20 mg of the compound once a day. In some embodiments, the loading dose is about 22 mg of the compound once a day. In some embodiments, the loading dose is about 24 mg of the compound once a day. In some embodiments, the loading dose is about 26 mg of the compound once a day. In some embodiments, the loading dose is about 28 mg of the compound once a day. In some embodiments, the loading dose is about 30 mg of the compound once a day. In some embodiments, the loading dose is about 32 mg of the compound once a day. In some embodiments, the loading dose is about 34 mg of the compound once a day. In some embodiments, the loading dose is about 36 mg of the compound once a day. In some embodiments, the loading dose is about 38 mg of the compound once a day. In some embodiments, the loading dose is about 40 mg of the compound once a day. In some embodiments, the loading dose is about 42 mg of the compound once a day. In some embodiments, the loading dose is about 44 mg of the compound once a day. In some embodiments, the loading dose is about 40 mg of the compound once a day. In some embodiments, the loading dose is about 46 mg of the compound once a day. In some embodiments, the loading dose is about 48 mg of the compound once a day. In some embodiments, the loading dose is about 50 mg of the compound once a day.

In some embodiments, the loading dose is about 2 mg to about 100 mg of the compound once a week. In some embodiments, the loading dose is about 2 mg to about 100 mg of the compound once a week. In some embodiments, the loading dose is about 5 mg to about 90 mg of the compound once a week. In some embodiments, the loading dose is about 10 mg to about 80 mg of the compound once a week. In some embodiments, the loading dose is about 10 mg to about 70 mg of the compound once a week. In some embodiments, the loading dose is about 10 mg to about 60 mg of the compound once a week. In some embodiments, the loading dose is about 10 mg to about 50 mg of the compound once a week. In some embodiments, the loading dose is about 10 mg to about 40 mg of the compound once a week. In some embodiments, the loading dose is about 10 mg to about 30 mg of the compound once a week. In some embodiments, the loading dose is about 10 mg to about 20 mg of the compound once a week. In some embodiments, the loading dose is about 2 mg of the compound once a week. In some embodiments, the loading dose is about 3 mg of the compound once a week. In some embodiments, the loading dose is about 4 mg of the compound once a week. In some embodiments, the loading dose is about 5 mg of the compound once a week. In some embodiments, the loading dose is about 10 mg of the compound once a week. In some embodiments, the loading dose is about 11 mg of the compound once a week. In some embodiments, the loading dose is about 12 mg of the compound once a week. In some embodiments, the loading dose is about 13 mg of the compound once a week. In some embodiments, the loading dose is about 14 mg of the compound once a week. In some embodiments, the loading dose is about 15 mg of the compound once a week. In some embodiments, the loading dose is about 16 mg of the compound once a week. In some embodiments, the loading dose is about 17 mg of the compound once a week. In some embodiments, the loading dose is about 18 mg of the compound once a week. In some embodiments, the loading dose is about 19 mg of the compound once a week. In some embodiments, the loading dose is about 20 mg of the compound once a week. In some embodiments, the loading dose is about 22 mg of the compound once a week. In some embodiments, the loading dose is about 24 mg of the compound once a week. In some embodiments, the loading dose is about 26 mg of the compound once a week. In some embodiments, the loading dose is about 28 mg of the compound once a week. In some embodiments, the loading dose is about 30 mg of the compound once a week. In some embodiments, the loading dose is about 32 mg of the compound once a week. In some embodiments, the loading dose is about 34 mg of the compound once a week. In some embodiments, the loading dose is about 36 mg of the compound once a week. In some embodiments, the loading dose is about 38 mg of the compound once a week. In some embodiments, the loading dose is about 40 mg of the compound once a week. In some embodiments, the loading dose is about 42 mg of the compound once a week. In some embodiments, the loading dose is about 44 mg of the compound once a week. In some embodiments, the loading dose is about 40 mg of the compound once a week. In some embodiments, the loading dose is about 46 mg of the compound once a week. In some embodiments, the loading dose is about 48 mg of the compound once a week. In some embodiments, the loading dose is about 50 mg of the compound once a week.

In some embodiments, the loading dose is about 2 mg to about 100 mg of the compound twice a week. In some embodiments, the loading dose is about 2 mg to about 100 mg of the compound twice a week. In some embodiments, the loading dose is about 5 mg to about 90 mg of the compound twice a week. In some embodiments, the loading dose is about 10 mg to about 80 mg of the compound twice a week. In some embodiments, the loading dose is about 10 mg to about 70 mg of the compound twice a week. In some embodiments, the loading dose is about 10 mg to about 60 mg of the compound twice a week. In some embodiments, the loading dose is about 10 mg to about 50 mg of the compound twice a week. In some embodiments, the loading dose is about 10 mg to about 40 mg of the compound twice a week. In some embodiments, the loading dose is about 10 mg to about 30 mg of the compound twice a week. In some embodiments, the loading dose is about 10 mg to about 20 mg of the compound twice a week. In some embodiments, the loading dose is about 2 mg of the compound twice a week. In some embodiments, the loading dose is about 3 mg of the compound twice a week. In some embodiments, the loading dose is about 4 mg of the compound twice a week. In some embodiments, the loading dose is about 5 mg of the compound twice a week. In some embodiments, the loading dose is about 10 mg of the compound twice a week. In some embodiments, the loading dose is about 11 mg of the compound twice a week. In some embodiments, the loading dose is about 12 mg of the compound twice a week. In some embodiments, the loading dose is about 13 mg of the compound twice a week. In some embodiments, the loading dose is about 14 mg of the compound twice a week. In some embodiments, the loading dose is about 15 mg of the compound twice a week. In some embodiments, the loading dose is about 16 mg of the compound twice a week. In some embodiments, the loading dose is about 17 mg of the compound twice a week. In some embodiments, the loading dose is about 18 mg of the compound twice a week. In some embodiments, the loading dose is about 19 mg of the compound twice a week. In some embodiments, the loading dose is about 20 mg of the compound twice a week. In some embodiments, the loading dose is about 22 mg of the compound twice a week. In some embodiments, the loading dose is about 24 mg of the compound twice a week. In some embodiments, the loading dose is about 26 mg of the compound twice a week. In some embodiments, the loading dose is about 28 mg of the compound twice a week. In some embodiments, the loading dose is about 30 mg of the compound twice a week. In some embodiments, the loading dose is about 32 mg of the compound twice a week. In some embodiments, the loading dose is about 34 mg of the compound twice a week. In some embodiments, the loading dose is about 36 mg of the compound twice a week. In some embodiments, the loading dose is about 38 mg of the compound twice a week. In some embodiments, the loading dose is about 40 mg of the compound twice a week. In some embodiments, the loading dose is about 42 mg of the compound twice a week. In some embodiments, the loading dose is about 44 mg of the compound twice a week. In some embodiments, the loading dose is about 40 mg of the compound twice a week. In some embodiments, the loading dose is about 46 mg of the compound twice a week. In some embodiments, the loading dose is about 48 mg of the compound twice a week. In some embodiments, the loading dose is about 50 mg of the compound twice a week.

The second time period, during which e.g. a maintenance dose is administered, may be at least about one week, or more, e.g. about one month or more (for example, about 1 month to about 2 months, about 1 month to about 3 months, about 1 month to about 4 months, about 1 month to about 5 months, about 1 month to about 6 months, about 1 month to about 9 months, 1 month to about 12 months, or more).

The method comprises administering a loading dose daily for a first time period, and administering a maintenance dose daily for a second time period. In some embodiments, the first time period is from one day to 6 days, and the second period is from one to 35 days. In some embodiments, the first time period is from one day to 6 days, and the second period is from one to 30 days. In some embodiments, the first time period is from one day to 6 days, and the second period is from one to 25 days. In some embodiments, the first time period is from one day to 6 days, and the second period is from one to 22 days. In some embodiments, the first time period is from one day to 6 days, and the second period is from one to 20 days. In some embodiments, the first time period is from one day to 5 days, and the second period is from one day to 35 days. In some embodiments, the first time period is from one day to 5 days, and the second period is from one to 30 days. In some embodiments, the first time period is from one day to 5 days, and the second period is from one day to 25 days. In some embodiments, the first time period is from one day to 5 days, and the second period is from one day to 22 days. In some embodiments, the first time period is from one day to 5 days, and the second period is from one day to 20 days. In some embodiments, the first time period is from one day to 4 days, and the second period is from one day to 35 days. In some embodiments, the first time period is from one day to 4 days, and the second period is from one to 30 days. In some embodiments, the first time period is from one day to 4 days, and the second period is from one day to 25 days. In some embodiments, the first time period is from one day to 4 days, and the second period is from one day to 22 days. In some embodiments, the first time period is from one day to 4 days, and the second period is from one day to 20 days. In some embodiments, the first time period is from one day to 3 days, and the second period is from one day to 35 days. In some embodiments, the first time period is from one day to 3 days, and the second period is from one to 30 days. In some embodiments, the first time period is from one day to 3 days, and the second period is from one day to 25 days. In some embodiments, the first time period is from one day to 3 days, and the second period is from one day to 22 days. In some embodiments, the first time period is from one day to 3 days, and the second period is from one day to 20 days. In some embodiments, the first time period is from one day to 2 days, and the second period is from one day to 35 days. In some embodiments, the first time period is from one day to 2 days, and the second period is from one to 30 days. In some embodiments, the first time period is from one day to 2 days, and the second period is from one day to 25 days. In some embodiments, the first time period is from one day to 2 days, and the second period is from one day to 22 days. In some embodiments, the first time period is from one day to 2 days, and the second period is from one day to 20 days. In other embodiments, the first period of time and the second period of time combined comprise 20 days. In some embodiments, the first period of time and the second period of time combined comprise 21 days. In some embodiments, the first period of time and the second period of time combined comprise 22 days. In some embodiments, the first period of time and the second period of time combined comprise 23 days. In some embodiments, the first period of time and the second period of time combined comprise 24 days. In some embodiments, the first period of time and the second period of time combined comprise 25 days. In some embodiments, the first period of time and the second period of time combined comprise 26 days. In some embodiments, the first period of time and the second period of time combined comprise 27 days. In some embodiments, the first period of time and the second period of time combined comprise 28 days. In some embodiments, the first period of time and the second period of time combined comprise 29 days. In some embodiments, the first period of time and the second period of time combined comprise 30 days. In some embodiments, the first period of time and the second period of time combined comprise 31 days. In some embodiments, the first period of time and the second period of time combined comprise 32 days. In some embodiments, the first period of time and the second period of time combined comprise 33 days. In some embodiments, the first period of time and the second period of time combined comprise 34 days. In some embodiments, the first period of time and the second period of time combined comprise 35 days. Disclosed methods may be administered for a cycle comprising a first period of time and a second period of time. In some embodiments, the cycle comprises 20 days. In some embodiments, the cycle comprises 21 days. In some embodiments, the cycle comprises 22 days. In some embodiments, the cycle comprises 23 days. In some embodiments, the cycle comprises 24 days. In some embodiments, the cycle comprises 25 days. In some embodiments, the cycle comprises 26 days. In some embodiments, the cycle comprises 27 days. In some embodiments, the cycle comprises 28 days. In some embodiments, the cycle comprises 29 days. In some embodiments, the cycle comprises 30 days. In some embodiments, the cycle comprises 31 days. In some embodiments, the cycle comprises 32 days. In some embodiments, the cycle comprises 33 days. In some embodiments, the cycle comprises 34 days. In some embodiments, the cycle comprises 35 days. In other embodiments, the method may be administered for one to 1200 cycles. In some embodiments, the method may be administered for 10 to 1000 cycles. In some embodiments, the method may be administered for 50 to 800 cycles. In some embodiments, the method may be administered for 70 to 700 cycles. In some embodiments, the method may be administered for 100 to 500 cycles.

In some embodiments, the loading dose is administered from 1 day to 20 days, and the maintenance dose is administered from 20 days to 37000 days. In some embodiments, the method comprises administering a loading dose of 5 mg of the compound daily for 3 days, followed by administering a maintenance dose of 10 mg of the compound daily. In some embodiments, the method comprises administering a loading dose of 5 mg of the compound daily for 4 days, followed by administering a maintenance dose of 10 mg of the compound daily. In some embodiments, the method comprises administering a loading dose of 5 mg of the compound daily for 5 days, followed by administering a maintenance dose of 10 mg of the compound daily. In some embodiments, the method comprises administering a loading dose of 5 mg of the compound daily for 6 days, followed by administering a maintenance dose of 10 mg of the compound daily. In some embodiments, the method comprises administering a loading dose of 5 mg of the compound daily for 7 days, followed by administering a maintenance dose of 10 mg of the compound daily. In some embodiments, the method comprises administering a loading dose of 5 mg of the compound daily for 8 days, followed by administering a maintenance dose of 10 mg of the compound daily. In some embodiments, the method comprises administering a loading dose of 5 mg of the compound daily for 9 days, followed by administering a maintenance dose of 10 mg of the compound daily. In some embodiments, the method comprises administering a loading dose of 5 mg of the compound daily for 10 days, followed by administering a maintenance dose of 10 mg of the compound daily. In some embodiments, the method comprises administering a loading dose of 7 mg of the compound daily for 3 days, followed by administering a maintenance dose of 10 mg of the compound daily. In some embodiments, the method comprises administering a loading dose of 7 mg of the compound daily for 4 days, followed by administering a maintenance dose of 10 mg of the compound daily. In some embodiments, the method comprises administering a loading dose of 7 mg of the compound daily for 5 days, followed by administering a maintenance dose of 10 mg of the compound daily. In some embodiments, the method comprises administering a loading dose of 7 mg of the compound daily for 6 days, followed by administering a maintenance dose of 10 mg of the compound daily. In some embodiments, the method comprises administering a loading dose of 7 mg of the compound daily for 7 days, followed by administering a maintenance dose of 10 mg of the compound daily. In some embodiments, the method comprises administering a loading dose of 7 mg of the compound daily for 8 days, followed by administering a maintenance dose of 10 mg of the compound daily. In some embodiments, the method comprises administering a loading dose of 7 mg of the compound daily for 9 days, followed by administering a maintenance dose of 10 mg of the compound daily. In some embodiments, the method comprises administering a loading dose of 7 mg of the compound daily for 10 days, followed by administering a maintenance dose of 10 mg of the compound daily. In some embodiments, the method comprises administering a loading dose of 8 mg of the compound daily for 3 days, followed by administering a maintenance dose of 10 mg of the compound daily. In some embodiments, the method comprises administering a loading dose of 8 mg of the compound daily for 4 days, followed by administering a maintenance dose of 10 mg of the compound daily. In some embodiments, the method comprises administering a loading dose of 8 mg of the compound daily for 5 days, followed by administering a maintenance dose of 10 mg of the compound daily. In some embodiments, the method comprises administering a loading dose of 8 mg of the compound daily for 6 days, followed by administering a maintenance dose of 10 mg of the compound daily. In some embodiments, the method comprises administering a loading dose of 8 mg of the compound daily for 7 days, followed by administering a maintenance dose of 10 mg of the compound daily. In some embodiments, the method comprises administering a loading dose of 8 mg of the compound daily for 8 days, followed by administering a maintenance dose of 10 mg of the compound daily. In some embodiments, the method comprises administering a loading dose of 8 mg of the compound daily for 9 days, followed by administering a maintenance dose of 10 mg of the compound daily. In some embodiments, the method comprises administering a loading dose of 8 mg of the compound daily for 10 days, followed by administering a maintenance dose of 10 mg of the compound daily. In some embodiments, the method comprises administering a loading dose of 10 mg of the compound daily for 3 days, followed by administering a maintenance dose of 10 mg of the compound daily. In some embodiments, the method comprises administering a loading dose of 10 mg of the compound daily for 4 days, followed by administering a maintenance dose of 10 mg of the compound daily. In some embodiments, the method comprises administering a loading dose of 10 mg of the compound daily for 5 days, followed by administering a maintenance dose of 10 mg of the compound daily. In some embodiments, the method comprises administering a loading dose of 10 mg of the compound daily for 6 days, followed by administering a maintenance dose of 10 mg of the compound daily. In some embodiments, the method comprises administering a loading dose of 10 mg of the compound daily for 7 days, followed by administering a maintenance dose of 10 mg of the compound daily. In some embodiments, the method comprises administering a loading dose of 10 mg of the compound daily for 8 days, followed by administering a maintenance dose of 10 mg of the compound daily. In some embodiments, the method comprises administering a loading dose of 10 mg of the compound daily for 9 days, followed by administering a maintenance dose of 10 mg of the compound daily. In some embodiments, the method comprises administering a loading dose of 10 mg of the compound daily for 10 days, followed by administering a maintenance dose of 10 mg of the compound daily. In some embodiments, the method comprises administering a loading dose of 12 mg of the compound daily for 3 days, followed by administering a maintenance dose of 10 mg of the compound daily. In some embodiments, the method comprises administering a loading dose of 12 mg of the compound daily for 4 days, followed by administering a maintenance dose of 10 mg of the compound daily. In some embodiments, the method comprises administering a loading dose of 12 mg of the compound daily for 5 days, followed by administering a maintenance dose of 10 mg of the compound daily. In some embodiments, the method comprises administering a loading dose of 12 mg of the compound daily for 6 days, followed by administering a maintenance dose of 10 mg of the compound daily. In some embodiments, the method comprises administering a loading dose of 12 mg of the compound daily for 7 days, followed by administering a maintenance dose of 10 mg of the compound daily. In some embodiments, the method comprises administering a loading dose of 12 mg of the compound daily for 8 days, followed by administering a maintenance dose of 10 mg of the compound daily. In some embodiments, the method comprises administering a loading dose of 12 mg of the compound daily for 9 days, followed by administering a maintenance dose of 10 mg of the compound daily. In some embodiments, the method comprises administering a loading dose of 12 mg of the compound daily for 10 days, followed by administering a maintenance dose of 10 mg of the compound daily. In some embodiments, the method comprises administering a loading dose of 15 mg of the compound daily for 3 days, followed by administering a maintenance dose of 10 mg of the compound daily. In some embodiments, the method comprises administering a loading dose of 15 mg of the compound daily for 4 days, followed by administering a maintenance dose of 10 mg of the compound daily. In some embodiments, the method comprises administering a loading dose of 15 mg of the compound daily for 5 days, followed by administering a maintenance dose of 10 mg of the compound daily. In some embodiments, the method comprises administering a loading dose of 15 mg of the compound daily for 6 days, followed by administering a maintenance dose of 10 mg of the compound daily. In some embodiments, the method comprises administering a loading dose of 15 mg of the compound daily for 7 days, followed by administering a maintenance dose of 10 mg of the compound daily. In some embodiments, the method comprises administering a loading dose of 15 mg of the compound daily for 8 days, followed by administering a maintenance dose of 10 mg of the compound daily. In some embodiments, the method comprises administering a loading dose of 15 mg of the compound daily for 9 days, followed by administering a maintenance dose of 10 mg of the compound daily. In some embodiments, the method comprises administering a loading dose of 15 mg of the compound daily for 10 days, followed by administering a maintenance dose of 10 mg of the compound daily. In some embodiments, the method comprises administering a loading dose of 5 mg of the compound daily for 3 days, followed by administering a maintenance dose of 10 mg of the compound every other day. In some embodiments, the method comprises administering a loading dose of 5 mg of the compound daily for 4 days, followed by administering a maintenance dose of 10 mg of the compound every other day. In some embodiments, the method comprises administering a loading dose of 5 mg of the compound daily for 5 days, followed by administering a maintenance dose of 10 mg of the compound every other day. In some embodiments, the method comprises administering a loading dose of 5 mg of the compound daily for 6 days, followed by administering a maintenance dose of 10 mg of the compound every other day. In some embodiments, the method comprises administering a loading dose of 5 mg of the compound daily for 7 days, followed by administering a maintenance dose of 10 mg of the compound every other day. In some embodiments, the method comprises administering a loading dose of 5 mg of the compound daily for 8 days, followed by administering a maintenance dose of 10 mg of the compound every other day. In some embodiments, the method comprises administering a loading dose of 5 mg of the compound daily for 9 days, followed by administering a maintenance dose of 10 mg of the compound every other day. In some embodiments, the method comprises administering a loading dose of 5 mg of the compound daily for 10 days, followed by administering a maintenance dose of 10 mg of the compound every other day. In some embodiments, the method comprises administering a loading dose of 7 mg of the compound daily for 3 days, followed by administering a maintenance dose of 10 mg of the compound every other day. In some embodiments, the method comprises administering a loading dose of 7 mg of the compound daily for 4 days, followed by administering a maintenance dose of 10 mg of the compound every other day. In some embodiments, the method comprises administering a loading dose of 7 mg of the compound daily for 5 days, followed by administering a maintenance dose of 10 mg of the compound every other day. In some embodiments, the method comprises administering a loading dose of 7 mg of the compound daily for 6 days, followed by administering a maintenance dose of 10 mg of the compound every other day. In some embodiments, the method comprises administering a loading dose of 7 mg of the compound daily for 7 days, followed by administering a maintenance dose of 10 mg of the compound every other day. In some embodiments, the method comprises administering a loading dose of 7 mg of the compound daily for 8 days, followed by administering a maintenance dose of 10 mg of the compound every other day. In some embodiments, the method comprises administering a loading dose of 7 mg of the compound daily for 9 days, followed by administering a maintenance dose of 10 mg of the compound every other day. In some embodiments, the method comprises administering a loading dose of 7 mg of the compound daily for 10 days, followed by administering a maintenance dose of 10 mg of the compound every other day. In some embodiments, the method comprises administering a loading dose of 8 mg of the compound daily for 3 days, followed by administering a maintenance dose of 10 mg of the compound every other day. In some embodiments, the method comprises administering a loading dose of 8 mg of the compound daily for 4 days, followed by administering a maintenance dose of 10 mg of the compound every other day. In some embodiments, the method comprises administering a loading dose of 8 mg of the compound daily for 5 days, followed by administering a maintenance dose of 10 mg of the compound every other day. In some embodiments, the method comprises administering a loading dose of 8 mg of the compound daily for 6 days, followed by administering a maintenance dose of 10 mg of the compound every other day. In some embodiments, the method comprises administering a loading dose of 8 mg of the compound daily for 7 days, followed by administering a maintenance dose of 10 mg of the compound every other day. In some embodiments, the method comprises administering a loading dose of 8 mg of the compound daily for 8 days, followed by administering a maintenance dose of 10 mg of the compound every other day. In some embodiments, the method comprises administering a loading dose of 8 mg of the compound daily for 9 days, followed by administering a maintenance dose of 10 mg of the compound every other day. In some embodiments, the method comprises administering a loading dose of 8 mg of the compound daily for 10 days, followed by administering a maintenance dose of 10 mg of the compound every other day. In some embodiments, the method comprises administering a loading dose of 10 mg of the compound daily for 3 days, followed by administering a maintenance dose of 10 mg of the compound every other day. In some embodiments, the method comprises administering a loading dose of 10 mg of the compound daily for 4 days, followed by administering a maintenance dose of 10 mg of the compound every other day. In some embodiments, the method comprises administering a loading dose of 10 mg of the compound daily for 5 days, followed by administering a maintenance dose of 10 mg of the compound every other day. In some embodiments, the method comprises administering a loading dose of 10 mg of the compound daily for 6 days, followed by administering a maintenance dose of 10 mg of the compound every other day. In some embodiments, the method comprises administering a loading dose of 10 mg of the compound daily for 7 days, followed by administering a maintenance dose of 10 mg of the compound every other day. In some embodiments, the method comprises administering a loading dose of 10 mg of the compound daily for 8 days, followed by administering a maintenance dose of 10 mg of the compound every other day. In some embodiments, the method comprises administering a loading dose of 10 mg of the compound daily for 9 days, followed by administering a maintenance dose of 10 mg of the compound every other day. In some embodiments, the method comprises administering a loading dose of 10 mg of the compound daily for 10 days, followed by administering a maintenance dose of 10 mg of the compound every other day. In some embodiments, the method comprises administering a loading dose of 12 mg of the compound daily for 3 days, followed by administering a maintenance dose of 10 mg of the compound every other day. In some embodiments, the method comprises administering a loading dose of 12 mg of the compound daily for 4 days, followed by administering a maintenance dose of 10 mg of the compound every other day. In some embodiments, the method comprises administering a loading dose of 12 mg of the compound daily for 5 days, followed by administering a maintenance dose of 10 mg of the compound every other day. In some embodiments, the method comprises administering a loading dose of 12 mg of the compound daily for 6 days, followed by administering a maintenance dose of 10 mg of the compound every other day. In some embodiments, the method comprises administering a loading dose of 12 mg of the compound daily for 7 days, followed by administering a maintenance dose of 10 mg of the compound every other day. In some embodiments, the method comprises administering a loading dose of 12 mg of the compound daily for 8 days, followed by administering a maintenance dose of 10 mg of the compound every other day. In some embodiments, the method comprises administering a loading dose of 12 mg of the compound daily for 9 days, followed by administering a maintenance dose of 10 mg of the compound every other day. In some embodiments, the method comprises administering a loading dose of 12 mg of the compound daily for 10 days, followed by administering a maintenance dose of 10 mg of the compound every other day. In some embodiments, the method comprises administering a loading dose of 15 mg of the compound daily for 3 days, followed by administering a maintenance dose of 10 mg of the compound every other day. In some embodiments, the method comprises administering a loading dose of 15 mg of the compound daily for 4 days, followed by administering a maintenance dose of 10 mg of the compound every other day. In some embodiments, the method comprises administering a loading dose of 15 mg of the compound daily for 5 days, followed by administering a maintenance dose of 10 mg of the compound every other day. In some embodiments, the method comprises administering a loading dose of 15 mg of the compound daily for 6 days, followed by administering a maintenance dose of 10 mg of the compound every other day. In some embodiments, the method comprises administering a loading dose of 15 mg of the compound daily for 7 days, followed by administering a maintenance dose of 10 mg of the compound every other day. In some embodiments, the method comprises administering a loading dose of 15 mg of the compound daily for 8 days, followed by administering a maintenance dose of 10 mg of the compound every other day. In some embodiments, the method comprises administering a loading dose of 15 mg of the compound daily for 9 days, followed by administering a maintenance dose of 10 mg of the compound every other day. In some embodiments, the method comprises administering a loading dose of 15 mg of the compound daily for 10 days, followed by administering a maintenance dose of 10 mg of the compound every other day. In some embodiments, the method comprises administering a loading dose of 5 mg of the compound daily for 3 days, followed by administering a maintenance dose of 10 mg of the compound once a week. In some embodiments, the method comprises administering a loading dose of 5 mg of the compound daily for 4 days, followed by administering a maintenance dose of 10 mg of the compound once a week. In some embodiments, the method comprises administering a loading dose of 5 mg of the compound daily for 5 days, followed by administering a maintenance dose of 10 mg of the compound once a week. In some embodiments, the method comprises administering a loading dose of 5 mg of the compound daily for 6 days, followed by administering a maintenance dose of 10 mg of the compound once a week. In some embodiments, the method comprises administering a loading dose of 5 mg of the compound daily for 7 days, followed by administering a maintenance dose of 10 mg of the compound once a week. In some embodiments, the method comprises administering a loading dose of 5 mg of the compound daily for 8 days, followed by administering a maintenance dose of 10 mg of the compound once a week. In some embodiments, the method comprises administering a loading dose of 5 mg of the compound daily for 9 days, followed by administering a maintenance dose of 10 mg of the compound once a week. In some embodiments, the method comprises administering a loading dose of 5 mg of the compound daily for 10 days, followed by administering a maintenance dose of 10 mg of the compound once a week. In some embodiments, the method comprises administering a loading dose of 7 mg of the compound daily for 3 days, followed by administering a maintenance dose of 10 mg of the compound once a week. In some embodiments, the method comprises administering a loading dose of 7 mg of the compound daily for 4 days, followed by administering a maintenance dose of 10 mg of the compound once a week. In some embodiments, the method comprises administering a loading dose of 7 mg of the compound daily for 5 days, followed by administering a maintenance dose of 10 mg of the compound once a week. In some embodiments, the method comprises administering a loading dose of 7 mg of the compound daily for 6 days, followed by administering a maintenance dose of 10 mg of the compound once a week. In some embodiments, the method comprises administering a loading dose of 7 mg of the compound daily for 7 days, followed by administering a maintenance dose of 10 mg of the compound once a week. In some embodiments, the method comprises administering a loading dose of 7 mg of the compound daily for 8 days, followed by administering a maintenance dose of 10 mg of the compound once a week. In some embodiments, the method comprises administering a loading dose of 7 mg of the compound daily for 9 days, followed by administering a maintenance dose of 10 mg of the compound once a week. In some embodiments, the method comprises administering a loading dose of 7 mg of the compound daily for 10 days, followed by administering a maintenance dose of 10 mg of the compound once a week. In some embodiments, the method comprises administering a loading dose of 8 mg of the compound daily for 3 days, followed by administering a maintenance dose of 10 mg of the compound once a week. In some embodiments, the method comprises administering a loading dose of 8 mg of the compound daily for 4 days, followed by administering a maintenance dose of 10 mg of the compound once a week. In some embodiments, the method comprises administering a loading dose of 8 mg of the compound daily for 5 days, followed by administering a maintenance dose of 10 mg of the compound once a week. In some embodiments, the method comprises administering a loading dose of 8 mg of the compound daily for 6 days, followed by administering a maintenance dose of 10 mg of the compound once a week. In some embodiments, the method comprises administering a loading dose of 8 mg of the compound daily for 7 days, followed by administering a maintenance dose of 10 mg of the compound once a week. In some embodiments, the method comprises administering a loading dose of 8 mg of the compound daily for 8 days, followed by administering a maintenance dose of 10 mg of the compound once a week. In some embodiments, the method comprises administering a loading dose of 8 mg of the compound daily for 9 days, followed by administering a maintenance dose of 10 mg of the compound once a week. In some embodiments, the method comprises administering a loading dose of 8 mg of the compound daily for 10 days, followed by administering a maintenance dose of 10 mg of the compound once a week. In some embodiments, the method comprises administering a loading dose of 10 mg of the compound daily for 3 days, followed by administering a maintenance dose of 10 mg of the compound once a week. In some embodiments, the method comprises administering a loading dose of 10 mg of the compound daily for 4 days, followed by administering a maintenance dose of 10 mg of the compound once a week. In some embodiments, the method comprises administering a loading dose of 10 mg of the compound daily for 5 days, followed by administering a maintenance dose of 10 mg of the compound once a week. In some embodiments, the method comprises administering a loading dose of 10 mg of the compound daily for 6 days, followed by administering a maintenance dose of 10 mg of the compound once a week. In some embodiments, the method comprises administering a loading dose of 10 mg of the compound daily for 7 days, followed by administering a maintenance dose of 10 mg of the compound once a week. In some embodiments, the method comprises administering a loading dose of 10 mg of the compound daily for 8 days, followed by administering a maintenance dose of 10 mg of the compound once a week. In some embodiments, the method comprises administering a loading dose of 10 mg of the compound daily for 9 days, followed by administering a maintenance dose of 10 mg of the compound once a week. In some embodiments, the method comprises administering a loading dose of 10 mg of the compound daily for 10 days, followed by administering a maintenance dose of 10 mg of the compound once a week. In some embodiments, the method comprises administering a loading dose of 12 mg of the compound daily for 3 days, followed by administering a maintenance dose of 10 mg of the compound once a week. In some embodiments, the method comprises administering a loading dose of 12 mg of the compound daily for 4 days, followed by administering a maintenance dose of 10 mg of the compound once a week. In some embodiments, the method comprises administering a loading dose of 12 mg of the compound daily for 5 days, followed by administering a maintenance dose of 10 mg of the compound once a week. In some embodiments, the method comprises administering a loading dose of 12 mg of the compound daily for 6 days, followed by administering a maintenance dose of 10 mg of the compound once a week. In some embodiments, the method comprises administering a loading dose of 12 mg of the compound daily for 7 days, followed by administering a maintenance dose of 10 mg of the compound once a week. In some embodiments, the method comprises administering a loading dose of 12 mg of the compound daily for 8 days, followed by administering a maintenance dose of 10 mg of the compound once a week. In some embodiments, the method comprises administering a loading dose of 12 mg of the compound daily for 9 days, followed by administering a maintenance dose of 10 mg of the compound once a week. In some embodiments, the method comprises administering a loading dose of 12 mg of the compound daily for 10 days, followed by administering a maintenance dose of 10 mg of the compound once a week. In some embodiments, the method comprises administering a loading dose of 15 mg of the compound daily for 3 days, followed by administering a maintenance dose of 10 mg of the compound once a week. In some embodiments, the method comprises administering a loading dose of 15 mg of the compound daily for 4 days, followed by administering a maintenance dose of 10 mg of the compound once a week. In some embodiments, the method comprises administering a loading dose of 15 mg of the compound daily for 5 days, followed by administering a maintenance dose of 10 mg of the compound once a week. In some embodiments, the method comprises administering a loading dose of 15 mg of the compound daily for 6 days, followed by administering a maintenance dose of 10 mg of the compound once a week. In some embodiments, the method comprises administering a loading dose of 15 mg of the compound daily for 7 days, followed by administering a maintenance dose of 10 mg of the compound once a week. In some embodiments, the method comprises administering a loading dose of 15 mg of the compound daily for 8 days, followed by administering a maintenance dose of 10 mg of the compound once a week. In some embodiments, the method comprises administering a loading dose of 15 mg of the compound daily for 9 days, followed by administering a maintenance dose of 10 mg of the compound once a week. In some embodiments, the method comprises administering a loading dose of 15 mg of the compound daily for 10 days, followed by administering a maintenance dose of 10 mg of the compound once a week. In some embodiments, the method comprises administering a loading dose of 5 mg of the compound daily for 3 days, followed by administering a maintenance dose of 10 mg of the compound twice a week. In some embodiments, the method comprises administering a loading dose of 5 mg of the compound daily for 4 days, followed by administering a maintenance dose of 10 mg of the compound twice a week. In some embodiments, the method comprises administering a loading dose of 5 mg of the compound daily for 5 days, followed by administering a maintenance dose of 10 mg of the compound twice a week. In some embodiments, the method comprises administering a loading dose of 5 mg of the compound daily for 6 days, followed by administering a maintenance dose of 10 mg of the compound twice a week. In some embodiments, the method comprises administering a loading dose of 5 mg of the compound daily for 7 days, followed by administering a maintenance dose of 10 mg of the compound twice a week. In some embodiments, the method comprises administering a loading dose of 5 mg of the compound daily for 8 days, followed by administering a maintenance dose of 10 mg of the compound twice a week. In some embodiments, the method comprises administering a loading dose of 5 mg of the compound daily for 9 days, followed by administering a maintenance dose of 10 mg of the compound twice a week. In some embodiments, the method comprises administering a loading dose of 5 mg of the compound daily for 10 days, followed by administering a maintenance dose of 10 mg of the compound twice a week. In some embodiments, the method comprises administering a loading dose of 7 mg of the compound daily for 3 days, followed by administering a maintenance dose of 10 mg of the compound twice a week. In some embodiments, the method comprises administering a loading dose of 7 mg of the compound daily for 4 days, followed by administering a maintenance dose of 10 mg of the compound twice a week. In some embodiments, the method comprises administering a loading dose of 7 mg of the compound daily for 5 days, followed by administering a maintenance dose of 10 mg of the compound twice a week. In some embodiments, the method comprises administering a loading dose of 7 mg of the compound daily for 6 days, followed by administering a maintenance dose of 10 mg of the compound twice a week. In some embodiments, the method comprises administering a loading dose of 7 mg of the compound daily for 7 days, followed by administering a maintenance dose of 10 mg of the compound twice a week. In some embodiments, the method comprises administering a loading dose of 7 mg of the compound daily for 8 days, followed by administering a maintenance dose of 10 mg of the compound twice a week. In some embodiments, the method comprises administering a loading dose of 7 mg of the compound daily for 9 days, followed by administering a maintenance dose of 10 mg of the compound twice a week. In some embodiments, the method comprises administering a loading dose of 7 mg of the compound daily for 10 days, followed by administering a maintenance dose of 10 mg of the compound twice a week. In some embodiments, the method comprises administering a loading dose of 8 mg of the compound daily for 3 days, followed by administering a maintenance dose of 10 mg of the compound twice a week. In some embodiments, the method comprises administering a loading dose of 8 mg of the compound daily for 4 days, followed by administering a maintenance dose of 10 mg of the compound twice a week. In some embodiments, the method comprises administering a loading dose of 8 mg of the compound daily for 5 days, followed by administering a maintenance dose of 10 mg of the compound twice a week. In some embodiments, the method comprises administering a loading dose of 8 mg of the compound daily for 6 days, followed by administering a maintenance dose of 10 mg of the compound twice a week. In some embodiments, the method comprises administering a loading dose of 8 mg of the compound daily for 7 days, followed by administering a maintenance dose of 10 mg of the compound twice a week. In some embodiments, the method comprises administering a loading dose of 8 mg of the compound daily for 8 days, followed by administering a maintenance dose of 10 mg of the compound twice a week. In some embodiments, the method comprises administering a loading dose of 8 mg of the compound daily for 9 days, followed by administering a maintenance dose of 10 mg of the compound twice a week. In some embodiments, the method comprises administering a loading dose of 8 mg of the compound daily for 10 days, followed by administering a maintenance dose of 10 mg of the compound twice a week. In some embodiments, the method comprises administering a loading dose of 10 mg of the compound daily for 3 days, followed by administering a maintenance dose of 10 mg of the compound twice a week. In some embodiments, the method comprises administering a loading dose of 10 mg of the compound daily for 4 days, followed by administering a maintenance dose of 10 mg of the compound twice a week. In some embodiments, the method comprises administering a loading dose of 10 mg of the compound daily for 5 days, followed by administering a maintenance dose of 10 mg of the compound twice a week. In some embodiments, the method comprises administering a loading dose of 10 mg of the compound daily for 6 days, followed by administering a maintenance dose of 10 mg of the compound twice a week. In some embodiments, the method comprises administering a loading dose of 10 mg of the compound daily for 7 days, followed by administering a maintenance dose of 10 mg of the compound twice a week. In some embodiments, the method comprises administering a loading dose of 10 mg of the compound daily for 8 days, followed by administering a maintenance dose of 10 mg of the compound twice a week. In some embodiments, the method comprises administering a loading dose of 10 mg of the compound daily for 9 days, followed by administering a maintenance dose of 10 mg of the compound twice a week. In some embodiments, the method comprises administering a loading dose of 10 mg of the compound daily for 10 days, followed by administering a maintenance dose of 10 mg of the compound twice a week. In some embodiments, the method comprises administering a loading dose of 12 mg of the compound daily for 3 days, followed by administering a maintenance dose of 10 mg of the compound twice a week. In some embodiments, the method comprises administering a loading dose of 12 mg of the compound daily for 4 days, followed by administering a maintenance dose of 10 mg of the compound twice a week. In some embodiments, the method comprises administering a loading dose of 12 mg of the compound daily for 5 days, followed by administering a maintenance dose of 10 mg of the compound twice a week. In some embodiments, the method comprises administering a loading dose of 12 mg of the compound daily for 6 days, followed by administering a maintenance dose of 10 mg of the compound twice a week. In some embodiments, the method comprises administering a loading dose of 12 mg of the compound daily for 7 days, followed by administering a maintenance dose of 10 mg of the compound twice a week. In some embodiments, the method comprises administering a loading dose of 12 mg of the compound daily for 8 days, followed by administering a maintenance dose of 10 mg of the compound twice a week. In some embodiments, the method comprises administering a loading dose of 12 mg of the compound daily for 9 days, followed by administering a maintenance dose of 10 mg of the compound twice a week. In some embodiments, the method comprises administering a loading dose of 12 mg of the compound daily for 10 days, followed by administering a maintenance dose of 10 mg of the compound twice a week. In some embodiments, the method comprises administering a loading dose of 15 mg of the compound daily for 3 days, followed by administering a maintenance dose of 10 mg of the compound twice a week. In some embodiments, the method comprises administering a loading dose of 15 mg of the compound daily for 4 days, followed by administering a maintenance dose of 10 mg of the compound twice a week. In some embodiments, the method comprises administering a loading dose of 15 mg of the compound daily for 5 days, followed by administering a maintenance dose of 10 mg of the compound twice a week. In some embodiments, the method comprises administering a loading dose of 15 mg of the compound daily for 6 days, followed by administering a maintenance dose of 10 mg of the compound twice a week. In some embodiments, the method comprises administering a loading dose of 15 mg of the compound daily for 7 days, followed by administering a maintenance dose of 10 mg of the compound twice a week. In some embodiments, the method comprises administering a loading dose of 15 mg of the compound daily for 8 days, followed by administering a maintenance dose of 10 mg of the compound twice a week. In some embodiments, the method comprises administering a loading dose of 15 mg of the compound daily for 9 days, followed by administering a maintenance dose of 10 mg of the compound twice a week. In some embodiments, the method comprises administering a loading dose of 15 mg of the compound daily for 10 days, followed by administering a maintenance dose of 10 mg of the compound twice a week. In some embodiments, the method comprises administering a loading dose of 5 mg of the compound daily for 3 days, followed by administering a maintenance dose of 10 mg of the compound three times a week. In some embodiments, the method comprises administering a loading dose of 5 mg of the compound daily for 4 days, followed by administering a maintenance dose of 10 mg of the compound three times a week. In some embodiments, the method comprises administering a loading dose of 5 mg of the compound daily for 5 days, followed by administering a maintenance dose of 10 mg of the compound three times a week. In some embodiments, the method comprises administering a loading dose of 5 mg of the compound daily for 6 days, followed by administering a maintenance dose of 10 mg of the compound three times a week. In some embodiments, the method comprises administering a loading dose of 5 mg of the compound daily for 7 days, followed by administering a maintenance dose of 10 mg of the compound three times a week. In some embodiments, the method comprises administering a loading dose of 5 mg of the compound daily for 8 days, followed by administering a maintenance dose of 10 mg of the compound three times a week. In some embodiments, the method comprises administering a loading dose of 5 mg of the compound daily for 9 days, followed by administering a maintenance dose of 10 mg of the compound three times a week. In some embodiments, the method comprises administering a loading dose of 5 mg of the compound daily for 10 days, followed by administering a maintenance dose of 10 mg of the compound three times a week. In some embodiments, the method comprises administering a loading dose of 7 mg of the compound daily for 3 days, followed by administering a maintenance dose of 10 mg of the compound three times a week. In some embodiments, the method comprises administering a loading dose of 7 mg of the compound daily for 4 days, followed by administering a maintenance dose of 10 mg of the compound three times a week. In some embodiments, the method comprises administering a loading dose of 7 mg of the compound daily for 5 days, followed by administering a maintenance dose of 10 mg of the compound three times a week. In some embodiments, the method comprises administering a loading dose of 7 mg of the compound daily for 6 days, followed by administering a maintenance dose of 10 mg of the compound three times a week. In some embodiments, the method comprises administering a loading dose of 7 mg of the compound daily for 7 days, followed by administering a maintenance dose of 10 mg of the compound three times a week. In some embodiments, the method comprises administering a loading dose of 7 mg of the compound daily for 8 days, followed by administering a maintenance dose of 10 mg of the compound three times a week. In some embodiments, the method comprises administering a loading dose of 7 mg of the compound daily for 9 days, followed by administering a maintenance dose of 10 mg of the compound three times a week. In some embodiments, the method comprises administering a loading dose of 7 mg of the compound daily for 10 days, followed by administering a maintenance dose of 10 mg of the compound three times a week. In some embodiments, the method comprises administering a loading dose of 8 mg of the compound daily for 3 days, followed by administering a maintenance dose of 10 mg of the compound three times a week. In some embodiments, the method comprises administering a loading dose of 8 mg of the compound daily for 4 days, followed by administering a maintenance dose of 10 mg of the compound three times a week. In some embodiments, the method comprises administering a loading dose of 8 mg of the compound daily for 5 days, followed by administering a maintenance dose of 10 mg of the compound three times a week. In some embodiments, the method comprises administering a loading dose of 8 mg of the compound daily for 6 days, followed by administering a maintenance dose of 10 mg of the compound three times a week. In some embodiments, the method comprises administering a loading dose of 8 mg of the compound daily for 7 days, followed by administering a maintenance dose of 10 mg of the compound three times a week. In some embodiments, the method comprises administering a loading dose of 8 mg of the compound daily for 8 days, followed by administering a maintenance dose of 10 mg of the compound three times a week. In some embodiments, the method comprises administering a loading dose of 8 mg of the compound daily for 9 days, followed by administering a maintenance dose of 10 mg of the compound three times a week. In some embodiments, the method comprises administering a loading dose of 8 mg of the compound daily for 10 days, followed by administering a maintenance dose of 10 mg of the compound three times a week. In some embodiments, the method comprises administering a loading dose of 10 mg of the compound daily for 3 days, followed by administering a maintenance dose of 10 mg of the compound three times a week. In some embodiments, the method comprises administering a loading dose of 10 mg of the compound daily for 4 days, followed by administering a maintenance dose of 10 mg of the compound three times a week. In some embodiments, the method comprises administering a loading dose of 10 mg of the compound daily for 5 days, followed by administering a maintenance dose of 10 mg of the compound three times a week. In some embodiments, the method comprises administering a loading dose of 10 mg of the compound daily for 6 days, followed by administering a maintenance dose of 10 mg of the compound three times a week. In some embodiments, the method comprises administering a loading dose of 10 mg of the compound daily for 7 days, followed by administering a maintenance dose of 10 mg of the compound three times a week. In some embodiments, the method comprises administering a loading dose of 10 mg of the compound daily for 8 days, followed by administering a maintenance dose of 10 mg of the compound three times a week. In some embodiments, the method comprises administering a loading dose of 10 mg of the compound daily for 9 days, followed by administering a maintenance dose of 10 mg of the compound three times a week. In some embodiments, the method comprises administering a loading dose of 10 mg of the compound daily for 10 days, followed by administering a maintenance dose of 10 mg of the compound three times a week. In some embodiments, the method comprises administering a loading dose of 12 mg of the compound daily for 3 days, followed by administering a maintenance dose of 10 mg of the compound three times a week. In some embodiments, the method comprises administering a loading dose of 12 mg of the compound daily for 4 days, followed by administering a maintenance dose of 10 mg of the compound three times a week. In some embodiments, the method comprises administering a loading dose of 12 mg of the compound daily for 5 days, followed by administering a maintenance dose of 10 mg of the compound three times a week. In some embodiments, the method comprises administering a loading dose of 12 mg of the compound daily for 6 days, followed by administering a maintenance dose of 10 mg of the compound three times a week. In some embodiments, the method comprises administering a loading dose of 12 mg of the compound daily for 7 days, followed by administering a maintenance dose of 10 mg of the compound three times a week. In some embodiments, the method comprises administering a loading dose of 12 mg of the compound daily for 8 days, followed by administering a maintenance dose of 10 mg of the compound three times a week. In some embodiments, the method comprises administering a loading dose of 12 mg of the compound daily for 9 days, followed by administering a maintenance dose of 10 mg of the compound three times a week. In some embodiments, the method comprises administering a loading dose of 12 mg of the compound daily for 10 days, followed by administering a maintenance dose of 10 mg of the compound three times a week. In some embodiments, the method comprises administering a loading dose of 15 mg of the compound daily for 3 days, followed by administering a maintenance dose of 10 mg of the compound three times a week. In some embodiments, the method comprises administering a loading dose of 15 mg of the compound daily for 4 days, followed by administering a maintenance dose of 10 mg of the compound three times a week. In some embodiments, the method comprises administering a loading dose of 15 mg of the compound daily for 5 days, followed by administering a maintenance dose of 10 mg of the compound three times a week. In some embodiments, the method comprises administering a loading dose of 15 mg of the compound daily for 6 days, followed by administering a maintenance dose of 10 mg of the compound three times a week. In some embodiments, the method comprises administering a loading dose of 15 mg of the compound daily for 7 days, followed by administering a maintenance dose of 10 mg of the compound three times a week. In some embodiments, the method comprises administering a loading dose of 15 mg of the compound daily for 8 days, followed by administering a maintenance dose of 10 mg of the compound three times a week. In some embodiments, the method comprises administering a loading dose of 15 mg of the compound daily for 9 days, followed by administering a maintenance dose of 10 mg of the compound three times a week. In some embodiments, the method comprises administering a loading dose of 15 mg of the compound daily for 10 days, followed by administering a maintenance dose of 10 mg of the compound three times a week.

In some embodiments, the loading dose is administered from 1 day to 20 days, and the maintenance dose is administered from 20 days to 37000 days. In some embodiments, the method comprises administering a loading dose of 5 mg of the compound daily for 3 days, followed by administering a maintenance dose of 20 mg of the compound daily. In some embodiments, the method comprises administering a loading dose of 5 mg of the compound daily for 4 days, followed by administering a maintenance dose of 20 mg of the compound daily. In some embodiments, the method comprises administering a loading dose of 5 mg of the compound daily for 5 days, followed by administering a maintenance dose of 20 mg of the compound daily. In some embodiments, the method comprises administering a loading dose of 5 mg of the compound daily for 6 days, followed by administering a maintenance dose of 20 mg of the compound daily. In some embodiments, the method comprises administering a loading dose of 5 mg of the compound daily for 7 days, followed by administering a maintenance dose of 20 mg of the compound daily. In some embodiments, the method comprises administering a loading dose of 5 mg of the compound daily for 8 days, followed by administering a maintenance dose of 20 mg of the compound daily. In some embodiments, the method comprises administering a loading dose of 5 mg of the compound daily for 9 days, followed by administering a maintenance dose of 20 mg of the compound daily. In some embodiments, the method comprises administering a loading dose of 5 mg of the compound daily for 10 days, followed by administering a maintenance dose of 20 mg of the compound daily. In some embodiments, the method comprises administering a loading dose of 7 mg of the compound daily for 3 days, followed by administering a maintenance dose of 20 mg of the compound daily. In some embodiments, the method comprises administering a loading dose of 7 mg of the compound daily for 4 days, followed by administering a maintenance dose of 20 mg of the compound daily. In some embodiments, the method comprises administering a loading dose of 7 mg of the compound daily for 5 days, followed by administering a maintenance dose of 20 mg of the compound daily. In some embodiments, the method comprises administering a loading dose of 7 mg of the compound daily for 6 days, followed by administering a maintenance dose of 20 mg of the compound daily. In some embodiments, the method comprises administering a loading dose of 7 mg of the compound daily for 7 days, followed by administering a maintenance dose of 20 mg of the compound daily. In some embodiments, the method comprises administering a loading dose of 7 mg of the compound daily for 8 days, followed by administering a maintenance dose of 20 mg of the compound daily. In some embodiments, the method comprises administering a loading dose of 7 mg of the compound daily for 9 days, followed by administering a maintenance dose of 20 mg of the compound daily. In some embodiments, the method comprises administering a loading dose of 7 mg of the compound daily for 10 days, followed by administering a maintenance dose of 20 mg of the compound daily. In some embodiments, the method comprises administering a loading dose of 8 mg of the compound daily for 3 days, followed by administering a maintenance dose of 20 mg of the compound daily. In some embodiments, the method comprises administering a loading dose of 8 mg of the compound daily for 4 days, followed by administering a maintenance dose of 20 mg of the compound daily. In some embodiments, the method comprises administering a loading dose of 8 mg of the compound daily for 5 days, followed by administering a maintenance dose of 20 mg of the compound daily. In some embodiments, the method comprises administering a loading dose of 8 mg of the compound daily for 6 days, followed by administering a maintenance dose of 20 mg of the compound daily. In some embodiments, the method comprises administering a loading dose of 8 mg of the compound daily for 7 days, followed by administering a maintenance dose of 20 mg of the compound daily. In some embodiments, the method comprises administering a loading dose of 8 mg of the compound daily for 8 days, followed by administering a maintenance dose of 20 mg of the compound daily. In some embodiments, the method comprises administering a loading dose of 8 mg of the compound daily for 9 days, followed by administering a maintenance dose of 20 mg of the compound daily. In some embodiments, the method comprises administering a loading dose of 8 mg of the compound daily for 10 days, followed by administering a maintenance dose of 20 mg of the compound daily. In some embodiments, the method comprises administering a loading dose of 20 mg of the compound daily for 3 days, followed by administering a maintenance dose of 20 mg of the compound daily. In some embodiments, the method comprises administering a loading dose of 10 mg of the compound daily for 4 days, followed by administering a maintenance dose of 20 mg of the compound daily. In some embodiments, the method comprises administering a loading dose of 10 mg of the compound daily for 5 days, followed by administering a maintenance dose of 20 mg of the compound daily. In some embodiments, the method comprises administering a loading dose of 10 mg of the compound daily for 6 days, followed by administering a maintenance dose of 20 mg of the compound daily. In some embodiments, the method comprises administering a loading dose of 10 mg of the compound daily for 7 days, followed by administering a maintenance dose of 20 mg of the compound daily. In some embodiments, the method comprises administering a loading dose of 10 mg of the compound daily for 8 days, followed by administering a maintenance dose of 20 mg of the compound daily. In some embodiments, the method comprises administering a loading dose of 10 mg of the compound daily for 9 days, followed by administering a maintenance dose of 20 mg of the compound daily. In some embodiments, the method comprises administering a loading dose of 10 mg of the compound daily for 10 days, followed by administering a maintenance dose of 20 mg of the compound daily. In some embodiments, the method comprises administering a loading dose of 12 mg of the compound daily for 3 days, followed by administering a maintenance dose of 20 mg of the compound daily. In some embodiments, the method comprises administering a loading dose of 12 mg of the compound daily for 4 days, followed by administering a maintenance dose of 20 mg of the compound daily. In some embodiments, the method comprises administering a loading dose of 12 mg of the compound daily for 5 days, followed by administering a maintenance dose of 20 mg of the compound daily. In some embodiments, the method comprises administering a loading dose of 12 mg of the compound daily for 6 days, followed by administering a maintenance dose of 20 mg of the compound daily. In some embodiments, the method comprises administering a loading dose of 12 mg of the compound daily for 7 days, followed by administering a maintenance dose of 20 mg of the compound daily. In some embodiments, the method comprises administering a loading dose of 12 mg of the compound daily for 8 days, followed by administering a maintenance dose of 20 mg of the compound daily. In some embodiments, the method comprises administering a loading dose of 12 mg of the compound daily for 9 days, followed by administering a maintenance dose of 20 mg of the compound daily. In some embodiments, the method comprises administering a loading dose of 12 mg of the compound daily for 10 days, followed by administering a maintenance dose of 20 mg of the compound daily. In some embodiments, the method comprises administering a loading dose of 15 mg of the compound daily for 3 days, followed by administering a maintenance dose of 20 mg of the compound daily. In some embodiments, the method comprises administering a loading dose of 15 mg of the compound daily for 4 days, followed by administering a maintenance dose of 20 mg of the compound daily. In some embodiments, the method comprises administering a loading dose of 15 mg of the compound daily for 5 days, followed by administering a maintenance dose of 20 mg of the compound daily. In some embodiments, the method comprises administering a loading dose of 15 mg of the compound daily for 6 days, followed by administering a maintenance dose of 20 mg of the compound daily. In some embodiments, the method comprises administering a loading dose of 15 mg of the compound daily for 7 days, followed by administering a maintenance dose of 20 mg of the compound daily. In some embodiments, the method comprises administering a loading dose of 15 mg of the compound daily for 8 days, followed by administering a maintenance dose of 20 mg of the compound daily. In some embodiments, the method comprises administering a loading dose of 15 mg of the compound daily for 9 days, followed by administering a maintenance dose of 20 mg of the compound daily. In some embodiments, the method comprises administering a loading dose of 15 mg of the compound daily for 10 days, followed by administering a maintenance dose of 20 mg of the compound daily. In some embodiments, the method comprises administering a loading dose of 15 mg of the compound daily for 20 days, followed by administering a maintenance dose of 20 mg of the compound daily. In some embodiments, the method comprises administering a loading dose of 5 mg of the compound daily for 3 days, followed by administering a maintenance dose of 20 mg of the compound every other day. In some embodiments, the method comprises administering a loading dose of 5 mg of the compound daily for 4 days, followed by administering a maintenance dose of 20 mg of the compound every other day. In some embodiments, the method comprises administering a loading dose of 5 mg of the compound daily for 5 days, followed by administering a maintenance dose of 20 mg of the compound every other day. In some embodiments, the method comprises administering a loading dose of 5 mg of the compound daily for 6 days, followed by administering a maintenance dose of 20 mg of the compound every other day. In some embodiments, the method comprises administering a loading dose of 5 mg of the compound daily for 7 days, followed by administering a maintenance dose of 20 mg of the compound every other day. In some embodiments, the method comprises administering a loading dose of 5 mg of the compound daily for 8 days, followed by administering a maintenance dose of 20 mg of the compound every other day. In some embodiments, the method comprises administering a loading dose of 5 mg of the compound daily for 9 days, followed by administering a maintenance dose of 20 mg of the compound every other day. In some embodiments, the method comprises administering a loading dose of 5 mg of the compound daily for 10 days, followed by administering a maintenance dose of 20 mg of the compound every other day. In some embodiments, the method comprises administering a loading dose of 7 mg of the compound daily for 3 days, followed by administering a maintenance dose of 20 mg of the compound every other day. In some embodiments, the method comprises administering a loading dose of 7 mg of the compound daily for 4 days, followed by administering a maintenance dose of 20 mg of the compound every other day. In some embodiments, the method comprises administering a loading dose of 7 mg of the compound daily for 5 days, followed by administering a maintenance dose of 20 mg of the compound every other day. In some embodiments, the method comprises administering a loading dose of 7 mg of the compound daily for 6 days, followed by administering a maintenance dose of 20 mg of the compound every other day. In some embodiments, the method comprises administering a loading dose of 7 mg of the compound daily for 7 days, followed by administering a maintenance dose of 20 mg of the compound every other day. In some embodiments, the method comprises administering a loading dose of 7 mg of the compound daily for 8 days, followed by administering a maintenance dose of 20 mg of the compound every other day. In some embodiments, the method comprises administering a loading dose of 7 mg of the compound daily for 9 days, followed by administering a maintenance dose of 20 mg of the compound every other day. In some embodiments, the method comprises administering a loading dose of 7 mg of the compound daily for 10 days, followed by administering a maintenance dose of 20 mg of the compound every other day. In some embodiments, the method comprises administering a loading dose of 8 mg of the compound daily for 3 days, followed by administering a maintenance dose of 20 mg of the compound every other day. In some embodiments, the method comprises administering a loading dose of 8 mg of the compound daily for 4 days, followed by administering a maintenance dose of 20 mg of the compound every other day. In some embodiments, the method comprises administering a loading dose of 8 mg of the compound daily for 5 days, followed by administering a maintenance dose of 20 mg of the compound every other day. In some embodiments, the method comprises administering a loading dose of 8 mg of the compound daily for 6 days, followed by administering a maintenance dose of 20 mg of the compound every other day. In some embodiments, the method comprises administering a loading dose of 8 mg of the compound daily for 7 days, followed by administering a maintenance dose of 20 mg of the compound every other day. In some embodiments, the method comprises administering a loading dose of 8 mg of the compound daily for 8 days, followed by administering a maintenance dose of 20 mg of the compound every other day. In some embodiments, the method comprises administering a loading dose of 8 mg of the compound daily for 9 days, followed by administering a maintenance dose of 20 mg of the compound every other day. In some embodiments, the method comprises administering a loading dose of 8 mg of the compound daily for 10 days, followed by administering a maintenance dose of 20 mg of the compound every other day. In some embodiments, the method comprises administering a loading dose of 10 mg of the compound daily for 3 days, followed by administering a maintenance dose of 20 mg of the compound every other day. In some embodiments, the method comprises administering a loading dose of 10 mg of the compound daily for 4 days, followed by administering a maintenance dose of 20 mg of the compound every other day. In some embodiments, the method comprises administering a loading dose of 10 mg of the compound daily for 5 days, followed by administering a maintenance dose of 20 mg of the compound every other day. In some embodiments, the method comprises administering a loading dose of 10 mg of the compound daily for 6 days, followed by administering a maintenance dose of 20 mg of the compound every other day. In some embodiments, the method comprises administering a loading dose of 10 mg of the compound daily for 7 days, followed by administering a maintenance dose of 20 mg of the compound every other day. In some embodiments, the method comprises administering a loading dose of 10 mg of the compound daily for 8 days, followed by administering a maintenance dose of 20 mg of the compound every other day. In some embodiments, the method comprises administering a loading dose of 10 mg of the compound daily for 9 days, followed by administering a maintenance dose of 20 mg of the compound every other day. In some embodiments, the method comprises administering a loading dose of 10 mg of the compound daily for 10 days, followed by administering a maintenance dose of 20 mg of the compound every other day. In some embodiments, the method comprises administering a loading dose of 12 mg of the compound daily for 3 days, followed by administering a maintenance dose of 20 mg of the compound every other day. In some embodiments, the method comprises administering a loading dose of 12 mg of the compound daily for 4 days, followed by administering a maintenance dose of 20 mg of the compound every other day. In some embodiments, the method comprises administering a loading dose of 12 mg of the compound daily for 5 days, followed by administering a maintenance dose of 20 mg of the compound every other day. In some embodiments, the method comprises administering a loading dose of 12 mg of the compound daily for 6 days, followed by administering a maintenance dose of 20 mg of the compound every other day. In some embodiments, the method comprises administering a loading dose of 12 mg of the compound daily for 7 days, followed by administering a maintenance dose of 20 mg of the compound every other day. In some embodiments, the method comprises administering a loading dose of 12 mg of the compound daily for 8 days, followed by administering a maintenance dose of 20 mg of the compound every other day. In some embodiments, the method comprises administering a loading dose of 12 mg of the compound daily for 9 days, followed by administering a maintenance dose of 20 mg of the compound every other day. In some embodiments, the method comprises administering a loading dose of 12 mg of the compound daily for 10 days, followed by administering a maintenance dose of 20 mg of the compound every other day. In some embodiments, the method comprises administering a loading dose of 15 mg of the compound daily for 3 days, followed by administering a maintenance dose of 20 mg of the compound every other day. In some embodiments, the method comprises administering a loading dose of 15 mg of the compound daily for 4 days, followed by administering a maintenance dose of 20 mg of the compound every other day. In some embodiments, the method comprises administering a loading dose of 15 mg of the compound daily for 5 days, followed by administering a maintenance dose of 20 mg of the compound every other day. In some embodiments, the method comprises administering a loading dose of 15 mg of the compound daily for 6 days, followed by administering a maintenance dose of 20 mg of the compound every other day. In some embodiments, the method comprises administering a loading dose of 15 mg of the compound daily for 7 days, followed by administering a maintenance dose of 20 mg of the compound every other day. In some embodiments, the method comprises administering a loading dose of 15 mg of the compound daily for 8 days, followed by administering a maintenance dose of 20 mg of the compound every other day. In some embodiments, the method comprises administering a loading dose of 15 mg of the compound daily for 9 days, followed by administering a maintenance dose of 20 mg of the compound every other day. In some embodiments, the method comprises administering a loading dose of 15 mg of the compound daily for 10 days, followed by administering a maintenance dose of 20 mg of the compound every other day. In some embodiments, the method comprises administering a loading dose of 5 mg of the compound daily for 3 days, followed by administering a maintenance dose of 20 mg of the compound once a week. In some embodiments, the method comprises administering a loading dose of 5 mg of the compound daily for 4 days, followed by administering a maintenance dose of 20 mg of the compound once a week. In some embodiments, the method comprises administering a loading dose of 5 mg of the compound daily for 5 days, followed by administering a maintenance dose of 20 mg of the compound once a week. In some embodiments, the method comprises administering a loading dose of 5 mg of the compound daily for 6 days, followed by administering a maintenance dose of 20 mg of the compound once a week. In some embodiments, the method comprises administering a loading dose of 5 mg of the compound daily for 7 days, followed by administering a maintenance dose of 20 mg of the compound once a week. In some embodiments, the method comprises administering a loading dose of 5 mg of the compound daily for 8 days, followed by administering a maintenance dose of 20 mg of the compound once a week. In some embodiments, the method comprises administering a loading dose of 5 mg of the compound daily for 9 days, followed by administering a maintenance dose of 20 mg of the compound once a week. In some embodiments, the method comprises administering a loading dose of 5 mg of the compound daily for 10 days, followed by administering a maintenance dose of 20 mg of the compound once a week. In some embodiments, the method comprises administering a loading dose of 7 mg of the compound daily for 3 days, followed by administering a maintenance dose of 20 mg of the compound once a week. In some embodiments, the method comprises administering a loading dose of 7 mg of the compound daily for 4 days, followed by administering a maintenance dose of 20 mg of the compound once a week. In some embodiments, the method comprises administering a loading dose of 7 mg of the compound daily for 5 days, followed by administering a maintenance dose of 20 mg of the compound once a week. In some embodiments, the method comprises administering a loading dose of 7 mg of the compound daily for 6 days, followed by administering a maintenance dose of 20 mg of the compound once a week. In some embodiments, the method comprises administering a loading dose of 7 mg of the compound daily for 7 days, followed by administering a maintenance dose of 20 mg of the compound once a week. In some embodiments, the method comprises administering a loading dose of 7 mg of the compound daily for 8 days, followed by administering a maintenance dose of 20 mg of the compound once a week. In some embodiments, the method comprises administering a loading dose of 7 mg of the compound daily for 9 days, followed by administering a maintenance dose of 20 mg of the compound once a week. In some embodiments, the method comprises administering a loading dose of 7 mg of the compound daily for 10 days, followed by administering a maintenance dose of 20 mg of the compound once a week. In some embodiments, the method comprises administering a loading dose of 8 mg of the compound daily for 3 days, followed by administering a maintenance dose of 20 mg of the compound once a week. In some embodiments, the method comprises administering a loading dose of 8 mg of the compound daily for 4 days, followed by administering a maintenance dose of 20 mg of the compound once a week. In some embodiments, the method comprises administering a loading dose of 8 mg of the compound daily for 5 days, followed by administering a maintenance dose of 20 mg of the compound once a week. In some embodiments, the method comprises administering a loading dose of 8 mg of the compound daily for 6 days, followed by administering a maintenance dose of 20 mg of the compound once a week. In some embodiments, the method comprises administering a loading dose of 8 mg of the compound daily for 7 days, followed by administering a maintenance dose of 20 mg of the compound once a week. In some embodiments, the method comprises administering a loading dose of 8 mg of the compound daily for 8 days, followed by administering a maintenance dose of 20 mg of the compound once a week. In some embodiments, the method comprises administering a loading dose of 8 mg of the compound daily for 9 days, followed by administering a maintenance dose of 20 mg of the compound once a week. In some embodiments, the method comprises administering a loading dose of 8 mg of the compound daily for 10 days, followed by administering a maintenance dose of 20 mg of the compound once a week. In some embodiments, the method comprises administering a loading dose of 10 mg of the compound daily for 3 days, followed by administering a maintenance dose of 20 mg of the compound once a week. In some embodiments, the method comprises administering a loading dose of 10 mg of the compound daily for 4 days, followed by administering a maintenance dose of 20 mg of the compound once a week. In some embodiments, the method comprises administering a loading dose of 10 mg of the compound daily for 5 days, followed by administering a maintenance dose of 20 mg of the compound once a week. In some embodiments, the method comprises administering a loading dose of 10 mg of the compound daily for 6 days, followed by administering a maintenance dose of 20 mg of the compound once a week. In some embodiments, the method comprises administering a loading dose of 10 mg of the compound daily for 7 days, followed by administering a maintenance dose of 20 mg of the compound once a week. In some embodiments, the method comprises administering a loading dose of 10 mg of the compound daily for 8 days, followed by administering a maintenance dose of 20 mg of the compound once a week. In some embodiments, the method comprises administering a loading dose of 10 mg of the compound daily for 9 days, followed by administering a maintenance dose of 20 mg of the compound once a week. In some embodiments, the method comprises administering a loading dose of 10 mg of the compound daily for 10 days, followed by administering a maintenance dose of 20 mg of the compound once a week. In some embodiments, the method comprises administering a loading dose of 12 mg of the compound daily for 3 days, followed by administering a maintenance dose of 20 mg of the compound once a week. In some embodiments, the method comprises administering a loading dose of 12 mg of the compound daily for 4 days, followed by administering a maintenance dose of 20 mg of the compound once a week. In some embodiments, the method comprises administering a loading dose of 12 mg of the compound daily for 5 days, followed by administering a maintenance dose of 20 mg of the compound once a week. In some embodiments, the method comprises administering a loading dose of 12 mg of the compound daily for 6 days, followed by administering a maintenance dose of 20 mg of the compound once a week. In some embodiments, the method comprises administering a loading dose of 12 mg of the compound daily for 7 days, followed by administering a maintenance dose of 20 mg of the compound once a week. In some embodiments, the method comprises administering a loading dose of 12 mg of the compound daily for 8 days, followed by administering a maintenance dose of 20 mg of the compound once a week. In some embodiments, the method comprises administering a loading dose of 12 mg of the compound daily for 9 days, followed by administering a maintenance dose of 20 mg of the compound once a week. In some embodiments, the method comprises administering a loading dose of 12 mg of the compound daily for 10 days, followed by administering a maintenance dose of 20 mg of the compound once a week. In some embodiments, the method comprises administering a loading dose of 15 mg of the compound daily for 3 days, followed by administering a maintenance dose of 20 mg of the compound once a week. In some embodiments, the method comprises administering a loading dose of 15 mg of the compound daily for 4 days, followed by administering a maintenance dose of 20 mg of the compound once a week. In some embodiments, the method comprises administering a loading dose of 15 mg of the compound daily for 5 days, followed by administering a maintenance dose of 20 mg of the compound once a week. In some embodiments, the method comprises administering a loading dose of 15 mg of the compound daily for 6 days, followed by administering a maintenance dose of 20 mg of the compound once a week. In some embodiments, the method comprises administering a loading dose of 15 mg of the compound daily for 7 days, followed by administering a maintenance dose of 20 mg of the compound once a week. In some embodiments, the method comprises administering a loading dose of 15 mg of the compound daily for 8 days, followed by administering a maintenance dose of 20 mg of the compound once a week. In some embodiments, the method comprises administering a loading dose of 15 mg of the compound daily for 9 days, followed by administering a maintenance dose of 20 mg of the compound once a week. In some embodiments, the method comprises administering a loading dose of 15 mg of the compound daily for 10 days, followed by administering a maintenance dose of 20 mg of the compound once a week. In some embodiments, the method comprises administering a loading dose of 5 mg of the compound daily for 3 days, followed by administering a maintenance dose of 20 mg of the compound twice a week. In some embodiments, the method comprises administering a loading dose of 5 mg of the compound daily for 4 days, followed by administering a maintenance dose of 20 mg of the compound twice a week. In some embodiments, the method comprises administering a loading dose of 5 mg of the compound daily for 5 days, followed by administering a maintenance dose of 20 mg of the compound twice a week. In some embodiments, the method comprises administering a loading dose of 5 mg of the compound daily for 6 days, followed by administering a maintenance dose of 20 mg of the compound twice a week. In some embodiments, the method comprises administering a loading dose of 5 mg of the compound daily for 7 days, followed by administering a maintenance dose of 20 mg of the compound twice a week. In some embodiments, the method comprises administering a loading dose of 5 mg of the compound daily for 8 days, followed by administering a maintenance dose of 20 mg of the compound twice a week. In some embodiments, the method comprises administering a loading dose of 5 mg of the compound daily for 9 days, followed by administering a maintenance dose of 20 mg of the compound twice a week. In some embodiments, the method comprises administering a loading dose of 5 mg of the compound daily for 10 days, followed by administering a maintenance dose of 20 mg of the compound twice a week. In some embodiments, the method comprises administering a loading dose of 7 mg of the compound daily for 3 days, followed by administering a maintenance dose of 20 mg of the compound twice a week. In some embodiments, the method comprises administering a loading dose of 7 mg of the compound daily for 4 days, followed by administering a maintenance dose of 20 mg of the compound twice a week. In some embodiments, the method comprises administering a loading dose of 7 mg of the compound daily for 5 days, followed by administering a maintenance dose of 20 mg of the compound twice a week. In some embodiments, the method comprises administering a loading dose of 7 mg of the compound daily for 6 days, followed by administering a maintenance dose of 20 mg of the compound twice a week. In some embodiments, the method comprises administering a loading dose of 7 mg of the compound daily for 7 days, followed by administering a maintenance dose of 20 mg of the compound twice a week. In some embodiments, the method comprises administering a loading dose of 7 mg of the compound daily for 8 days, followed by administering a maintenance dose of 20 mg of the compound twice a week. In some embodiments, the method comprises administering a loading dose of 7 mg of the compound daily for 9 days, followed by administering a maintenance dose of 20 mg of the compound twice a week. In some embodiments, the method comprises administering a loading dose of 7 mg of the compound daily for 10 days, followed by administering a maintenance dose of 20 mg of the compound twice a week. In some embodiments, the method comprises administering a loading dose of 8 mg of the compound daily for 3 days, followed by administering a maintenance dose of 20 mg of the compound twice a week. In some embodiments, the method comprises administering a loading dose of 8 mg of the compound daily for 4 days, followed by administering a maintenance dose of 20 mg of the compound twice a week. In some embodiments, the method comprises administering a loading dose of 8 mg of the compound daily for 5 days, followed by administering a maintenance dose of 20 mg of the compound twice a week. In some embodiments, the method comprises administering a loading dose of 8 mg of the compound daily for 6 days, followed by administering a maintenance dose of 20 mg of the compound twice a week. In some embodiments, the method comprises administering a loading dose of 8 mg of the compound daily for 7 days, followed by administering a maintenance dose of 20 mg of the compound twice a week. In some embodiments, the method comprises administering a loading dose of 8 mg of the compound daily for 8 days, followed by administering a maintenance dose of 20 mg of the compound twice a week. In some embodiments, the method comprises administering a loading dose of 8 mg of the compound daily for 9 days, followed by administering a maintenance dose of 20 mg of the compound twice a week. In some embodiments, the method comprises administering a loading dose of 8 mg of the compound daily for 10 days, followed by administering a maintenance dose of 20 mg of the compound twice a week. In some embodiments, the method comprises administering a loading dose of 10 mg of the compound daily for 3 days, followed by administering a maintenance dose of 20 mg of the compound twice a week. In some embodiments, the method comprises administering a loading dose of 10 mg of the compound daily for 4 days, followed by administering a maintenance dose of 20 mg of the compound twice a week. In some embodiments, the method comprises administering a loading dose of 10 mg of the compound daily for 5 days, followed by administering a maintenance dose of 20 mg of the compound twice a week. In some embodiments, the method comprises administering a loading dose of 10 mg of the compound daily for 6 days, followed by administering a maintenance dose of 20 mg of the compound twice a week. In some embodiments, the method comprises administering a loading dose of 10 mg of the compound daily for 7 days, followed by administering a maintenance dose of 20 mg of the compound twice a week. In some embodiments, the method comprises administering a loading dose of 10 mg of the compound daily for 8 days, followed by administering a maintenance dose of 20 mg of the compound twice a week. In some embodiments, the method comprises administering a loading dose of 10 mg of the compound daily for 9 days, followed by administering a maintenance dose of 20 mg of the compound twice a week. In some embodiments, the method comprises administering a loading dose of 10 mg of the compound daily for 10 days, followed by administering a maintenance dose of 20 mg of the compound twice a week. In some embodiments, the method comprises administering a loading dose of 12 mg of the compound daily for 3 days, followed by administering a maintenance dose of 20 mg of the compound twice a week. In some embodiments, the method comprises administering a loading dose of 12 mg of the compound daily for 4 days, followed by administering a maintenance dose of 20 mg of the compound twice a week. In some embodiments, the method comprises administering a loading dose of 12 mg of the compound daily for 5 days, followed by administering a maintenance dose of 20 mg of the compound twice a week. In some embodiments, the method comprises administering a loading dose of 12 mg of the compound daily for 6 days, followed by administering a maintenance dose of 20 mg of the compound twice a week. In some embodiments, the method comprises administering a loading dose of 12 mg of the compound daily for 7 days, followed by administering a maintenance dose of 20 mg of the compound twice a week. In some embodiments, the method comprises administering a loading dose of 12 mg of the compound daily for 8 days, followed by administering a maintenance dose of 20 mg of the compound twice a week. In some embodiments, the method comprises administering a loading dose of 12 mg of the compound daily for 9 days, followed by administering a maintenance dose of 20 mg of the compound twice a week. In some embodiments, the method comprises administering a loading dose of 12 mg of the compound daily for 10 days, followed by administering a maintenance dose of 10 mg of the compound twice a week. In some embodiments, the method comprises administering a loading dose of 15 mg of the compound daily for 3 days, followed by administering a maintenance dose of 20 mg of the compound twice a week. In some embodiments, the method comprises administering a loading dose of 15 mg of the compound daily for 4 days, followed by administering a maintenance dose of 20 mg of the compound twice a week. In some embodiments, the method comprises administering a loading dose of 15 mg of the compound daily for 5 days, followed by administering a maintenance dose of 20 mg of the compound twice a week. In some embodiments, the method comprises administering a loading dose of 15 mg of the compound daily for 6 days, followed by administering a maintenance dose of 20 mg of the compound twice a week. In some embodiments, the method comprises administering a loading dose of 15 mg of the compound daily for 7 days, followed by administering a maintenance dose of 10 mg of the compound twice a week. In some embodiments, the method comprises administering a loading dose of 15 mg of the compound daily for 8 days, followed by administering a maintenance dose of 20 mg of the compound twice a week. In some embodiments, the method comprises administering a loading dose of 15 mg of the compound daily for 9 days, followed by administering a maintenance dose of 20 mg of the compound twice a week. In some embodiments, the method comprises administering a loading dose of 15 mg of the compound daily for 10 days, followed by administering a maintenance dose of 10 mg of the compound twice a week. In some embodiments, the method comprises administering a loading dose of 5 mg of the compound daily for 3 days, followed by administering a maintenance dose of 20 mg of the compound three times a week. In some embodiments, the method comprises administering a loading dose of 5 mg of the compound daily for 4 days, followed by administering a maintenance dose of 20 mg of the compound three times a week. In some embodiments, the method comprises administering a loading dose of 5 mg of the compound daily for 5 days, followed by administering a maintenance dose of 20 mg of the compound three times a week. In some embodiments, the method comprises administering a loading dose of 5 mg of the compound daily for 6 days, followed by administering a maintenance dose of 20 mg of the compound three times a week. In some embodiments, the method comprises administering a loading dose of 5 mg of the compound daily for 7 days, followed by administering a maintenance dose of 20 mg of the compound three times a week. In some embodiments, the method comprises administering a loading dose of 5 mg of the compound daily for 8 days, followed by administering a maintenance dose of 20 mg of the compound three times a week. In some embodiments, the method comprises administering a loading dose of 5 mg of the compound daily for 9 days, followed by administering a maintenance dose of 20 mg of the compound three times a week. In some embodiments, the method comprises administering a loading dose of 5 mg of the compound daily for 10 days, followed by administering a maintenance dose of 20 mg of the compound three times a week. In some embodiments, the method comprises administering a loading dose of 7 mg of the compound daily for 3 days, followed by administering a maintenance dose of 20 mg of the compound three times a week. In some embodiments, the method comprises administering a loading dose of 7 mg of the compound daily for 4 days, followed by administering a maintenance dose of 20 mg of the compound three times a week. In some embodiments, the method comprises administering a loading dose of 7 mg of the compound daily for 5 days, followed by administering a maintenance dose of 20 mg of the compound three times a week. In some embodiments, the method comprises administering a loading dose of 7 mg of the compound daily for 6 days, followed by administering a maintenance dose of 20 mg of the compound three times a week. In some embodiments, the method comprises administering a loading dose of 7 mg of the compound daily for 7 days, followed by administering a maintenance dose of 20 mg of the compound three times a week. In some embodiments, the method comprises administering a loading dose of 7 mg of the compound daily for 8 days, followed by administering a maintenance dose of 20 mg of the compound three times a week. In some embodiments, the method comprises administering a loading dose of 7 mg of the compound daily for 9 days, followed by administering a maintenance dose of 20 mg of the compound three times a week. In some embodiments, the method comprises administering a loading dose of 7 mg of the compound daily for 10 days, followed by administering a maintenance dose of 20 mg of the compound three times a week. In some embodiments, the method comprises administering a loading dose of 8 mg of the compound daily for 3 days, followed by administering a maintenance dose of 20 mg of the compound three times a week. In some embodiments, the method comprises administering a loading dose of 8 mg of the compound daily for 4 days, followed by administering a maintenance dose of 20 mg of the compound three times a week. In some embodiments, the method comprises administering a loading dose of 8 mg of the compound daily for 5 days, followed by administering a maintenance dose of 20 mg of the compound three times a week. In some embodiments, the method comprises administering a loading dose of 8 mg of the compound daily for 6 days, followed by administering a maintenance dose of 20 mg of the compound three times a week. In some embodiments, the method comprises administering a loading dose of 8 mg of the compound daily for 7 days, followed by administering a maintenance dose of 20 mg of the compound three times a week. In some embodiments, the method comprises administering a loading dose of 8 mg of the compound daily for 8 days, followed by administering a maintenance dose of 20 mg of the compound three times a week. In some embodiments, the method comprises administering a loading dose of 8 mg of the compound daily for 9 days, followed by administering a maintenance dose of 20 mg of the compound three times a week. In some embodiments, the method comprises administering a loading dose of 8 mg of the compound daily for 10 days, followed by administering a maintenance dose of 10 mg of the compound three times a week. In some embodiments, the method comprises administering a loading dose of 20 mg of the compound daily for 3 days, followed by administering a maintenance dose of 20 mg of the compound three times a week. In some embodiments, the method comprises administering a loading dose of 10 mg of the compound daily for 4 days, followed by administering a maintenance dose of 20 mg of the compound three times a week. In some embodiments, the method comprises administering a loading dose of 10 mg of the compound daily for 5 days, followed by administering a maintenance dose of 20 mg of the compound three times a week. In some embodiments, the method comprises administering a loading dose of 10 mg of the compound daily for 6 days, followed by administering a maintenance dose of 20 mg of the compound three times a week. In some embodiments, the method comprises administering a loading dose of 10 mg of the compound daily for 7 days, followed by administering a maintenance dose of 20 mg of the compound three times a week. In some embodiments, the method comprises administering a loading dose of 10 mg of the compound daily for 8 days, followed by administering a maintenance dose of 20 mg of the compound three times a week. In some embodiments, the method comprises administering a loading dose of 10 mg of the compound daily for 9 days, followed by administering a maintenance dose of 20 mg of the compound three times a week. In some embodiments, the method comprises administering a loading dose of 10 mg of the compound daily for 10 days, followed by administering a maintenance dose of 20 mg of the compound three times a week. In some embodiments, the method comprises administering a loading dose of 12 mg of the compound daily for 3 days, followed by administering a maintenance dose of 20 mg of the compound three times a week. In some embodiments, the method comprises administering a loading dose of 12 mg of the compound daily for 4 days, followed by administering a maintenance dose of 20 mg of the compound three times a week. In some embodiments, the method comprises administering a loading dose of 12 mg of the compound daily for 5 days, followed by administering a maintenance dose of 20 mg of the compound three times a week. In some embodiments, the method comprises administering a loading dose of 12 mg of the compound daily for 6 days, followed by administering a maintenance dose of 20 mg of the compound three times a week. In some embodiments, the method comprises administering a loading dose of 12 mg of the compound daily for 7 days, followed by administering a maintenance dose of 20 mg of the compound three times a week. In some embodiments, the method comprises administering a loading dose of 12 mg of the compound daily for 8 days, followed by administering a maintenance dose of 20 mg of the compound three times a week. In some embodiments, the method comprises administering a loading dose of 12 mg of the compound daily for 9 days, followed by administering a maintenance dose of 20 mg of the compound three times a week. In some embodiments, the method comprises administering a loading dose of 12 mg of the compound daily for 10 days, followed by administering a maintenance dose of 10 mg of the compound three times a week. In some embodiments, the method comprises administering a loading dose of 15 mg of the compound daily for 3 days, followed by administering a maintenance dose of 20 mg of the compound three times a week. In some embodiments, the method comprises administering a loading dose of 15 mg of the compound daily for 4 days, followed by administering a maintenance dose of 20 mg of the compound three times a week. In some embodiments, the method comprises administering a loading dose of 15 mg of the compound daily for 5 days, followed by administering a maintenance dose of 20 mg of the compound three times a week. In some embodiments, the method comprises administering a loading dose of 15 mg of the compound daily for 6 days, followed by administering a maintenance dose of 20 mg of the compound three times a week. In some embodiments, the method comprises administering a loading dose of 15 mg of the compound daily for 7 days, followed by administering a maintenance dose of 20 mg of the compound three times a week. In some embodiments, the method comprises administering a loading dose of 15 mg of the compound daily for 8 days, followed by administering a maintenance dose of 20 mg of the compound three times a week. In some embodiments, the method comprises administering a loading dose of 15 mg of the compound daily for 9 days, followed by administering a maintenance dose of 20 mg of the compound three times a week. In some embodiments, the method comprises administering a loading dose of 15 mg of the compound daily for 10 days, followed by administering a maintenance dose of 20 mg of the compound three times a week.

In some embodiments, the loading dose is administered from 1 day to 20 days, and the maintenance dose is administered from 20 days to 37000 days. In some embodiments, the method comprises administering a loading dose of 5 mg of the compound daily for 3 days, followed by administering a maintenance dose of 30 mg of the compound daily. In some embodiments, the method comprises administering a loading dose of 5 mg of the compound daily for 4 days, followed by administering a maintenance dose of 30 mg of the compound daily. In some embodiments, the method comprises administering a loading dose of 5 mg of the compound daily for 5 days, followed by administering a maintenance dose of 30 mg of the compound daily. In some embodiments, the method comprises administering a loading dose of 5 mg of the compound daily for 6 days, followed by administering a maintenance dose of 30 mg of the compound daily. In some embodiments, the method comprises administering a loading dose of 5 mg of the compound daily for 7 days, followed by administering a maintenance dose of 30 mg of the compound daily. In some embodiments, the method comprises administering a loading dose of 5 mg of the compound daily for 8 days, followed by administering a maintenance dose of 30 mg of the compound daily. In some embodiments, the method comprises administering a loading dose of 5 mg of the compound daily for 9 days, followed by administering a maintenance dose of 30 mg of the compound daily. In some embodiments, the method comprises administering a loading dose of 5 mg of the compound daily for 10 days, followed by administering a maintenance dose of 30 mg of the compound daily. In some embodiments, the method comprises administering a loading dose of 7 mg of the compound daily for 3 days, followed by administering a maintenance dose of 30 mg of the compound daily. In some embodiments, the method comprises administering a loading dose of 7 mg of the compound daily for 4 days, followed by administering a maintenance dose of 30 mg of the compound daily. In some embodiments, the method comprises administering a loading dose of 7 mg of the compound daily for 5 days, followed by administering a maintenance dose of 30 mg of the compound daily. In some embodiments, the method comprises administering a loading dose of 7 mg of the compound daily for 6 days, followed by administering a maintenance dose of 30 mg of the compound daily. In some embodiments, the method comprises administering a loading dose of 7 mg of the compound daily for 7 days, followed by administering a maintenance dose of 30 mg of the compound daily. In some embodiments, the method comprises administering a loading dose of 7 mg of the compound daily for 8 days, followed by administering a maintenance dose of 30 mg of the compound daily. In some embodiments, the method comprises administering a loading dose of 7 mg of the compound daily for 9 days, followed by administering a maintenance dose of 30 mg of the compound daily. In some embodiments, the method comprises administering a loading dose of 7 mg of the compound daily for 10 days, followed by administering a maintenance dose of 30 mg of the compound daily. In some embodiments, the method comprises administering a loading dose of 8 mg of the compound daily for 3 days, followed by administering a maintenance dose of 30 mg of the compound daily. In some embodiments, the method comprises administering a loading dose of 8 mg of the compound daily for 4 days, followed by administering a maintenance dose of 30 mg of the compound daily. In some embodiments, the method comprises administering a loading dose of 8 mg of the compound daily for 5 days, followed by administering a maintenance dose of 30 mg of the compound daily. In some embodiments, the method comprises administering a loading dose of 8 mg of the compound daily for 6 days, followed by administering a maintenance dose of 30 mg of the compound daily. In some embodiments, the method comprises administering a loading dose of 8 mg of the compound daily for 7 days, followed by administering a maintenance dose of 30 mg of the compound daily. In some embodiments, the method comprises administering a loading dose of 8 mg of the compound daily for 8 days, followed by administering a maintenance dose of 30 mg of the compound daily. In some embodiments, the method comprises administering a loading dose of 8 mg of the compound daily for 9 days, followed by administering a maintenance dose of 30 mg of the compound daily. In some embodiments, the method comprises administering a loading dose of 8 mg of the compound daily for 10 days, followed by administering a maintenance dose of 30 mg of the compound daily. In some embodiments, the method comprises administering a loading dose of 10 mg of the compound daily for 3 days, followed by administering a maintenance dose of 30 mg of the compound daily. In some embodiments, the method comprises administering a loading dose of 30 mg of the compound daily for 4 days, followed by administering a maintenance dose of 30 mg of the compound daily. In some embodiments, the method comprises administering a loading dose of 10 mg of the compound daily for 5 days, followed by administering a maintenance dose of 30 mg of the compound daily. In some embodiments, the method comprises administering a loading dose of 10 mg of the compound daily for 6 days, followed by administering a maintenance dose of 30 mg of the compound daily. In some embodiments, the method comprises administering a loading dose of 10 mg of the compound daily for 7 days, followed by administering a maintenance dose of 30 mg of the compound daily. In some embodiments, the method comprises administering a loading dose of 10 mg of the compound daily for 8 days, followed by administering a maintenance dose of 30 mg of the compound daily. In some embodiments, the method comprises administering a loading dose of 10 mg of the compound daily for 9 days, followed by administering a maintenance dose of 30 mg of the compound daily. In some embodiments, the method comprises administering a loading dose of 10 mg of the compound daily for 10 days, followed by administering a maintenance dose of 30 mg of the compound daily. In some embodiments, the method comprises administering a loading dose of 12 mg of the compound daily for 3 days, followed by administering a maintenance dose of 30 mg of the compound daily. In some embodiments, the method comprises administering a loading dose of 12 mg of the compound daily for 4 days, followed by administering a maintenance dose of 30 mg of the compound daily. In some embodiments, the method comprises administering a loading dose of 12 mg of the compound daily for 5 days, followed by administering a maintenance dose of 30 mg of the compound daily. In some embodiments, the method comprises administering a loading dose of 12 mg of the compound daily for 6 days, followed by administering a maintenance dose of 30 mg of the compound daily. In some embodiments, the method comprises administering a loading dose of 12 mg of the compound daily for 7 days, followed by administering a maintenance dose of 30 mg of the compound daily. In some embodiments, the method comprises administering a loading dose of 12 mg of the compound daily for 8 days, followed by administering a maintenance dose of 30 mg of the compound daily. In some embodiments, the method comprises administering a loading dose of 12 mg of the compound daily for 9 days, followed by administering a maintenance dose of 30 mg of the compound daily. In some embodiments, the method comprises administering a loading dose of 12 mg of the compound daily for 10 days, followed by administering a maintenance dose of 30 mg of the compound daily. In some embodiments, the method comprises administering a loading dose of 15 mg of the compound daily for 3 days, followed by administering a maintenance dose of 30 mg of the compound daily. In some embodiments, the method comprises administering a loading dose of 15 mg of the compound daily for 4 days, followed by administering a maintenance dose of 30 mg of the compound daily. In some embodiments, the method comprises administering a loading dose of 15 mg of the compound daily for 5 days, followed by administering a maintenance dose of 30 mg of the compound daily. In some embodiments, the method comprises administering a loading dose of 15 mg of the compound daily for 6 days, followed by administering a maintenance dose of 30 mg of the compound daily. In some embodiments, the method comprises administering a loading dose of 15 mg of the compound daily for 7 days, followed by administering a maintenance dose of 30 mg of the compound daily. In some embodiments, the method comprises administering a loading dose of 15 mg of the compound daily for 8 days, followed by administering a maintenance dose of 30 mg of the compound daily. In some embodiments, the method comprises administering a loading dose of 15 mg of the compound daily for 9 days, followed by administering a maintenance dose of 30 mg of the compound daily. In some embodiments, the method comprises administering a loading dose of 15 mg of the compound daily for 10 days, followed by administering a maintenance dose of 30 mg of the compound daily. In some embodiments, the method comprises administering a loading dose of 5 mg of the compound daily for 3 days, followed by administering a maintenance dose of 30 mg of the compound every other day. In some embodiments, the method comprises administering a loading dose of 5 mg of the compound daily for 4 days, followed by administering a maintenance dose of 30 mg of the compound every other day. In some embodiments, the method comprises administering a loading dose of 5 mg of the compound daily for 5 days, followed by administering a maintenance dose of 30 mg of the compound every other day. In some embodiments, the method comprises administering a loading dose of 5 mg of the compound daily for 6 days, followed by administering a maintenance dose of 30 mg of the compound every other day. In some embodiments, the method comprises administering a loading dose of 5 mg of the compound daily for 7 days, followed by administering a maintenance dose of 30 mg of the compound every other day. In some embodiments, the method comprises administering a loading dose of 5 mg of the compound daily for 8 days, followed by administering a maintenance dose of 30 mg of the compound every other day. In some embodiments, the method comprises administering a loading dose of 5 mg of the compound daily for 9 days, followed by administering a maintenance dose of 30 mg of the compound every other day. In some embodiments, the method comprises administering a loading dose of 5 mg of the compound daily for 10 days, followed by administering a maintenance dose of 30 mg of the compound every other day. In some embodiments, the method comprises administering a loading dose of 7 mg of the compound daily for 3 days, followed by administering a maintenance dose of 30 mg of the compound every other day. In some embodiments, the method comprises administering a loading dose of 7 mg of the compound daily for 4 days, followed by administering a maintenance dose of 30 mg of the compound every other day. In some embodiments, the method comprises administering a loading dose of 7 mg of the compound daily for 5 days, followed by administering a maintenance dose of 30 mg of the compound every other day. In some embodiments, the method comprises administering a loading dose of 7 mg of the compound daily for 6 days, followed by administering a maintenance dose of 30 mg of the compound every other day. In some embodiments, the method comprises administering a loading dose of 7 mg of the compound daily for 7 days, followed by administering a maintenance dose of 30 mg of the compound every other day. In some embodiments, the method comprises administering a loading dose of 7 mg of the compound daily for 8 days, followed by administering a maintenance dose of 30 mg of the compound every other day. In some embodiments, the method comprises administering a loading dose of 7 mg of the compound daily for 9 days, followed by administering a maintenance dose of 30 mg of the compound every other day. In some embodiments, the method comprises administering a loading dose of 7 mg of the compound daily for 10 days, followed by administering a maintenance dose of 30 mg of the compound every other day. In some embodiments, the method comprises administering a loading dose of 8 mg of the compound daily for 3 days, followed by administering a maintenance dose of 30 mg of the compound every other day. In some embodiments, the method comprises administering a loading dose of 8 mg of the compound daily for 4 days, followed by administering a maintenance dose of 30 mg of the compound every other day. In some embodiments, the method comprises administering a loading dose of 8 mg of the compound daily for 5 days, followed by administering a maintenance dose of 30 mg of the compound every other day. In some embodiments, the method comprises administering a loading dose of 8 mg of the compound daily for 6 days, followed by administering a maintenance dose of 30 mg of the compound every other day. In some embodiments, the method comprises administering a loading dose of 8 mg of the compound daily for 7 days, followed by administering a maintenance dose of 30 mg of the compound every other day. In some embodiments, the method comprises administering a loading dose of 8 mg of the compound daily for 8 days, followed by administering a maintenance dose of 30 mg of the compound every other day. In some embodiments, the method comprises administering a loading dose of 8 mg of the compound daily for 9 days, followed by administering a maintenance dose of 30 mg of the compound every other day. In some embodiments, the method comprises administering a loading dose of 8 mg of the compound daily for 10 days, followed by administering a maintenance dose of 30 mg of the compound every other day. In some embodiments, the method comprises administering a loading dose of 10 mg of the compound daily for 3 days, followed by administering a maintenance dose of 30 mg of the compound every other day. In some embodiments, the method comprises administering a loading dose of 10 mg of the compound daily for 4 days, followed by administering a maintenance dose of 30 mg of the compound every other day. In some embodiments, the method comprises administering a loading dose of 10 mg of the compound daily for 5 days, followed by administering a maintenance dose of 30 mg of the compound every other day. In some embodiments, the method comprises administering a loading dose of 10 mg of the compound daily for 6 days, followed by administering a maintenance dose of 30 mg of the compound every other day. In some embodiments, the method comprises administering a loading dose of 10 mg of the compound daily for 7 days, followed by administering a maintenance dose of 30 mg of the compound every other day. In some embodiments, the method comprises administering a loading dose of 10 mg of the compound daily for 8 days, followed by administering a maintenance dose of 30 mg of the compound every other day. In some embodiments, the method comprises administering a loading dose of 10 mg of the compound daily for 9 days, followed by administering a maintenance dose of 30 mg of the compound every other day. In some embodiments, the method comprises administering a loading dose of 10 mg of the compound daily for 10 days, followed by administering a maintenance dose of 30 mg of the compound every other day. In some embodiments, the method comprises administering a loading dose of 12 mg of the compound daily for 3 days, followed by administering a maintenance dose of 30 mg of the compound every other day. In some embodiments, the method comprises administering a loading dose of 12 mg of the compound daily for 4 days, followed by administering a maintenance dose of 30 mg of the compound every other day. In some embodiments, the method comprises administering a loading dose of 12 mg of the compound daily for 5 days, followed by administering a maintenance dose of 30 mg of the compound every other day. In some embodiments, the method comprises administering a loading dose of 12 mg of the compound daily for 6 days, followed by administering a maintenance dose of 30 mg of the compound every other day. In some embodiments, the method comprises administering a loading dose of 12 mg of the compound daily for 7 days, followed by administering a maintenance dose of 30 mg of the compound every other day. In some embodiments, the method comprises administering a loading dose of 12 mg of the compound daily for 8 days, followed by administering a maintenance dose of 30 mg of the compound every other day. In some embodiments, the method comprises administering a loading dose of 12 mg of the compound daily for 9 days, followed by administering a maintenance dose of 30 mg of the compound every other day. In some embodiments, the method comprises administering a loading dose of 12 mg of the compound daily for 10 days, followed by administering a maintenance dose of 30 mg of the compound every other day. In some embodiments, the method comprises administering a loading dose of 15 mg of the compound daily for 3 days, followed by administering a maintenance dose of 30 mg of the compound every other day. In some embodiments, the method comprises administering a loading dose of 15 mg of the compound daily for 4 days, followed by administering a maintenance dose of 30 mg of the compound every other day. In some embodiments, the method comprises administering a loading dose of 15 mg of the compound daily for 5 days, followed by administering a maintenance dose of 30 mg of the compound every other day. In some embodiments, the method comprises administering a loading dose of 15 mg of the compound daily for 6 days, followed by administering a maintenance dose of 30 mg of the compound every other day. In some embodiments, the method comprises administering a loading dose of 15 mg of the compound daily for 7 days, followed by administering a maintenance dose of 30 mg of the compound every other day. In some embodiments, the method comprises administering a loading dose of 15 mg of the compound daily for 8 days, followed by administering a maintenance dose of 30 mg of the compound every other day. In some embodiments, the method comprises administering a loading dose of 15 mg of the compound daily for 9 days, followed by administering a maintenance dose of 30 mg of the compound every other day. In some embodiments, the method comprises administering a loading dose of 15 mg of the compound daily for 10 days, followed by administering a maintenance dose of 30 mg of the compound every other day. In some embodiments, the method comprises administering a loading dose of 5 mg of the compound daily for 3 days, followed by administering a maintenance dose of 30 mg of the compound once a week. In some embodiments, the method comprises administering a loading dose of 5 mg of the compound daily for 4 days, followed by administering a maintenance dose of 30 mg of the compound once a week. In some embodiments, the method comprises administering a loading dose of 5 mg of the compound daily for 5 days, followed by administering a maintenance dose of 30 mg of the compound once a week. In some embodiments, the method comprises administering a loading dose of 5 mg of the compound daily for 6 days, followed by administering a maintenance dose of 30 mg of the compound once a week. In some embodiments, the method comprises administering a loading dose of 5 mg of the compound daily for 7 days, followed by administering a maintenance dose of 30 mg of the compound once a week. In some embodiments, the method comprises administering a loading dose of 5 mg of the compound daily for 8 days, followed by administering a maintenance dose of 30 mg of the compound once a week. In some embodiments, the method comprises administering a loading dose of 5 mg of the compound daily for 9 days, followed by administering a maintenance dose of 30 mg of the compound once a week. In some embodiments, the method comprises administering a loading dose of 5 mg of the compound daily for 10 days, followed by administering a maintenance dose of 30 mg of the compound once a week. In some embodiments, the method comprises administering a loading dose of 7 mg of the compound daily for 3 days, followed by administering a maintenance dose of 30 mg of the compound once a week. In some embodiments, the method comprises administering a loading dose of 7 mg of the compound daily for 4 days, followed by administering a maintenance dose of 30 mg of the compound once a week. In some embodiments, the method comprises administering a loading dose of 7 mg of the compound daily for 5 days, followed by administering a maintenance dose of 30 mg of the compound once a week. In some embodiments, the method comprises administering a loading dose of 7 mg of the compound daily for 6 days, followed by administering a maintenance dose of 30 mg of the compound once a week. In some embodiments, the method comprises administering a loading dose of 7 mg of the compound daily for 7 days, followed by administering a maintenance dose of 30 mg of the compound once a week. In some embodiments, the method comprises administering a loading dose of 7 mg of the compound daily for 8 days, followed by administering a maintenance dose of 30 mg of the compound once a week. In some embodiments, the method comprises administering a loading dose of 7 mg of the compound daily for 9 days, followed by administering a maintenance dose of 30 mg of the compound once a week. In some embodiments, the method comprises administering a loading dose of 7 mg of the compound daily for 10 days, followed by administering a maintenance dose of 30 mg of the compound once a week. In some embodiments, the method comprises administering a loading dose of 8 mg of the compound daily for 3 days, followed by administering a maintenance dose of 30 mg of the compound once a week. In some embodiments, the method comprises administering a loading dose of 8 mg of the compound daily for 4 days, followed by administering a maintenance dose of 30 mg of the compound once a week. In some embodiments, the method comprises administering a loading dose of 8 mg of the compound daily for 5 days, followed by administering a maintenance dose of 30 mg of the compound once a week. In some embodiments, the method comprises administering a loading dose of 8 mg of the compound daily for 6 days, followed by administering a maintenance dose of 30 mg of the compound once a week. In some embodiments, the method comprises administering a loading dose of 8 mg of the compound daily for 7 days, followed by administering a maintenance dose of 30 mg of the compound once a week. In some embodiments, the method comprises administering a loading dose of 8 mg of the compound daily for 8 days, followed by administering a maintenance dose of 30 mg of the compound once a week. In some embodiments, the method comprises administering a loading dose of 8 mg of the compound daily for 9 days, followed by administering a maintenance dose of 30 mg of the compound once a week. In some embodiments, the method comprises administering a loading dose of 8 mg of the compound daily for 10 days, followed by administering a maintenance dose of 30 mg of the compound once a week. In some embodiments, the method comprises administering a loading dose of 10 mg of the compound daily for 3 days, followed by administering a maintenance dose of 30 mg of the compound once a week. In some embodiments, the method comprises administering a loading dose of 10 mg of the compound daily for 4 days, followed by administering a maintenance dose of 30 mg of the compound once a week. In some embodiments, the method comprises administering a loading dose of 10 mg of the compound daily for 5 days, followed by administering a maintenance dose of 30 mg of the compound once a week. In some embodiments, the method comprises administering a loading dose of 10 mg of the compound daily for 6 days, followed by administering a maintenance dose of 30 mg of the compound once a week. In some embodiments, the method comprises administering a loading dose of 10 mg of the compound daily for 7 days, followed by administering a maintenance dose of 30 mg of the compound once a week. In some embodiments, the method comprises administering a loading dose of 10 mg of the compound daily for 8 days, followed by administering a maintenance dose of 30 mg of the compound once a week. In some embodiments, the method comprises administering a loading dose of 10 mg of the compound daily for 9 days, followed by administering a maintenance dose of 30 mg of the compound once a week. In some embodiments, the method comprises administering a loading dose of 10 mg of the compound daily for 10 days, followed by administering a maintenance dose of 30 mg of the compound once a week. In some embodiments, the method comprises administering a loading dose of 12 mg of the compound daily for 3 days, followed by administering a maintenance dose of 30 mg of the compound once a week. In some embodiments, the method comprises administering a loading dose of 12 mg of the compound daily for 4 days, followed by administering a maintenance dose of 30 mg of the compound once a week. In some embodiments, the method comprises administering a loading dose of 12 mg of the compound daily for 5 days, followed by administering a maintenance dose of 30 mg of the compound once a week. In some embodiments, the method comprises administering a loading dose of 12 mg of the compound daily for 6 days, followed by administering a maintenance dose of 30 mg of the compound once a week. In some embodiments, the method comprises administering a loading dose of 12 mg of the compound daily for 7 days, followed by administering a maintenance dose of 30 mg of the compound once a week. In some embodiments, the method comprises administering a loading dose of 12 mg of the compound daily for 8 days, followed by administering a maintenance dose of 30 mg of the compound once a week. In some embodiments, the method comprises administering a loading dose of 12 mg of the compound daily for 9 days, followed by administering a maintenance dose of 30 mg of the compound once a week. In some embodiments, the method comprises administering a loading dose of 12 mg of the compound daily for 10 days, followed by administering a maintenance dose of 30 mg of the compound once a week. In some embodiments, the method comprises administering a loading dose of 15 mg of the compound daily for 3 days, followed by administering a maintenance dose of 30 mg of the compound once a week. In some embodiments, the method comprises administering a loading dose of 15 mg of the compound daily for 4 days, followed by administering a maintenance dose of 30 mg of the compound once a week. In some embodiments, the method comprises administering a loading dose of 15 mg of the compound daily for 5 days, followed by administering a maintenance dose of 30 mg of the compound once a week. In some embodiments, the method comprises administering a loading dose of 15 mg of the compound daily for 6 days, followed by administering a maintenance dose of 30 mg of the compound once a week. In some embodiments, the method comprises administering a loading dose of 15 mg of the compound daily for 7 days, followed by administering a maintenance dose of 30 mg of the compound once a week. In some embodiments, the method comprises administering a loading dose of 15 mg of the compound daily for 8 days, followed by administering a maintenance dose of 30 mg of the compound once a week. In some embodiments, the method comprises administering a loading dose of 15 mg of the compound daily for 9 days, followed by administering a maintenance dose of 30 mg of the compound once a week. In some embodiments, the method comprises administering a loading dose of 15 mg of the compound daily for 10 days, followed by administering a maintenance dose of 30 mg of the compound once a week. In some embodiments, the method comprises administering a loading dose of 5 mg of the compound daily for 3 days, followed by administering a maintenance dose of 30 mg of the compound twice a week. In some embodiments, the method comprises administering a loading dose of 5 mg of the compound daily for 4 days, followed by administering a maintenance dose of 30 mg of the compound twice a week. In some embodiments, the method comprises administering a loading dose of 5 mg of the compound daily for 5 days, followed by administering a maintenance dose of 30 mg of the compound twice a week. In some embodiments, the method comprises administering a loading dose of 5 mg of the compound daily for 6 days, followed by administering a maintenance dose of 30 mg of the compound twice a week. In some embodiments, the method comprises administering a loading dose of 5 mg of the compound daily for 7 days, followed by administering a maintenance dose of 30 mg of the compound twice a week. In some embodiments, the method comprises administering a loading dose of 5 mg of the compound daily for 8 days, followed by administering a maintenance dose of 30 mg of the compound twice a week. In some embodiments, the method comprises administering a loading dose of 5 mg of the compound daily for 9 days, followed by administering a maintenance dose of 30 mg of the compound twice a week. In some embodiments, the method comprises administering a loading dose of 5 mg of the compound daily for 10 days, followed by administering a maintenance dose of 30 mg of the compound twice a week. In some embodiments, the method comprises administering a loading dose of 7 mg of the compound daily for 3 days, followed by administering a maintenance dose of 30 mg of the compound twice a week. In some embodiments, the method comprises administering a loading dose of 7 mg of the compound daily for 4 days, followed by administering a maintenance dose of 30 mg of the compound twice a week. In some embodiments, the method comprises administering a loading dose of 7 mg of the compound daily for 5 days, followed by administering a maintenance dose of 30 mg of the compound twice a week. In some embodiments, the method comprises administering a loading dose of 7 mg of the compound daily for 6 days, followed by administering a maintenance dose of 30 mg of the compound twice a week. In some embodiments, the method comprises administering a loading dose of 7 mg of the compound daily for 7 days, followed by administering a maintenance dose of 30 mg of the compound twice a week. In some embodiments, the method comprises administering a loading dose of 7 mg of the compound daily for 8 days, followed by administering a maintenance dose of 30 mg of the compound twice a week. In some embodiments, the method comprises administering a loading dose of 7 mg of the compound daily for 9 days, followed by administering a maintenance dose of 30 mg of the compound twice a week. In some embodiments, the method comprises administering a loading dose of 7 mg of the compound daily for 10 days, followed by administering a maintenance dose of 30 mg of the compound twice a week. In some embodiments, the method comprises administering a loading dose of 8 mg of the compound daily for 3 days, followed by administering a maintenance dose of 30 mg of the compound twice a week. In some embodiments, the method comprises administering a loading dose of 8 mg of the compound daily for 4 days, followed by administering a maintenance dose of 30 mg of the compound twice a week. In some embodiments, the method comprises administering a loading dose of 8 mg of the compound daily for 5 days, followed by administering a maintenance dose of 30 mg of the compound twice a week. In some embodiments, the method comprises administering a loading dose of 8 mg of the compound daily for 6 days, followed by administering a maintenance dose of 30 mg of the compound twice a week. In some embodiments, the method comprises administering a loading dose of 8 mg of the compound daily for 7 days, followed by administering a maintenance dose of 30 mg of the compound twice a week. In some embodiments, the method comprises administering a loading dose of 8 mg of the compound daily for 8 days, followed by administering a maintenance dose of 30 mg of the compound twice a week. In some embodiments, the method comprises administering a loading dose of 8 mg of the compound daily for 9 days, followed by administering a maintenance dose of 30 mg of the compound twice a week. In some embodiments, the method comprises administering a loading dose of 8 mg of the compound daily for 10 days, followed by administering a maintenance dose of 30 mg of the compound twice a week. In some embodiments, the method comprises administering a loading dose of 10 mg of the compound daily for 3 days, followed by administering a maintenance dose of 30 mg of the compound twice a week. In some embodiments, the method comprises administering a loading dose of 10 mg of the compound daily for 4 days, followed by administering a maintenance dose of 30 mg of the compound twice a week. In some embodiments, the method comprises administering a loading dose of 10 mg of the compound daily for 5 days, followed by administering a maintenance dose of 30 mg of the compound twice a week. In some embodiments, the method comprises administering a loading dose of 10 mg of the compound daily for 6 days, followed by administering a maintenance dose of 30 mg of the compound twice a week. In some embodiments, the method comprises administering a loading dose of 10 mg of the compound daily for 7 days, followed by administering a maintenance dose of 30 mg of the compound twice a week. In some embodiments, the method comprises administering a loading dose of 10 mg of the compound daily for 8 days, followed by administering a maintenance dose of 30 mg of the compound twice a week. In some embodiments, the method comprises administering a loading dose of 10 mg of the compound daily for 9 days, followed by administering a maintenance dose of 30 mg of the compound twice a week. In some embodiments, the method comprises administering a loading dose of 10 mg of the compound daily for 10 days, followed by administering a maintenance dose of 30 mg of the compound twice a week. In some embodiments, the method comprises administering a loading dose of 12 mg of the compound daily for 3 days, followed by administering a maintenance dose of 30 mg of the compound twice a week. In some embodiments, the method comprises administering a loading dose of 12 mg of the compound daily for 4 days, followed by administering a maintenance dose of 30 mg of the compound twice a week. In some embodiments, the method comprises administering a loading dose of 12 mg of the compound daily for 5 days, followed by administering a maintenance dose of 30 mg of the compound twice a week. In some embodiments, the method comprises administering a loading dose of 12 mg of the compound daily for 6 days, followed by administering a maintenance dose of 30 mg of the compound twice a week. In some embodiments, the method comprises administering a loading dose of 12 mg of the compound daily for 7 days, followed by administering a maintenance dose of 30 mg of the compound twice a week. In some embodiments, the method comprises administering a loading dose of 12 mg of the compound daily for 8 days, followed by administering a maintenance dose of 30 mg of the compound twice a week. In some embodiments, the method comprises administering a loading dose of 12 mg of the compound daily for 9 days, followed by administering a maintenance dose of 30 mg of the compound twice a week. In some embodiments, the method comprises administering a loading dose of 12 mg of the compound daily for 10 days, followed by administering a maintenance dose of 30 mg of the compound twice a week. In some embodiments, the method comprises administering a loading dose of 15 mg of the compound daily for 3 days, followed by administering a maintenance dose of 30 mg of the compound twice a week. In some embodiments, the method comprises administering a loading dose of 15 mg of the compound daily for 4 days, followed by administering a maintenance dose of 30 mg of the compound twice a week. In some embodiments, the method comprises administering a loading dose of 15 mg of the compound daily for 5 days, followed by administering a maintenance dose of 30 mg of the compound twice a week. In some embodiments, the method comprises administering a loading dose of 15 mg of the compound daily for 6 days, followed by administering a maintenance dose of 30 mg of the compound twice a week. In some embodiments, the method comprises administering a loading dose of 15 mg of the compound daily for 7 days, followed by administering a maintenance dose of 30 mg of the compound twice a week. In some embodiments, the method comprises administering a loading dose of 15 mg of the compound daily for 8 days, followed by administering a maintenance dose of 30 mg of the compound twice a week. In some embodiments, the method comprises administering a loading dose of 15 mg of the compound daily for 9 days, followed by administering a maintenance dose of 30 mg of the compound twice a week. In some embodiments, the method comprises administering a loading dose of 15 mg of the compound daily for 10 days, followed by administering a maintenance dose of 30 mg of the compound twice a week. In some embodiments, the method comprises administering a loading dose of 5 mg of the compound daily for 3 days, followed by administering a maintenance dose of 30 mg of the compound three times a week. In some embodiments, the method comprises administering a loading dose of 5 mg of the compound daily for 4 days, followed by administering a maintenance dose of 30 mg of the compound three times a week. In some embodiments, the method comprises administering a loading dose of 5 mg of the compound daily for 5 days, followed by administering a maintenance dose of 30 mg of the compound three times a week. In some embodiments, the method comprises administering a loading dose of 5 mg of the compound daily for 6 days, followed by administering a maintenance dose of 30 mg of the compound three times a week. In some embodiments, the method comprises administering a loading dose of 5 mg of the compound daily for 7 days, followed by administering a maintenance dose of 30 mg of the compound three times a week. In some embodiments, the method comprises administering a loading dose of 5 mg of the compound daily for 8 days, followed by administering a maintenance dose of 30 mg of the compound three times a week. In some embodiments, the method comprises administering a loading dose of 5 mg of the compound daily for 9 days, followed by administering a maintenance dose of 30 mg of the compound three times a week. In some embodiments, the method comprises administering a loading dose of 5 mg of the compound daily for 10 days, followed by administering a maintenance dose of 30 mg of the compound three times a week. In some embodiments, the method comprises administering a loading dose of 7 mg of the compound daily for 3 days, followed by administering a maintenance dose of 30 mg of the compound three times a week. In some embodiments, the method comprises administering a loading dose of 7 mg of the compound daily for 4 days, followed by administering a maintenance dose of 30 mg of the compound three times a week. In some embodiments, the method comprises administering a loading dose of 7 mg of the compound daily for 5 days, followed by administering a maintenance dose of 30 mg of the compound three times a week. In some embodiments, the method comprises administering a loading dose of 7 mg of the compound daily for 6 days, followed by administering a maintenance dose of 30 mg of the compound three times a week. In some embodiments, the method comprises administering a loading dose of 7 mg of the compound daily for 7 days, followed by administering a maintenance dose of 30 mg of the compound three times a week. In some embodiments, the method comprises administering a loading dose of 7 mg of the compound daily for 8 days, followed by administering a maintenance dose of 30 mg of the compound three times a week. In some embodiments, the method comprises administering a loading dose of 7 mg of the compound daily for 9 days, followed by administering a maintenance dose of 30 mg of the compound three times a week. In some embodiments, the method comprises administering a loading dose of 7 mg of the compound daily for 10 days, followed by administering a maintenance dose of 30 mg of the compound three times a week. In some embodiments, the method comprises administering a loading dose of 8 mg of the compound daily for 3 days, followed by administering a maintenance dose of 30 mg of the compound three times a week. In some embodiments, the method comprises administering a loading dose of 8 mg of the compound daily for 4 days, followed by administering a maintenance dose of 30 mg of the compound three times a week. In some embodiments, the method comprises administering a loading dose of 8 mg of the compound daily for 5 days, followed by administering a maintenance dose of 30 mg of the compound three times a week. In some embodiments, the method comprises administering a loading dose of 8 mg of the compound daily for 6 days, followed by administering a maintenance dose of 30 mg of the compound three times a week. In some embodiments, the method comprises administering a loading dose of 8 mg of the compound daily for 7 days, followed by administering a maintenance dose of 30 mg of the compound three times a week. In some embodiments, the method comprises administering a loading dose of 8 mg of the compound daily for 8 days, followed by administering a maintenance dose of 30 mg of the compound three times a week. In some embodiments, the method comprises administering a loading dose of 8 mg of the compound daily for 9 days, followed by administering a maintenance dose of 30 mg of the compound three times a week. In some embodiments, the method comprises administering a loading dose of 8 mg of the compound daily for 10 days, followed by administering a maintenance dose of 30 mg of the compound three times a week. In some embodiments, the method comprises administering a loading dose of 10 mg of the compound daily for 3 days, followed by administering a maintenance dose of 30 mg of the compound three times a week. In some embodiments, the method comprises administering a loading dose of 10 mg of the compound daily for 4 days, followed by administering a maintenance dose of 30 mg of the compound three times a week. In some embodiments, the method comprises administering a loading dose of 10 mg of the compound daily for 5 days, followed by administering a maintenance dose of 30 mg of the compound three times a week. In some embodiments, the method comprises administering a loading dose of 10 mg of the compound daily for 6 days, followed by administering a maintenance dose of 30 mg of the compound three times a week. In some embodiments, the method comprises administering a loading dose of 10 mg of the compound daily for 7 days, followed by administering a maintenance dose of 30 mg of the compound three times a week. In some embodiments, the method comprises administering a loading dose of 10 mg of the compound daily for 8 days, followed by administering a maintenance dose of 30 mg of the compound three times a week. In some embodiments, the method comprises administering a loading dose of 10 mg of the compound daily for 9 days, followed by administering a maintenance dose of 30 mg of the compound three times a week. In some embodiments, the method comprises administering a loading dose of 10 mg of the compound daily for 10 days, followed by administering a maintenance dose of 30 mg of the compound three times a week. In some embodiments, the method comprises administering a loading dose of 12 mg of the compound daily for 3 days, followed by administering a maintenance dose of 30 mg of the compound three times a week. In some embodiments, the method comprises administering a loading dose of 12 mg of the compound daily for 4 days, followed by administering a maintenance dose of 30 mg of the compound three times a week. In some embodiments, the method comprises administering a loading dose of 12 mg of the compound daily for 5 days, followed by administering a maintenance dose of 30 mg of the compound three times a week. In some embodiments, the method comprises administering a loading dose of 12 mg of the compound daily for 6 days, followed by administering a maintenance dose of 30 mg of the compound three times a week. In some embodiments, the method comprises administering a loading dose of 12 mg of the compound daily for 7 days, followed by administering a maintenance dose of 30 mg of the compound three times a week. In some embodiments, the method comprises administering a loading dose of 12 mg of the compound daily for 8 days, followed by administering a maintenance dose of 30 mg of the compound three times a week. In some embodiments, the method comprises administering a loading dose of 12 mg of the compound daily for 9 days, followed by administering a maintenance dose of 30 mg of the compound three times a week. In some embodiments, the method comprises administering a loading dose of 12 mg of the compound daily for 10 days, followed by administering a maintenance dose of 30 mg of the compound three times a week. In some embodiments, the method comprises administering a loading dose of 15 mg of the compound daily for 3 days, followed by administering a maintenance dose of 30 mg of the compound three times a week. In some embodiments, the method comprises administering a loading dose of 15 mg of the compound daily for 4 days, followed by administering a maintenance dose of 30 mg of the compound three times a week. In some embodiments, the method comprises administering a loading dose of 15 mg of the compound daily for 5 days, followed by administering a maintenance dose of 30 mg of the compound three times a week. In some embodiments, the method comprises administering a loading dose of 15 mg of the compound daily for 6 days, followed by administering a maintenance dose of 30 mg of the compound three times a week. In some embodiments, the method comprises administering a loading dose of 15 mg of the compound daily for 7 days, followed by administering a maintenance dose of 30 mg of the compound three times a week. In some embodiments, the method comprises administering a loading dose of 15 mg of the compound daily for 8 days, followed by administering a maintenance dose of 30 mg of the compound three times a week. In some embodiments, the method comprises administering a loading dose of 15 mg of the compound daily for 9 days, followed by administering a maintenance dose of 30 mg of the compound three times a week. In some embodiments, the method comprises administering a loading dose of 15 mg of the compound daily for 10 days, followed by administering a maintenance dose of 30 mg of the compound three times a week.

In some embodiments, the loading dose is administered from 1 day to 20 days, and the maintenance dose is administered from 20 days to 37000 days. In some embodiments, the method comprises administering a loading dose of 5 mg of the compound daily for 3 days, followed by administering a maintenance dose of 40 mg of the compound daily. In some embodiments, the method comprises administering a loading dose of 5 mg of the compound daily for 4 days, followed by administering a maintenance dose of 40 mg of the compound daily. In some embodiments, the method comprises administering a loading dose of 5 mg of the compound daily for 5 days, followed by administering a maintenance dose of 40 mg of the compound daily. In some embodiments, the method comprises administering a loading dose of 5 mg of the compound daily for 6 days, followed by administering a maintenance dose of 40 mg of the compound daily. In some embodiments, the method comprises administering a loading dose of 5 mg of the compound daily for 7 days, followed by administering a maintenance dose of 40 mg of the compound daily. In some embodiments, the method comprises administering a loading dose of 5 mg of the compound daily for 8 days, followed by administering a maintenance dose of 40 mg of the compound daily. In some embodiments, the method comprises administering a loading dose of 5 mg of the compound daily for 9 days, followed by administering a maintenance dose of 40 mg of the compound daily. In some embodiments, the method comprises administering a loading dose of 5 mg of the compound daily for 10 days, followed by administering a maintenance dose of 40 mg of the compound daily. In some embodiments, the method comprises administering a loading dose of 7 mg of the compound daily for 3 days, followed by administering a maintenance dose of 40 mg of the compound daily. In some embodiments, the method comprises administering a loading dose of 7 mg of the compound daily for 4 days, followed by administering a maintenance dose of 40 mg of the compound daily. In some embodiments, the method comprises administering a loading dose of 7 mg of the compound daily for 5 days, followed by administering a maintenance dose of 40 mg of the compound daily. In some embodiments, the method comprises administering a loading dose of 7 mg of the compound daily for 6 days, followed by administering a maintenance dose of 40 mg of the compound daily. In some embodiments, the method comprises administering a loading dose of 7 mg of the compound daily for 7 days, followed by administering a maintenance dose of 40 mg of the compound daily. In some embodiments, the method comprises administering a loading dose of 7 mg of the compound daily for 8 days, followed by administering a maintenance dose of 40 mg of the compound daily. In some embodiments, the method comprises administering a loading dose of 7 mg of the compound daily for 9 days, followed by administering a maintenance dose of 40 mg of the compound daily. In some embodiments, the method comprises administering a loading dose of 7 mg of the compound daily for 40 days, followed by administering a maintenance dose of 40 mg of the compound daily. In some embodiments, the method comprises administering a loading dose of 8 mg of the compound daily for 3 days, followed by administering a maintenance dose of 40 mg of the compound daily. In some embodiments, the method comprises administering a loading dose of 8 mg of the compound daily for 4 days, followed by administering a maintenance dose of 40 mg of the compound daily. In some embodiments, the method comprises administering a loading dose of 8 mg of the compound daily for 5 days, followed by administering a maintenance dose of 40 mg of the compound daily. In some embodiments, the method comprises administering a loading dose of 8 mg of the compound daily for 6 days, followed by administering a maintenance dose of 40 mg of the compound daily. In some embodiments, the method comprises administering a loading dose of 8 mg of the compound daily for 7 days, followed by administering a maintenance dose of 40 mg of the compound daily. In some embodiments, the method comprises administering a loading dose of 8 mg of the compound daily for 8 days, followed by administering a maintenance dose of 40 mg of the compound daily. In some embodiments, the method comprises administering a loading dose of 8 mg of the compound daily for 9 days, followed by administering a maintenance dose of 40 mg of the compound daily. In some embodiments, the method comprises administering a loading dose of 8 mg of the compound daily for 10 days, followed by administering a maintenance dose of 40 mg of the compound daily. In some embodiments, the method comprises administering a loading dose of 10 mg of the compound daily for 3 days, followed by administering a maintenance dose of 40 mg of the compound daily. In some embodiments, the method comprises administering a loading dose of 10 mg of the compound daily for 4 days, followed by administering a maintenance dose of 40 mg of the compound daily. In some embodiments, the method comprises administering a loading dose of 10 mg of the compound daily for 5 days, followed by administering a maintenance dose of 40 mg of the compound daily. In some embodiments, the method comprises administering a loading dose of 10 mg of the compound daily for 6 days, followed by administering a maintenance dose of 40 mg of the compound daily. In some embodiments, the method comprises administering a loading dose of 10 mg of the compound daily for 7 days, followed by administering a maintenance dose of 40 mg of the compound daily. In some embodiments, the method comprises administering a loading dose of 10 mg of the compound daily for 8 days, followed by administering a maintenance dose of 40 mg of the compound daily. In some embodiments, the method comprises administering a loading dose of 10 mg of the compound daily for 9 days, followed by administering a maintenance dose of 40 mg of the compound daily. In some embodiments, the method comprises administering a loading dose of 10 mg of the compound daily for 10 days, followed by administering a maintenance dose of 40 mg of the compound daily. In some embodiments, the method comprises administering a loading dose of 12 mg of the compound daily for 3 days, followed by administering a maintenance dose of 40 mg of the compound daily. In some embodiments, the method comprises administering a loading dose of 12 mg of the compound daily for 4 days, followed by administering a maintenance dose of 40 mg of the compound daily. In some embodiments, the method comprises administering a loading dose of 12 mg of the compound daily for 5 days, followed by administering a maintenance dose of 40 mg of the compound daily. In some embodiments, the method comprises administering a loading dose of 12 mg of the compound daily for 6 days, followed by administering a maintenance dose of 40 mg of the compound daily. In some embodiments, the method comprises administering a loading dose of 12 mg of the compound daily for 7 days, followed by administering a maintenance dose of 40 mg of the compound daily. In some embodiments, the method comprises administering a loading dose of 12 mg of the compound daily for 8 days, followed by administering a maintenance dose of 40 mg of the compound daily. In some embodiments, the method comprises administering a loading dose of 12 mg of the compound daily for 9 days, followed by administering a maintenance dose of 40 mg of the compound daily. In some embodiments, the method comprises administering a loading dose of 12 mg of the compound daily for 40 days, followed by administering a maintenance dose of 40 mg of the compound daily. In some embodiments, the method comprises administering a loading dose of 15 mg of the compound daily for 3 days, followed by administering a maintenance dose of 40 mg of the compound daily. In some embodiments, the method comprises administering a loading dose of 15 mg of the compound daily for 4 days, followed by administering a maintenance dose of 40 mg of the compound daily. In some embodiments, the method comprises administering a loading dose of 15 mg of the compound daily for 5 days, followed by administering a maintenance dose of 40 mg of the compound daily. In some embodiments, the method comprises administering a loading dose of 15 mg of the compound daily for 6 days, followed by administering a maintenance dose of 40 mg of the compound daily. In some embodiments, the method comprises administering a loading dose of 15 mg of the compound daily for 7 days, followed by administering a maintenance dose of 40 mg of the compound daily. In some embodiments, the method comprises administering a loading dose of 15 mg of the compound daily for 8 days, followed by administering a maintenance dose of 40 mg of the compound daily. In some embodiments, the method comprises administering a loading dose of 15 mg of the compound daily for 9 days, followed by administering a maintenance dose of 40 mg of the compound daily. In some embodiments, the method comprises administering a loading dose of 15 mg of the compound daily for 10 days, followed by administering a maintenance dose of 40 mg of the compound daily. In some embodiments, the method comprises administering a loading dose of 5 mg of the compound daily for 3 days, followed by administering a maintenance dose of 40 mg of the compound every other day. In some embodiments, the method comprises administering a loading dose of 5 mg of the compound daily for 4 days, followed by administering a maintenance dose of 40 mg of the compound every other day. In some embodiments, the method comprises administering a loading dose of 5 mg of the compound daily for 5 days, followed by administering a maintenance dose of 40 mg of the compound every other day. In some embodiments, the method comprises administering a loading dose of 5 mg of the compound daily for 6 days, followed by administering a maintenance dose of 40 mg of the compound every other day. In some embodiments, the method comprises administering a loading dose of 5 mg of the compound daily for 7 days, followed by administering a maintenance dose of 40 mg of the compound every other day. In some embodiments, the method comprises administering a loading dose of 5 mg of the compound daily for 8 days, followed by administering a maintenance dose of 40 mg of the compound every other day. In some embodiments, the method comprises administering a loading dose of 5 mg of the compound daily for 9 days, followed by administering a maintenance dose of 40 mg of the compound every other day. In some embodiments, the method comprises administering a loading dose of 5 mg of the compound daily for 10 days, followed by administering a maintenance dose of 40 mg of the compound every other day. In some embodiments, the method comprises administering a loading dose of 7 mg of the compound daily for 3 days, followed by administering a maintenance dose of 40 mg of the compound every other day. In some embodiments, the method comprises administering a loading dose of 7 mg of the compound daily for 4 days, followed by administering a maintenance dose of 40 mg of the compound every other day. In some embodiments, the method comprises administering a loading dose of 7 mg of the compound daily for 5 days, followed by administering a maintenance dose of 40 mg of the compound every other day. In some embodiments, the method comprises administering a loading dose of 7 mg of the compound daily for 6 days, followed by administering a maintenance dose of 40 mg of the compound every other day. In some embodiments, the method comprises administering a loading dose of 7 mg of the compound daily for 7 days, followed by administering a maintenance dose of 40 mg of the compound every other day. In some embodiments, the method comprises administering a loading dose of 7 mg of the compound daily for 8 days, followed by administering a maintenance dose of 40 mg of the compound every other day. In some embodiments, the method comprises administering a loading dose of 7 mg of the compound daily for 9 days, followed by administering a maintenance dose of 40 mg of the compound every other day. In some embodiments, the method comprises administering a loading dose of 7 mg of the compound daily for 10 days, followed by administering a maintenance dose of 40 mg of the compound every other day. In some embodiments, the method comprises administering a loading dose of 8 mg of the compound daily for 3 days, followed by administering a maintenance dose of 40 mg of the compound every other day. In some embodiments, the method comprises administering a loading dose of 8 mg of the compound daily for 4 days, followed by administering a maintenance dose of 40 mg of the compound every other day. In some embodiments, the method comprises administering a loading dose of 8 mg of the compound daily for 5 days, followed by administering a maintenance dose of 40 mg of the compound every other day. In some embodiments, the method comprises administering a loading dose of 8 mg of the compound daily for 6 days, followed by administering a maintenance dose of 40 mg of the compound every other day. In some embodiments, the method comprises administering a loading dose of 8 mg of the compound daily for 7 days, followed by administering a maintenance dose of 40 mg of the compound every other day. In some embodiments, the method comprises administering a loading dose of 8 mg of the compound daily for 8 days, followed by administering a maintenance dose of 40 mg of the compound every other day. In some embodiments, the method comprises administering a loading dose of 8 mg of the compound daily for 9 days, followed by administering a maintenance dose of 40 mg of the compound every other day. In some embodiments, the method comprises administering a loading dose of 8 mg of the compound daily for 10 days, followed by administering a maintenance dose of 40 mg of the compound every other day. In some embodiments, the method comprises administering a loading dose of 10 mg of the compound daily for 3 days, followed by administering a maintenance dose of 40 mg of the compound every other day. In some embodiments, the method comprises administering a loading dose of 10 mg of the compound daily for 4 days, followed by administering a maintenance dose of 40 mg of the compound every other day. In some embodiments, the method comprises administering a loading dose of 10 mg of the compound daily for 5 days, followed by administering a maintenance dose of 40 mg of the compound every other day. In some embodiments, the method comprises administering a loading dose of 10 mg of the compound daily for 6 days, followed by administering a maintenance dose of 40 mg of the compound every other day. In some embodiments, the method comprises administering a loading dose of 10 mg of the compound daily for 7 days, followed by administering a maintenance dose of 40 mg of the compound every other day. In some embodiments, the method comprises administering a loading dose of 10 mg of the compound daily for 8 days, followed by administering a maintenance dose of 40 mg of the compound every other day. In some embodiments, the method comprises administering a loading dose of 10 mg of the compound daily for 9 days, followed by administering a maintenance dose of 40 mg of the compound every other day. In some embodiments, the method comprises administering a loading dose of 10 mg of the compound daily for 10 days, followed by administering a maintenance dose of 40 mg of the compound every other day. In some embodiments, the method comprises administering a loading dose of 12 mg of the compound daily for 3 days, followed by administering a maintenance dose of 40 mg of the compound every other day. In some embodiments, the method comprises administering a loading dose of 12 mg of the compound daily for 4 days, followed by administering a maintenance dose of 40 mg of the compound every other day. In some embodiments, the method comprises administering a loading dose of 12 mg of the compound daily for 5 days, followed by administering a maintenance dose of 40 mg of the compound every other day. In some embodiments, the method comprises administering a loading dose of 12 mg of the compound daily for 6 days, followed by administering a maintenance dose of 40 mg of the compound every other day. In some embodiments, the method comprises administering a loading dose of 12 mg of the compound daily for 7 days, followed by administering a maintenance dose of 40 mg of the compound every other day. In some embodiments, the method comprises administering a loading dose of 12 mg of the compound daily for 8 days, followed by administering a maintenance dose of 40 mg of the compound every other day. In some embodiments, the method comprises administering a loading dose of 12 mg of the compound daily for 9 days, followed by administering a maintenance dose of 40 mg of the compound every other day. In some embodiments, the method comprises administering a loading dose of 12 mg of the compound daily for 10 days, followed by administering a maintenance dose of 40 mg of the compound every other day. In some embodiments, the method comprises administering a loading dose of 15 mg of the compound daily for 3 days, followed by administering a maintenance dose of 40 mg of the compound every other day. In some embodiments, the method comprises administering a loading dose of 15 mg of the compound daily for 4 days, followed by administering a maintenance dose of 40 mg of the compound every other day. In some embodiments, the method comprises administering a loading dose of 15 mg of the compound daily for 5 days, followed by administering a maintenance dose of 40 mg of the compound every other day. In some embodiments, the method comprises administering a loading dose of 15 mg of the compound daily for 6 days, followed by administering a maintenance dose of 40 mg of the compound every other day. In some embodiments, the method comprises administering a loading dose of 15 mg of the compound daily for 7 days, followed by administering a maintenance dose of 40 mg of the compound every other day. In some embodiments, the method comprises administering a loading dose of 15 mg of the compound daily for 8 days, followed by administering a maintenance dose of 40 mg of the compound every other day. In some embodiments, the method comprises administering a loading dose of 15 mg of the compound daily for 9 days, followed by administering a maintenance dose of 40 mg of the compound every other day. In some embodiments, the method comprises administering a loading dose of 15 mg of the compound daily for 10 days, followed by administering a maintenance dose of 40 mg of the compound every other day. In some embodiments, the method comprises administering a loading dose of 5 mg of the compound daily for 3 days, followed by administering a maintenance dose of 40 mg of the compound once a week. In some embodiments, the method comprises administering a loading dose of 5 mg of the compound daily for 4 days, followed by administering a maintenance dose of 40 mg of the compound once a week. In some embodiments, the method comprises administering a loading dose of 5 mg of the compound daily for 5 days, followed by administering a maintenance dose of 40 mg of the compound once a week. In some embodiments, the method comprises administering a loading dose of 5 mg of the compound daily for 6 days, followed by administering a maintenance dose of 40 mg of the compound once a week. In some embodiments, the method comprises administering a loading dose of 5 mg of the compound daily for 7 days, followed by administering a maintenance dose of 40 mg of the compound once a week. In some embodiments, the method comprises administering a loading dose of 5 mg of the compound daily for 8 days, followed by administering a maintenance dose of 40 mg of the compound once a week. In some embodiments, the method comprises administering a loading dose of 5 mg of the compound daily for 9 days, followed by administering a maintenance dose of 40 mg of the compound once a week. In some embodiments, the method comprises administering a loading dose of 5 mg of the compound daily for 10 days, followed by administering a maintenance dose of 40 mg of the compound once a week. In some embodiments, the method comprises administering a loading dose of 7 mg of the compound daily for 3 days, followed by administering a maintenance dose of 40 mg of the compound once a week. In some embodiments, the method comprises administering a loading dose of 7 mg of the compound daily for 4 days, followed by administering a maintenance dose of 40 mg of the compound once a week. In some embodiments, the method comprises administering a loading dose of 7 mg of the compound daily for 5 days, followed by administering a maintenance dose of 40 mg of the compound once a week. In some embodiments, the method comprises administering a loading dose of 7 mg of the compound daily for 6 days, followed by administering a maintenance dose of 40 mg of the compound once a week. In some embodiments, the method comprises administering a loading dose of 7 mg of the compound daily for 7 days, followed by administering a maintenance dose of 40 mg of the compound once a week. In some embodiments, the method comprises administering a loading dose of 7 mg of the compound daily for 8 days, followed by administering a maintenance dose of 40 mg of the compound once a week. In some embodiments, the method comprises administering a loading dose of 7 mg of the compound daily for 9 days, followed by administering a maintenance dose of 40 mg of the compound once a week. In some embodiments, the method comprises administering a loading dose of 7 mg of the compound daily for 10 days, followed by administering a maintenance dose of 40 mg of the compound once a week. In some embodiments, the method comprises administering a loading dose of 8 mg of the compound daily for 3 days, followed by administering a maintenance dose of 40 mg of the compound once a week. In some embodiments, the method comprises administering a loading dose of 8 mg of the compound daily for 4 days, followed by administering a maintenance dose of 40 mg of the compound once a week. In some embodiments, the method comprises administering a loading dose of 8 mg of the compound daily for 5 days, followed by administering a maintenance dose of 40 mg of the compound once a week. In some embodiments, the method comprises administering a loading dose of 8 mg of the compound daily for 6 days, followed by administering a maintenance dose of 40 mg of the compound once a week. In some embodiments, the method comprises administering a loading dose of 8 mg of the compound daily for 7 days, followed by administering a maintenance dose of 40 mg of the compound once a week. In some embodiments, the method comprises administering a loading dose of 8 mg of the compound daily for 8 days, followed by administering a maintenance dose of 40 mg of the compound once a week. In some embodiments, the method comprises administering a loading dose of 8 mg of the compound daily for 9 days, followed by administering a maintenance dose of 40 mg of the compound once a week. In some embodiments, the method comprises administering a loading dose of 8 mg of the compound daily for 10 days, followed by administering a maintenance dose of 40 mg of the compound once a week. In some embodiments, the method comprises administering a loading dose of 10 mg of the compound daily for 3 days, followed by administering a maintenance dose of 40 mg of the compound once a week. In some embodiments, the method comprises administering a loading dose of 10 mg of the compound daily for 4 days, followed by administering a maintenance dose of 40 mg of the compound once a week. In some embodiments, the method comprises administering a loading dose of 10 mg of the compound daily for 5 days, followed by administering a maintenance dose of 40 mg of the compound once a week. In some embodiments, the method comprises administering a loading dose of 10 mg of the compound daily for 6 days, followed by administering a maintenance dose of 40 mg of the compound once a week. In some embodiments, the method comprises administering a loading dose of 10 mg of the compound daily for 7 days, followed by administering a maintenance dose of 40 mg of the compound once a week. In some embodiments, the method comprises administering a loading dose of 10 mg of the compound daily for 8 days, followed by administering a maintenance dose of 40 mg of the compound once a week. In some embodiments, the method comprises administering a loading dose of 10 mg of the compound daily for 9 days, followed by administering a maintenance dose of 40 mg of the compound once a week. In some embodiments, the method comprises administering a loading dose of 10 mg of the compound daily for 40 days, followed by administering a maintenance dose of 10 mg of the compound once a week. In some embodiments, the method comprises administering a loading dose of 12 mg of the compound daily for 3 days, followed by administering a maintenance dose of 40 mg of the compound once a week.

In some embodiments, the method comprises administering a loading dose of 12 mg of the compound daily for 4 days, followed by administering a maintenance dose of 40 mg of the compound once a week. In some embodiments, the method comprises administering a loading dose of 12 mg of the compound daily for 5 days, followed by administering a maintenance dose of 40 mg of the compound once a week. In some embodiments, the method comprises administering a loading dose of 12 mg of the compound daily for 6 days, followed by administering a maintenance dose of 40 mg of the compound once a week. In some embodiments, the method comprises administering a loading dose of 12 mg of the compound daily for 7 days, followed by administering a maintenance dose of 40 mg of the compound once a week. In some embodiments, the method comprises administering a loading dose of 12 mg of the compound daily for 8 days, followed by administering a maintenance dose of 40 mg of the compound once a week. In some embodiments, the method comprises administering a loading dose of 12 mg of the compound daily for 9 days, followed by administering a maintenance dose of 40 mg of the compound once a week. In some embodiments, the method comprises administering a loading dose of 12 mg of the compound daily for 10 days, followed by administering a maintenance dose of 40 mg of the compound once a week. In some embodiments, the method comprises administering a loading dose of 15 mg of the compound daily for 3 days, followed by administering a maintenance dose of 40 mg of the compound once a week. In some embodiments, the method comprises administering a loading dose of 15 mg of the compound daily for 4 days, followed by administering a maintenance dose of 40 mg of the compound once a week. In some embodiments, the method comprises administering a loading dose of 15 mg of the compound daily for 5 days, followed by administering a maintenance dose of 40 mg of the compound once a week. In some embodiments, the method comprises administering a loading dose of 15 mg of the compound daily for 6 days, followed by administering a maintenance dose of 40 mg of the compound once a week. In some embodiments, the method comprises administering a loading dose of 15 mg of the compound daily for 7 days, followed by administering a maintenance dose of 40 mg of the compound once a week. In some embodiments, the method comprises administering a loading dose of 15 mg of the compound daily for 8 days, followed by administering a maintenance dose of 40 mg of the compound once a week. In some embodiments, the method comprises administering a loading dose of 15 mg of the compound daily for 9 days, followed by administering a maintenance dose of 40 mg of the compound once a week. In some embodiments, the method comprises administering a loading dose of 15 mg of the compound daily for 10 days, followed by administering a maintenance dose of 40 mg of the compound once a week. In some embodiments, the method comprises administering a loading dose of 5 mg of the compound daily for 3 days, followed by administering a maintenance dose of 40 mg of the compound twice a week. In some embodiments, the method comprises administering a loading dose of 5 mg of the compound daily for 4 days, followed by administering a maintenance dose of 40 mg of the compound twice a week. In some embodiments, the method comprises administering a loading dose of 5 mg of the compound daily for 5 days, followed by administering a maintenance dose of 40 mg of the compound twice a week. In some embodiments, the method comprises administering a loading dose of 5 mg of the compound daily for 6 days, followed by administering a maintenance dose of 40 mg of the compound twice a week. In some embodiments, the method comprises administering a loading dose of 5 mg of the compound daily for 7 days, followed by administering a maintenance dose of 40 mg of the compound twice a week. In some embodiments, the method comprises administering a loading dose of 5 mg of the compound daily for 8 days, followed by administering a maintenance dose of 40 mg of the compound twice a week. In some embodiments, the method comprises administering a loading dose of 5 mg of the compound daily for 9 days, followed by administering a maintenance dose of 40 mg of the compound twice a week. In some embodiments, the method comprises administering a loading dose of 5 mg of the compound daily for 10 days, followed by administering a maintenance dose of 40 mg of the compound twice a week. In some embodiments, the method comprises administering a loading dose of 7 mg of the compound daily for 3 days, followed by administering a maintenance dose of 40 mg of the compound twice a week. In some embodiments, the method comprises administering a loading dose of 7 mg of the compound daily for 4 days, followed by administering a maintenance dose of 40 mg of the compound twice a week. In some embodiments, the method comprises administering a loading dose of 7 mg of the compound daily for 5 days, followed by administering a maintenance dose of 40 mg of the compound twice a week. In some embodiments, the method comprises administering a loading dose of 7 mg of the compound daily for 6 days, followed by administering a maintenance dose of 40 mg of the compound twice a week. In some embodiments, the method comprises administering a loading dose of 7 mg of the compound daily for 7 days, followed by administering a maintenance dose of 40 mg of the compound twice a week. In some embodiments, the method comprises administering a loading dose of 7 mg of the compound daily for 8 days, followed by administering a maintenance dose of 40 mg of the compound twice a week. In some embodiments, the method comprises administering a loading dose of 7 mg of the compound daily for 9 days, followed by administering a maintenance dose of 40 mg of the compound twice a week. In some embodiments, the method comprises administering a loading dose of 7 mg of the compound daily for 10 days, followed by administering a maintenance dose of 40 mg of the compound twice a week. In some embodiments, the method comprises administering a loading dose of 8 mg of the compound daily for 3 days, followed by administering a maintenance dose of 40 mg of the compound twice a week. In some embodiments, the method comprises administering a loading dose of 8 mg of the compound daily for 4 days, followed by administering a maintenance dose of 40 mg of the compound twice a week. In some embodiments, the method comprises administering a loading dose of 8 mg of the compound daily for 5 days, followed by administering a maintenance dose of 40 mg of the compound twice a week. In some embodiments, the method comprises administering a loading dose of 8 mg of the compound daily for 6 days, followed by administering a maintenance dose of 40 mg of the compound twice a week. In some embodiments, the method comprises administering a loading dose of 8 mg of the compound daily for 7 days, followed by administering a maintenance dose of 40 mg of the compound twice a week. In some embodiments, the method comprises administering a loading dose of 8 mg of the compound daily for 8 days, followed by administering a maintenance dose of 40 mg of the compound twice a week. In some embodiments, the method comprises administering a loading dose of 8 mg of the compound daily for 9 days, followed by administering a maintenance dose of 40 mg of the compound twice a week. In some embodiments, the method comprises administering a loading dose of 8 mg of the compound daily for 10 days, followed by administering a maintenance dose of 40 mg of the compound twice a week. In some embodiments, the method comprises administering a loading dose of 10 mg of the compound daily for 3 days, followed by administering a maintenance dose of 40 mg of the compound twice a week. In some embodiments, the method comprises administering a loading dose of 10 mg of the compound daily for 4 days, followed by administering a maintenance dose of 40 mg of the compound twice a week. In some embodiments, the method comprises administering a loading dose of 10 mg of the compound daily for 5 days, followed by administering a maintenance dose of 40 mg of the compound twice a week. In some embodiments, the method comprises administering a loading dose of 10 mg of the compound daily for 6 days, followed by administering a maintenance dose of 40 mg of the compound twice a week. In some embodiments, the method comprises administering a loading dose of 10 mg of the compound daily for 7 days, followed by administering a maintenance dose of 40 mg of the compound twice a week. In some embodiments, the method comprises administering a loading dose of 10 mg of the compound daily for 8 days, followed by administering a maintenance dose of 40 mg of the compound twice a week. In some embodiments, the method comprises administering a loading dose of 10 mg of the compound daily for 9 days, followed by administering a maintenance dose of 40 mg of the compound twice a week. In some embodiments, the method comprises administering a loading dose of 10 mg of the compound daily for 10 days, followed by administering a maintenance dose of 40 mg of the compound twice a week. In some embodiments, the method comprises administering a loading dose of 12 mg of the compound daily for 3 days, followed by administering a maintenance dose of 40 mg of the compound twice a week. In some embodiments, the method comprises administering a loading dose of 12 mg of the compound daily for 4 days, followed by administering a maintenance dose of 40 mg of the compound twice a week. In some embodiments, the method comprises administering a loading dose of 12 mg of the compound daily for 5 days, followed by administering a maintenance dose of 40 mg of the compound twice a week. In some embodiments, the method comprises administering a loading dose of 12 mg of the compound daily for 6 days, followed by administering a maintenance dose of 40 mg of the compound twice a week. In some embodiments, the method comprises administering a loading dose of 12 mg of the compound daily for 7 days, followed by administering a maintenance dose of 40 mg of the compound twice a week. In some embodiments, the method comprises administering a loading dose of 12 mg of the compound daily for 8 days, followed by administering a maintenance dose of 40 mg of the compound twice a week. In some embodiments, the method comprises administering a loading dose of 12 mg of the compound daily for 9 days, followed by administering a maintenance dose of 40 mg of the compound twice a week. In some embodiments, the method comprises administering a loading dose of 12 mg of the compound daily for 10 days, followed by administering a maintenance dose of 40 mg of the compound twice a week. In some embodiments, the method comprises administering a loading dose of 15 mg of the compound daily for 3 days, followed by administering a maintenance dose of 40 mg of the compound twice a week. In some embodiments, the method comprises administering a loading dose of 15 mg of the compound daily for 4 days, followed by administering a maintenance dose of 40 mg of the compound twice a week. In some embodiments, the method comprises administering a loading dose of 15 mg of the compound daily for 5 days, followed by administering a maintenance dose of 40 mg of the compound twice a week. In some embodiments, the method comprises administering a loading dose of 15 mg of the compound daily for 6 days, followed by administering a maintenance dose of 40 mg of the compound twice a week. In some embodiments, the method comprises administering a loading dose of 15 mg of the compound daily for 7 days, followed by administering a maintenance dose of 40 mg of the compound twice a week. In some embodiments, the method comprises administering a loading dose of 15 mg of the compound daily for 8 days, followed by administering a maintenance dose of 40 mg of the compound twice a week. In some embodiments, the method comprises administering a loading dose of 15 mg of the compound daily for 9 days, followed by administering a maintenance dose of 40 mg of the compound twice a week. In some embodiments, the method comprises administering a loading dose of 15 mg of the compound daily for 10 days, followed by administering a maintenance dose of 40 mg of the compound twice a week. In some embodiments, the method comprises administering a loading dose of 5 mg of the compound daily for 3 days, followed by administering a maintenance dose of 40 mg of the compound three times a week. In some embodiments, the method comprises administering a loading dose of 5 mg of the compound daily for 4 days, followed by administering a maintenance dose of 40 mg of the compound three times a week. In some embodiments, the method comprises administering a loading dose of 5 mg of the compound daily for 5 days, followed by administering a maintenance dose of 40 mg of the compound three times a week. In some embodiments, the method comprises administering a loading dose of 5 mg of the compound daily for 6 days, followed by administering a maintenance dose of 40 mg of the compound three times a week. In some embodiments, the method comprises administering a loading dose of 5 mg of the compound daily for 7 days, followed by administering a maintenance dose of 40 mg of the compound three times a week. In some embodiments, the method comprises administering a loading dose of 5 mg of the compound daily for 8 days, followed by administering a maintenance dose of 40 mg of the compound three times a week. In some embodiments, the method comprises administering a loading dose of 5 mg of the compound daily for 9 days, followed by administering a maintenance dose of 40 mg of the compound three times a week. In some embodiments, the method comprises administering a loading dose of 5 mg of the compound daily for 10 days, followed by administering a maintenance dose of 40 mg of the compound three times a week. In some embodiments, the method comprises administering a loading dose of 7 mg of the compound daily for 3 days, followed by administering a maintenance dose of 40 mg of the compound three times a week. In some embodiments, the method comprises administering a loading dose of 7 mg of the compound daily for 4 days, followed by administering a maintenance dose of 40 mg of the compound three times a week. In some embodiments, the method comprises administering a loading dose of 7 mg of the compound daily for 5 days, followed by administering a maintenance dose of 40 mg of the compound three times a week. In some embodiments, the method comprises administering a loading dose of 7 mg of the compound daily for 6 days, followed by administering a maintenance dose of 40 mg of the compound three times a week. In some embodiments, the method comprises administering a loading dose of 7 mg of the compound daily for 7 days, followed by administering a maintenance dose of 40 mg of the compound three times a week. In some embodiments, the method comprises administering a loading dose of 7 mg of the compound daily for 8 days, followed by administering a maintenance dose of 40 mg of the compound three times a week. In some embodiments, the method comprises administering a loading dose of 7 mg of the compound daily for 9 days, followed by administering a maintenance dose of 40 mg of the compound three times a week. In some embodiments, the method comprises administering a loading dose of 7 mg of the compound daily for 10 days, followed by administering a maintenance dose of 40 mg of the compound three times a week. In some embodiments, the method comprises administering a loading dose of 8 mg of the compound daily for 3 days, followed by administering a maintenance dose of 40 mg of the compound three times a week. In some embodiments, the method comprises administering a loading dose of 8 mg of the compound daily for 4 days, followed by administering a maintenance dose of 40 mg of the compound three times a week. In some embodiments, the method comprises administering a loading dose of 8 mg of the compound daily for 5 days, followed by administering a maintenance dose of 40 mg of the compound three times a week. In some embodiments, the method comprises administering a loading dose of 8 mg of the compound daily for 6 days, followed by administering a maintenance dose of 40 mg of the compound three times a week. In some embodiments, the method comprises administering a loading dose of 8 mg of the compound daily for 7 days, followed by administering a maintenance dose of 40 mg of the compound three times a week. In some embodiments, the method comprises administering a loading dose of 8 mg of the compound daily for 8 days, followed by administering a maintenance dose of 40 mg of the compound three times a week. In some embodiments, the method comprises administering a loading dose of 8 mg of the compound daily for 9 days, followed by administering a maintenance dose of 40 mg of the compound three times a week. In some embodiments, the method comprises administering a loading dose of 8 mg of the compound daily for 10 days, followed by administering a maintenance dose of 40 mg of the compound three times a week. In some embodiments, the method comprises administering a loading dose of 10 mg of the compound daily for 3 days, followed by administering a maintenance dose of 40 mg of the compound three times a week. In some embodiments, the method comprises administering a loading dose of 10 mg of the compound daily for 4 days, followed by administering a maintenance dose of 40 mg of the compound three times a week. In some embodiments, the method comprises administering a loading dose of 10 mg of the compound daily for 5 days, followed by administering a maintenance dose of 40 mg of the compound three times a week. In some embodiments, the method comprises administering a loading dose of 10 mg of the compound daily for 6 days, followed by administering a maintenance dose of 40 mg of the compound three times a week. In some embodiments, the method comprises administering a loading dose of 10 mg of the compound daily for 7 days, followed by administering a maintenance dose of 40 mg of the compound three times a week. In some embodiments, the method comprises administering a loading dose of 10 mg of the compound daily for 8 days, followed by administering a maintenance dose of 40 mg of the compound three times a week. In some embodiments, the method comprises administering a loading dose of 10 mg of the compound daily for 9 days, followed by administering a maintenance dose of 40 mg of the compound three times a week. In some embodiments, the method comprises administering a loading dose of 10 mg of the compound daily for 10 days, followed by administering a maintenance dose of 40 mg of the compound three times a week. In some embodiments, the method comprises administering a loading dose of 12 mg of the compound daily for 3 days, followed by administering a maintenance dose of 40 mg of the compound three times a week. In some embodiments, the method comprises administering a loading dose of 12 mg of the compound daily for 4 days, followed by administering a maintenance dose of 40 mg of the compound three times a week. In some embodiments, the method comprises administering a loading dose of 12 mg of the compound daily for 5 days, followed by administering a maintenance dose of 40 mg of the compound three times a week. In some embodiments, the method comprises administering a loading dose of 12 mg of the compound daily for 6 days, followed by administering a maintenance dose of 40 mg of the compound three times a week. In some embodiments, the method comprises administering a loading dose of 12 mg of the compound daily for 7 days, followed by administering a maintenance dose of 40 mg of the compound three times a week. In some embodiments, the method comprises administering a loading dose of 12 mg of the compound daily for 8 days, followed by administering a maintenance dose of 40 mg of the compound three times a week. In some embodiments, the method comprises administering a loading dose of 12 mg of the compound daily for 9 days, followed by administering a maintenance dose of 40 mg of the compound three times a week. In some embodiments, the method comprises administering a loading dose of 12 mg of the compound daily for 10 days, followed by administering a maintenance dose of 40 mg of the compound three times a week. In some embodiments, the method comprises administering a loading dose of 15 mg of the compound daily for 3 days, followed by administering a maintenance dose of 40 mg of the compound three times a week. In some embodiments, the method comprises administering a loading dose of 15 mg of the compound daily for 4 days, followed by administering a maintenance dose of 40 mg of the compound three times a week. In some embodiments, the method comprises administering a loading dose of 15 mg of the compound daily for 5 days, followed by administering a maintenance dose of 40 mg of the compound three times a week. In some embodiments, the method comprises administering a loading dose of 15 mg of the compound daily for 6 days, followed by administering a maintenance dose of 40 mg of the compound three times a week. In some embodiments, the method comprises administering a loading dose of 15 mg of the compound daily for 7 days, followed by administering a maintenance dose of 40 mg of the compound three times a week. In some embodiments, the method comprises administering a loading dose of 15 mg of the compound daily for 8 days, followed by administering a maintenance dose of 40 mg of the compound three times a week. In some embodiments, the method comprises administering a loading dose of 15 mg of the compound daily for 9 days, followed by administering a maintenance dose of 40 mg of the compound three times a week. In some embodiments, the method comprises administering a loading dose of 15 mg of the compound daily for 10 days, followed by administering a maintenance dose of 40 mg of the compound three times a week.

In some embodiments, the loading dose is administered from 1 day to 20 days, and the maintenance dose is administered from 20 days to 37000 days. In some embodiments, the method comprises administering a loading dose of 5 mg of the compound daily for 3 days, followed by administering a maintenance dose of 50 mg of the compound daily. In some embodiments, the method comprises administering a loading dose of 5 mg of the compound daily for 4 days, followed by administering a maintenance dose of 50 mg of the compound daily. In some embodiments, the method comprises administering a loading dose of 5 mg of the compound daily for 5 days, followed by administering a maintenance dose of 50 mg of the compound daily. In some embodiments, the method comprises administering a loading dose of 5 mg of the compound daily for 6 days, followed by administering a maintenance dose of 50 mg of the compound daily. In some embodiments, the method comprises administering a loading dose of 5 mg of the compound daily for 7 days, followed by administering a maintenance dose of 50 mg of the compound daily. In some embodiments, the method comprises administering a loading dose of 5 mg of the compound daily for 8 days, followed by administering a maintenance dose of 50 mg of the compound daily. In some embodiments, the method comprises administering a loading dose of 5 mg of the compound daily for 9 days, followed by administering a maintenance dose of 50 mg of the compound daily. In some embodiments, the method comprises administering a loading dose of 5 mg of the compound daily for 10 days, followed by administering a maintenance dose of 50 mg of the compound daily. In some embodiments, the method comprises administering a loading dose of 7 mg of the compound daily for 3 days, followed by administering a maintenance dose of 50 mg of the compound daily. In some embodiments, the method comprises administering a loading dose of 7 mg of the compound daily for 4 days, followed by administering a maintenance dose of 50 mg of the compound daily. In some embodiments, the method comprises administering a loading dose of 7 mg of the compound daily for 5 days, followed by administering a maintenance dose of 50 mg of the compound daily. In some embodiments, the method comprises administering a loading dose of 7 mg of the compound daily for 6 days, followed by administering a maintenance dose of 50 mg of the compound daily. In some embodiments, the method comprises administering a loading dose of 7 mg of the compound daily for 7 days, followed by administering a maintenance dose of 50 mg of the compound daily. In some embodiments, the method comprises administering a loading dose of 7 mg of the compound daily for 8 days, followed by administering a maintenance dose of 50 mg of the compound daily. In some embodiments, the method comprises administering a loading dose of 7 mg of the compound daily for 9 days, followed by administering a maintenance dose of 50 mg of the compound daily. In some embodiments, the method comprises administering a loading dose of 7 mg of the compound daily for 40 days, followed by administering a maintenance dose of 50 mg of the compound daily. In some embodiments, the method comprises administering a loading dose of 8 mg of the compound daily for 3 days, followed by administering a maintenance dose of 50 mg of the compound daily. In some embodiments, the method comprises administering a loading dose of 8 mg of the compound daily for 4 days, followed by administering a maintenance dose of 50 mg of the compound daily. In some embodiments, the method comprises administering a loading dose of 8 mg of the compound daily for 5 days, followed by administering a maintenance dose of 50 mg of the compound daily. In some embodiments, the method comprises administering a loading dose of 8 mg of the compound daily for 6 days, followed by administering a maintenance dose of 50 mg of the compound daily. In some embodiments, the method comprises administering a loading dose of 8 mg of the compound daily for 7 days, followed by administering a maintenance dose of 50 mg of the compound daily. In some embodiments, the method comprises administering a loading dose of 8 mg of the compound daily for 8 days, followed by administering a maintenance dose of 50 mg of the compound daily. In some embodiments, the method comprises administering a loading dose of 8 mg of the compound daily for 9 days, followed by administering a maintenance dose of 50 mg of the compound daily. In some embodiments, the method comprises administering a loading dose of 8 mg of the compound daily for 10 days, followed by administering a maintenance dose of 50 mg of the compound daily. In some embodiments, the method comprises administering a loading dose of 10 mg of the compound daily for 3 days, followed by administering a maintenance dose of 50 mg of the compound daily. In some embodiments, the method comprises administering a loading dose of 10 mg of the compound daily for 4 days, followed by administering a maintenance dose of 50 mg of the compound daily. In some embodiments, the method comprises administering a loading dose of 10 mg of the compound daily for 5 days, followed by administering a maintenance dose of 50 mg of the compound daily. In some embodiments, the method comprises administering a loading dose of 10 mg of the compound daily for 6 days, followed by administering a maintenance dose of 50 mg of the compound daily. In some embodiments, the method comprises administering a loading dose of 10 mg of the compound daily for 7 days, followed by administering a maintenance dose of 50 mg of the compound daily. In some embodiments, the method comprises administering a loading dose of 10 mg of the compound daily for 8 days, followed by administering a maintenance dose of 50 mg of the compound daily. In some embodiments, the method comprises administering a loading dose of 10 mg of the compound daily for 9 days, followed by administering a maintenance dose of 50 mg of the compound daily. In some embodiments, the method comprises administering a loading dose of 10 mg of the compound daily for 10 days, followed by administering a maintenance dose of 50 mg of the compound daily. In some embodiments, the method comprises administering a loading dose of 12 mg of the compound daily for 3 days, followed by administering a maintenance dose of 50 mg of the compound daily. In some embodiments, the method comprises administering a loading dose of 12 mg of the compound daily for 4 days, followed by administering a maintenance dose of 50 mg of the compound daily. In some embodiments, the method comprises administering a loading dose of 12 mg of the compound daily for 5 days, followed by administering a maintenance dose of 50 mg of the compound daily. In some embodiments, the method comprises administering a loading dose of 12 mg of the compound daily for 6 days, followed by administering a maintenance dose of 50 mg of the compound daily. In some embodiments, the method comprises administering a loading dose of 12 mg of the compound daily for 7 days, followed by administering a maintenance dose of 50 mg of the compound daily. In some embodiments, the method comprises administering a loading dose of 12 mg of the compound daily for 8 days, followed by administering a maintenance dose of 50 mg of the compound daily. In some embodiments, the method comprises administering a loading dose of 12 mg of the compound daily for 9 days, followed by administering a maintenance dose of 50 mg of the compound daily. In some embodiments, the method comprises administering a loading dose of 12 mg of the compound daily for 40 days, followed by administering a maintenance dose of 50 mg of the compound daily. In some embodiments, the method comprises administering a loading dose of 15 mg of the compound daily for 3 days, followed by administering a maintenance dose of 50 mg of the compound daily. In some embodiments, the method comprises administering a loading dose of 15 mg of the compound daily for 4 days, followed by administering a maintenance dose of 50 mg of the compound daily. In some embodiments, the method comprises administering a loading dose of 15 mg of the compound daily for 5 days, followed by administering a maintenance dose of 50 mg of the compound daily. In some embodiments, the method comprises administering a loading dose of 15 mg of the compound daily for 6 days, followed by administering a maintenance dose of 50 mg of the compound daily. In some embodiments, the method comprises administering a loading dose of 15 mg of the compound daily for 7 days, followed by administering a maintenance dose of 50 mg of the compound daily. In some embodiments, the method comprises administering a loading dose of 15 mg of the compound daily for 8 days, followed by administering a maintenance dose of 50 mg of the compound daily. In some embodiments, the method comprises administering a loading dose of 15 mg of the compound daily for 9 days, followed by administering a maintenance dose of 50 mg of the compound daily. In some embodiments, the method comprises administering a loading dose of 15 mg of the compound daily for 10 days, followed by administering a maintenance dose of 50 mg of the compound daily. In some embodiments, the method comprises administering a loading dose of 5 mg of the compound daily for 3 days, followed by administering a maintenance dose of 50 mg of the compound every other day. In some embodiments, the method comprises administering a loading dose of 5 mg of the compound daily for 4 days, followed by administering a maintenance dose of 50 mg of the compound every other day. In some embodiments, the method comprises administering a loading dose of 5 mg of the compound daily for 5 days, followed by administering a maintenance dose of 50 mg of the compound every other day. In some embodiments, the method comprises administering a loading dose of 5 mg of the compound daily for 6 days, followed by administering a maintenance dose of 50 mg of the compound every other day. In some embodiments, the method comprises administering a loading dose of 5 mg of the compound daily for 7 days, followed by administering a maintenance dose of 50 mg of the compound every other day. In some embodiments, the method comprises administering a loading dose of 5 mg of the compound daily for 8 days, followed by administering a maintenance dose of 50 mg of the compound every other day. In some embodiments, the method comprises administering a loading dose of 5 mg of the compound daily for 9 days, followed by administering a maintenance dose of 50 mg of the compound every other day. In some embodiments, the method comprises administering a loading dose of 5 mg of the compound daily for 10 days, followed by administering a maintenance dose of 50 mg of the compound every other day. In some embodiments, the method comprises administering a loading dose of 7 mg of the compound daily for 3 days, followed by administering a maintenance dose of 50 mg of the compound every other day. In some embodiments, the method comprises administering a loading dose of 7 mg of the compound daily for 4 days, followed by administering a maintenance dose of 50 mg of the compound every other day. In some embodiments, the method comprises administering a loading dose of 7 mg of the compound daily for 5 days, followed by administering a maintenance dose of 50 mg of the compound every other day. In some embodiments, the method comprises administering a loading dose of 7 mg of the compound daily for 6 days, followed by administering a maintenance dose of 50 mg of the compound every other day. In some embodiments, the method comprises administering a loading dose of 7 mg of the compound daily for 7 days, followed by administering a maintenance dose of 50 mg of the compound every other day. In some embodiments, the method comprises administering a loading dose of 7 mg of the compound daily for 8 days, followed by administering a maintenance dose of 50 mg of the compound every other day. In some embodiments, the method comprises administering a loading dose of 7 mg of the compound daily for 9 days, followed by administering a maintenance dose of 50 mg of the compound every other day. In some embodiments, the method comprises administering a loading dose of 7 mg of the compound daily for 10 days, followed by administering a maintenance dose of 50 mg of the compound every other day. In some embodiments, the method comprises administering a loading dose of 8 mg of the compound daily for 3 days, followed by administering a maintenance dose of 50 mg of the compound every other day. In some embodiments, the method comprises administering a loading dose of 8 mg of the compound daily for 4 days, followed by administering a maintenance dose of 50 mg of the compound every other day. In some embodiments, the method comprises administering a loading dose of 8 mg of the compound daily for 5 days, followed by administering a maintenance dose of 50 mg of the compound every other day. In some embodiments, the method comprises administering a loading dose of 8 mg of the compound daily for 6 days, followed by administering a maintenance dose of 50 mg of the compound every other day. In some embodiments, the method comprises administering a loading dose of 8 mg of the compound daily for 7 days, followed by administering a maintenance dose of 50 mg of the compound every other day. In some embodiments, the method comprises administering a loading dose of 8 mg of the compound daily for 8 days, followed by administering a maintenance dose of 50 mg of the compound every other day. In some embodiments, the method comprises administering a loading dose of 8 mg of the compound daily for 9 days, followed by administering a maintenance dose of 50 mg of the compound every other day. In some embodiments, the method comprises administering a loading dose of 8 mg of the compound daily for 10 days, followed by administering a maintenance dose of 50 mg of the compound every other day. In some embodiments, the method comprises administering a loading dose of 10 mg of the compound daily for 3 days, followed by administering a maintenance dose of 50 mg of the compound every other day. In some embodiments, the method comprises administering a loading dose of 10 mg of the compound daily for 4 days, followed by administering a maintenance dose of 50 mg of the compound every other day. In some embodiments, the method comprises administering a loading dose of 10 mg of the compound daily for 5 days, followed by administering a maintenance dose of 50 mg of the compound every other day. In some embodiments, the method comprises administering a loading dose of 10 mg of the compound daily for 6 days, followed by administering a maintenance dose of 50 mg of the compound every other day. In some embodiments, the method comprises administering a loading dose of 10 mg of the compound daily for 7 days, followed by administering a maintenance dose of 50 mg of the compound every other day. In some embodiments, the method comprises administering a loading dose of 10 mg of the compound daily for 8 days, followed by administering a maintenance dose of 50 mg of the compound every other day. In some embodiments, the method comprises administering a loading dose of 10 mg of the compound daily for 9 days, followed by administering a maintenance dose of 50 mg of the compound every other day. In some embodiments, the method comprises administering a loading dose of 10 mg of the compound daily for 10 days, followed by administering a maintenance dose of 50 mg of the compound every other day. In some embodiments, the method comprises administering a loading dose of 12 mg of the compound daily for 3 days, followed by administering a maintenance dose of 50 mg of the compound every other day. In some embodiments, the method comprises administering a loading dose of 12 mg of the compound daily for 4 days, followed by administering a maintenance dose of 50 mg of the compound every other day. In some embodiments, the method comprises administering a loading dose of 12 mg of the compound daily for 5 days, followed by administering a maintenance dose of 50 mg of the compound every other day. In some embodiments, the method comprises administering a loading dose of 12 mg of the compound daily for 6 days, followed by administering a maintenance dose of 50 mg of the compound every other day. In some embodiments, the method comprises administering a loading dose of 12 mg of the compound daily for 7 days, followed by administering a maintenance dose of 50 mg of the compound every other day. In some embodiments, the method comprises administering a loading dose of 12 mg of the compound daily for 8 days, followed by administering a maintenance dose of 50 mg of the compound every other day. In some embodiments, the method comprises administering a loading dose of 12 mg of the compound daily for 9 days, followed by administering a maintenance dose of 50 mg of the compound every other day. In some embodiments, the method comprises administering a loading dose of 12 mg of the compound daily for 10 days, followed by administering a maintenance dose of 50 mg of the compound every other day. In some embodiments, the method comprises administering a loading dose of 15 mg of the compound daily for 3 days, followed by administering a maintenance dose of 50 mg of the compound every other day. In some embodiments, the method comprises administering a loading dose of 15 mg of the compound daily for 4 days, followed by administering a maintenance dose of 50 mg of the compound every other day. In some embodiments, the method comprises administering a loading dose of 15 mg of the compound daily for 5 days, followed by administering a maintenance dose of 50 mg of the compound every other day. In some embodiments, the method comprises administering a loading dose of 15 mg of the compound daily for 6 days, followed by administering a maintenance dose of 50 mg of the compound every other day. In some embodiments, the method comprises administering a loading dose of 15 mg of the compound daily for 7 days, followed by administering a maintenance dose of 50 mg of the compound every other day. In some embodiments, the method comprises administering a loading dose of 15 mg of the compound daily for 8 days, followed by administering a maintenance dose of 50 mg of the compound every other day. In some embodiments, the method comprises administering a loading dose of 15 mg of the compound daily for 9 days, followed by administering a maintenance dose of 50 mg of the compound every other day. In some embodiments, the method comprises administering a loading dose of 15 mg of the compound daily for 10 days, followed by administering a maintenance dose of 50 mg of the compound every other day. In some embodiments, the method comprises administering a loading dose of 5 mg of the compound daily for 3 days, followed by administering a maintenance dose of 50 mg of the compound once a week. In some embodiments, the method comprises administering a loading dose of 5 mg of the compound daily for 4 days, followed by administering a maintenance dose of 50 mg of the compound once a week. In some embodiments, the method comprises administering a loading dose of 5 mg of the compound daily for 5 days, followed by administering a maintenance dose of 50 mg of the compound once a week. In some embodiments, the method comprises administering a loading dose of 5 mg of the compound daily for 6 days, followed by administering a maintenance dose of 50 mg of the compound once a week. In some embodiments, the method comprises administering a loading dose of 5 mg of the compound daily for 7 days, followed by administering a maintenance dose of 50 mg of the compound once a week. In some embodiments, the method comprises administering a loading dose of 5 mg of the compound daily for 8 days, followed by administering a maintenance dose of 50 mg of the compound once a week. In some embodiments, the method comprises administering a loading dose of 5 mg of the compound daily for 9 days, followed by administering a maintenance dose of 50 mg of the compound once a week. In some embodiments, the method comprises administering a loading dose of 5 mg of the compound daily for 10 days, followed by administering a maintenance dose of 50 mg of the compound once a week. In some embodiments, the method comprises administering a loading dose of 7 mg of the compound daily for 3 days, followed by administering a maintenance dose of 50 mg of the compound once a week. In some embodiments, the method comprises administering a loading dose of 7 mg of the compound daily for 4 days, followed by administering a maintenance dose of 50 mg of the compound once a week. In some embodiments, the method comprises administering a loading dose of 7 mg of the compound daily for 5 days, followed by administering a maintenance dose of 50 mg of the compound once a week. In some embodiments, the method comprises administering a loading dose of 7 mg of the compound daily for 6 days, followed by administering a maintenance dose of 50 mg of the compound once a week. In some embodiments, the method comprises administering a loading dose of 7 mg of the compound daily for 7 days, followed by administering a maintenance dose of 50 mg of the compound once a week. In some embodiments, the method comprises administering a loading dose of 7 mg of the compound daily for 8 days, followed by administering a maintenance dose of 50 mg of the compound once a week. In some embodiments, the method comprises administering a loading dose of 7 mg of the compound daily for 9 days, followed by administering a maintenance dose of 50 mg of the compound once a week. In some embodiments, the method comprises administering a loading dose of 7 mg of the compound daily for 10 days, followed by administering a maintenance dose of 50 mg of the compound once a week. In some embodiments, the method comprises administering a loading dose of 8 mg of the compound daily for 3 days, followed by administering a maintenance dose of 50 mg of the compound once a week. In some embodiments, the method comprises administering a loading dose of 8 mg of the compound daily for 4 days, followed by administering a maintenance dose of 50 mg of the compound once a week. In some embodiments, the method comprises administering a loading dose of 8 mg of the compound daily for 5 days, followed by administering a maintenance dose of 50 mg of the compound once a week. In some embodiments, the method comprises administering a loading dose of 8 mg of the compound daily for 6 days, followed by administering a maintenance dose of 50 mg of the compound once a week. In some embodiments, the method comprises administering a loading dose of 8 mg of the compound daily for 7 days, followed by administering a maintenance dose of 50 mg of the compound once a week. In some embodiments, the method comprises administering a loading dose of 8 mg of the compound daily for 8 days, followed by administering a maintenance dose of 50 mg of the compound once a week. In some embodiments, the method comprises administering a loading dose of 8 mg of the compound daily for 9 days, followed by administering a maintenance dose of 50 mg of the compound once a week. In some embodiments, the method comprises administering a loading dose of 8 mg of the compound daily for 10 days, followed by administering a maintenance dose of 50 mg of the compound once a week. In some embodiments, the method comprises administering a loading dose of 10 mg of the compound daily for 3 days, followed by administering a maintenance dose of 50 mg of the compound once a week. In some embodiments, the method comprises administering a loading dose of 10 mg of the compound daily for 4 days, followed by administering a maintenance dose of 50 mg of the compound once a week. In some embodiments, the method comprises administering a loading dose of 10 mg of the compound daily for 5 days, followed by administering a maintenance dose of 50 mg of the compound once a week. In some embodiments, the method comprises administering a loading dose of 10 mg of the compound daily for 6 days, followed by administering a maintenance dose of 50 mg of the compound once a week. In some embodiments, the method comprises administering a loading dose of 10 mg of the compound daily for 7 days, followed by administering a maintenance dose of 50 mg of the compound once a week. In some embodiments, the method comprises administering a loading dose of 10 mg of the compound daily for 8 days, followed by administering a maintenance dose of 50 mg of the compound once a week. In some embodiments, the method comprises administering a loading dose of 10 mg of the compound daily for 9 days, followed by administering a maintenance dose of 50 mg of the compound once a week. In some embodiments, the method comprises administering a loading dose of 10 mg of the compound daily for 40 days, followed by administering a maintenance dose of 10 mg of the compound once a week. In some embodiments, the method comprises administering a loading dose of 12 mg of the compound daily for 3 days, followed by administering a maintenance dose of 50 mg of the compound once a week. In some embodiments, the method comprises administering a loading dose of 12 mg of the compound daily for 4 days, followed by administering a maintenance dose of 50 mg of the compound once a week. In some embodiments, the method comprises administering a loading dose of 12 mg of the compound daily for 5 days, followed by administering a maintenance dose of 50 mg of the compound once a week. In some embodiments, the method comprises administering a loading dose of 12 mg of the compound daily for 6 days, followed by administering a maintenance dose of 50 mg of the compound once a week. In some embodiments, the method comprises administering a loading dose of 12 mg of the compound daily for 7 days, followed by administering a maintenance dose of 50 mg of the compound once a week. In some embodiments, the method comprises administering a loading dose of 12 mg of the compound daily for 8 days, followed by administering a maintenance dose of 50 mg of the compound once a week. In some embodiments, the method comprises administering a loading dose of 12 mg of the compound daily for 9 days, followed by administering a maintenance dose of 50 mg of the compound once a week. In some embodiments, the method comprises administering a loading dose of 12 mg of the compound daily for 10 days, followed by administering a maintenance dose of 50 mg of the compound once a week. In some embodiments, the method comprises administering a loading dose of 15 mg of the compound daily for 3 days, followed by administering a maintenance dose of 50 mg of the compound once a week. In some embodiments, the method comprises administering a loading dose of 15 mg of the compound daily for 4 days, followed by administering a maintenance dose of 50 mg of the compound once a week. In some embodiments, the method comprises administering a loading dose of 15 mg of the compound daily for 5 days, followed by administering a maintenance dose of 50 mg of the compound once a week. In some embodiments, the method comprises administering a loading dose of 15 mg of the compound daily for 6 days, followed by administering a maintenance dose of 50 mg of the compound once a week. In some embodiments, the method comprises administering a loading dose of 15 mg of the compound daily for 7 days, followed by administering a maintenance dose of 50 mg of the compound once a week. In some embodiments, the method comprises administering a loading dose of 15 mg of the compound daily for 8 days, followed by administering a maintenance dose of 50 mg of the compound once a week. In some embodiments, the method comprises administering a loading dose of 15 mg of the compound daily for 9 days, followed by administering a maintenance dose of 50 mg of the compound once a week. In some embodiments, the method comprises administering a loading dose of 15 mg of the compound daily for 10 days, followed by administering a maintenance dose of 50 mg of the compound once a week. In some embodiments, the method comprises administering a loading dose of 5 mg of the compound daily for 3 days, followed by administering a maintenance dose of 50 mg of the compound twice a week. In some embodiments, the method comprises administering a loading dose of 5 mg of the compound daily for 4 days, followed by administering a maintenance dose of 50 mg of the compound twice a week. In some embodiments, the method comprises administering a loading dose of 5 mg of the compound daily for 5 days, followed by administering a maintenance dose of 50 mg of the compound twice a week. In some embodiments, the method comprises administering a loading dose of 5 mg of the compound daily for 6 days, followed by administering a maintenance dose of 50 mg of the compound twice a week. In some embodiments, the method comprises administering a loading dose of 5 mg of the compound daily for 7 days, followed by administering a maintenance dose of 50 mg of the compound twice a week. In some embodiments, the method comprises administering a loading dose of 5 mg of the compound daily for 8 days, followed by administering a maintenance dose of 50 mg of the compound twice a week. In some embodiments, the method comprises administering a loading dose of 5 mg of the compound daily for 9 days, followed by administering a maintenance dose of 50 mg of the compound twice a week. In some embodiments, the method comprises administering a loading dose of 5 mg of the compound daily for 10 days, followed by administering a maintenance dose of 50 mg of the compound twice a week. In some embodiments, the method comprises administering a loading dose of 7 mg of the compound daily for 3 days, followed by administering a maintenance dose of 50 mg of the compound twice a week. In some embodiments, the method comprises administering a loading dose of 7 mg of the compound daily for 4 days, followed by administering a maintenance dose of 50 mg of the compound twice a week. In some embodiments, the method comprises administering a loading dose of 7 mg of the compound daily for 5 days, followed by administering a maintenance dose of 50 mg of the compound twice a week. In some embodiments, the method comprises administering a loading dose of 7 mg of the compound daily for 6 days, followed by administering a maintenance dose of 50 mg of the compound twice a week. In some embodiments, the method comprises administering a loading dose of 7 mg of the compound daily for 7 days, followed by administering a maintenance dose of 50 mg of the compound twice a week. In some embodiments, the method comprises administering a loading dose of 7 mg of the compound daily for 8 days, followed by administering a maintenance dose of 50 mg of the compound twice a week. In some embodiments, the method comprises administering a loading dose of 7 mg of the compound daily for 9 days, followed by administering a maintenance dose of 50 mg of the compound twice a week. In some embodiments, the method comprises administering a loading dose of 7 mg of the compound daily for 10 days, followed by administering a maintenance dose of 50 mg of the compound twice a week. In some embodiments, the method comprises administering a loading dose of 8 mg of the compound daily for 3 days, followed by administering a maintenance dose of 50 mg of the compound twice a week. In some embodiments, the method comprises administering a loading dose of 8 mg of the compound daily for 4 days, followed by administering a maintenance dose of 50 mg of the compound twice a week. In some embodiments, the method comprises administering a loading dose of 8 mg of the compound daily for 5 days, followed by administering a maintenance dose of 50 mg of the compound twice a week. In some embodiments, the method comprises administering a loading dose of 8 mg of the compound daily for 6 days, followed by administering a maintenance dose of 50 mg of the compound twice a week. In some embodiments, the method comprises administering a loading dose of 8 mg of the compound daily for 7 days, followed by administering a maintenance dose of 50 mg of the compound twice a week. In some embodiments, the method comprises administering a loading dose of 8 mg of the compound daily for 8 days, followed by administering a maintenance dose of 50 mg of the compound twice a week. In some embodiments, the method comprises administering a loading dose of 8 mg of the compound daily for 9 days, followed by administering a maintenance dose of 50 mg of the compound twice a week. In some embodiments, the method comprises administering a loading dose of 8 mg of the compound daily for 10 days, followed by administering a maintenance dose of 50 mg of the compound twice a week. In some embodiments, the method comprises administering a loading dose of 10 mg of the compound daily for 3 days, followed by administering a maintenance dose of 50 mg of the compound twice a week. In some embodiments, the method comprises administering a loading dose of 10 mg of the compound daily for 4 days, followed by administering a maintenance dose of 50 mg of the compound twice a week. In some embodiments, the method comprises administering a loading dose of 10 mg of the compound daily for 5 days, followed by administering a maintenance dose of 50 mg of the compound twice a week. In some embodiments, the method comprises administering a loading dose of 10 mg of the compound daily for 6 days, followed by administering a maintenance dose of 50 mg of the compound twice a week. In some embodiments, the method comprises administering a loading dose of 10 mg of the compound daily for 7 days, followed by administering a maintenance dose of 50 mg of the compound twice a week. In some embodiments, the method comprises administering a loading dose of 10 mg of the compound daily for 8 days, followed by administering a maintenance dose of 50 mg of the compound twice a week. In some embodiments, the method comprises administering a loading dose of 10 mg of the compound daily for 9 days, followed by administering a maintenance dose of 50 mg of the compound twice a week. In some embodiments, the method comprises administering a loading dose of 10 mg of the compound daily for 10 days, followed by administering a maintenance dose of 50 mg of the compound twice a week. In some embodiments, the method comprises administering a loading dose of 12 mg of the compound daily for 3 days, followed by administering a maintenance dose of 50 mg of the compound twice a week. In some embodiments, the method comprises administering a loading dose of 12 mg of the compound daily for 4 days, followed by administering a maintenance dose of 50 mg of the compound twice a week. In some embodiments, the method comprises administering a loading dose of 12 mg of the compound daily for 5 days, followed by administering a maintenance dose of 50 mg of the compound twice a week. In some embodiments, the method comprises administering a loading dose of 12 mg of the compound daily for 6 days, followed by administering a maintenance dose of 50 mg of the compound twice a week. In some embodiments, the method comprises administering a loading dose of 12 mg of the compound daily for 7 days, followed by administering a maintenance dose of 50 mg of the compound twice a week. In some embodiments, the method comprises administering a loading dose of 12 mg of the compound daily for 8 days, followed by administering a maintenance dose of 50 mg of the compound twice a week. In some embodiments, the method comprises administering a loading dose of 12 mg of the compound daily for 9 days, followed by administering a maintenance dose of 50 mg of the compound twice a week. In some embodiments, the method comprises administering a loading dose of 12 mg of the compound daily for 10 days, followed by administering a maintenance dose of 50 mg of the compound twice a week. In some embodiments, the method comprises administering a loading dose of 15 mg of the compound daily for 3 days, followed by administering a maintenance dose of 50 mg of the compound twice a week. In some embodiments, the method comprises administering a loading dose of 15 mg of the compound daily for 4 days, followed by administering a maintenance dose of 50 mg of the compound twice a week. In some embodiments, the method comprises administering a loading dose of 15 mg of the compound daily for 5 days, followed by administering a maintenance dose of 50 mg of the compound twice a week. In some embodiments, the method comprises administering a loading dose of 15 mg of the compound daily for 6 days, followed by administering a maintenance dose of 50 mg of the compound twice a week. In some embodiments, the method comprises administering a loading dose of 15 mg of the compound daily for 7 days, followed by administering a maintenance dose of 50 mg of the compound twice a week. In some embodiments, the method comprises administering a loading dose of 15 mg of the compound daily for 8 days, followed by administering a maintenance dose of 50 mg of the compound twice a week. In some embodiments, the method comprises administering a loading dose of 15 mg of the compound daily for 9 days, followed by administering a maintenance dose of 50 mg of the compound twice a week. In some embodiments, the method comprises administering a loading dose of 15 mg of the compound daily for 10 days, followed by administering a maintenance dose of 50 mg of the compound twice a week. In some embodiments, the method comprises administering a loading dose of 5 mg of the compound daily for 3 days, followed by administering a maintenance dose of 50 mg of the compound three times a week. In some embodiments, the method comprises administering a loading dose of 5 mg of the compound daily for 4 days, followed by administering a maintenance dose of 50 mg of the compound three times a week. In some embodiments, the method comprises administering a loading dose of 5 mg of the compound daily for 5 days, followed by administering a maintenance dose of 50 mg of the compound three times a week. In some embodiments, the method comprises administering a loading dose of 5 mg of the compound daily for 6 days, followed by administering a maintenance dose of 50 mg of the compound three times a week. In some embodiments, the method comprises administering a loading dose of 5 mg of the compound daily for 7 days, followed by administering a maintenance dose of 50 mg of the compound three times a week. In some embodiments, the method comprises administering a loading dose of 5 mg of the compound daily for 8 days, followed by administering a maintenance dose of 50 mg of the compound three times a week. In some embodiments, the method comprises administering a loading dose of 5 mg of the compound daily for 9 days, followed by administering a maintenance dose of 50 mg of the compound three times a week. In some embodiments, the method comprises administering a loading dose of 5 mg of the compound daily for 10 days, followed by administering a maintenance dose of 50 mg of the compound three times a week. In some embodiments, the method comprises administering a loading dose of 7 mg of the compound daily for 3 days, followed by administering a maintenance dose of 50 mg of the compound three times a week. In some embodiments, the method comprises administering a loading dose of 7 mg of the compound daily for 4 days, followed by administering a maintenance dose of 50 mg of the compound three times a week. In some embodiments, the method comprises administering a loading dose of 7 mg of the compound daily for 5 days, followed by administering a maintenance dose of 50 mg of the compound three times a week. In some embodiments, the method comprises administering a loading dose of 7 mg of the compound daily for 6 days, followed by administering a maintenance dose of 50 mg of the compound three times a week. In some embodiments, the method comprises administering a loading dose of 7 mg of the compound daily for 7 days, followed by administering a maintenance dose of 50 mg of the compound three times a week. In some embodiments, the method comprises administering a loading dose of 7 mg of the compound daily for 8 days, followed by administering a maintenance dose of 50 mg of the compound three times a week. In some embodiments, the method comprises administering a loading dose of 7 mg of the compound daily for 9 days, followed by administering a maintenance dose of 50 mg of the compound three times a week. In some embodiments, the method comprises administering a loading dose of 7 mg of the compound daily for 10 days, followed by administering a maintenance dose of 50 mg of the compound three times a week. In some embodiments, the method comprises administering a loading dose of 8 mg of the compound daily for 3 days, followed by administering a maintenance dose of 50 mg of the compound three times a week. In some embodiments, the method comprises administering a loading dose of 8 mg of the compound daily for 4 days, followed by administering a maintenance dose of 50 mg of the compound three times a week. In some embodiments, the method comprises administering a loading dose of 8 mg of the compound daily for 5 days, followed by administering a maintenance dose of 50 mg of the compound three times a week. In some embodiments, the method comprises administering a loading dose of 8 mg of the compound daily for 6 days, followed by administering a maintenance dose of 50 mg of the compound three times a week. In some embodiments, the method comprises administering a loading dose of 8 mg of the compound daily for 7 days, followed by administering a maintenance dose of 50 mg of the compound three times a week. In some embodiments, the method comprises administering a loading dose of 8 mg of the compound daily for 8 days, followed by administering a maintenance dose of 50 mg of the compound three times a week. In some embodiments, the method comprises administering a loading dose of 8 mg of the compound daily for 9 days, followed by administering a maintenance dose of 50 mg of the compound three times a week. In some embodiments, the method comprises administering a loading dose of 8 mg of the compound daily for 10 days, followed by administering a maintenance dose of 50 mg of the compound three times a week. In some embodiments, the method comprises administering a loading dose of 10 mg of the compound daily for 3 days, followed by administering a maintenance dose of 50 mg of the compound three times a week. In some embodiments, the method comprises administering a loading dose of 10 mg of the compound daily for 4 days, followed by administering a maintenance dose of 50 mg of the compound three times a week. In some embodiments, the method comprises administering a loading dose of 10 mg of the compound daily for 5 days, followed by administering a maintenance dose of 50 mg of the compound three times a week. In some embodiments, the method comprises administering a loading dose of 10 mg of the compound daily for 6 days, followed by administering a maintenance dose of 50 mg of the compound three times a week. In some embodiments, the method comprises administering a loading dose of 10 mg of the compound daily for 7 days, followed by administering a maintenance dose of 50 mg of the compound three times a week. In some embodiments, the method comprises administering a loading dose of 10 mg of the compound daily for 8 days, followed by administering a maintenance dose of 50 mg of the compound three times a week. In some embodiments, the method comprises administering a loading dose of 10 mg of the compound daily for 9 days, followed by administering a maintenance dose of 50 mg of the compound three times a week. In some embodiments, the method comprises administering a loading dose of 10 mg of the compound daily for 10 days, followed by administering a maintenance dose of 50 mg of the compound three times a week. In some embodiments, the method comprises administering a loading dose of 12 mg of the compound daily for 3 days, followed by administering a maintenance dose of 50 mg of the compound three times a week. In some embodiments, the method comprises administering a loading dose of 12 mg of the compound daily for 4 days, followed by administering a maintenance dose of 50 mg of the compound three times a week. In some embodiments, the method comprises administering a loading dose of 12 mg of the compound daily for 5 days, followed by administering a maintenance dose of 50 mg of the compound three times a week. In some embodiments, the method comprises administering a loading dose of 12 mg of the compound daily for 6 days, followed by administering a maintenance dose of 50 mg of the compound three times a week. In some embodiments, the method comprises administering a loading dose of 12 mg of the compound daily for 7 days, followed by administering a maintenance dose of 50 mg of the compound three times a week. In some embodiments, the method comprises administering a loading dose of 12 mg of the compound daily for 8 days, followed by administering a maintenance dose of 50 mg of the compound three times a week. In some embodiments, the method comprises administering a loading dose of 12 mg of the compound daily for 9 days, followed by administering a maintenance dose of 50 mg of the compound three times a week. In some embodiments, the method comprises administering a loading dose of 12 mg of the compound daily for 10 days, followed by administering a maintenance dose of 50 mg of the compound three times a week. In some embodiments, the method comprises administering a loading dose of 15 mg of the compound daily for 3 days, followed by administering a maintenance dose of 50 mg of the compound three times a week. In some embodiments, the method comprises administering a loading dose of 15 mg of the compound daily for 4 days, followed by administering a maintenance dose of 50 mg of the compound three times a week. In some embodiments, the method comprises administering a loading dose of 15 mg of the compound daily for 5 days, followed by administering a maintenance dose of 50 mg of the compound three times a week. In some embodiments, the method comprises administering a loading dose of 15 mg of the compound daily for 6 days, followed by administering a maintenance dose of 50 mg of the compound three times a week. In some embodiments, the method comprises administering a loading dose of 15 mg of the compound daily for 7 days, followed by administering a maintenance dose of 50 mg of the compound three times a week. In some embodiments, the method comprises administering a loading dose of 15 mg of the compound daily for 8 days, followed by administering a maintenance dose of 50 mg of the compound three times a week. In some embodiments, the method comprises administering a loading dose of 15 mg of the compound daily for 9 days, followed by administering a maintenance dose of 50 mg of the compound three times a week. In some embodiments, the method comprises administering a loading dose of 15 mg of the compound daily for 10 days, followed by administering a maintenance dose of 50 mg of the compound three times a week.

In some embodiments, the loading dose is administered from 1 day to 20 days, and the maintenance dose is administered from 20 days to 37000 days. In some embodiments, the method comprises administering a loading dose of 20 mg of the compound daily for 3 days, followed by administering a maintenance dose of 6 mg of the compound daily. In some embodiments, the method comprises administering a loading dose of 20 mg of the compound daily for 4 days, followed by administering a maintenance dose of 6 mg of the compound daily. In some embodiments, the method comprises administering a loading dose of 20 mg of the compound daily for 5 days, followed by administering a maintenance dose of 6 mg of the compound daily. In some embodiments, the method comprises administering a loading dose of 20 mg of the compound daily for 6 days, followed by administering a maintenance dose of 6 mg of the compound daily. In some embodiments, the method comprises administering a loading dose of 20 mg of the compound daily for 7 days, followed by administering a maintenance dose of 6 mg of the compound daily. In some embodiments, the method comprises administering a loading dose of 20 mg of the compound daily for 8 days, followed by administering a maintenance dose of 6 mg of the compound daily. In some embodiments, the method comprises administering a loading dose of 20 mg of the compound daily for 9 days, followed by administering a maintenance dose of 6 mg of the compound daily. In some embodiments, the method comprises administering a loading dose of 20 mg of the compound daily for 10 days, followed by administering a maintenance dose of 6 mg of the compound daily. In some embodiments, the method comprises administering a loading dose of 30 mg of the compound daily for 3 days, followed by administering a maintenance dose of 6 mg of the compound daily. In some embodiments, the method comprises administering a loading dose of 30 mg of the compound daily for 4 days, followed by administering a maintenance dose of 6 mg of the compound daily. In some embodiments, the method comprises administering a loading dose of 30 mg of the compound daily for 5 days, followed by administering a maintenance dose of 6 mg of the compound daily. In some embodiments, the method comprises administering a loading dose of 30 mg of the compound daily for 6 days, followed by administering a maintenance dose of 6 mg of the compound daily. In some embodiments, the method comprises administering a loading dose of 30 mg of the compound daily for 7 days, followed by administering a maintenance dose of 6 mg of the compound daily. In some embodiments, the method comprises administering a loading dose of 30 mg of the compound daily for 8 days, followed by administering a maintenance dose of 6 mg of the compound daily. In some embodiments, the method comprises administering a loading dose of 30 mg of the compound daily for 9 days, followed by administering a maintenance dose of 6 mg of the compound daily. In some embodiments, the method comprises administering a loading dose of 30 mg of the compound daily for 10 days, followed by administering a maintenance dose of 6 mg of the compound daily. In some embodiments, the method comprises administering a loading dose of 40 mg of the compound daily for 3 days, followed by administering a maintenance dose of 6 mg of the compound daily. In some embodiments, the method comprises administering a loading dose of 40 mg of the compound daily for 4 days, followed by administering a maintenance dose of 6 mg of the compound daily. In some embodiments, the method comprises administering a loading dose of 40 mg of the compound daily for 5 days, followed by administering a maintenance dose of 6 mg of the compound daily. In some embodiments, the method comprises administering a loading dose of 40 mg of the compound daily for 6 days, followed by administering a maintenance dose of 6 mg of the compound daily. In some embodiments, the method comprises administering a loading dose of 40 mg of the compound daily for 7 days, followed by administering a maintenance dose of 6 mg of the compound daily. In some embodiments, the method comprises administering a loading dose of 40 mg of the compound daily for 8 days, followed by administering a maintenance dose of 6 mg of the compound daily. In some embodiments, the method comprises administering a loading dose of 40 mg of the compound daily for 9 days, followed by administering a maintenance dose of 6 mg of the compound daily. In some embodiments, the method comprises administering a loading dose of 40 mg of the compound daily for 10 days, followed by administering a maintenance dose of 6 mg of the compound daily. In some embodiments, the method comprises administering a loading dose of 50 mg of the compound daily for 3 days, followed by administering a maintenance dose of 6 mg of the compound daily. In some embodiments, the method comprises administering a loading dose of 50 mg of the compound daily for 4 days, followed by administering a maintenance dose of 6 mg of the compound daily. In some embodiments, the method comprises administering a loading dose of 50 mg of the compound daily for 5 days, followed by administering a maintenance dose of 6 mg of the compound daily. In some embodiments, the method comprises administering a loading dose of 50 mg of the compound daily for 6 days, followed by administering a maintenance dose of 6 mg of the compound daily. In some embodiments, the method comprises administering a loading dose of 50 mg of the compound daily for 7 days, followed by administering a maintenance dose of 6 mg of the compound daily. In some embodiments, the method comprises administering a loading dose of 50 mg of the compound daily for 8 days, followed by administering a maintenance dose of 6 mg of the compound daily. In some embodiments, the method comprises administering a loading dose of 50 mg of the compound daily for 9 days, followed by administering a maintenance dose of 6 mg of the compound daily. In some embodiments, the method comprises administering a loading dose of 50 mg of the compound daily for 10 days, followed by administering a maintenance dose of 6 mg of the compound daily. In some embodiments, the method comprises administering a loading dose of 60 mg of the compound daily for 3 days, followed by administering a maintenance dose of 6 mg of the compound daily. In some embodiments, the method comprises administering a loading dose of 60 mg of the compound daily for 4 days, followed by administering a maintenance dose of 6 mg of the compound daily. In some embodiments, the method comprises administering a loading dose of 60 mg of the compound daily for 5 days, followed by administering a maintenance dose of 6 mg of the compound daily. In some embodiments, the method comprises administering a loading dose of 60 mg of the compound daily for 6 days, followed by administering a maintenance dose of 6 mg of the compound daily. In some embodiments, the method comprises administering a loading dose of 60 mg of the compound daily for 7 days, followed by administering a maintenance dose of 6 mg of the compound daily. In some embodiments, the method comprises administering a loading dose of 60 mg of the compound daily for 8 days, followed by administering a maintenance dose of 6 mg of the compound daily. In some embodiments, the method comprises administering a loading dose of 60 mg of the compound daily for 9 days, followed by administering a maintenance dose of 6 mg of the compound daily. In some embodiments, the method comprises administering a loading dose of 60 mg of the compound daily for 10 days, followed by administering a maintenance dose of 6 mg of the compound daily. In some embodiments, the method comprises administering a loading dose of 70 mg of the compound daily for 3 days, followed by administering a maintenance dose of 6 mg of the compound daily. In some embodiments, the method comprises administering a loading dose of 70 mg of the compound daily for 4 days, followed by administering a maintenance dose of 6 mg of the compound daily. In some embodiments, the method comprises administering a loading dose of 70 mg of the compound daily for 5 days, followed by administering a maintenance dose of 6 mg of the compound daily. In some embodiments, the method comprises administering a loading dose of 70 mg of the compound daily for 6 days, followed by administering a maintenance dose of 6 mg of the compound daily. In some embodiments, the method comprises administering a loading dose of 70 mg of the compound daily for 7 days, followed by administering a maintenance dose of 6 mg of the compound daily. In some embodiments, the method comprises administering a loading dose of 70 mg of the compound daily for 8 days, followed by administering a maintenance dose of 6 mg of the compound daily. In some embodiments, the method comprises administering a loading dose of 70 mg of the compound daily for 9 days, followed by administering a maintenance dose of 6 mg of the compound daily. In some embodiments, the method comprises administering a loading dose of 70 mg of the compound daily for 10 days, followed by administering a maintenance dose of 6 mg of the compound daily.

In some embodiments, the loading dose is administered from 1 day to 20 days, and the maintenance dose is administered from 20 days to 37000 days. In some embodiments, the method comprises administering a loading dose of 20 mg of the compound daily for 3 days, followed by administering a maintenance dose of 8 mg of the compound daily. In some embodiments, the method comprises administering a loading dose of 20 mg of the compound daily for 4 days, followed by administering a maintenance dose of 8 mg of the compound daily. In some embodiments, the method comprises administering a loading dose of 20 mg of the compound daily for 5 days, followed by administering a maintenance dose of 8 mg of the compound daily. In some embodiments, the method comprises administering a loading dose of 20 mg of the compound daily for 6 days, followed by administering a maintenance dose of 8 mg of the compound daily. In some embodiments, the method comprises administering a loading dose of 20 mg of the compound daily for 7 days, followed by administering a maintenance dose of 8 mg of the compound daily. In some embodiments, the method comprises administering a loading dose of 20 mg of the compound daily for 8 days, followed by administering a maintenance dose of 8 mg of the compound daily. In some embodiments, the method comprises administering a loading dose of 20 mg of the compound daily for 9 days, followed by administering a maintenance dose of 8 mg of the compound daily. In some embodiments, the method comprises administering a loading dose of 20 mg of the compound daily for 10 days, followed by administering a maintenance dose of 8 mg of the compound daily. In some embodiments, the method comprises administering a loading dose of 30 mg of the compound daily for 3 days, followed by administering a maintenance dose of 8 mg of the compound daily. In some embodiments, the method comprises administering a loading dose of 30 mg of the compound daily for 4 days, followed by administering a maintenance dose of 8 mg of the compound daily. In some embodiments, the method comprises administering a loading dose of 30 mg of the compound daily for 5 days, followed by administering a maintenance dose of 8 mg of the compound daily. In some embodiments, the method comprises administering a loading dose of 30 mg of the compound daily for 6 days, followed by administering a maintenance dose of 8 mg of the compound daily. In some embodiments, the method comprises administering a loading dose of 30 mg of the compound daily for 7 days, followed by administering a maintenance dose of 8 mg of the compound daily. In some embodiments, the method comprises administering a loading dose of 30 mg of the compound daily for 8 days, followed by administering a maintenance dose of 8 mg of the compound daily. In some embodiments, the method comprises administering a loading dose of 30 mg of the compound daily for 9 days, followed by administering a maintenance dose of 8 mg of the compound daily. In some embodiments, the method comprises administering a loading dose of 30 mg of the compound daily for 10 days, followed by administering a maintenance dose of 8 mg of the compound daily. In some embodiments, the method comprises administering a loading dose of 40 mg of the compound daily for 3 days, followed by administering a maintenance dose of 8 mg of the compound daily. In some embodiments, the method comprises administering a loading dose of 40 mg of the compound daily for 4 days, followed by administering a maintenance dose of 8 mg of the compound daily. In some embodiments, the method comprises administering a loading dose of 40 mg of the compound daily for 5 days, followed by administering a maintenance dose of 8 mg of the compound daily. In some embodiments, the method comprises administering a loading dose of 40 mg of the compound daily for 6 days, followed by administering a maintenance dose of 8 mg of the compound daily. In some embodiments, the method comprises administering a loading dose of 40 mg of the compound daily for 7 days, followed by administering a maintenance dose of 8 mg of the compound daily. In some embodiments, the method comprises administering a loading dose of 40 mg of the compound daily for 8 days, followed by administering a maintenance dose of 8 mg of the compound daily. In some embodiments, the method comprises administering a loading dose of 40 mg of the compound daily for 9 days, followed by administering a maintenance dose of 8 mg of the compound daily. In some embodiments, the method comprises administering a loading dose of 40 mg of the compound daily for 10 days, followed by administering a maintenance dose of 8 mg of the compound daily. In some embodiments, the method comprises administering a loading dose of 50 mg of the compound daily for 3 days, followed by administering a maintenance dose of 8 mg of the compound daily. In some embodiments, the method comprises administering a loading dose of 50 mg of the compound daily for 4 days, followed by administering a maintenance dose of 8 mg of the compound daily. In some embodiments, the method comprises administering a loading dose of 50 mg of the compound daily for 5 days, followed by administering a maintenance dose of 8 mg of the compound daily. In some embodiments, the method comprises administering a loading dose of 50 mg of the compound daily for 6 days, followed by administering a maintenance dose of 8 mg of the compound daily. In some embodiments, the method comprises administering a loading dose of 50 mg of the compound daily for 7 days, followed by administering a maintenance dose of 8 mg of the compound daily. In some embodiments, the method comprises administering a loading dose of 50 mg of the compound daily for 8 days, followed by administering a maintenance dose of 8 mg of the compound daily. In some embodiments, the method comprises administering a loading dose of 50 mg of the compound daily for 9 days, followed by administering a maintenance dose of 8 mg of the compound daily. In some embodiments, the method comprises administering a loading dose of 50 mg of the compound daily for 10 days, followed by administering a maintenance dose of 8 mg of the compound daily. In some embodiments, the method comprises administering a loading dose of 60 mg of the compound daily for 3 days, followed by administering a maintenance dose of 8 mg of the compound daily. In some embodiments, the method comprises administering a loading dose of 60 mg of the compound daily for 4 days, followed by administering a maintenance dose of 8 mg of the compound daily. In some embodiments, the method comprises administering a loading dose of 60 mg of the compound daily for 5 days, followed by administering a maintenance dose of 8 mg of the compound daily. In some embodiments, the method comprises administering a loading dose of 60 mg of the compound daily for 6 days, followed by administering a maintenance dose of 8 mg of the compound daily. In some embodiments, the method comprises administering a loading dose of 60 mg of the compound daily for 7 days, followed by administering a maintenance dose of 8 mg of the compound daily. In some embodiments, the method comprises administering a loading dose of 60 mg of the compound daily for 8 days, followed by administering a maintenance dose of 8 mg of the compound daily. In some embodiments, the method comprises administering a loading dose of 60 mg of the compound daily for 9 days, followed by administering a maintenance dose of 8 mg of the compound daily. In some embodiments, the method comprises administering a loading dose of 60 mg of the compound daily for 10 days, followed by administering a maintenance dose of 8 mg of the compound daily. In some embodiments, the method comprises administering a loading dose of 70 mg of the compound daily for 3 days, followed by administering a maintenance dose of 8 mg of the compound daily. In some embodiments, the method comprises administering a loading dose of 70 mg of the compound daily for 4 days, followed by administering a maintenance dose of 8 mg of the compound daily. In some embodiments, the method comprises administering a loading dose of 70 mg of the compound daily for 5 days, followed by administering a maintenance dose of 8 mg of the compound daily. In some embodiments, the method comprises administering a loading dose of 70 mg of the compound daily for 6 days, followed by administering a maintenance dose of 8 mg of the compound daily. In some embodiments, the method comprises administering a loading dose of 70 mg of the compound daily for 7 days, followed by administering a maintenance dose of 8 mg of the compound daily. In some embodiments, the method comprises administering a loading dose of 70 mg of the compound daily for 8 days, followed by administering a maintenance dose of 8 mg of the compound daily. In some embodiments, the method comprises administering a loading dose of 70 mg of the compound daily for 9 days, followed by administering a maintenance dose of 8 mg of the compound daily. In some embodiments, the method comprises administering a loading dose of 70 mg of the compound daily for 10 days, followed by administering a maintenance dose of 8 mg of the compound daily.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 10 mg of the compound daily. In some embodiments, the method comprises administering a loading dose of 25 mg of the compound daily for 4 days, followed by administering a maintenance dose of 10 mg of the compound daily. In some embodiments, the method comprises administering a loading dose of 25 mg of the compound daily for 5 days, followed by administering a maintenance dose of 10 mg of the compound daily. In some embodiments, the method comprises administering a loading dose of 25 mg of the compound daily for 6 days, followed by administering a maintenance dose of 10 mg of the compound daily. In some embodiments, the method comprises administering a loading dose of 25 mg of the compound daily for 7 days, followed by administering a maintenance dose of 10 mg of the compound daily. In some embodiments, the method comprises administering a loading dose of 25 mg of the compound daily for 8 days, followed by administering a maintenance dose of 10 mg of the compound daily. In some embodiments, the method comprises administering a loading dose of 25 mg of the compound daily for 9 days, followed by administering a maintenance dose of 10 mg of the compound daily. In some embodiments, the method comprises administering a loading dose of 25 mg of the compound daily for 10 days, followed by administering a maintenance dose of 10 mg of the compound daily. In some embodiments, the method comprises administering a loading dose of 30 mg of the compound daily for 3 days, followed by administering a maintenance dose of 10 mg of the compound daily. In some embodiments, the method comprises administering a loading dose of 30 mg of the compound daily for 4 days, followed by administering a maintenance dose of 10 mg of the compound daily. In some embodiments, the method comprises administering a loading dose of 30 mg of the compound daily for 5 days, followed by administering a maintenance dose of 10 mg of the compound daily. In some embodiments, the method comprises administering a loading dose of 30 mg of the compound daily for 6 days, followed by administering a maintenance dose of 10 mg of the compound daily. In some embodiments, the method comprises administering a loading dose of 30 mg of the compound daily for 7 days, followed by administering a maintenance dose of 10 mg of the compound daily. In some embodiments, the method comprises administering a loading dose of 30 mg of the compound daily for 8 days, followed by administering a maintenance dose of 10 mg of the compound daily. In some embodiments, the method comprises administering a loading dose of 30 mg of the compound daily for 9 days, followed by administering a maintenance dose of 10 mg of the compound daily. In some embodiments, the method comprises administering a loading dose of 30 mg of the compound daily for 10 days, followed by administering a maintenance dose of 10 mg of the compound daily. In some embodiments, the method comprises administering a loading dose of 40 mg of the compound daily for 3 days, followed by administering a maintenance dose of 10 mg of the compound daily. In some embodiments, the method comprises administering a loading dose of 40 mg of the compound daily for 4 days, followed by administering a maintenance dose of 10 mg of the compound daily. In some embodiments, the method comprises administering a loading dose of 40 mg of the compound daily for 5 days, followed by administering a maintenance dose of 10 mg of the compound daily. In some embodiments, the method comprises administering a loading dose of 40 mg of the compound daily for 6 days, followed by administering a maintenance dose of 10 mg of the compound daily. In some embodiments, the method comprises administering a loading dose of 40 mg of the compound daily for 7 days, followed by administering a maintenance dose of 10 mg of the compound daily. In some embodiments, the method comprises administering a loading dose of 40 mg of the compound daily for 8 days, followed by administering a maintenance dose of 10 mg of the compound daily. In some embodiments, the method comprises administering a loading dose of 40 mg of the compound daily for 9 days, followed by administering a maintenance dose of 10 mg of the compound daily. In some embodiments, the method comprises administering a loading dose of 40 mg of the compound daily for 10 days, followed by administering a maintenance dose of 10 mg of the compound daily. In some embodiments, the method comprises administering a loading dose of 50 mg of the compound daily for 3 days, followed by administering a maintenance dose of 10 mg of the compound daily. In some embodiments, the method comprises administering a loading dose of 50 mg of the compound daily for 4 days, followed by administering a maintenance dose of 10 mg of the compound daily. In some embodiments, the method comprises administering a loading dose of 50 mg of the compound daily for 5 days, followed by administering a maintenance dose of 10 mg of the compound daily. In some embodiments, the method comprises administering a loading dose of 50 mg of the compound daily for 6 days, followed by administering a maintenance dose of 10 mg of the compound daily. In some embodiments, the method comprises administering a loading dose of 50 mg of the compound daily for 7 days, followed by administering a maintenance dose of 10 mg of the compound daily. In some embodiments, the method comprises administering a loading dose of 50 mg of the compound daily for 8 days, followed by administering a maintenance dose of 10 mg of the compound daily. In some embodiments, the method comprises administering a loading dose of 50 mg of the compound daily for 9 days, followed by administering a maintenance dose of 10 mg of the compound daily. In some embodiments, the method comprises administering a loading dose of 50 mg of the compound daily for 10 days, followed by administering a maintenance dose of 10 mg of the compound daily. In some embodiments, the method comprises administering a loading dose of 60 mg of the compound daily for 3 days, followed by administering a maintenance dose of 10 mg of the compound daily. In some embodiments, the method comprises administering a loading dose of 60 mg of the compound daily for 4 days, followed by administering a maintenance dose of 10 mg of the compound daily. In some embodiments, the method comprises administering a loading dose of 60 mg of the compound daily for 5 days, followed by administering a maintenance dose of 10 mg of the compound daily. In some embodiments, the method comprises administering a loading dose of 60 mg of the compound daily for 6 days, followed by administering a maintenance dose of 10 mg of the compound daily. In some embodiments, the method comprises administering a loading dose of 60 mg of the compound daily for 7 days, followed by administering a maintenance dose of 10 mg of the compound daily. In some embodiments, the method comprises administering a loading dose of 60 mg of the compound daily for 8 days, followed by administering a maintenance dose of 10 mg of the compound daily. In some embodiments, the method comprises administering a loading dose of 60 mg of the compound daily for 9 days, followed by administering a maintenance dose of 10 mg of the compound daily. In some embodiments, the method comprises administering a loading dose of 60 mg of the compound daily for 10 days, followed by administering a maintenance dose of 10 mg of the compound daily. In some embodiments, the method comprises administering a loading dose of 70 mg of the compound daily for 3 days, followed by administering a maintenance dose of 10 mg of the compound daily. In some embodiments, the method comprises administering a loading dose of 70 mg of the compound daily for 4 days, followed by administering a maintenance dose of 10 mg of the compound daily. In some embodiments, the method comprises administering a loading dose of 70 mg of the compound daily for 5 days, followed by administering a maintenance dose of 10 mg of the compound daily. In some embodiments, the method comprises administering a loading dose of 70 mg of the compound daily for 6 days, followed by administering a maintenance dose of 10 mg of the compound daily. In some embodiments, the method comprises administering a loading dose of 70 mg of the compound daily for 7 days, followed by administering a maintenance dose of 10 mg of the compound daily. In some embodiments, the method comprises administering a loading dose of 70 mg of the compound daily for 8 days, followed by administering a maintenance dose of 10 mg of the compound daily. In some embodiments, the method comprises administering a loading dose of 70 mg of the compound daily for 9 days, followed by administering a maintenance dose of 10 mg of the compound daily. In some embodiments, the method comprises administering a loading dose of 70 mg of the compound daily for 10 days, followed by administering a maintenance dose of 10 mg of the compound daily.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 20 mg of the compound daily. In some embodiments, the method comprises administering a loading dose of 25 mg of the compound daily for 4 days, followed by administering a maintenance dose of 20 mg of the compound daily. In some embodiments, the method comprises administering a loading dose of 25 mg of the compound daily for 5 days, followed by administering a maintenance dose of 20 mg of the compound daily. In some embodiments, the method comprises administering a loading dose of 25 mg of the compound daily for 6 days, followed by administering a maintenance dose of 20 mg of the compound daily. In some embodiments, the method comprises administering a loading dose of 25 mg of the compound daily for 7 days, followed by administering a maintenance dose of 20 mg of the compound daily. In some embodiments, the method comprises administering a loading dose of 25 mg of the compound daily for 8 days, followed by administering a maintenance dose of 20 mg of the compound daily. In some embodiments, the method comprises administering a loading dose of 25 mg of the compound daily for 9 days, followed by administering a maintenance dose of 20 mg of the compound daily. In some embodiments, the method comprises administering a loading dose of 25 mg of the compound daily for 10 days, followed by administering a maintenance dose of 20 mg of the compound daily. In some embodiments, the method comprises administering a loading dose of 30 mg of the compound daily for 3 days, followed by administering a maintenance dose of 20 mg of the compound daily. In some embodiments, the method comprises administering a loading dose of 30 mg of the compound daily for 4 days, followed by administering a maintenance dose of 20 mg of the compound daily. In some embodiments, the method comprises administering a loading dose of 30 mg of the compound daily for 5 days, followed by administering a maintenance dose of 20 mg of the compound daily. In some embodiments, the method comprises administering a loading dose of 30 mg of the compound daily for 6 days, followed by administering a maintenance dose of 20 mg of the compound daily. In some embodiments, the method comprises administering a loading dose of 30 mg of the compound daily for 7 days, followed by administering a maintenance dose of 20 mg of the compound daily. In some embodiments, the method comprises administering a loading dose of 30 mg of the compound daily for 8 days, followed by administering a maintenance dose of 20 mg of the compound daily. In some embodiments, the method comprises administering a loading dose of 30 mg of the compound daily for 9 days, followed by administering a maintenance dose of 20 mg of the compound daily. In some embodiments, the method comprises administering a loading dose of 30 mg of the compound daily for 10 days, followed by administering a maintenance dose of 20 mg of the compound daily. In some embodiments, the method comprises administering a loading dose of 40 mg of the compound daily for 3 days, followed by administering a maintenance dose of 20 mg of the compound daily. In some embodiments, the method comprises administering a loading dose of 40 mg of the compound daily for 4 days, followed by administering a maintenance dose of 20 mg of the compound daily. In some embodiments, the method comprises administering a loading dose of 40 mg of the compound daily for 5 days, followed by administering a maintenance dose of 20 mg of the compound daily. In some embodiments, the method comprises administering a loading dose of 40 mg of the compound daily for 6 days, followed by administering a maintenance dose of 20 mg of the compound daily. In some embodiments, the method comprises administering a loading dose of 40 mg of the compound daily for 7 days, followed by administering a maintenance dose of 20 mg of the compound daily. In some embodiments, the method comprises administering a loading dose of 40 mg of the compound daily for 8 days, followed by administering a maintenance dose of 20 mg of the compound daily. In some embodiments, the method comprises administering a loading dose of 40 mg of the compound daily for 9 days, followed by administering a maintenance dose of 20 mg of the compound daily. In some embodiments, the method comprises administering a loading dose of 40 mg of the compound daily for 10 days, followed by administering a maintenance dose of 20 mg of the compound daily. In some embodiments, the method comprises administering a loading dose of 50 mg of the compound daily for 3 days, followed by administering a maintenance dose of 20 mg of the compound daily. In some embodiments, the method comprises administering a loading dose of 50 mg of the compound daily for 4 days, followed by administering a maintenance dose of 20 mg of the compound daily. In some embodiments, the method comprises administering a loading dose of 50 mg of the compound daily for 5 days, followed by administering a maintenance dose of 20 mg of the compound daily. In some embodiments, the method comprises administering a loading dose of 50 mg of the compound daily for 6 days, followed by administering a maintenance dose of 20 mg of the compound daily. In some embodiments, the method comprises administering a loading dose of 50 mg of the compound daily for 7 days, followed by administering a maintenance dose of 20 mg of the compound daily. In some embodiments, the method comprises administering a loading dose of 50 mg of the compound daily for 8 days, followed by administering a maintenance dose of 20 mg of the compound daily. In some embodiments, the method comprises administering a loading dose of 50 mg of the compound daily for 9 days, followed by administering a maintenance dose of 20 mg of the compound daily. In some embodiments, the method comprises administering a loading dose of 50 mg of the compound daily for 10 days, followed by administering a maintenance dose of 20 mg of the compound daily. In some embodiments, the method comprises administering a loading dose of 60 mg of the compound daily for 3 days, followed by administering a maintenance dose of 20 mg of the compound daily. In some embodiments, the method comprises administering a loading dose of 60 mg of the compound daily for 4 days, followed by administering a maintenance dose of 20 mg of the compound daily. In some embodiments, the method comprises administering a loading dose of 60 mg of the compound daily for 5 days, followed by administering a maintenance dose of 20 mg of the compound daily. In some embodiments, the method comprises administering a loading dose of 60 mg of the compound daily for 6 days, followed by administering a maintenance dose of 20 mg of the compound daily. In some embodiments, the method comprises administering a loading dose of 60 mg of the compound daily for 7 days, followed by administering a maintenance dose of 20 mg of the compound daily. In some embodiments, the method comprises administering a loading dose of 60 mg of the compound daily for 8 days, followed by administering a maintenance dose of 20 mg of the compound daily. In some embodiments, the method comprises administering a loading dose of 60 mg of the compound daily for 9 days, followed by administering a maintenance dose of 20 mg of the compound daily. In some embodiments, the method comprises administering a loading dose of 60 mg of the compound daily for 10 days, followed by administering a maintenance dose of 20 mg of the compound daily. In some embodiments, the method comprises administering a loading dose of 70 mg of the compound daily for 3 days, followed by administering a maintenance dose of 20 mg of the compound daily. In some embodiments, the method comprises administering a loading dose of 70 mg of the compound daily for 4 days, followed by administering a maintenance dose of 20 mg of the compound daily. In some embodiments, the method comprises administering a loading dose of 70 mg of the compound daily for 5 days, followed by administering a maintenance dose of 20 mg of the compound daily. In some embodiments, the method comprises administering a loading dose of 70 mg of the compound daily for 6 days, followed by administering a maintenance dose of 20 mg of the compound daily. In some embodiments, the method comprises administering a loading dose of 70 mg of the compound daily for 7 days, followed by administering a maintenance dose of 20 mg of the compound daily. In some embodiments, the method comprises administering a loading dose of 70 mg of the compound daily for 8 days, followed by administering a maintenance dose of 20 mg of the compound daily. In some embodiments, the method comprises administering a loading dose of 70 mg of the compound daily for 9 days, followed by administering a maintenance dose of 20 mg of the compound daily. In some embodiments, the method comprises administering a loading dose of 70 mg of the compound daily for 10 days, followed by administering a maintenance dose of 20 mg of the compound daily.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 30 mg of the compound daily. In some embodiments, the method comprises administering a loading dose of 25 mg of the compound daily for 4 days, followed by administering a maintenance dose of 30 mg of the compound daily. In some embodiments, the method comprises administering a loading dose of 25 mg of the compound daily for 5 days, followed by administering a maintenance dose of 30 mg of the compound daily. In some embodiments, the method comprises administering a loading dose of 25 mg of the compound daily for 6 days, followed by administering a maintenance dose of 30 mg of the compound daily. In some embodiments, the method comprises administering a loading dose of 25 mg of the compound daily for 7 days, followed by administering a maintenance dose of 30 mg of the compound daily. In some embodiments, the method comprises administering a loading dose of 25 mg of the compound daily for 8 days, followed by administering a maintenance dose of 30 mg of the compound daily. In some embodiments, the method comprises administering a loading dose of 25 mg of the compound daily for 9 days, followed by administering a maintenance dose of 30 mg of the compound daily. In some embodiments, the method comprises administering a loading dose of 25 mg of the compound daily for 10 days, followed by administering a maintenance dose of 30 mg of the compound daily. In some embodiments, the method comprises administering a loading dose of 30 mg of the compound daily for 3 days, followed by administering a maintenance dose of 30 mg of the compound daily. In some embodiments, the method comprises administering a loading dose of 30 mg of the compound daily for 4 days, followed by administering a maintenance dose of 30 mg of the compound daily. In some embodiments, the method comprises administering a loading dose of 30 mg of the compound daily for 5 days, followed by administering a maintenance dose of 30 mg of the compound daily. In some embodiments, the method comprises administering a loading dose of 30 mg of the compound daily for 6 days, followed by administering a maintenance dose of 30 mg of the compound daily. In some embodiments, the method comprises administering a loading dose of 30 mg of the compound daily for 7 days, followed by administering a maintenance dose of 30 mg of the compound daily. In some embodiments, the method comprises administering a loading dose of 30 mg of the compound daily for 8 days, followed by administering a maintenance dose of 30 mg of the compound daily. In some embodiments, the method comprises administering a loading dose of 30 mg of the compound daily for 9 days, followed by administering a maintenance dose of 30 mg of the compound daily. In some embodiments, the method comprises administering a loading dose of 30 mg of the compound daily for 10 days, followed by administering a maintenance dose of 30 mg of the compound daily. In some embodiments, the method comprises administering a loading dose of 40 mg of the compound daily for 3 days, followed by administering a maintenance dose of 30 mg of the compound daily. In some embodiments, the method comprises administering a loading dose of 40 mg of the compound daily for 4 days, followed by administering a maintenance dose of 30 mg of the compound daily. In some embodiments, the method comprises administering a loading dose of 40 mg of the compound daily for 5 days, followed by administering a maintenance dose of 30 mg of the compound daily. In some embodiments, the method comprises administering a loading dose of 40 mg of the compound daily for 6 days, followed by administering a maintenance dose of 30 mg of the compound daily. In some embodiments, the method comprises administering a loading dose of 40 mg of the compound daily for 7 days, followed by administering a maintenance dose of 30 mg of the compound daily. In some embodiments, the method comprises administering a loading dose of 40 mg of the compound daily for 8 days, followed by administering a maintenance dose of 30 mg of the compound daily. In some embodiments, the method comprises administering a loading dose of 40 mg of the compound daily for 9 days, followed by administering a maintenance dose of 30 mg of the compound daily. In some embodiments, the method comprises administering a loading dose of 40 mg of the compound daily for 10 days, followed by administering a maintenance dose of 30 mg of the compound daily. In some embodiments, the method comprises administering a loading dose of 50 mg of the compound daily for 3 days, followed by administering a maintenance dose of 30 mg of the compound daily. In some embodiments, the method comprises administering a loading dose of 50 mg of the compound daily for 4 days, followed by administering a maintenance dose of 30 mg of the compound daily. In some embodiments, the method comprises administering a loading dose of 50 mg of the compound daily for 5 days, followed by administering a maintenance dose of 30 mg of the compound daily. In some embodiments, the method comprises administering a loading dose of 50 mg of the compound daily for 6 days, followed by administering a maintenance dose of 30 mg of the compound daily. In some embodiments, the method comprises administering a loading dose of 50 mg of the compound daily for 7 days, followed by administering a maintenance dose of 30 mg of the compound daily. In some embodiments, the method comprises administering a loading dose of 50 mg of the compound daily for 8 days, followed by administering a maintenance dose of 30 mg of the compound daily. In some embodiments, the method comprises administering a loading dose of 50 mg of the compound daily for 9 days, followed by administering a maintenance dose of 30 mg of the compound daily. In some embodiments, the method comprises administering a loading dose of 50 mg of the compound daily for 10 days, followed by administering a maintenance dose of 30 mg of the compound daily. In some embodiments, the method comprises administering a loading dose of 60 mg of the compound daily for 3 days, followed by administering a maintenance dose of 30 mg of the compound daily. In some embodiments, the method comprises administering a loading dose of 60 mg of the compound daily for 4 days, followed by administering a maintenance dose of 30 mg of the compound daily. In some embodiments, the method comprises administering a loading dose of 60 mg of the compound daily for 5 days, followed by administering a maintenance dose of 30 mg of the compound daily. In some embodiments, the method comprises administering a loading dose of 60 mg of the compound daily for 6 days, followed by administering a maintenance dose of 30 mg of the compound daily. In some embodiments, the method comprises administering a loading dose of 60 mg of the compound daily for 7 days, followed by administering a maintenance dose of 30 mg of the compound daily. In some embodiments, the method comprises administering a loading dose of 60 mg of the compound daily for 8 days, followed by administering a maintenance dose of 30 mg of the compound daily. In some embodiments, the method comprises administering a loading dose of 60 mg of the compound daily for 9 days, followed by administering a maintenance dose of 30 mg of the compound daily. In some embodiments, the method comprises administering a loading dose of 60 mg of the compound daily for 10 days, followed by administering a maintenance dose of 30 mg of the compound daily. In some embodiments, the method comprises administering a loading dose of 70 mg of the compound daily for 3 days, followed by administering a maintenance dose of 30 mg of the compound daily. In some embodiments, the method comprises administering a loading dose of 70 mg of the compound daily for 4 days, followed by administering a maintenance dose of 30 mg of the compound daily. In some embodiments, the method comprises administering a loading dose of 70 mg of the compound daily for 5 days, followed by administering a maintenance dose of 30 mg of the compound daily. In some embodiments, the method comprises administering a loading dose of 70 mg of the compound daily for 6 days, followed by administering a maintenance dose of 30 mg of the compound daily. In some embodiments, the method comprises administering a loading dose of 70 mg of the compound daily for 7 days, followed by administering a maintenance dose of 30 mg of the compound daily. In some embodiments, the method comprises administering a loading dose of 70 mg of the compound daily for 8 days, followed by administering a maintenance dose of 30 mg of the compound daily. In some embodiments, the method comprises administering a loading dose of 70 mg of the compound daily for 9 days, followed by administering a maintenance dose of 30 mg of the compound daily. In some embodiments, the method comprises administering a loading dose of 70 mg of the compound daily for 10 days, followed by administering a maintenance dose of 30 mg of the compound daily.

In some embodiments, the loading dose is administered from 1 day to 20 days, and the maintenance dose is administered from 20 days to 37000 days. In some embodiments, the method comprises administering a loading dose of 20 mg of the compound daily for 3 days, followed by administering a maintenance dose of 6 mg of the compound every other day. In some embodiments, the method comprises administering a loading dose of 20 mg of the compound daily for 4 days, followed by administering a maintenance dose of 6 mg of the compound every other day. In some embodiments, the method comprises administering a loading dose of 20 mg of the compound daily for 5 days, followed by administering a maintenance dose of 6 mg of the compound every other day. In some embodiments, the method comprises administering a loading dose of 20 mg of the compound daily for 6 days, followed by administering a maintenance dose of 6 mg of the compound every other day. In some embodiments, the method comprises administering a loading dose of 20 mg of the compound daily for 7 days, followed by administering a maintenance dose of 6 mg of the compound every other day. In some embodiments, the method comprises administering a loading dose of 20 mg of the compound daily for 8 days, followed by administering a maintenance dose of 6 mg of the compound every other day. In some embodiments, the method comprises administering a loading dose of 20 mg of the compound daily for 9 days, followed by administering a maintenance dose of 6 mg of the compound every other day. In some embodiments, the method comprises administering a loading dose of 20 mg of the compound daily for 10 days, followed by administering a maintenance dose of 6 mg of the compound every other day. In some embodiments, the method comprises administering a loading dose of 30 mg of the compound daily for 3 days, followed by administering a maintenance dose of 6 mg of the compound every other day. In some embodiments, the method comprises administering a loading dose of 30 mg of the compound daily for 4 days, followed by administering a maintenance dose of 6 mg of the compound every other day. In some embodiments, the method comprises administering a loading dose of 30 mg of the compound daily for 5 days, followed by administering a maintenance dose of 6 mg of the compound every other day. In some embodiments, the method comprises administering a loading dose of 30 mg of the compound daily for 6 days, followed by administering a maintenance dose of 6 mg of the compound every other day. In some embodiments, the method comprises administering a loading dose of 30 mg of the compound daily for 7 days, followed by administering a maintenance dose of 6 mg of the compound every other day. In some embodiments, the method comprises administering a loading dose of 30 mg of the compound daily for 8 days, followed by administering a maintenance dose of 6 mg of the compound every other day. In some embodiments, the method comprises administering a loading dose of 30 mg of the compound daily for 9 days, followed by administering a maintenance dose of 6 mg of the compound every other day. In some embodiments, the method comprises administering a loading dose of 30 mg of the compound daily for 10 days, followed by administering a maintenance dose of 6 mg of the compound every other day. In some embodiments, the method comprises administering a loading dose of 40 mg of the compound daily for 3 days, followed by administering a maintenance dose of 6 mg of the compound every other day. In some embodiments, the method comprises administering a loading dose of 40 mg of the compound daily for 4 days, followed by administering a maintenance dose of 6 mg of the compound every other day. In some embodiments, the method comprises administering a loading dose of 40 mg of the compound daily for 5 days, followed by administering a maintenance dose of 6 mg of the compound every other day. In some embodiments, the method comprises administering a loading dose of 40 mg of the compound every other day for 6 days, followed by administering a maintenance dose of 6 mg of the compound daily. In some embodiments, the method comprises administering a loading dose of 40 mg of the compound every other day for 7 days, followed by administering a maintenance dose of 6 mg of the compound every other day. In some embodiments, the method comprises administering a loading dose of 40 mg of the compound daily for 8 days, followed by administering a maintenance dose of 6 mg of the compound every other day. In some embodiments, the method comprises administering a loading dose of 40 mg of the compound daily for 9 days, followed by administering a maintenance dose of 6 mg of the compound every other day. In some embodiments, the method comprises administering a loading dose of 40 mg of the compound daily for 10 days, followed by administering a maintenance dose of 6 mg of the compound every other day. In some embodiments, the method comprises administering a loading dose of 50 mg of the compound daily for 3 days, followed by administering a maintenance dose of 6 mg of the compound every other day. In some embodiments, the method comprises administering a loading dose of 50 mg of the compound daily for 4 days, followed by administering a maintenance dose of 6 mg of the compound every other day. In some embodiments, the method comprises administering a loading dose of 50 mg of the compound daily for 5 days, followed by administering a maintenance dose of 6 mg of the compound every other day. In some embodiments, the method comprises administering a loading dose of 50 mg of the compound daily for 6 days, followed by administering a maintenance dose of 6 mg of the compound every other day. In some embodiments, the method comprises administering a loading dose of 50 mg of the compound daily for 7 days, followed by administering a maintenance dose of 6 mg of the compound every other day. In some embodiments, the method comprises administering a loading dose of 50 mg of the compound daily for 8 days, followed by administering a maintenance dose of 6 mg of the compound every other day. In some embodiments, the method comprises administering a loading dose of 50 mg of the compound daily for 9 days, followed by administering a maintenance dose of 6 mg of the compound every other day. In some embodiments, the method comprises administering a loading dose of 50 mg of the compound daily for 10 days, followed by administering a maintenance dose of 6 mg of the compound every other day. In some embodiments, the method comprises administering a loading dose of 60 mg of the compound daily for 3 days, followed by administering a maintenance dose of 6 mg of the compound every other day. In some embodiments, the method comprises administering a loading dose of 60 mg of the compound daily for 4 days, followed by administering a maintenance dose of 6 mg of the compound every other day. In some embodiments, the method comprises administering a loading dose of 60 mg of the compound daily for 5 days, followed by administering a maintenance dose of 6 mg of the compound every other day. In some embodiments, the method comprises administering a loading dose of 60 mg of the compound daily for 6 days, followed by administering a maintenance dose of 6 mg of the compound every other day. In some embodiments, the method comprises administering a loading dose of 60 mg of the compound daily for 7 days, followed by administering a maintenance dose of 6 mg of the compound every other day. In some embodiments, the method comprises administering a loading dose of 60 mg of the compound daily for 8 days, followed by administering a maintenance dose of 6 mg of the compound every other day. In some embodiments, the method comprises administering a loading dose of 60 mg of the compound daily for 9 days, followed by administering a maintenance dose of 6 mg of the compound every other day. In some embodiments, the method comprises administering a loading dose of 60 mg of the compound daily for 10 days, followed by administering a maintenance dose of 6 mg of the compound every other day. In some embodiments, the method comprises administering a loading dose of 70 mg of the compound daily for 3 days, followed by administering a maintenance dose of 6 mg of the compound every other day. In some embodiments, the method comprises administering a loading dose of 70 mg of the compound daily for 4 days, followed by administering a maintenance dose of 6 mg of the compound every other day. In some embodiments, the method comprises administering a loading dose of 70 mg of the compound daily for 5 days, followed by administering a maintenance dose of 6 mg of the compound every other day. In some embodiments, the method comprises administering a loading dose of 70 mg of the compound daily for 6 days, followed by administering a maintenance dose of 6 mg of the compound every other day. In some embodiments, the method comprises administering a loading dose of 70 mg of the compound daily for 7 days, followed by administering a maintenance dose of 6 mg of the compound every other day. In some embodiments, the method comprises administering a loading dose of 70 mg of the compound daily for 8 days, followed by administering a maintenance dose of 6 mg of the compound every other day. In some embodiments, the method comprises administering a loading dose of 70 mg of the compound daily for 9 days, followed by administering a maintenance dose of 6 mg of the compound every other day. In some embodiments, the method comprises administering a loading dose of 70 mg of the compound daily for 10 days, followed by administering a maintenance dose of 6 mg of the compound every other day.

In some embodiments, the loading dose is administered from 1 day to 20 days, and the maintenance dose is administered from 20 days to 37000 days. In some embodiments, the method comprises administering a loading dose of 20 mg of the compound daily for 3 days, followed by administering a maintenance dose of 8 mg of the compound every other day. In some embodiments, the method comprises administering a loading dose of 20 mg of the compound daily for 4 days, followed by administering a maintenance dose of 8 mg of the compound every other day. In some embodiments, the method comprises administering a loading dose of 20 mg of the compound daily for 5 days, followed by administering a maintenance dose of 8 mg of the compound every other day. In some embodiments, the method comprises administering a loading dose of 20 mg of the compound daily for 6 days, followed by administering a maintenance dose of 8 mg of the compound every other day. In some embodiments, the method comprises administering a loading dose of 20 mg of the compound daily for 7 days, followed by administering a maintenance dose of 8 mg of the compound every other day. In some embodiments, the method comprises administering a loading dose of 20 mg of the compound daily for 8 days, followed by administering a maintenance dose of 8 mg of the compound every other day. In some embodiments, the method comprises administering a loading dose of 20 mg of the compound daily for 9 days, followed by administering a maintenance dose of 8 mg of the compound every other day. In some embodiments, the method comprises administering a loading dose of 20 mg of the compound daily for 10 days, followed by administering a maintenance dose of 8 mg of the compound every other day. In some embodiments, the method comprises administering a loading dose of 30 mg of the compound daily for 3 days, followed by administering a maintenance dose of 8 mg of the compound every other day. In some embodiments, the method comprises administering a loading dose of 30 mg of the compound daily for 4 days, followed by administering a maintenance dose of 8 mg of the compound every other day. In some embodiments, the method comprises administering a loading dose of 30 mg of the compound daily for 5 days, followed by administering a maintenance dose of 8 mg of the compound every other day. In some embodiments, the method comprises administering a loading dose of 30 mg of the compound daily for 6 days, followed by administering a maintenance dose of 8 mg of the compound every other day. In some embodiments, the method comprises administering a loading dose of 30 mg of the compound daily for 7 days, followed by administering a maintenance dose of 8 mg of the compound every other day. In some embodiments, the method comprises administering a loading dose of 30 mg of the compound daily for 8 days, followed by administering a maintenance dose of 8 mg of the compound every other day. In some embodiments, the method comprises administering a loading dose of 30 mg of the compound daily for 9 days, followed by administering a maintenance dose of 8 mg of the compound every other day. In some embodiments, the method comprises administering a loading dose of 30 mg of the compound daily for 10 days, followed by administering a maintenance dose of 8 mg of the compound every other day. In some embodiments, the method comprises administering a loading dose of 40 mg of the compound daily for 3 days, followed by administering a maintenance dose of 8 mg of the compound every other day. In some embodiments, the method comprises administering a loading dose of 40 mg of the compound daily for 4 days, followed by administering a maintenance dose of 8 mg of the compound every other day. In some embodiments, the method comprises administering a loading dose of 40 mg of the compound daily for 5 days, followed by administering a maintenance dose of 8 mg of the compound every other day. In some embodiments, the method comprises administering a loading dose of 40 mg of the compound daily for 6 days, followed by administering a maintenance dose of 8 mg of the compound every other day. In some embodiments, the method comprises administering a loading dose of 40 mg of the compound daily for 7 days, followed by administering a maintenance dose of 8 mg of the compound every other day. In some embodiments, the method comprises administering a loading dose of 40 mg of the compound daily for 8 days, followed by administering a maintenance dose of 8 mg of the compound every other day. In some embodiments, the method comprises administering a loading dose of 40 mg of the compound daily for 9 days, followed by administering a maintenance dose of 8 mg of the compound every other day. In some embodiments, the method comprises administering a loading dose of 40 mg of the compound daily for 10 days, followed by administering a maintenance dose of 8 mg of the compound every other day. In some embodiments, the method comprises administering a loading dose of 50 mg of the compound daily for 3 days, followed by administering a maintenance dose of 8 mg of the compound every other day. In some embodiments, the method comprises administering a loading dose of 50 mg of the compound daily for 4 days, followed by administering a maintenance dose of 8 mg of the compound every other day. In some embodiments, the method comprises administering a loading dose of 50 mg of the compound daily for 5 days, followed by administering a maintenance dose of 8 mg of the compound every other day. In some embodiments, the method comprises administering a loading dose of 50 mg of the compound daily for 6 days, followed by administering a maintenance dose of 8 mg of the compound every other day. In some embodiments, the method comprises administering a loading dose of 50 mg of the compound daily for 7 days, followed by administering a maintenance dose of 8 mg of the compound every other day. In some embodiments, the method comprises administering a loading dose of 50 mg of the compound daily for 8 days, followed by administering a maintenance dose of 8 mg of the compound every other day. In some embodiments, the method comprises administering a loading dose of 50 mg of the compound daily for 9 days, followed by administering a maintenance dose of 8 mg of the compound every other day. In some embodiments, the method comprises administering a loading dose of 50 mg of the compound daily for 10 days, followed by administering a maintenance dose of 8 mg of the compound every other day. In some embodiments, the method comprises administering a loading dose of 60 mg of the compound daily for 3 days, followed by administering a maintenance dose of 8 mg of the compound every other day. In some embodiments, the method comprises administering a loading dose of 60 mg of the compound daily for 4 days, followed by administering a maintenance dose of 8 mg of the compound every other day. In some embodiments, the method comprises administering a loading dose of 60 mg of the compound daily for 5 days, followed by administering a maintenance dose of 8 mg of the compound every other day. In some embodiments, the method comprises administering a loading dose of 60 mg of the compound daily for 6 days, followed by administering a maintenance dose of 8 mg of the compound every other day. In some embodiments, the method comprises administering a loading dose of 60 mg of the compound daily for 7 days, followed by administering a maintenance dose of 8 mg of the compound every other day. In some embodiments, the method comprises administering a loading dose of 60 mg of the compound daily for 8 days, followed by administering a maintenance dose of 8 mg of the compound every other day. In some embodiments, the method comprises administering a loading dose of 60 mg of the compound daily for 9 days, followed by administering a maintenance dose of 8 mg of the compound every other day.

In some embodiments, the method comprises administering a loading dose of 60 mg of the compound daily for 10 days, followed by administering a maintenance dose of 8 mg of the compound every other day. In some embodiments, the method comprises administering a loading dose of 70 mg of the compound daily for 3 days, followed by administering a maintenance dose of 8 mg of the compound every other day. In some embodiments, the method comprises administering a loading dose of 70 mg of the compound daily for 4 days, followed by administering a maintenance dose of 8 mg of the compound every other day. In some embodiments, the method comprises administering a loading dose of 70 mg of the compound daily for 5 days, followed by administering a maintenance dose of 8 mg of the compound every other day. In some embodiments, the method comprises administering a loading dose of 70 mg of the compound daily for 6 days, followed by administering a maintenance dose of 8 mg of the compound every other day. In some embodiments, the method comprises administering a loading dose of 70 mg of the compound daily for 7 days, followed by administering a maintenance dose of 8 mg of the compound every other day. In some embodiments, the method comprises administering a loading dose of 70 mg of the compound daily for 8 days, followed by administering a maintenance dose of 8 mg of the compound every other day. In some embodiments, the method comprises administering a loading dose of 70 mg of the compound daily for 9 days, followed by administering a maintenance dose of 8 mg of the compound every other day. In some embodiments, the method comprises administering a loading dose of 70 mg of the compound daily for 10 days, followed by administering a maintenance dose of 8 mg of the compound every other day.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 10 mg of the compound every other day. In some embodiments, the method comprises administering a loading dose of 25 mg of the compound daily for 4 days, followed by administering a maintenance dose of 10 mg of the compound every other day. In some embodiments, the method comprises administering a loading dose of 25 mg of the compound daily for 5 days, followed by administering a maintenance dose of 10 mg of the compound every other day. In some embodiments, the method comprises administering a loading dose of 25 mg of the compound daily for 6 days, followed by administering a maintenance dose of 10 mg of the compound every other day. In some embodiments, the method comprises administering a loading dose of 25 mg of the compound daily for 7 days, followed by administering a maintenance dose of 10 mg of the compound every other day. In some embodiments, the method comprises administering a loading dose of 25 mg of the compound daily for 8 days, followed by administering a maintenance dose of 10 mg of the compound every other day. In some embodiments, the method comprises administering a loading dose of 25 mg of the compound daily for 9 days, followed by administering a maintenance dose of 10 mg of the compound every other day. In some embodiments, the method comprises administering a loading dose of 25 mg of the compound daily for 10 days, followed by administering a maintenance dose of 10 mg of the compound every other day. In some embodiments, the method comprises administering a loading dose of 30 mg of the compound daily for 3 days, followed by administering a maintenance dose of 10 mg of the compound every other day. In some embodiments, the method comprises administering a loading dose of 30 mg of the compound daily for 4 days, followed by administering a maintenance dose of 10 mg of the compound every other day. In some embodiments, the method comprises administering a loading dose of 30 mg of the compound daily for 5 days, followed by administering a maintenance dose of 10 mg of the compound every other day. In some embodiments, the method comprises administering a loading dose of 30 mg of the compound daily for 6 days, followed by administering a maintenance dose of 10 mg of the compound every other day. In some embodiments, the method comprises administering a loading dose of 30 mg of the compound daily for 7 days, followed by administering a maintenance dose of 10 mg of the compound every other day. In some embodiments, the method comprises administering a loading dose of 30 mg of the compound daily for 8 days, followed by administering a maintenance dose of 10 mg of the compound every other day. In some embodiments, the method comprises administering a loading dose of 30 mg of the compound daily for 9 days, followed by administering a maintenance dose of 10 mg of the compound every other day. In some embodiments, the method comprises administering a loading dose of 30 mg of the compound daily for 10 days, followed by administering a maintenance dose of 10 mg of the compound every other day. In some embodiments, the method comprises administering a loading dose of 40 mg of the compound daily for 3 days, followed by administering a maintenance dose of 10 mg of the compound every other day. In some embodiments, the method comprises administering a loading dose of 40 mg of the compound daily for 4 days, followed by administering a maintenance dose of 10 mg of the compound every other day. In some embodiments, the method comprises administering a loading dose of 40 mg of the compound daily for 5 days, followed by administering a maintenance dose of 10 mg of the compound every other day. In some embodiments, the method comprises administering a loading dose of 40 mg of the compound daily for 6 days, followed by administering a maintenance dose of 10 mg of the compound every other day. In some embodiments, the method comprises administering a loading dose of 40 mg of the compound daily for 7 days, followed by administering a maintenance dose of 10 mg of the compound every other day. In some embodiments, the method comprises administering a loading dose of 40 mg of the compound daily for 8 days, followed by administering a maintenance dose of 10 mg of the compound every other day. In some embodiments, the method comprises administering a loading dose of 40 mg of the compound daily for 9 days, followed by administering a maintenance dose of 10 mg of the compound every other day. In some embodiments, the method comprises administering a loading dose of 40 mg of the compound daily for 10 days, followed by administering a maintenance dose of 10 mg of the compound every other day. In some embodiments, the method comprises administering a loading dose of 50 mg of the compound daily for 3 days, followed by administering a maintenance dose of 10 mg of the compound every other day. In some embodiments, the method comprises administering a loading dose of 50 mg of the compound daily for 4 days, followed by administering a maintenance dose of 10 mg of the compound every other day. In some embodiments, the method comprises administering a loading dose of 50 mg of the compound daily for 5 days, followed by administering a maintenance dose of 10 mg of the compound every other day. In some embodiments, the method comprises administering a loading dose of 50 mg of the compound daily for 6 days, followed by administering a maintenance dose of 10 mg of the compound every other day. In some embodiments, the method comprises administering a loading dose of 50 mg of the compound daily for 7 days, followed by administering a maintenance dose of 10 mg of the compound every other day. In some embodiments, the method comprises administering a loading dose of 50 mg of the compound daily for 8 days, followed by administering a maintenance dose of 10 mg of the compound every other day. In some embodiments, the method comprises administering a loading dose of 50 mg of the compound daily for 9 days, followed by administering a maintenance dose of 10 mg of the compound every other day. In some embodiments, the method comprises administering a loading dose of 50 mg of the compound daily for 10 days, followed by administering a maintenance dose of 10 mg of the compound every other day. In some embodiments, the method comprises administering a loading dose of 60 mg of the compound daily for 3 days, followed by administering a maintenance dose of 10 mg of the compound every other day. In some embodiments, the method comprises administering a loading dose of 60 mg of the compound daily for 4 days, followed by administering a maintenance dose of 10 mg of the compound every other day. In some embodiments, the method comprises administering a loading dose of 60 mg of the compound daily for 5 days, followed by administering a maintenance dose of 10 mg of the compound every other day. In some embodiments, the method comprises administering a loading dose of 60 mg of the compound daily for 6 days, followed by administering a maintenance dose of 10 mg of the compound every other day. In some embodiments, the method comprises administering a loading dose of 60 mg of the compound daily for 7 days, followed by administering a maintenance dose of 10 mg of the compound every other day. In some embodiments, the method comprises administering a loading dose of 60 mg of the compound daily for 8 days, followed by administering a maintenance dose of 10 mg of the compound every other day. In some embodiments, the method comprises administering a loading dose of 60 mg of the compound daily for 9 days, followed by administering a maintenance dose of 10 mg of the compound every other day. In some embodiments, the method comprises administering a loading dose of 60 mg of the compound daily for 10 days, followed by administering a maintenance dose of 10 mg of the compound every other day. In some embodiments, the method comprises administering a loading dose of 70 mg of the compound daily for 3 days, followed by administering a maintenance dose of 10 mg of the compound every other day. In some embodiments, the method comprises administering a loading dose of 70 mg of the compound daily for 4 days, followed by administering a maintenance dose of 10 mg of the compound every other day. In some embodiments, the method comprises administering a loading dose of 70 mg of the compound daily for 5 days, followed by administering a maintenance dose of 10 mg of the compound every other day. In some embodiments, the method comprises administering a loading dose of 70 mg of the compound daily for 6 days, followed by administering a maintenance dose of 10 mg of the compound every other day. In some embodiments, the method comprises administering a loading dose of 70 mg of the compound daily for 7 days, followed by administering a maintenance dose of 10 mg of the compound every other day. In some embodiments, the method comprises administering a loading dose of 70 mg of the compound daily for 8 days, followed by administering a maintenance dose of 10 mg of the compound every other day. In some embodiments, the method comprises administering a loading dose of 70 mg of the compound daily for 9 days, followed by administering a maintenance dose of 10 mg of the compound every other day. In some embodiments, the method comprises administering a loading dose of 70 mg of the compound daily for 10 days, followed by administering a maintenance dose of 10 mg of the compound every other day.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 20 mg of the compound every other day. In some embodiments, the method comprises administering a loading dose of 25 mg of the compound daily for 4 days, followed by administering a maintenance dose of 20 mg of the compound every other day. In some embodiments, the method comprises administering a loading dose of 25 mg of the compound daily for 5 days, followed by administering a maintenance dose of 20 mg of the compound every other day. In some embodiments, the method comprises administering a loading dose of 25 mg of the compound daily for 6 days, followed by administering a maintenance dose of 20 mg of the compound every other day. In some embodiments, the method comprises administering a loading dose of 25 mg of the compound daily for 7 days, followed by administering a maintenance dose of 20 mg of the compound every other day. In some embodiments, the method comprises administering a loading dose of 25 mg of the compound daily for 8 days, followed by administering a maintenance dose of 20 mg of the compound every other day. In some embodiments, the method comprises administering a loading dose of 25 mg of the compound daily for 9 days, followed by administering a maintenance dose of 20 mg of the compound every other day. In some embodiments, the method comprises administering a loading dose of 25 mg of the compound daily for 10 days, followed by administering a maintenance dose of 20 mg of the compound every other day. In some embodiments, the method comprises administering a loading dose of 30 mg of the compound daily for 3 days, followed by administering a maintenance dose of 20 mg of the compound every other day. In some embodiments, the method comprises administering a loading dose of 30 mg of the compound daily for 4 days, followed by administering a maintenance dose of 20 mg of the compound every other day. In some embodiments, the method comprises administering a loading dose of 30 mg of the compound daily for 5 days, followed by administering a maintenance dose of 20 mg of the compound every other day. In some embodiments, the method comprises administering a loading dose of 30 mg of the compound daily for 6 days, followed by administering a maintenance dose of 20 mg of the compound every other day. In some embodiments, the method comprises administering a loading dose of 30 mg of the compound daily for 7 days, followed by administering a maintenance dose of 20 mg of the compound every other day. In some embodiments, the method comprises administering a loading dose of 30 mg of the compound daily for 8 days, followed by administering a maintenance dose of 20 mg of the compound every other day. In some embodiments, the method comprises administering a loading dose of 30 mg of the compound daily for 9 days, followed by administering a maintenance dose of 20 mg of the compound every other day. In some embodiments, the method comprises administering a loading dose of 30 mg of the compound daily for 10 days, followed by administering a maintenance dose of 20 mg of the compound every other day. In some embodiments, the method comprises administering a loading dose of 40 mg of the compound daily for 3 days, followed by administering a maintenance dose of 20 mg of the compound every other day. In some embodiments, the method comprises administering a loading dose of 40 mg of the compound daily for 4 days, followed by administering a maintenance dose of 20 mg of the compound every other day. In some embodiments, the method comprises administering a loading dose of 40 mg of the compound daily for 5 days, followed by administering a maintenance dose of 20 mg of the compound every other day. In some embodiments, the method comprises administering a loading dose of 40 mg of the compound daily for 6 days, followed by administering a maintenance dose of 20 mg of the compound every other day. In some embodiments, the method comprises administering a loading dose of 40 mg of the compound daily for 7 days, followed by administering a maintenance dose of 20 mg of the compound every other day. In some embodiments, the method comprises administering a loading dose of 40 mg of the compound daily for 8 days, followed by administering a maintenance dose of 20 mg of the compound every other day. In some embodiments, the method comprises administering a loading dose of 40 mg of the compound daily for 9 days, followed by administering a maintenance dose of 20 mg of the compound every other day. In some embodiments, the method comprises administering a loading dose of 40 mg of the compound daily for 10 days, followed by administering a maintenance dose of 20 mg of the compound every other day. In some embodiments, the method comprises administering a loading dose of 50 mg of the compound daily for 3 days, followed by administering a maintenance dose of 20 mg of the compound every other day. In some embodiments, the method comprises administering a loading dose of 50 mg of the compound daily for 4 days, followed by administering a maintenance dose of 20 mg of the compound every other day. In some embodiments, the method comprises administering a loading dose of 50 mg of the compound daily for 5 days, followed by administering a maintenance dose of 20 mg of the compound every other day. In some embodiments, the method comprises administering a loading dose of 50 mg of the compound daily for 6 days, followed by administering a maintenance dose of 20 mg of the compound every other day. In some embodiments, the method comprises administering a loading dose of 50 mg of the compound daily for 7 days, followed by administering a maintenance dose of 20 mg of the compound every other day. In some embodiments, the method comprises administering a loading dose of 50 mg of the compound daily for 8 days, followed by administering a maintenance dose of 20 mg of the compound every other day. In some embodiments, the method comprises administering a loading dose of 50 mg of the compound daily for 9 days, followed by administering a maintenance dose of 20 mg of the compound every other day. In some embodiments, the method comprises administering a loading dose of 50 mg of the compound daily for 10 days, followed by administering a maintenance dose of 20 mg of the compound every other day. In some embodiments, the method comprises administering a loading dose of 60 mg of the compound daily for 3 days, followed by administering a maintenance dose of 20 mg of the compound every other day. In some embodiments, the method comprises administering a loading dose of 60 mg of the compound daily for 4 days, followed by administering a maintenance dose of 20 mg of the compound every other day. In some embodiments, the method comprises administering a loading dose of 60 mg of the compound daily for 5 days, followed by administering a maintenance dose of 20 mg of the compound every other day. In some embodiments, the method comprises administering a loading dose of 60 mg of the compound daily for 6 days, followed by administering a maintenance dose of 20 mg of the compound every other day. In some embodiments, the method comprises administering a loading dose of 60 mg of the compound daily for 7 days, followed by administering a maintenance dose of 20 mg of the compound every other day. In some embodiments, the method comprises administering a loading dose of 60 mg of the compound daily for 8 days, followed by administering a maintenance dose of 20 mg of the compound every other day. In some embodiments, the method comprises administering a loading dose of 60 mg of the compound daily for 9 days, followed by administering a maintenance dose of 20 mg of the compound every other day. In some embodiments, the method comprises administering a loading dose of 60 mg of the compound daily for 10 days, followed by administering a maintenance dose of 20 mg of the compound every other day. In some embodiments, the method comprises administering a loading dose of 70 mg of the compound daily for 3 days, followed by administering a maintenance dose of 20 mg of the compound every other day. In some embodiments, the method comprises administering a loading dose of 70 mg of the compound daily for 4 days, followed by administering a maintenance dose of 20 mg of the compound every other day. In some embodiments, the method comprises administering a loading dose of 70 mg of the compound daily for 5 days, followed by administering a maintenance dose of 20 mg of the compound every other day. In some embodiments, the method comprises administering a loading dose of 70 mg of the compound daily for 6 days, followed by administering a maintenance dose of 20 mg of the compound every other day. In some embodiments, the method comprises administering a loading dose of 70 mg of the compound daily for 7 days, followed by administering a maintenance dose of 20 mg of the compound every other day. In some embodiments, the method comprises administering a loading dose of 70 mg of the compound daily for 8 days, followed by administering a maintenance dose of 20 mg of the compound every other day. In some embodiments, the method comprises administering a loading dose of 70 mg of the compound daily for 9 days, followed by administering a maintenance dose of 20 mg of the compound every other day. In some embodiments, the method comprises administering a loading dose of 70 mg of the compound daily for 10 days, followed by administering a maintenance dose of 20 mg of the compound every other day.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 30 mg of the compound every other day. In some embodiments, the method comprises administering a loading dose of 25 mg of the compound daily for 4 days, followed by administering a maintenance dose of 30 mg of the compound every other day. In some embodiments, the method comprises administering a loading dose of 25 mg of the compound daily for 5 days, followed by administering a maintenance dose of 30 mg of the compound every other day. In some embodiments, the method comprises administering a loading dose of 25 mg of the compound daily for 6 days, followed by administering a maintenance dose of 30 mg of the compound every other day. In some embodiments, the method comprises administering a loading dose of 25 mg of the compound daily for 7 days, followed by administering a maintenance dose of 30 mg of the compound every other day. In some embodiments, the method comprises administering a loading dose of 25 mg of the compound daily for 8 days, followed by administering a maintenance dose of 30 mg of the compound every other day. In some embodiments, the method comprises administering a loading dose of 25 mg of the compound daily for 9 days, followed by administering a maintenance dose of 30 mg of the compound every other day. In some embodiments, the method comprises administering a loading dose of 25 mg of the compound daily for 10 days, followed by administering a maintenance dose of 30 mg of the compound every other day. In some embodiments, the method comprises administering a loading dose of 30 mg of the compound daily for 3 days, followed by administering a maintenance dose of 30 mg of the compound every other day. In some embodiments, the method comprises administering a loading dose of 30 mg of the compound daily for 4 days, followed by administering a maintenance dose of 30 mg of the compound every other day. In some embodiments, the method comprises administering a loading dose of 30 mg of the compound daily for 5 days, followed by administering a maintenance dose of 30 mg of the compound every other day. In some embodiments, the method comprises administering a loading dose of 30 mg of the compound daily for 6 days, followed by administering a maintenance dose of 30 mg of the compound every other day. In some embodiments, the method comprises administering a loading dose of 30 mg of the compound daily for 7 days, followed by administering a maintenance dose of 30 mg of the compound every other day. In some embodiments, the method comprises administering a loading dose of 30 mg of the compound daily for 8 days, followed by administering a maintenance dose of 30 mg of the compound every other day. In some embodiments, the method comprises administering a loading dose of 30 mg of the compound daily for 9 days, followed by administering a maintenance dose of 30 mg of the compound every other day. In some embodiments, the method comprises administering a loading dose of 30 mg of the compound daily for 10 days, followed by administering a maintenance dose of 30 mg of the compound every other day. In some embodiments, the method comprises administering a loading dose of 40 mg of the compound daily for 3 days, followed by administering a maintenance dose of 30 mg of the compound every other day. In some embodiments, the method comprises administering a loading dose of 40 mg of the compound daily for 4 days, followed by administering a maintenance dose of 30 mg of the compound every other day. In some embodiments, the method comprises administering a loading dose of 40 mg of the compound daily for 5 days, followed by administering a maintenance dose of 30 mg of the compound every other day. In some embodiments, the method comprises administering a loading dose of 40 mg of the compound daily for 6 days, followed by administering a maintenance dose of 30 mg of the compound every other day. In some embodiments, the method comprises administering a loading dose of 40 mg of the compound daily for 7 days, followed by administering a maintenance dose of 30 mg of the compound every other day. In some embodiments, the method comprises administering a loading dose of 40 mg of the compound daily for 8 days, followed by administering a maintenance dose of 30 mg of the compound every other day. In some embodiments, the method comprises administering a loading dose of 40 mg of the compound daily for 9 days, followed by administering a maintenance dose of 30 mg of the compound every other day. In some embodiments, the method comprises administering a loading dose of 40 mg of the compound daily for 10 days, followed by administering a maintenance dose of 30 mg of the compound every other day. In some embodiments, the method comprises administering a loading dose of 50 mg of the compound daily for 3 days, followed by administering a maintenance dose of 30 mg of the compound every other day. In some embodiments, the method comprises administering a loading dose of 50 mg of the compound daily for 4 days, followed by administering a maintenance dose of 30 mg of the compound every other day. In some embodiments, the method comprises administering a loading dose of 50 mg of the compound daily for 5 days, followed by administering a maintenance dose of 30 mg of the compound every other day. In some embodiments, the method comprises administering a loading dose of 50 mg of the compound daily for 6 days, followed by administering a maintenance dose of 30 mg of the compound every other day. In some embodiments, the method comprises administering a loading dose of 50 mg of the compound daily for 7 days, followed by administering a maintenance dose of 30 mg of the compound every other day. In some embodiments, the method comprises administering a loading dose of 50 mg of the compound daily for 8 days, followed by administering a maintenance dose of 30 mg of the compound every other day. In some embodiments, the method comprises administering a loading dose of 50 mg of the compound daily for 9 days, followed by administering a maintenance dose of 30 mg of the compound every other day. In some embodiments, the method comprises administering a loading dose of 50 mg of the compound daily for 10 days, followed by administering a maintenance dose of 30 mg of the compound every other day. In some embodiments, the method comprises administering a loading dose of 60 mg of the compound daily for 3 days, followed by administering a maintenance dose of 30 mg of the compound every other day. In some embodiments, the method comprises administering a loading dose of 60 mg of the compound daily for 4 days, followed by administering a maintenance dose of 30 mg of the compound every other day. In some embodiments, the method comprises administering a loading dose of 60 mg of the compound daily for 5 days, followed by administering a maintenance dose of 30 mg of the compound every other day. In some embodiments, the method comprises administering a loading dose of 60 mg of the compound daily for 6 days, followed by administering a maintenance dose of 30 mg of the compound every other day. In some embodiments, the method comprises administering a loading dose of 60 mg of the compound daily for 7 days, followed by administering a maintenance dose of 30 mg of the compound every other day. In some embodiments, the method comprises administering a loading dose of 60 mg of the compound daily for 8 days, followed by administering a maintenance dose of 30 mg of the compound every other day. In some embodiments, the method comprises administering a loading dose of 60 mg of the compound daily for 9 days, followed by administering a maintenance dose of 30 mg of the compound every other day. In some embodiments, the method comprises administering a loading dose of 60 mg of the compound daily for 10 days, followed by administering a maintenance dose of 30 mg of the compound every other day. In some embodiments, the method comprises administering a loading dose of 70 mg of the compound daily for 3 days, followed by administering a maintenance dose of 30 mg of the compound every other day. In some embodiments, the method comprises administering a loading dose of 70 mg of the compound daily for 4 days, followed by administering a maintenance dose of 30 mg of the compound every other day. In some embodiments, the method comprises administering a loading dose of 70 mg of the compound daily for 5 days, followed by administering a maintenance dose of 30 mg of the compound every other day. In some embodiments, the method comprises administering a loading dose of 70 mg of the compound daily for 6 days, followed by administering a maintenance dose of 30 mg of the compound every other day. In some embodiments, the method comprises administering a loading dose of 70 mg of the compound daily for 7 days, followed by administering a maintenance dose of 30 mg of the compound every other day. In some embodiments, the method comprises administering a loading dose of 70 mg of the compound daily for 8 days, followed by administering a maintenance dose of 30 mg of the compound every other day. In some embodiments, the method comprises administering a loading dose of 70 mg of the compound daily for 9 days, followed by administering a maintenance dose of 30 mg of the compound every other day. In some embodiments, the method comprises administering a loading dose of 70 mg of the compound daily for 10 days, followed by administering a maintenance dose of 30 mg of the compound every other day.

In some embodiments, the loading dose is administered from 1 day to 20 days, and the maintenance dose is administered from 20 days to 37000 days. In some embodiments, the method comprises administering a loading dose of 20 mg of the compound daily for 3 days, followed by administering a maintenance dose of 6 mg of the compound once a week. In some embodiments, the method comprises administering a loading dose of 20 mg of the compound daily for 4 days, followed by administering a maintenance dose of 6 mg of the compound once a week. In some embodiments, the method comprises administering a loading dose of 20 mg of the compound daily for 5 days, followed by administering a maintenance dose of 6 mg of the compound once a week. In some embodiments, the method comprises administering a loading dose of 20 mg of the compound daily for 6 days, followed by administering a maintenance dose of 6 mg of the compound once a week. In some embodiments, the method comprises administering a loading dose of 20 mg of the compound daily for 7 days, followed by administering a maintenance dose of 6 mg of the compound once a week. In some embodiments, the method comprises administering a loading dose of 20 mg of the compound daily for 8 days, followed by administering a maintenance dose of 6 mg of the compound once a week. In some embodiments, the method comprises administering a loading dose of 20 mg of the compound daily for 9 days, followed by administering a maintenance dose of 6 mg of the compound once a week. In some embodiments, the method comprises administering a loading dose of 20 mg of the compound daily for 10 days, followed by administering a maintenance dose of 6 mg of the compound once a week. In some embodiments, the method comprises administering a loading dose of 30 mg of the compound daily for 3 days, followed by administering a maintenance dose of 6 mg of the compound once a week. In some embodiments, the method comprises administering a loading dose of 30 mg of the compound daily for 4 days, followed by administering a maintenance dose of 6 mg of the compound once a week. In some embodiments, the method comprises administering a loading dose of 30 mg of the compound daily for 5 days, followed by administering a maintenance dose of 6 mg of the compound once a week. In some embodiments, the method comprises administering a loading dose of 30 mg of the compound daily for 6 days, followed by administering a maintenance dose of 6 mg of the compound once a week. In some embodiments, the method comprises administering a loading dose of 30 mg of the compound daily for 7 days, followed by administering a maintenance dose of 6 mg of the compound once a week. In some embodiments, the method comprises administering a loading dose of 30 mg of the compound daily for 8 days, followed by administering a maintenance dose of 6 mg of the compound once a week. In some embodiments, the method comprises administering a loading dose of 30 mg of the compound daily for 9 days, followed by administering a maintenance dose of 6 mg of the compound once a week. In some embodiments, the method comprises administering a loading dose of 30 mg of the compound daily for 10 days, followed by administering a maintenance dose of 6 mg of the compound once a week. In some embodiments, the method comprises administering a loading dose of 40 mg of the compound daily for 3 days, followed by administering a maintenance dose of 6 mg of the compound once a week. In some embodiments, the method comprises administering a loading dose of 40 mg of the compound daily for 4 days, followed by administering a maintenance dose of 6 mg of the compound once a week. In some embodiments, the method comprises administering a loading dose of 40 mg of the compound daily for 5 days, followed by administering a maintenance dose of 6 mg of the compound once a week. In some embodiments, the method comprises administering a loading dose of 40 mg of the compound daily for 6 days, followed by administering a maintenance dose of 6 mg of the compound once a week. In some embodiments, the method comprises administering a loading dose of 40 mg of the compound daily for 7 days, followed by administering a maintenance dose of 6 mg of the compound once a week. In some embodiments, the method comprises administering a loading dose of 40 mg of the compound daily for 8 days, followed by administering a maintenance dose of 6 mg of the compound once a week. In some embodiments, the method comprises administering a loading dose of 40 mg of the compound daily for 9 days, followed by administering a maintenance dose of 6 mg of the compound once a week. In some embodiments, the method comprises administering a loading dose of 40 mg of the compound daily for 10 days, followed by administering a maintenance dose of 6 mg of the compound once a week. In some embodiments, the method comprises administering a loading dose of 50 mg of the compound daily for 3 days, followed by administering a maintenance dose of 6 mg of the compound once a week. In some embodiments, the method comprises administering a loading dose of 50 mg of the compound daily for 4 days, followed by administering a maintenance dose of 6 mg of the compound once a week. In some embodiments, the method comprises administering a loading dose of 50 mg of the compound daily for 5 days, followed by administering a maintenance dose of 6 mg of the compound once a week. In some embodiments, the method comprises administering a loading dose of 50 mg of the compound daily for 6 days, followed by administering a maintenance dose of 6 mg of the compound once a week. In some embodiments, the method comprises administering a loading dose of 50 mg of the compound daily for 7 days, followed by administering a maintenance dose of 6 mg of the compound once a week. In some embodiments, the method comprises administering a loading dose of 50 mg of the compound daily for 8 days, followed by administering a maintenance dose of 6 mg of the compound once a week. In some embodiments, the method comprises administering a loading dose of 50 mg of the compound daily for 9 days, followed by administering a maintenance dose of 6 mg of the compound once a week. In some embodiments, the method comprises administering a loading dose of 50 mg of the compound daily for 10 days, followed by administering a maintenance dose of 6 mg of the compound once a week. In some embodiments, the method comprises administering a loading dose of 60 mg of the compound daily for 3 days, followed by administering a maintenance dose of 6 mg of the compound once a week. In some embodiments, the method comprises administering a loading dose of 60 mg of the compound daily for 4 days, followed by administering a maintenance dose of 6 mg of the compound once a week. In some embodiments, the method comprises administering a loading dose of 60 mg of the compound daily for 5 days, followed by administering a maintenance dose of 6 mg of the compound once a week. In some embodiments, the method comprises administering a loading dose of 60 mg of the compound daily for 6 days, followed by administering a maintenance dose of 6 mg of the compound once a week. In some embodiments, the method comprises administering a loading dose of 60 mg of the compound daily for 7 days, followed by administering a maintenance dose of 6 mg of the compound once a week. In some embodiments, the method comprises administering a loading dose of 60 mg of the compound daily for 8 days, followed by administering a maintenance dose of 6 mg of the compound once a week. In some embodiments, the method comprises administering a loading dose of 60 mg of the compound daily for 9 days, followed by administering a maintenance dose of 6 mg of the compound once a week. In some embodiments, the method comprises administering a loading dose of 60 mg of the compound daily for 10 days, followed by administering a maintenance dose of 6 mg of the compound once a week. In some embodiments, the method comprises administering a loading dose of 70 mg of the compound daily for 3 days, followed by administering a maintenance dose of 6 mg of the compound once a week. In some embodiments, the method comprises administering a loading dose of 70 mg of the compound daily for 4 days, followed by administering a maintenance dose of 6 mg of the compound once a week. In some embodiments, the method comprises administering a loading dose of 70 mg of the compound daily for 5 days, followed by administering a maintenance dose of 6 mg of the compound once a week. In some embodiments, the method comprises administering a loading dose of 70 mg of the compound daily for 6 days, followed by administering a maintenance dose of 6 mg of the compound once a week. In some embodiments, the method comprises administering a loading dose of 70 mg of the compound daily for 7 days, followed by administering a maintenance dose of 6 mg of the compound once a week. In some embodiments, the method comprises administering a loading dose of 70 mg of the compound daily for 8 days, followed by administering a maintenance dose of 6 mg of the compound once a week. In some embodiments, the method comprises administering a loading dose of 70 mg of the compound daily for 9 days, followed by administering a maintenance dose of 6 mg of the compound once a week. In some embodiments, the method comprises administering a loading dose of 70 mg of the compound daily for 10 days, followed by administering a maintenance dose of 6 mg of the compound once a week.

In some embodiments, the loading dose is administered from 1 day to 20 days, and the maintenance dose is administered from 20 days to 37000 days. In some embodiments, the method comprises administering a loading dose of 20 mg of the compound daily for 3 days, followed by administering a maintenance dose of 8 mg of the compound once a week. In some embodiments, the method comprises administering a loading dose of 20 mg of the compound daily for 4 days, followed by administering a maintenance dose of 8 mg of the compound once a week. In some embodiments, the method comprises administering a loading dose of 20 mg of the compound daily for 5 days, followed by administering a maintenance dose of 8 mg of the compound once a week. In some embodiments, the method comprises administering a loading dose of 20 mg of the compound daily for 6 days, followed by administering a maintenance dose of 8 mg of the compound once a week. In some embodiments, the method comprises administering a loading dose of 20 mg of the compound daily for 7 days, followed by administering a maintenance dose of 8 mg of the compound once a week. In some embodiments, the method comprises administering a loading dose of 20 mg of the compound daily for 8 days, followed by administering a maintenance dose of 8 mg of the compound once a week. In some embodiments, the method comprises administering a loading dose of 20 mg of the compound daily for 9 days, followed by administering a maintenance dose of 8 mg of the compound once a week. In some embodiments, the method comprises administering a loading dose of 20 mg of the compound daily for 10 days, followed by administering a maintenance dose of 8 mg of the compound once a week. In some embodiments, the method comprises administering a loading dose of 30 mg of the compound daily for 3 days, followed by administering a maintenance dose of 8 mg of the compound once a week. In some embodiments, the method comprises administering a loading dose of 30 mg of the compound daily for 4 days, followed by administering a maintenance dose of 8 mg of the compound once a week. In some embodiments, the method comprises administering a loading dose of 30 mg of the compound daily for 5 days, followed by administering a maintenance dose of 8 mg of the compound once a week. In some embodiments, the method comprises administering a loading dose of 30 mg of the compound daily for 6 days, followed by administering a maintenance dose of 8 mg of the compound once a week. In some embodiments, the method comprises administering a loading dose of 30 mg of the compound daily for 7 days, followed by administering a maintenance dose of 8 mg of the compound once a week. In some embodiments, the method comprises administering a loading dose of 30 mg of the compound daily for 8 days, followed by administering a maintenance dose of 8 mg of the compound once a week. In some embodiments, the method comprises administering a loading dose of 30 mg of the compound daily for 9 days, followed by administering a maintenance dose of 8 mg of the compound once a week. In some embodiments, the method comprises administering a loading dose of 30 mg of the compound daily for 10 days, followed by administering a maintenance dose of 8 mg of the compound once a week. In some embodiments, the method comprises administering a loading dose of 40 mg of the compound daily for 3 days, followed by administering a maintenance dose of 8 mg of the compound once a week. In some embodiments, the method comprises administering a loading dose of 40 mg of the compound daily for 4 days, followed by administering a maintenance dose of 8 mg of the compound once a week. In some embodiments, the method comprises administering a loading dose of 40 mg of the compound daily for 5 days, followed by administering a maintenance dose of 8 mg of the compound once a week. In some embodiments, the method comprises administering a loading dose of 40 mg of the compound daily for 6 days, followed by administering a maintenance dose of 8 mg of the compound once a week. In some embodiments, the method comprises administering a loading dose of 40 mg of the compound daily for 7 days, followed by administering a maintenance dose of 8 mg of the compound once a week. In some embodiments, the method comprises administering a loading dose of 40 mg of the compound daily for 8 days, followed by administering a maintenance dose of 8 mg of the compound once a week. In some embodiments, the method comprises administering a loading dose of 40 mg of the compound daily for 9 days, followed by administering a maintenance dose of 8 mg of the compound once a week. In some embodiments, the method comprises administering a loading dose of 40 mg of the compound daily for 10 days, followed by administering a maintenance dose of 8 mg of the compound once a week. In some embodiments, the method comprises administering a loading dose of 50 mg of the compound daily for 3 days, followed by administering a maintenance dose of 8 mg of the compound once a week. In some embodiments, the method comprises administering a loading dose of 50 mg of the compound daily for 4 days, followed by administering a maintenance dose of 8 mg of the compound once a week. In some embodiments, the method comprises administering a loading dose of 50 mg of the compound daily for 5 days, followed by administering a maintenance dose of 8 mg of the compound once a week. In some embodiments, the method comprises administering a loading dose of 50 mg of the compound daily for 6 days, followed by administering a maintenance dose of 8 mg of the compound once a week. In some embodiments, the method comprises administering a loading dose of 50 mg of the compound daily for 7 days, followed by administering a maintenance dose of 8 mg of the compound once a week. In some embodiments, the method comprises administering a loading dose of 50 mg of the compound daily for 8 days, followed by administering a maintenance dose of 8 mg of the compound once a week. In some embodiments, the method comprises administering a loading dose of 50 mg of the compound daily for 9 days, followed by administering a maintenance dose of 8 mg of the compound once a week. In some embodiments, the method comprises administering a loading dose of 50 mg of the compound daily for 10 days, followed by administering a maintenance dose of 8 mg of the compound once a week. In some embodiments, the method comprises administering a loading dose of 60 mg of the compound daily for 3 days, followed by administering a maintenance dose of 8 mg of the compound once a week. In some embodiments, the method comprises administering a loading dose of 60 mg of the compound daily for 4 days, followed by administering a maintenance dose of 8 mg of the compound once a week. In some embodiments, the method comprises administering a loading dose of 60 mg of the compound daily for 5 days, followed by administering a maintenance dose of 8 mg of the compound once a week. In some embodiments, the method comprises administering a loading dose of 60 mg of the compound daily for 6 days, followed by administering a maintenance dose of 8 mg of the compound once a week. In some embodiments, the method comprises administering a loading dose of 60 mg of the compound daily for 7 days, followed by administering a maintenance dose of 8 mg of the compound once a week. In some embodiments, the method comprises administering a loading dose of 60 mg of the compound daily for 8 days, followed by administering a maintenance dose of 8 mg of the compound once a week. In some embodiments, the method comprises administering a loading dose of 60 mg of the compound daily for 9 days, followed by administering a maintenance dose of 8 mg of the compound once a week. In some embodiments, the method comprises administering a loading dose of 60 mg of the compound daily for 10 days, followed by administering a maintenance dose of 8 mg of the compound once a week. In some embodiments, the method comprises administering a loading dose of 70 mg of the compound daily for 3 days, followed by administering a maintenance dose of 8 mg of the compound once a week. In some embodiments, the method comprises administering a loading dose of 70 mg of the compound daily for 4 days, followed by administering a maintenance dose of 8 mg of the compound once a week. In some embodiments, the method comprises administering a loading dose of 70 mg of the compound daily for 5 days, followed by administering a maintenance dose of 8 mg of the compound once a week. In some embodiments, the method comprises administering a loading dose of 70 mg of the compound daily for 6 days, followed by administering a maintenance dose of 8 mg of the compound once a week. In some embodiments, the method comprises administering a loading dose of 70 mg of the compound daily for 7 days, followed by administering a maintenance dose of 8 mg of the compound once a week. In some embodiments, the method comprises administering a loading dose of 70 mg of the compound daily for 8 days, followed by administering a maintenance dose of 8 mg of the compound once a week. In some embodiments, the method comprises administering a loading dose of 70 mg of the compound daily for 9 days, followed by administering a maintenance dose of 8 mg of the compound once a week. In some embodiments, the method comprises administering a loading dose of 70 mg of the compound daily for 10 days, followed by administering a maintenance dose of 8 mg of the compound once a week.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 10 mg of the compound once a week. In some embodiments, the method comprises administering a loading dose of 25 mg of the compound daily for 4 days, followed by administering a maintenance dose of 10 mg of the compound once a week. In some embodiments, the method comprises administering a loading dose of 25 mg of the compound daily for 5 days, followed by administering a maintenance dose of 10 mg of the compound once a week. In some embodiments, the method comprises administering a loading dose of 25 mg of the compound daily for 6 days, followed by administering a maintenance dose of 10 mg of the compound once a week. In some embodiments, the method comprises administering a loading dose of 25 mg of the compound daily for 7 days, followed by administering a maintenance dose of 10 mg of the compound once a week. In some embodiments, the method comprises administering a loading dose of 25 mg of the compound daily for 8 days, followed by administering a maintenance dose of 10 mg of the compound once a week. In some embodiments, the method comprises administering a loading dose of 25 mg of the compound daily for 9 days, followed by administering a maintenance dose of 10 mg of the compound once a week. In some embodiments, the method comprises administering a loading dose of 25 mg of the compound daily for 10 days, followed by administering a maintenance dose of 10 mg of the compound once a week. In some embodiments, the method comprises administering a loading dose of 30 mg of the compound daily for 3 days, followed by administering a maintenance dose of 10 mg of the compound once a week. In some embodiments, the method comprises administering a loading dose of 30 mg of the compound daily for 4 days, followed by administering a maintenance dose of 10 mg of the compound once a week. In some embodiments, the method comprises administering a loading dose of 30 mg of the compound daily for 5 days, followed by administering a maintenance dose of 10 mg of the compound once a week. In some embodiments, the method comprises administering a loading dose of 30 mg of the compound daily for 6 days, followed by administering a maintenance dose of 10 mg of the compound once a week. In some embodiments, the method comprises administering a loading dose of 30 mg of the compound daily for 7 days, followed by administering a maintenance dose of 10 mg of the compound once a week. In some embodiments, the method comprises administering a loading dose of 30 mg of the compound daily for 8 days, followed by administering a maintenance dose of 10 mg of the compound once a week. In some embodiments, the method comprises administering a loading dose of 30 mg of the compound daily for 9 days, followed by administering a maintenance dose of 10 mg of the compound once a week. In some embodiments, the method comprises administering a loading dose of 30 mg of the compound daily for 10 days, followed by administering a maintenance dose of 10 mg of the compound once a week. In some embodiments, the method comprises administering a loading dose of 40 mg of the compound daily for 3 days, followed by administering a maintenance dose of 10 mg of the compound once a week. In some embodiments, the method comprises administering a loading dose of 40 mg of the compound daily for 4 days, followed by administering a maintenance dose of 10 mg of the compound once a week. In some embodiments, the method comprises administering a loading dose of 40 mg of the compound daily for 5 days, followed by administering a maintenance dose of 10 mg of the compound once a week. In some embodiments, the method comprises administering a loading dose of 40 mg of the compound daily for 6 days, followed by administering a maintenance dose of 10 mg of the compound once a week. In some embodiments, the method comprises administering a loading dose of 40 mg of the compound daily for 7 days, followed by administering a maintenance dose of 10 mg of the compound once a week. In some embodiments, the method comprises administering a loading dose of 40 mg of the compound daily for 8 days, followed by administering a maintenance dose of 10 mg of the compound once a week. In some embodiments, the method comprises administering a loading dose of 40 mg of the compound daily for 9 days, followed by administering a maintenance dose of 10 mg of the compound once a week. In some embodiments, the method comprises administering a loading dose of 40 mg of the compound daily for 10 days, followed by administering a maintenance dose of 10 mg of the compound once a week. In some embodiments, the method comprises administering a loading dose of 50 mg of the compound daily for 3 days, followed by administering a maintenance dose of 10 mg of the compound once a week. In some embodiments, the method comprises administering a loading dose of 50 mg of the compound daily for 4 days, followed by administering a maintenance dose of 10 mg of the compound once a week. In some embodiments, the method comprises administering a loading dose of 50 mg of the compound daily for 5 days, followed by administering a maintenance dose of 10 mg of the compound once a week. In some embodiments, the method comprises administering a loading dose of 50 mg of the compound daily for 6 days, followed by administering a maintenance dose of 10 mg of the compound once a week. In some embodiments, the method comprises administering a loading dose of 50 mg of the compound daily for 7 days, followed by administering a maintenance dose of 10 mg of the compound once a week. In some embodiments, the method comprises administering a loading dose of 50 mg of the compound daily for 8 days, followed by administering a maintenance dose of 10 mg of the compound once a week. In some embodiments, the method comprises administering a loading dose of 50 mg of the compound daily for 9 days, followed by administering a maintenance dose of 10 mg of the compound once a week. In some embodiments, the method comprises administering a loading dose of 50 mg of the compound daily for 10 days, followed by administering a maintenance dose of 10 mg of the compound once a week. In some embodiments, the method comprises administering a loading dose of 60 mg of the compound daily for 3 days, followed by administering a maintenance dose of 10 mg of the compound once a week. In some embodiments, the method comprises administering a loading dose of 60 mg of the compound daily for 4 days, followed by administering a maintenance dose of 10 mg of the compound once a week. In some embodiments, the method comprises administering a loading dose of 60 mg of the compound daily for 5 days, followed by administering a maintenance dose of 10 mg of the compound once a week. In some embodiments, the method comprises administering a loading dose of 60 mg of the compound daily for 6 days, followed by administering a maintenance dose of 10 mg of the compound once a week. In some embodiments, the method comprises administering a loading dose of 60 mg of the compound daily for 7 days, followed by administering a maintenance dose of 10 mg of the compound once a week. In some embodiments, the method comprises administering a loading dose of 60 mg of the compound daily for 8 days, followed by administering a maintenance dose of 10 mg of the compound once a week. In some embodiments, the method comprises administering a loading dose of 60 mg of the compound daily for 9 days, followed by administering a maintenance dose of 10 mg of the compound once a week. In some embodiments, the method comprises administering a loading dose of 60 mg of the compound daily for 10 days, followed by administering a maintenance dose of 10 mg of the compound once a week. In some embodiments, the method comprises administering a loading dose of 70 mg of the compound daily for 3 days, followed by administering a maintenance dose of 10 mg of the compound once a week. In some embodiments, the method comprises administering a loading dose of 70 mg of the compound daily for 4 days, followed by administering a maintenance dose of 10 mg of the compound once a week. In some embodiments, the method comprises administering a loading dose of 70 mg of the compound daily for 5 days, followed by administering a maintenance dose of 10 mg of the compound once a week. In some embodiments, the method comprises administering a loading dose of 70 mg of the compound daily for 6 days, followed by administering a maintenance dose of 10 mg of the compound once a week. In some embodiments, the method comprises administering a loading dose of 70 mg of the compound daily for 7 days, followed by administering a maintenance dose of 10 mg of the compound once a week. In some embodiments, the method comprises administering a loading dose of 70 mg of the compound daily for 8 days, followed by administering a maintenance dose of 10 mg of the compound once a week. In some embodiments, the method comprises administering a loading dose of 70 mg of the compound daily for 9 days, followed by administering a maintenance dose of 10 mg of the compound once a week. In some embodiments, the method comprises administering a loading dose of 70 mg of the compound daily for 10 days, followed by administering a maintenance dose of 10 mg of the compound once a week.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 20 mg of the compound once a week. In some embodiments, the method comprises administering a loading dose of 25 mg of the compound daily for 4 days, followed by administering a maintenance dose of 20 mg of the compound once a week. In some embodiments, the method comprises administering a loading dose of 25 mg of the compound daily for 5 days, followed by administering a maintenance dose of 20 mg of the compound once a week. In some embodiments, the method comprises administering a loading dose of 25 mg of the compound daily for 6 days, followed by administering a maintenance dose of 20 mg of the compound once a week. In some embodiments, the method comprises administering a loading dose of 25 mg of the compound daily for 7 days, followed by administering a maintenance dose of 20 mg of the compound once a week. In some embodiments, the method comprises administering a loading dose of 25 mg of the compound daily for 8 days, followed by administering a maintenance dose of 20 mg of the compound once a week. In some embodiments, the method comprises administering a loading dose of 25 mg of the compound daily for 9 days, followed by administering a maintenance dose of 20 mg of the compound once a week. In some embodiments, the method comprises administering a loading dose of 25 mg of the compound daily for 10 days, followed by administering a maintenance dose of 20 mg of the compound once a week. In some embodiments, the method comprises administering a loading dose of 30 mg of the compound daily for 3 days, followed by administering a maintenance dose of 20 mg of the compound once a week. In some embodiments, the method comprises administering a loading dose of 30 mg of the compound daily for 4 days, followed by administering a maintenance dose of 20 mg of the compound once a week. In some embodiments, the method comprises administering a loading dose of 30 mg of the compound daily for 5 days, followed by administering a maintenance dose of 20 mg of the compound once a week. In some embodiments, the method comprises administering a loading dose of 30 mg of the compound daily for 6 days, followed by administering a maintenance dose of 20 mg of the compound once a week. In some embodiments, the method comprises administering a loading dose of 30 mg of the compound daily for 7 days, followed by administering a maintenance dose of 20 mg of the compound once a week. In some embodiments, the method comprises administering a loading dose of 30 mg of the compound daily for 8 days, followed by administering a maintenance dose of 20 mg of the compound once a week. In some embodiments, the method comprises administering a loading dose of 30 mg of the compound daily for 9 days, followed by administering a maintenance dose of 20 mg of the compound once a week. In some embodiments, the method comprises administering a loading dose of 30 mg of the compound daily for 10 days, followed by administering a maintenance dose of 20 mg of the compound once a week. In some embodiments, the method comprises administering a loading dose of 40 mg of the compound daily for 3 days, followed by administering a maintenance dose of 20 mg of the compound once a week. In some embodiments, the method comprises administering a loading dose of 40 mg of the compound daily for 4 days, followed by administering a maintenance dose of 20 mg of the compound once a week. In some embodiments, the method comprises administering a loading dose of 40 mg of the compound daily for 5 days, followed by administering a maintenance dose of 20 mg of the compound once a week. In some embodiments, the method comprises administering a loading dose of 40 mg of the compound daily for 6 days, followed by administering a maintenance dose of 20 mg of the compound once a week. In some embodiments, the method comprises administering a loading dose of 40 mg of the compound daily for 7 days, followed by administering a maintenance dose of 20 mg of the compound once a week. In some embodiments, the method comprises administering a loading dose of 40 mg of the compound daily for 8 days, followed by administering a maintenance dose of 20 mg of the compound once a week. In some embodiments, the method comprises administering a loading dose of 40 mg of the compound daily for 9 days, followed by administering a maintenance dose of 20 mg of the compound once a week. In some embodiments, the method comprises administering a loading dose of 40 mg of the compound daily for 10 days, followed by administering a maintenance dose of 20 mg of the compound once a week. In some embodiments, the method comprises administering a loading dose of 50 mg of the compound daily for 3 days, followed by administering a maintenance dose of 20 mg of the compound once a week. In some embodiments, the method comprises administering a loading dose of 50 mg of the compound daily for 4 days, followed by administering a maintenance dose of 20 mg of the compound once a week. In some embodiments, the method comprises administering a loading dose of 50 mg of the compound daily for 5 days, followed by administering a maintenance dose of 20 mg of the compound once a week. In some embodiments, the method comprises administering a loading dose of 50 mg of the compound daily for 6 days, followed by administering a maintenance dose of 20 mg of the compound once a week. In some embodiments, the method comprises administering a loading dose of 50 mg of the compound daily for 7 days, followed by administering a maintenance dose of 20 mg of the compound once a week. In some embodiments, the method comprises administering a loading dose of 50 mg of the compound daily for 8 days, followed by administering a maintenance dose of 20 mg of the compound once a week. In some embodiments, the method comprises administering a loading dose of 50 mg of the compound daily for 9 days, followed by administering a maintenance dose of 20 mg of the compound once a week. In some embodiments, the method comprises administering a loading dose of 50 mg of the compound daily for 10 days, followed by administering a maintenance dose of 20 mg of the compound once a week. In some embodiments, the method comprises administering a loading dose of 60 mg of the compound daily for 3 days, followed by administering a maintenance dose of 20 mg of the compound once a week. In some embodiments, the method comprises administering a loading dose of 60 mg of the compound daily for 4 days, followed by administering a maintenance dose of 20 mg of the compound once a week. In some embodiments, the method comprises administering a loading dose of 60 mg of the compound daily for 5 days, followed by administering a maintenance dose of 20 mg of the compound once a week. In some embodiments, the method comprises administering a loading dose of 60 mg of the compound daily for 6 days, followed by administering a maintenance dose of 20 mg of the compound once a week. In some embodiments, the method comprises administering a loading dose of 60 mg of the compound daily for 7 days, followed by administering a maintenance dose of 20 mg of the compound once a week. In some embodiments, the method comprises administering a loading dose of 60 mg of the compound daily for 8 days, followed by administering a maintenance dose of 20 mg of the compound once a week. In some embodiments, the method comprises administering a loading dose of 60 mg of the compound daily for 9 days, followed by administering a maintenance dose of 20 mg of the compound once a week. In some embodiments, the method comprises administering a loading dose of 60 mg of the compound daily for 10 days, followed by administering a maintenance dose of 20 mg of the compound once a week. In some embodiments, the method comprises administering a loading dose of 70 mg of the compound daily for 3 days, followed by administering a maintenance dose of 20 mg of the compound once a week. In some embodiments, the method comprises administering a loading dose of 70 mg of the compound daily for 4 days, followed by administering a maintenance dose of 20 mg of the compound once a week. In some embodiments, the method comprises administering a loading dose of 70 mg of the compound daily for 5 days, followed by administering a maintenance dose of 20 mg of the compound once a week. In some embodiments, the method comprises administering a loading dose of 70 mg of the compound daily for 6 days, followed by administering a maintenance dose of 20 mg of the compound once a week. In some embodiments, the method comprises administering a loading dose of 70 mg of the compound daily for 7 days, followed by administering a maintenance dose of 20 mg of the compound once a week. In some embodiments, the method comprises administering a loading dose of 70 mg of the compound daily for 8 days, followed by administering a maintenance dose of 20 mg of the compound once a week. In some embodiments, the method comprises administering a loading dose of 70 mg of the compound daily for 9 days, followed by administering a maintenance dose of 20 mg of the compound once a week. In some embodiments, the method comprises administering a loading dose of 70 mg of the compound daily for 10 days, followed by administering a maintenance dose of 20 mg of the compound once a week.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 30 mg of the compound once a week. In some embodiments, the method comprises administering a loading dose of 25 mg of the compound daily for 4 days, followed by administering a maintenance dose of 30 mg of the compound once a week. In some embodiments, the method comprises administering a loading dose of 25 mg of the compound daily for 5 days, followed by administering a maintenance dose of 30 mg of the compound once a week. In some embodiments, the method comprises administering a loading dose of 25 mg of the compound daily for 6 days, followed by administering a maintenance dose of 30 mg of the compound once a week. In some embodiments, the method comprises administering a loading dose of 25 mg of the compound daily for 7 days, followed by administering a maintenance dose of 30 mg of the compound once a week. In some embodiments, the method comprises administering a loading dose of 25 mg of the compound daily for 8 days, followed by administering a maintenance dose of 30 mg of the compound once a week. In some embodiments, the method comprises administering a loading dose of 25 mg of the compound daily for 9 days, followed by administering a maintenance dose of 30 mg of the compound once a week. In some embodiments, the method comprises administering a loading dose of 25 mg of the compound daily for 10 days, followed by administering a maintenance dose of 30 mg of the compound once a week. In some embodiments, the method comprises administering a loading dose of 30 mg of the compound daily for 3 days, followed by administering a maintenance dose of 30 mg of the compound once a week. In some embodiments, the method comprises administering a loading dose of 30 mg of the compound daily for 4 days, followed by administering a maintenance dose of 30 mg of the compound once a week. In some embodiments, the method comprises administering a loading dose of 30 mg of the compound daily for 5 days, followed by administering a maintenance dose of 30 mg of the compound once a week. In some embodiments, the method comprises administering a loading dose of 30 mg of the compound daily for 6 days, followed by administering a maintenance dose of 30 mg of the compound once a week. In some embodiments, the method comprises administering a loading dose of 30 mg of the compound daily for 7 days, followed by administering a maintenance dose of 30 mg of the compound once a week. In some embodiments, the method comprises administering a loading dose of 30 mg of the compound daily for 8 days, followed by administering a maintenance dose of 30 mg of the compound once a week. In some embodiments, the method comprises administering a loading dose of 30 mg of the compound daily for 9 days, followed by administering a maintenance dose of 30 mg of the compound once a week. In some embodiments, the method comprises administering a loading dose of 30 mg of the compound daily for 10 days, followed by administering a maintenance dose of 30 mg of the compound once a week. In some embodiments, the method comprises administering a loading dose of 40 mg of the compound daily for 3 days, followed by administering a maintenance dose of 30 mg of the compound once a week. In some embodiments, the method comprises administering a loading dose of 40 mg of the compound daily for 4 days, followed by administering a maintenance dose of 30 mg of the compound once a week. In some embodiments, the method comprises administering a loading dose of 40 mg of the compound daily for 5 days, followed by administering a maintenance dose of 30 mg of the compound once a week. In some embodiments, the method comprises administering a loading dose of 40 mg of the compound daily for 6 days, followed by administering a maintenance dose of 30 mg of the compound once a week. In some embodiments, the method comprises administering a loading dose of 40 mg of the compound daily for 7 days, followed by administering a maintenance dose of 30 mg of the compound once a week. In some embodiments, the method comprises administering a loading dose of 40 mg of the compound daily for 8 days, followed by administering a maintenance dose of 30 mg of the compound once a week. In some embodiments, the method comprises administering a loading dose of 40 mg of the compound daily for 9 days, followed by administering a maintenance dose of 30 mg of the compound once a week. In some embodiments, the method comprises administering a loading dose of 40 mg of the compound daily for 10 days, followed by administering a maintenance dose of 30 mg of the compound once a week. In some embodiments, the method comprises administering a loading dose of 50 mg of the compound daily for 3 days, followed by administering a maintenance dose of 30 mg of the compound once a week. In some embodiments, the method comprises administering a loading dose of 50 mg of the compound daily for 4 days, followed by administering a maintenance dose of 30 mg of the compound once a week. In some embodiments, the method comprises administering a loading dose of 50 mg of the compound daily for 5 days, followed by administering a maintenance dose of 30 mg of the compound once a week. In some embodiments, the method comprises administering a loading dose of 50 mg of the compound daily for 6 days, followed by administering a maintenance dose of 30 mg of the compound once a week. In some embodiments, the method comprises administering a loading dose of 50 mg of the compound daily for 7 days, followed by administering a maintenance dose of 30 mg of the compound once a week. In some embodiments, the method comprises administering a loading dose of 50 mg of the compound daily for 8 days, followed by administering a maintenance dose of 30 mg of the compound once a week. In some embodiments, the method comprises administering a loading dose of 50 mg of the compound daily for 9 days, followed by administering a maintenance dose of 30 mg of the compound once a week.

In some embodiments, the method comprises administering a loading dose of 50 mg of the compound daily for 10 days, followed by administering a maintenance dose of 30 mg of the compound once a week. In some embodiments, the method comprises administering a loading dose of 60 mg of the compound daily for 3 days, followed by administering a maintenance dose of 30 mg of the compound once a week. In some embodiments, the method comprises administering a loading dose of 60 mg of the compound daily for 4 days, followed by administering a maintenance dose of 30 mg of the compound once a week. In some embodiments, the method comprises administering a loading dose of 60 mg of the compound daily for 5 days, followed by administering a maintenance dose of 30 mg of the compound once a week. In some embodiments, the method comprises administering a loading dose of 60 mg of the compound daily for 6 days, followed by administering a maintenance dose of 30 mg of the compound once a week. In some embodiments, the method comprises administering a loading dose of 60 mg of the compound daily for 7 days, followed by administering a maintenance dose of 30 mg of the compound once a week. In some embodiments, the method comprises administering a loading dose of 60 mg of the compound daily for 8 days, followed by administering a maintenance dose of 30 mg of the compound once a week. In some embodiments, the method comprises administering a loading dose of 60 mg of the compound daily for 9 days, followed by administering a maintenance dose of 30 mg of the compound once a week. In some embodiments, the method comprises administering a loading dose of 60 mg of the compound daily for 10 days, followed by administering a maintenance dose of 30 mg of the compound once a week. In some embodiments, the method comprises administering a loading dose of 70 mg of the compound daily for 3 days, followed by administering a maintenance dose of 30 mg of the compound once a week. In some embodiments, the method comprises administering a loading dose of 70 mg of the compound daily for 4 days, followed by administering a maintenance dose of 30 mg of the compound once a week. In some embodiments, the method comprises administering a loading dose of 70 mg of the compound daily for 5 days, followed by administering a maintenance dose of 30 mg of the compound once a week. In some embodiments, the method comprises administering a loading dose of 70 mg of the compound daily for 6 days, followed by administering a maintenance dose of 30 mg of the compound once a week. In some embodiments, the method comprises administering a loading dose of 70 mg of the compound daily for 7 days, followed by administering a maintenance dose of 30 mg of the compound once a week. In some embodiments, the method comprises administering a loading dose of 70 mg of the compound daily for 8 days, followed by administering a maintenance dose of 30 mg of the compound once a week. In some embodiments, the method comprises administering a loading dose of 70 mg of the compound daily for 9 days, followed by administering a maintenance dose of 30 mg of the compound once a week. In some embodiments, the method comprises administering a loading dose of 70 mg of the compound daily for 10 days, followed by administering a maintenance dose of 30 mg of the compound once a week.

In some embodiments, the loading dose is administered from 1 day to 20 days, and the maintenance dose is administered from 20 days to 37000 days. In some embodiments, the method comprises administering a loading dose of 20 mg of the compound daily for 3 days, followed by administering a maintenance dose of 6 mg of the compound twice a week. In some embodiments, the method comprises administering a loading dose of 20 mg of the compound daily for 4 days, followed by administering a maintenance dose of 6 mg of the compound twice a week. In some embodiments, the method comprises administering a loading dose of 20 mg of the compound daily for 5 days, followed by administering a maintenance dose of 6 mg of the compound twice a week. In some embodiments, the method comprises administering a loading dose of 20 mg of the compound daily for 6 days, followed by administering a maintenance dose of 6 mg of the compound twice a week. In some embodiments, the method comprises administering a loading dose of 20 mg of the compound daily for 7 days, followed by administering a maintenance dose of 6 mg of the compound twice a week. In some embodiments, the method comprises administering a loading dose of 20 mg of the compound daily for 8 days, followed by administering a maintenance dose of 6 mg of the compound twice a week. In some embodiments, the method comprises administering a loading dose of 20 mg of the compound daily for 9 days, followed by administering a maintenance dose of 6 mg of the compound twice a week. In some embodiments, the method comprises administering a loading dose of 20 mg of the compound daily for 10 days, followed by administering a maintenance dose of 6 mg of the compound twice a week. In some embodiments, the method comprises administering a loading dose of 30 mg of the compound daily for 3 days, followed by administering a maintenance dose of 6 mg of the compound twice a week. In some embodiments, the method comprises administering a loading dose of 30 mg of the compound daily for 4 days, followed by administering a maintenance dose of 6 mg of the compound twice a week. In some embodiments, the method comprises administering a loading dose of 30 mg of the compound daily for 5 days, followed by administering a maintenance dose of 6 mg of the compound twice a week. In some embodiments, the method comprises administering a loading dose of 30 mg of the compound daily for 6 days, followed by administering a maintenance dose of 6 mg of the compound twice a week. In some embodiments, the method comprises administering a loading dose of 30 mg of the compound daily for 7 days, followed by administering a maintenance dose of 6 mg of the compound twice a week. In some embodiments, the method comprises administering a loading dose of 30 mg of the compound daily for 8 days, followed by administering a maintenance dose of 6 mg of the compound twice a week. In some embodiments, the method comprises administering a loading dose of 30 mg of the compound daily for 9 days, followed by administering a maintenance dose of 6 mg of the compound twice a week. In some embodiments, the method comprises administering a loading dose of 30 mg of the compound daily for 10 days, followed by administering a maintenance dose of 6 mg of the compound twice a week. In some embodiments, the method comprises administering a loading dose of 40 mg of the compound daily for 3 days, followed by administering a maintenance dose of 6 mg of the compound twice a week. In some embodiments, the method comprises administering a loading dose of 40 mg of the compound daily for 4 days, followed by administering a maintenance dose of 6 mg of the compound twice a week. In some embodiments, the method comprises administering a loading dose of 40 mg of the compound daily for 5 days, followed by administering a maintenance dose of 6 mg of the compound twice a week. In some embodiments, the method comprises administering a loading dose of 40 mg of the compound daily for 6 days, followed by administering a maintenance dose of 6 mg of the compound twice a week. In some embodiments, the method comprises administering a loading dose of 40 mg of the compound daily for 7 days, followed by administering a maintenance dose of 6 mg of the compound twice a week. In some embodiments, the method comprises administering a loading dose of 40 mg of the compound daily for 8 days, followed by administering a maintenance dose of 6 mg of the compound twice a week. In some embodiments, the method comprises administering a loading dose of 40 mg of the compound daily for 9 days, followed by administering a maintenance dose of 6 mg of the compound twice a week. In some embodiments, the method comprises administering a loading dose of 40 mg of the compound daily for 10 days, followed by administering a maintenance dose of 6 mg of the compound twice a week. In some embodiments, the method comprises administering a loading dose of 50 mg of the compound daily for 3 days, followed by administering a maintenance dose of 6 mg of the compound twice a week. In some embodiments, the method comprises administering a loading dose of 50 mg of the compound daily for 4 days, followed by administering a maintenance dose of 6 mg of the compound twice a week. In some embodiments, the method comprises administering a loading dose of 50 mg of the compound daily for 5 days, followed by administering a maintenance dose of 6 mg of the compound twice a week. In some embodiments, the method comprises administering a loading dose of 50 mg of the compound daily for 6 days, followed by administering a maintenance dose of 6 mg of the compound twice a week. In some embodiments, the method comprises administering a loading dose of 50 mg of the compound daily for 7 days, followed by administering a maintenance dose of 6 mg of the compound twice a week. In some embodiments, the method comprises administering a loading dose of 50 mg of the compound daily for 8 days, followed by administering a maintenance dose of 6 mg of the compound twice a week. In some embodiments, the method comprises administering a loading dose of 50 mg of the compound daily for 9 days, followed by administering a maintenance dose of 6 mg of the compound twice a week. In some embodiments, the method comprises administering a loading dose of 50 mg of the compound daily for 10 days, followed by administering a maintenance dose of 6 mg of the compound twice a week. In some embodiments, the method comprises administering a loading dose of 60 mg of the compound daily for 3 days, followed by administering a maintenance dose of 6 mg of the compound twice a week. In some embodiments, the method comprises administering a loading dose of 60 mg of the compound daily for 4 days, followed by administering a maintenance dose of 6 mg of the compound twice a week. In some embodiments, the method comprises administering a loading dose of 60 mg of the compound daily for 5 days, followed by administering a maintenance dose of 6 mg of the compound twice a week. In some embodiments, the method comprises administering a loading dose of 60 mg of the compound daily for 6 days, followed by administering a maintenance dose of 6 mg of the compound twice a week. In some embodiments, the method comprises administering a loading dose of 60 mg of the compound daily for 7 days, followed by administering a maintenance dose of 6 mg of the compound twice a week. In some embodiments, the method comprises administering a loading dose of 60 mg of the compound daily for 8 days, followed by administering a maintenance dose of 6 mg of the compound twice a week. In some embodiments, the method comprises administering a loading dose of 60 mg of the compound daily for 9 days, followed by administering a maintenance dose of 6 mg of the compound twice a week. In some embodiments, the method comprises administering a loading dose of 60 mg of the compound daily for 10 days, followed by administering a maintenance dose of 6 mg of the compound twice a week. In some embodiments, the method comprises administering a loading dose of 70 mg of the compound daily for 3 days, followed by administering a maintenance dose of 6 mg of the compound twice a week. In some embodiments, the method comprises administering a loading dose of 70 mg of the compound daily for 4 days, followed by administering a maintenance dose of 6 mg of the compound twice a week. In some embodiments, the method comprises administering a loading dose of 70 mg of the compound daily for 5 days, followed by administering a maintenance dose of 6 mg of the compound twice a week. In some embodiments, the method comprises administering a loading dose of 70 mg of the compound daily for 6 days, followed by administering a maintenance dose of 6 mg of the compound twice a week. In some embodiments, the method comprises administering a loading dose of 70 mg of the compound daily for 7 days, followed by administering a maintenance dose of 6 mg of the compound twice a week. In some embodiments, the method comprises administering a loading dose of 70 mg of the compound daily for 8 days, followed by administering a maintenance dose of 6 mg of the compound twice a week. In some embodiments, the method comprises administering a loading dose of 70 mg of the compound daily for 9 days, followed by administering a maintenance dose of 6 mg of the compound twice a week. In some embodiments, the method comprises administering a loading dose of 70 mg of the compound daily for 10 days, followed by administering a maintenance dose of 6 mg of the compound twice a week.

In some embodiments, the loading dose is administered from 1 day to 20 days, and the maintenance dose is administered from 20 days to 37000 days. In some embodiments, the method comprises administering a loading dose of 20 mg of the compound daily for 3 days, followed by administering a maintenance dose of 8 mg of the compound twice a week. In some embodiments, the method comprises administering a loading dose of 20 mg of the compound daily for 4 days, followed by administering a maintenance dose of 8 mg of the compound twice a week. In some embodiments, the method comprises administering a loading dose of 20 mg of the compound daily for 5 days, followed by administering a maintenance dose of 8 mg of the compound twice a week. In some embodiments, the method comprises administering a loading dose of 20 mg of the compound daily for 6 days, followed by administering a maintenance dose of 8 mg of the compound twice a week. In some embodiments, the method comprises administering a loading dose of 20 mg of the compound daily for 7 days, followed by administering a maintenance dose of 8 mg of the compound twice a week. In some embodiments, the method comprises administering a loading dose of 20 mg of the compound daily for 8 days, followed by administering a maintenance dose of 8 mg of the compound twice a week. In some embodiments, the method comprises administering a loading dose of 20 mg of the compound daily for 9 days, followed by administering a maintenance dose of 8 mg of the compound twice a week. In some embodiments, the method comprises administering a loading dose of 20 mg of the compound daily for 10 days, followed by administering a maintenance dose of 8 mg of the compound twice a week. In some embodiments, the method comprises administering a loading dose of 30 mg of the compound daily for 3 days, followed by administering a maintenance dose of 8 mg of the compound twice a week. In some embodiments, the method comprises administering a loading dose of 30 mg of the compound daily for 4 days, followed by administering a maintenance dose of 8 mg of the compound twice a week. In some embodiments, the method comprises administering a loading dose of 30 mg of the compound daily for 5 days, followed by administering a maintenance dose of 8 mg of the compound twice a week. In some embodiments, the method comprises administering a loading dose of 30 mg of the compound daily for 6 days, followed by administering a maintenance dose of 8 mg of the compound twice a week. In some embodiments, the method comprises administering a loading dose of 30 mg of the compound daily for 7 days, followed by administering a maintenance dose of 8 mg of the compound twice a week. In some embodiments, the method comprises administering a loading dose of 30 mg of the compound daily for 8 days, followed by administering a maintenance dose of 8 mg of the compound twice a week. In some embodiments, the method comprises administering a loading dose of 30 mg of the compound daily for 9 days, followed by administering a maintenance dose of 8 mg of the compound twice a week. In some embodiments, the method comprises administering a loading dose of 30 mg of the compound daily for 10 days, followed by administering a maintenance dose of 8 mg of the compound twice a week. In some embodiments, the method comprises administering a loading dose of 40 mg of the compound daily for 3 days, followed by administering a maintenance dose of 8 mg of the compound twice a week. In some embodiments, the method comprises administering a loading dose of 40 mg of the compound daily for 4 days, followed by administering a maintenance dose of 8 mg of the compound twice a week. In some embodiments, the method comprises administering a loading dose of 40 mg of the compound daily for 5 days, followed by administering a maintenance dose of 8 mg of the compound twice a week. In some embodiments, the method comprises administering a loading dose of 40 mg of the compound daily for 6 days, followed by administering a maintenance dose of 8 mg of the compound twice a week. In some embodiments, the method comprises administering a loading dose of 40 mg of the compound daily for 7 days, followed by administering a maintenance dose of 8 mg of the compound twice a week. In some embodiments, the method comprises administering a loading dose of 40 mg of the compound daily for 8 days, followed by administering a maintenance dose of 8 mg of the compound twice a week. In some embodiments, the method comprises administering a loading dose of 40 mg of the compound daily for 9 days, followed by administering a maintenance dose of 8 mg of the compound twice a week. In some embodiments, the method comprises administering a loading dose of 40 mg of the compound daily for 10 days, followed by administering a maintenance dose of 8 mg of the compound twice a week. In some embodiments, the method comprises administering a loading dose of 50 mg of the compound daily for 3 days, followed by administering a maintenance dose of 8 mg of the compound twice a week. In some embodiments, the method comprises administering a loading dose of 50 mg of the compound daily for 4 days, followed by administering a maintenance dose of 8 mg of the compound twice a week. In some embodiments, the method comprises administering a loading dose of 50 mg of the compound daily for 5 days, followed by administering a maintenance dose of 8 mg of the compound twice a week. In some embodiments, the method comprises administering a loading dose of 50 mg of the compound daily for 6 days, followed by administering a maintenance dose of 8 mg of the compound twice a week. In some embodiments, the method comprises administering a loading dose of 50 mg of the compound daily for 7 days, followed by administering a maintenance dose of 8 mg of the compound twice a week.

In some embodiments, the method comprises administering a loading dose of 50 mg of the compound daily for 8 days, followed by administering a maintenance dose of 8 mg of the compound twice a week. In some embodiments, the method comprises administering a loading dose of 50 mg of the compound daily for 9 days, followed by administering a maintenance dose of 8 mg of the compound twice a week. In some embodiments, the method comprises administering a loading dose of 50 mg of the compound daily for 10 days, followed by administering a maintenance dose of 8 mg of the compound twice a week. In some embodiments, the method comprises administering a loading dose of 60 mg of the compound daily for 3 days, followed by administering a maintenance dose of 8 mg of the compound twice a week. In some embodiments, the method comprises administering a loading dose of 60 mg of the compound daily for 4 days, followed by administering a maintenance dose of 8 mg of the compound twice a week. In some embodiments, the method comprises administering a loading dose of 60 mg of the compound daily for 5 days, followed by administering a maintenance dose of 8 mg of the compound twice a week. In some embodiments, the method comprises administering a loading dose of 60 mg of the compound daily for 6 days, followed by administering a maintenance dose of 8 mg of the compound twice a week. In some embodiments, the method comprises administering a loading dose of 60 mg of the compound daily for 7 days, followed by administering a maintenance dose of 8 mg of the compound twice a week. In some embodiments, the method comprises administering a loading dose of 60 mg of the compound daily for 8 days, followed by administering a maintenance dose of 8 mg of the compound twice a week. In some embodiments, the method comprises administering a loading dose of 60 mg of the compound daily for 9 days, followed by administering a maintenance dose of 8 mg of the compound twice a week. In some embodiments, the method comprises administering a loading dose of 60 mg of the compound daily for 10 days, followed by administering a maintenance dose of 8 mg of the compound twice a week. In some embodiments, the method comprises administering a loading dose of 70 mg of the compound daily for 3 days, followed by administering a maintenance dose of 8 mg of the compound twice a week. In some embodiments, the method comprises administering a loading dose of 70 mg of the compound daily for 4 days, followed by administering a maintenance dose of 8 mg of the compound twice a week. In some embodiments, the method comprises administering a loading dose of 70 mg of the compound daily for 5 days, followed by administering a maintenance dose of 8 mg of the compound twice a week. In some embodiments, the method comprises administering a loading dose of 70 mg of the compound daily for 6 days, followed by administering a maintenance dose of 8 mg of the compound twice a week. In some embodiments, the method comprises administering a loading dose of 70 mg of the compound daily for 7 days, followed by administering a maintenance dose of 8 mg of the compound twice a week. In some embodiments, the method comprises administering a loading dose of 70 mg of the compound daily for 8 days, followed by administering a maintenance dose of 8 mg of the compound twice a week. In some embodiments, the method comprises administering a loading dose of 70 mg of the compound daily for 9 days, followed by administering a maintenance dose of 8 mg of the compound twice a week. In some embodiments, the method comprises administering a loading dose of 70 mg of the compound daily for 10 days, followed by administering a maintenance dose of 8 mg of the compound twice a week.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 10 mg of the compound twice a week. In some embodiments, the method comprises administering a loading dose of 25 mg of the compound daily for 4 days, followed by administering a maintenance dose of 10 mg of the compound twice a week. In some embodiments, the method comprises administering a loading dose of 25 mg of the compound daily for 5 days, followed by administering a maintenance dose of 10 mg of the compound twice a week. In some embodiments, the method comprises administering a loading dose of 25 mg of the compound daily for 6 days, followed by administering a maintenance dose of 10 mg of the compound twice a week. In some embodiments, the method comprises administering a loading dose of 25 mg of the compound daily for 7 days, followed by administering a maintenance dose of 10 mg of the compound twice a week. In some embodiments, the method comprises administering a loading dose of 25 mg of the compound daily for 8 days, followed by administering a maintenance dose of 10 mg of the compound twice a week. In some embodiments, the method comprises administering a loading dose of 25 mg of the compound daily for 9 days, followed by administering a maintenance dose of 10 mg of the compound twice a week. In some embodiments, the method comprises administering a loading dose of 25 mg of the compound daily for 10 days, followed by administering a maintenance dose of 10 mg of the compound twice a week. In some embodiments, the method comprises administering a loading dose of 30 mg of the compound daily for 3 days, followed by administering a maintenance dose of 10 mg of the compound twice a week. In some embodiments, the method comprises administering a loading dose of 30 mg of the compound daily for 4 days, followed by administering a maintenance dose of 10 mg of the compound twice a week. In some embodiments, the method comprises administering a loading dose of 30 mg of the compound daily for 5 days, followed by administering a maintenance dose of 10 mg of the compound twice a week. In some embodiments, the method comprises administering a loading dose of 30 mg of the compound daily for 6 days, followed by administering a maintenance dose of 10 mg of the compound twice a week. In some embodiments, the method comprises administering a loading dose of 30 mg of the compound daily for 7 days, followed by administering a maintenance dose of 10 mg of the compound twice a week. In some embodiments, the method comprises administering a loading dose of 30 mg of the compound daily for 8 days, followed by administering a maintenance dose of 10 mg of the compound twice a week. In some embodiments, the method comprises administering a loading dose of 30 mg of the compound daily for 9 days, followed by administering a maintenance dose of 10 mg of the compound twice a week. In some embodiments, the method comprises administering a loading dose of 30 mg of the compound daily for 10 days, followed by administering a maintenance dose of 10 mg of the compound twice a week. In some embodiments, the method comprises administering a loading dose of 40 mg of the compound daily for 3 days, followed by administering a maintenance dose of 10 mg of the compound twice a week. In some embodiments, the method comprises administering a loading dose of 40 mg of the compound daily for 4 days, followed by administering a maintenance dose of 10 mg of the compound twice a week. In some embodiments, the method comprises administering a loading dose of 40 mg of the compound daily for 5 days, followed by administering a maintenance dose of 10 mg of the compound twice a week. In some embodiments, the method comprises administering a loading dose of 40 mg of the compound daily for 6 days, followed by administering a maintenance dose of 10 mg of the compound twice a week. In some embodiments, the method comprises administering a loading dose of 40 mg of the compound daily for 7 days, followed by administering a maintenance dose of 10 mg of the compound twice a week. In some embodiments, the method comprises administering a loading dose of 40 mg of the compound daily for 8 days, followed by administering a maintenance dose of 10 mg of the compound twice a week. In some embodiments, the method comprises administering a loading dose of 40 mg of the compound daily for 9 days, followed by administering a maintenance dose of 10 mg of the compound twice a week. In some embodiments, the method comprises administering a loading dose of 40 mg of the compound daily for 10 days, followed by administering a maintenance dose of 10 mg of the compound twice a week. In some embodiments, the method comprises administering a loading dose of 50 mg of the compound daily for 3 days, followed by administering a maintenance dose of 10 mg of the compound twice a week. In some embodiments, the method comprises administering a loading dose of 50 mg of the compound daily for 4 days, followed by administering a maintenance dose of 10 mg of the compound twice a week. In some embodiments, the method comprises administering a loading dose of 50 mg of the compound daily for 5 days, followed by administering a maintenance dose of 10 mg of the compound twice a week. In some embodiments, the method comprises administering a loading dose of 50 mg of the compound daily for 6 days, followed by administering a maintenance dose of 10 mg of the compound twice a week. In some embodiments, the method comprises administering a loading dose of 50 mg of the compound daily for 7 days, followed by administering a maintenance dose of 10 mg of the compound twice a week. In some embodiments, the method comprises administering a loading dose of 50 mg of the compound daily for 8 days, followed by administering a maintenance dose of 10 mg of the compound twice a week. In some embodiments, the method comprises administering a loading dose of 50 mg of the compound daily for 9 days, followed by administering a maintenance dose of 10 mg of the compound twice a week. In some embodiments, the method comprises administering a loading dose of 50 mg of the compound daily for 10 days, followed by administering a maintenance dose of 10 mg of the compound twice a week. In some embodiments, the method comprises administering a loading dose of 60 mg of the compound daily for 3 days, followed by administering a maintenance dose of 10 mg of the compound twice a week. In some embodiments, the method comprises administering a loading dose of 60 mg of the compound daily for 4 days, followed by administering a maintenance dose of 10 mg of the compound twice a week. In some embodiments, the method comprises administering a loading dose of 60 mg of the compound daily for 5 days, followed by administering a maintenance dose of 10 mg of the compound twice a week. In some embodiments, the method comprises administering a loading dose of 60 mg of the compound daily for 6 days, followed by administering a maintenance dose of 10 mg of the compound twice a week. In some embodiments, the method comprises administering a loading dose of 60 mg of the compound daily for 7 days, followed by administering a maintenance dose of 10 mg of the compound twice a week. In some embodiments, the method comprises administering a loading dose of 60 mg of the compound daily for 8 days, followed by administering a maintenance dose of 10 mg of the compound twice a week. In some embodiments, the method comprises administering a loading dose of 60 mg of the compound daily for 9 days, followed by administering a maintenance dose of 10 mg of the compound twice a week. In some embodiments, the method comprises administering a loading dose of 60 mg of the compound daily for 10 days, followed by administering a maintenance dose of 10 mg of the compound twice a week. In some embodiments, the method comprises administering a loading dose of 70 mg of the compound daily for 3 days, followed by administering a maintenance dose of 10 mg of the compound twice a week. In some embodiments, the method comprises administering a loading dose of 70 mg of the compound daily for 4 days, followed by administering a maintenance dose of 10 mg of the compound twice a week. In some embodiments, the method comprises administering a loading dose of 70 mg of the compound daily for 5 days, followed by administering a maintenance dose of 10 mg of the compound twice a week. In some embodiments, the method comprises administering a loading dose of 70 mg of the compound daily for 6 days, followed by administering a maintenance dose of 10 mg of the compound twice a week. In some embodiments, the method comprises administering a loading dose of 70 mg of the compound daily for 7 days, followed by administering a maintenance dose of 10 mg of the compound twice a week. In some embodiments, the method comprises administering a loading dose of 70 mg of the compound daily for 8 days, followed by administering a maintenance dose of 10 mg of the compound twice a week. In some embodiments, the method comprises administering a loading dose of 70 mg of the compound daily for 9 days, followed by administering a maintenance dose of 10 mg of the compound twice a week. In some embodiments, the method comprises administering a loading dose of 70 mg of the compound daily for 10 days, followed by administering a maintenance dose of 10 mg of the compound twice a week.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 20 mg of the compound twice a week. In some embodiments, the method comprises administering a loading dose of 25 mg of the compound daily for 4 days, followed by administering a maintenance dose of 20 mg of the compound twice a week. In some embodiments, the method comprises administering a loading dose of 25 mg of the compound daily for 5 days, followed by administering a maintenance dose of 20 mg of the compound twice a week. In some embodiments, the method comprises administering a loading dose of 25 mg of the compound daily for 6 days, followed by administering a maintenance dose of 20 mg of the compound twice a week. In some embodiments, the method comprises administering a loading dose of 25 mg of the compound daily for 7 days, followed by administering a maintenance dose of 20 mg of the compound twice a week. In some embodiments, the method comprises administering a loading dose of 25 mg of the compound daily for 8 days, followed by administering a maintenance dose of 20 mg of the compound twice a week. In some embodiments, the method comprises administering a loading dose of 25 mg of the compound daily for 9 days, followed by administering a maintenance dose of 20 mg of the compound twice a week. In some embodiments, the method comprises administering a loading dose of 25 mg of the compound daily for 10 days, followed by administering a maintenance dose of 20 mg of the compound twice a week. In some embodiments, the method comprises administering a loading dose of 30 mg of the compound daily for 3 days, followed by administering a maintenance dose of 20 mg of the compound twice a week. In some embodiments, the method comprises administering a loading dose of 30 mg of the compound daily for 4 days, followed by administering a maintenance dose of 20 mg of the compound twice a week. In some embodiments, the method comprises administering a loading dose of 30 mg of the compound daily for 5 days, followed by administering a maintenance dose of 20 mg of the compound twice a week. In some embodiments, the method comprises administering a loading dose of 30 mg of the compound daily for 6 days, followed by administering a maintenance dose of 20 mg of the compound twice a week. In some embodiments, the method comprises administering a loading dose of 30 mg of the compound daily for 7 days, followed by administering a maintenance dose of 20 mg of the compound twice a week. In some embodiments, the method comprises administering a loading dose of 30 mg of the compound daily for 8 days, followed by administering a maintenance dose of 20 mg of the compound twice a week. In some embodiments, the method comprises administering a loading dose of 30 mg of the compound daily for 9 days, followed by administering a maintenance dose of 20 mg of the compound twice a week. In some embodiments, the method comprises administering a loading dose of 30 mg of the compound daily for 10 days, followed by administering a maintenance dose of 20 mg of the compound twice a week. In some embodiments, the method comprises administering a loading dose of 40 mg of the compound daily for 3 days, followed by administering a maintenance dose of 20 mg of the compound twice a week. In some embodiments, the method comprises administering a loading dose of 40 mg of the compound daily for 4 days, followed by administering a maintenance dose of 20 mg of the compound twice a week. In some embodiments, the method comprises administering a loading dose of 40 mg of the compound daily for 5 days, followed by administering a maintenance dose of 20 mg of the compound twice a week. In some embodiments, the method comprises administering a loading dose of 40 mg of the compound daily for 6 days, followed by administering a maintenance dose of 20 mg of the compound twice a week. In some embodiments, the method comprises administering a loading dose of 40 mg of the compound daily for 7 days, followed by administering a maintenance dose of 20 mg of the compound twice a week. In some embodiments, the method comprises administering a loading dose of 40 mg of the compound daily for 8 days, followed by administering a maintenance dose of 20 mg of the compound twice a week. In some embodiments, the method comprises administering a loading dose of 40 mg of the compound daily for 9 days, followed by administering a maintenance dose of 20 mg of the compound twice a week. In some embodiments, the method comprises administering a loading dose of 40 mg of the compound daily for 10 days, followed by administering a maintenance dose of 20 mg of the compound twice a week. In some embodiments, the method comprises administering a loading dose of 50 mg of the compound daily for 3 days, followed by administering a maintenance dose of 20 mg of the compound twice a week. In some embodiments, the method comprises administering a loading dose of 50 mg of the compound daily for 4 days, followed by administering a maintenance dose of 20 mg of the compound twice a week. In some embodiments, the method comprises administering a loading dose of 50 mg of the compound daily for 5 days, followed by administering a maintenance dose of 20 mg of the compound twice a week.

In some embodiments, the method comprises administering a loading dose of 50 mg of the compound daily for 6 days, followed by administering a maintenance dose of 20 mg of the compound twice a week. In some embodiments, the method comprises administering a loading dose of 50 mg of the compound daily for 7 days, followed by administering a maintenance dose of 20 mg of the compound twice a week. In some embodiments, the method comprises administering a loading dose of 50 mg of the compound daily for 8 days, followed by administering a maintenance dose of 20 mg of the compound twice a week. In some embodiments, the method comprises administering a loading dose of 50 mg of the compound daily for 9 days, followed by administering a maintenance dose of 20 mg of the compound twice a week. In some embodiments, the method comprises administering a loading dose of 50 mg of the compound daily for 10 days, followed by administering a maintenance dose of 20 mg of the compound twice a week. In some embodiments, the method comprises administering a loading dose of 60 mg of the compound daily for 3 days, followed by administering a maintenance dose of 20 mg of the compound twice a week. In some embodiments, the method comprises administering a loading dose of 60 mg of the compound daily for 4 days, followed by administering a maintenance dose of 20 mg of the compound twice a week. In some embodiments, the method comprises administering a loading dose of 60 mg of the compound daily for 5 days, followed by administering a maintenance dose of 20 mg of the compound twice a week. In some embodiments, the method comprises administering a loading dose of 60 mg of the compound daily for 6 days, followed by administering a maintenance dose of 20 mg of the compound twice a week. In some embodiments, the method comprises administering a loading dose of 60 mg of the compound daily for 7 days, followed by administering a maintenance dose of 20 mg of the compound twice a week. In some embodiments, the method comprises administering a loading dose of 60 mg of the compound daily for 8 days, followed by administering a maintenance dose of 20 mg of the compound twice a week. In some embodiments, the method comprises administering a loading dose of 60 mg of the compound daily for 9 days, followed by administering a maintenance dose of 20 mg of the compound twice a week. In some embodiments, the method comprises administering a loading dose of 60 mg of the compound daily for 10 days, followed by administering a maintenance dose of 20 mg of the compound twice a week. In some embodiments, the method comprises administering a loading dose of 70 mg of the compound daily for 3 days, followed by administering a maintenance dose of 20 mg of the compound twice a week. In some embodiments, the method comprises administering a loading dose of 70 mg of the compound daily for 4 days, followed by administering a maintenance dose of 20 mg of the compound twice a week. In some embodiments, the method comprises administering a loading dose of 70 mg of the compound daily for 5 days, followed by administering a maintenance dose of 20 mg of the compound twice a week. In some embodiments, the method comprises administering a loading dose of 70 mg of the compound daily for 6 days, followed by administering a maintenance dose of 20 mg of the compound twice a week. In some embodiments, the method comprises administering a loading dose of 70 mg of the compound daily for 7 days, followed by administering a maintenance dose of 20 mg of the compound twice a week. In some embodiments, the method comprises administering a loading dose of 70 mg of the compound daily for 8 days, followed by administering a maintenance dose of 20 mg of the compound twice a week. In some embodiments, the method comprises administering a loading dose of 70 mg of the compound daily for 9 days, followed by administering a maintenance dose of 20 mg of the compound twice a week. In some embodiments, the method comprises administering a loading dose of 70 mg of the compound daily for 10 days, followed by administering a maintenance dose of 20 mg of the compound twice a week.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 30 mg of the compound twice a week. In some embodiments, the method comprises administering a loading dose of 25 mg of the compound daily for 4 days, followed by administering a maintenance dose of 30 mg of the compound twice a week. In some embodiments, the method comprises administering a loading dose of 25 mg of the compound daily for 5 days, followed by administering a maintenance dose of 30 mg of the compound twice a week. In some embodiments, the method comprises administering a loading dose of 25 mg of the compound daily for 6 days, followed by administering a maintenance dose of 30 mg of the compound twice a week. In some embodiments, the method comprises administering a loading dose of 25 mg of the compound daily for 7 days, followed by administering a maintenance dose of 30 mg of the compound twice a week. In some embodiments, the method comprises administering a loading dose of 25 mg of the compound daily for 8 days, followed by administering a maintenance dose of 30 mg of the compound twice a week. In some embodiments, the method comprises administering a loading dose of 25 mg of the compound daily for 9 days, followed by administering a maintenance dose of 30 mg of the compound twice a week. In some embodiments, the method comprises administering a loading dose of 25 mg of the compound daily for 10 days, followed by administering a maintenance dose of 30 mg of the compound twice a week. In some embodiments, the method comprises administering a loading dose of 30 mg of the compound daily for 3 days, followed by administering a maintenance dose of 30 mg of the compound twice a week. In some embodiments, the method comprises administering a loading dose of 30 mg of the compound daily for 4 days, followed by administering a maintenance dose of 30 mg of the compound twice a week. In some embodiments, the method comprises administering a loading dose of 30 mg of the compound daily for 5 days, followed by administering a maintenance dose of 30 mg of the compound twice a week. In some embodiments, the method comprises administering a loading dose of 30 mg of the compound daily for 6 days, followed by administering a maintenance dose of 30 mg of the compound twice a week. In some embodiments, the method comprises administering a loading dose of 30 mg of the compound daily for 7 days, followed by administering a maintenance dose of 30 mg of the compound twice a week. In some embodiments, the method comprises administering a loading dose of 30 mg of the compound daily for 8 days, followed by administering a maintenance dose of 30 mg of the compound twice a week. In some embodiments, the method comprises administering a loading dose of 30 mg of the compound daily for 9 days, followed by administering a maintenance dose of 30 mg of the compound twice a week. In some embodiments, the method comprises administering a loading dose of 30 mg of the compound daily for 10 days, followed by administering a maintenance dose of 30 mg of the compound twice a week. In some embodiments, the method comprises administering a loading dose of 40 mg of the compound daily for 3 days, followed by administering a maintenance dose of 30 mg of the compound twice a week. In some embodiments, the method comprises administering a loading dose of 40 mg of the compound daily for 4 days, followed by administering a maintenance dose of 30 mg of the compound twice a week. In some embodiments, the method comprises administering a loading dose of 40 mg of the compound daily for 5 days, followed by administering a maintenance dose of 30 mg of the compound twice a week. In some embodiments, the method comprises administering a loading dose of 40 mg of the compound daily for 6 days, followed by administering a maintenance dose of 30 mg of the compound twice a week. In some embodiments, the method comprises administering a loading dose of 40 mg of the compound daily for 7 days, followed by administering a maintenance dose of 30 mg of the compound twice a week. In some embodiments, the method comprises administering a loading dose of 40 mg of the compound daily for 8 days, followed by administering a maintenance dose of 30 mg of the compound twice a week. In some embodiments, the method comprises administering a loading dose of 40 mg of the compound daily for 9 days, followed by administering a maintenance dose of 30 mg of the compound twice a week. In some embodiments, the method comprises administering a loading dose of 40 mg of the compound daily for 10 days, followed by administering a maintenance dose of 30 mg of the compound twice a week. In some embodiments, the method comprises administering a loading dose of 50 mg of the compound daily for 3 days, followed by administering a maintenance dose of 30 mg of the compound twice a week. In some embodiments, the method comprises administering a loading dose of 50 mg of the compound daily for 4 days, followed by administering a maintenance dose of 30 mg of the compound twice a week. In some embodiments, the method comprises administering a loading dose of 50 mg of the compound daily for 5 days, followed by administering a maintenance dose of 30 mg of the compound twice a week. In some embodiments, the method comprises administering a loading dose of 50 mg of the compound daily for 6 days, followed by administering a maintenance dose of 30 mg of the compound twice a week. In some embodiments, the method comprises administering a loading dose of 50 mg of the compound daily for 7 days, followed by administering a maintenance dose of 30 mg of the compound twice a week. In some embodiments, the method comprises administering a loading dose of 50 mg of the compound daily for 8 days, followed by administering a maintenance dose of 30 mg of the compound twice a week. In some embodiments, the method comprises administering a loading dose of 50 mg of the compound daily for 9 days, followed by administering a maintenance dose of 30 mg of the compound twice a week. In some embodiments, the method comprises administering a loading dose of 50 mg of the compound daily for 10 days, followed by administering a maintenance dose of 30 mg of the compound twice a week. In some embodiments, the method comprises administering a loading dose of 60 mg of the compound daily for 3 days, followed by administering a maintenance dose of 30 mg of the compound twice a week. In some embodiments, the method comprises administering a loading dose of 60 mg of the compound daily for 4 days, followed by administering a maintenance dose of 30 mg of the compound twice a week. In some embodiments, the method comprises administering a loading dose of 60 mg of the compound daily for 5 days, followed by administering a maintenance dose of 30 mg of the compound twice a week. In some embodiments, the method comprises administering a loading dose of 60 mg of the compound daily for 6 days, followed by administering a maintenance dose of 30 mg of the compound twice a week. In some embodiments, the method comprises administering a loading dose of 60 mg of the compound daily for 7 days, followed by administering a maintenance dose of 30 mg of the compound twice a week. In some embodiments, the method comprises administering a loading dose of 60 mg of the compound daily for 8 days, followed by administering a maintenance dose of 30 mg of the compound twice a week. In some embodiments, the method comprises administering a loading dose of 60 mg of the compound daily for 9 days, followed by administering a maintenance dose of 30 mg of the compound twice a week. In some embodiments, the method comprises administering a loading dose of 60 mg of the compound daily for 10 days, followed by administering a maintenance dose of 30 mg of the compound twice a week. In some embodiments, the method comprises administering a loading dose of 70 mg of the compound daily for 3 days, followed by administering a maintenance dose of 30 mg of the compound twice a week. In some embodiments, the method comprises administering a loading dose of 70 mg of the compound daily for 4 days, followed by administering a maintenance dose of 30 mg of the compound twice a week. In some embodiments, the method comprises administering a loading dose of 70 mg of the compound daily for 5 days, followed by administering a maintenance dose of 30 mg of the compound twice a week. In some embodiments, the method comprises administering a loading dose of 70 mg of the compound daily for 6 days, followed by administering a maintenance dose of 30 mg of the compound twice a week. In some embodiments, the method comprises administering a loading dose of 70 mg of the compound daily for 7 days, followed by administering a maintenance dose of 30 mg of the compound twice a week. In some embodiments, the method comprises administering a loading dose of 70 mg of the compound daily for 8 days, followed by administering a maintenance dose of 30 mg of the compound twice a week. In some embodiments, the method comprises administering a loading dose of 70 mg of the compound daily for 9 days, followed by administering a maintenance dose of 30 mg of the compound twice a week. In some embodiments, the method comprises administering a loading dose of 70 mg of the compound daily for 10 days, followed by administering a maintenance dose of 30 mg of the compound twice a week.

In some embodiments, the loading dose is administered from 1 day to 20 days, and the maintenance dose is administered from 20 days to 37000 days. In some embodiments, the method comprises administering a loading dose of 20 mg of the compound daily for 3 days, followed by administering a maintenance dose of 6 mg of the compound three times a week. In some embodiments, the method comprises administering a loading dose of 20 mg of the compound daily for 4 days, followed by administering a maintenance dose of 6 mg of the compound three times a week. In some embodiments, the method comprises administering a loading dose of 20 mg of the compound daily for 5 days, followed by administering a maintenance dose of 6 mg of the compound three times a week. In some embodiments, the method comprises administering a loading dose of 20 mg of the compound daily for 6 days, followed by administering a maintenance dose of 6 mg of the compound three times a week. In some embodiments, the method comprises administering a loading dose of 20 mg of the compound daily for 7 days, followed by administering a maintenance dose of 6 mg of the compound three times a week. In some embodiments, the method comprises administering a loading dose of 20 mg of the compound daily for 8 days, followed by administering a maintenance dose of 6 mg of the compound three times a week. In some embodiments, the method comprises administering a loading dose of 20 mg of the compound daily for 9 days, followed by administering a maintenance dose of 6 mg of the compound three times a week. In some embodiments, the method comprises administering a loading dose of 20 mg of the compound daily for 10 days, followed by administering a maintenance dose of 6 mg of the compound three times a week. In some embodiments, the method comprises administering a loading dose of 30 mg of the compound daily for 3 days, followed by administering a maintenance dose of 6 mg of the compound three times a week. In some embodiments, the method comprises administering a loading dose of 30 mg of the compound daily for 4 days, followed by administering a maintenance dose of 6 mg of the compound three times a week. In some embodiments, the method comprises administering a loading dose of 30 mg of the compound daily for 5 days, followed by administering a maintenance dose of 6 mg of the compound three times a week. In some embodiments, the method comprises administering a loading dose of 30 mg of the compound daily for 6 days, followed by administering a maintenance dose of 6 mg of the compound three times a week. In some embodiments, the method comprises administering a loading dose of 30 mg of the compound daily for 7 days, followed by administering a maintenance dose of 6 mg of the compound three times a week. In some embodiments, the method comprises administering a loading dose of 30 mg of the compound daily for 8 days, followed by administering a maintenance dose of 6 mg of the compound three times a week. In some embodiments, the method comprises administering a loading dose of 30 mg of the compound daily for 9 days, followed by administering a maintenance dose of 6 mg of the compound three times a week. In some embodiments, the method comprises administering a loading dose of 30 mg of the compound daily for 10 days, followed by administering a maintenance dose of 6 mg of the compound three times a week. In some embodiments, the method comprises administering a loading dose of 40 mg of the compound daily for 3 days, followed by administering a maintenance dose of 6 mg of the compound three times a week. In some embodiments, the method comprises administering a loading dose of 40 mg of the compound daily for 4 days, followed by administering a maintenance dose of 6 mg of the compound three times a week. In some embodiments, the method comprises administering a loading dose of 40 mg of the compound daily for 5 days, followed by administering a maintenance dose of 6 mg of the compound three times a week. In some embodiments, the method comprises administering a loading dose of 40 mg of the compound daily for 6 days, followed by administering a maintenance dose of 6 mg of the compound three times a week. In some embodiments, the method comprises administering a loading dose of 40 mg of the compound daily for 7 days, followed by administering a maintenance dose of 6 mg of the compound three times a week. In some embodiments, the method comprises administering a loading dose of 40 mg of the compound daily for 8 days, followed by administering a maintenance dose of 6 mg of the compound three times a week. In some embodiments, the method comprises administering a loading dose of 40 mg of the compound daily for 9 days, followed by administering a maintenance dose of 6 mg of the compound three times a week. In some embodiments, the method comprises administering a loading dose of 40 mg of the compound daily for 10 days, followed by administering a maintenance dose of 6 mg of the compound three times a week. In some embodiments, the method comprises administering a loading dose of 50 mg of the compound daily for 3 days, followed by administering a maintenance dose of 6 mg of the compound three times a week. In some embodiments, the method comprises administering a loading dose of 50 mg of the compound daily for 4 days, followed by administering a maintenance dose of 6 mg of the compound three times a week. In some embodiments, the method comprises administering a loading dose of 50 mg of the compound daily for 5 days, followed by administering a maintenance dose of 6 mg of the compound three times a week. In some embodiments, the method comprises administering a loading dose of 50 mg of the compound daily for 6 days, followed by administering a maintenance dose of 6 mg of the compound three times a week. In some embodiments, the method comprises administering a loading dose of 50 mg of the compound daily for 7 days, followed by administering a maintenance dose of 6 mg of the compound three times a week. In some embodiments, the method comprises administering a loading dose of 50 mg of the compound daily for 8 days, followed by administering a maintenance dose of 6 mg of the compound three times a week. In some embodiments, the method comprises administering a loading dose of 50 mg of the compound daily for 9 days, followed by administering a maintenance dose of 6 mg of the compound three times a week. In some embodiments, the method comprises administering a loading dose of 50 mg of the compound daily for 10 days, followed by administering a maintenance dose of 6 mg of the compound three times a week. In some embodiments, the method comprises administering a loading dose of 60 mg of the compound daily for 3 days, followed by administering a maintenance dose of 6 mg of the compound three times a week. In some embodiments, the method comprises administering a loading dose of 60 mg of the compound daily for 4 days, followed by administering a maintenance dose of 6 mg of the compound three times a week. In some embodiments, the method comprises administering a loading dose of 60 mg of the compound daily for 5 days, followed by administering a maintenance dose of 6 mg of the compound three times a week. In some embodiments, the method comprises administering a loading dose of 60 mg of the compound daily for 6 days, followed by administering a maintenance dose of 6 mg of the compound three times a week. In some embodiments, the method comprises administering a loading dose of 60 mg of the compound daily for 7 days, followed by administering a maintenance dose of 6 mg of the compound three times a week. In some embodiments, the method comprises administering a loading dose of 60 mg of the compound daily for 8 days, followed by administering a maintenance dose of 6 mg of the compound three times a week. In some embodiments, the method comprises administering a loading dose of 60 mg of the compound daily for 9 days, followed by administering a maintenance dose of 6 mg of the compound three times a week. In some embodiments, the method comprises administering a loading dose of 60 mg of the compound daily for 10 days, followed by administering a maintenance dose of 6 mg of the compound three times a week. In some embodiments, the method comprises administering a loading dose of 70 mg of the compound daily for 3 days, followed by administering a maintenance dose of 6 mg of the compound three times a week. In some embodiments, the method comprises administering a loading dose of 70 mg of the compound daily for 4 days, followed by administering a maintenance dose of 6 mg of the compound three times a week. In some embodiments, the method comprises administering a loading dose of 70 mg of the compound daily for 5 days, followed by administering a maintenance dose of 6 mg of the compound three times a week. In some embodiments, the method comprises administering a loading dose of 70 mg of the compound daily for 6 days, followed by administering a maintenance dose of 6 mg of the compound three times a week. In some embodiments, the method comprises administering a loading dose of 70 mg of the compound daily for 7 days, followed by administering a maintenance dose of 6 mg of the compound three times a week. In some embodiments, the method comprises administering a loading dose of 70 mg of the compound daily for 8 days, followed by administering a maintenance dose of 6 mg of the compound three times a week. In some embodiments, the method comprises administering a loading dose of 70 mg of the compound daily for 9 days, followed by administering a maintenance dose of 6 mg of the compound three times a week. In some embodiments, the method comprises administering a loading dose of 70 mg of the compound daily for 10 days, followed by administering a maintenance dose of 6 mg of the compound three times a week.

In some embodiments, the loading dose is administered from 1 day to 20 days, and the maintenance dose is administered from 20 days to 37000 days. In some embodiments, the method comprises administering a loading dose of 20 mg of the compound daily for 3 days, followed by administering a maintenance dose of 8 mg of the compound three times a week. In some embodiments, the method comprises administering a loading dose of 20 mg of the compound daily for 4 days, followed by administering a maintenance dose of 8 mg of the compound three times a week. In some embodiments, the method comprises administering a loading dose of 20 mg of the compound daily for 5 days, followed by administering a maintenance dose of 8 mg of the compound three times a week. In some embodiments, the method comprises administering a loading dose of 20 mg of the compound daily for 6 days, followed by administering a maintenance dose of 8 mg of the compound three times a week. In some embodiments, the method comprises administering a loading dose of 20 mg of the compound daily for 7 days, followed by administering a maintenance dose of 8 mg of the compound three times a week. In some embodiments, the method comprises administering a loading dose of 20 mg of the compound daily for 8 days, followed by administering a maintenance dose of 8 mg of the compound three times a week. In some embodiments, the method comprises administering a loading dose of 20 mg of the compound daily for 9 days, followed by administering a maintenance dose of 8 mg of the compound three times a week. In some embodiments, the method comprises administering a loading dose of 20 mg of the compound daily for 10 days, followed by administering a maintenance dose of 8 mg of the compound three times a week. In some embodiments, the method comprises administering a loading dose of 30 mg of the compound daily for 3 days, followed by administering a maintenance dose of 8 mg of the compound three times a week. In some embodiments, the method comprises administering a loading dose of 30 mg of the compound daily for 4 days, followed by administering a maintenance dose of 8 mg of the compound three times a week. In some embodiments, the method comprises administering a loading dose of 30 mg of the compound daily for 5 days, followed by administering a maintenance dose of 8 mg of the compound three times a week. In some embodiments, the method comprises administering a loading dose of 30 mg of the compound daily for 6 days, followed by administering a maintenance dose of 8 mg of the compound three times a week. In some embodiments, the method comprises administering a loading dose of 30 mg of the compound daily for 7 days, followed by administering a maintenance dose of 8 mg of the compound three times a week. In some embodiments, the method comprises administering a loading dose of 30 mg of the compound daily for 8 days, followed by administering a maintenance dose of 8 mg of the compound three times a week. In some embodiments, the method comprises administering a loading dose of 30 mg of the compound daily for 9 days, followed by administering a maintenance dose of 8 mg of the compound three times a week. In some embodiments, the method comprises administering a loading dose of 30 mg of the compound daily for 10 days, followed by administering a maintenance dose of 8 mg of the compound three times a week. In some embodiments, the method comprises administering a loading dose of 40 mg of the compound daily for 3 days, followed by administering a maintenance dose of 8 mg of the compound three times a week. In some embodiments, the method comprises administering a loading dose of 40 mg of the compound daily for 4 days, followed by administering a maintenance dose of 8 mg of the compound three times a week. In some embodiments, the method comprises administering a loading dose of 40 mg of the compound daily for 5 days, followed by administering a maintenance dose of 8 mg of the compound three times a week. In some embodiments, the method comprises administering a loading dose of 40 mg of the compound daily for 6 days, followed by administering a maintenance dose of 8 mg of the compound three times a week. In some embodiments, the method comprises administering a loading dose of 40 mg of the compound daily for 7 days, followed by administering a maintenance dose of 8 mg of the compound three times a week. In some embodiments, the method comprises administering a loading dose of 40 mg of the compound daily for 8 days, followed by administering a maintenance dose of 8 mg of the compound three times a week. In some embodiments, the method comprises administering a loading dose of 40 mg of the compound daily for 9 days, followed by administering a maintenance dose of 8 mg of the compound three times a week. In some embodiments, the method comprises administering a loading dose of 40 mg of the compound daily for 10 days, followed by administering a maintenance dose of 8 mg of the compound three times a week. In some embodiments, the method comprises administering a loading dose of 50 mg of the compound daily for 3 days, followed by administering a maintenance dose of 8 mg of the compound three times a week. In some embodiments, the method comprises administering a loading dose of 50 mg of the compound daily for 4 days, followed by administering a maintenance dose of 8 mg of the compound three times a week. In some embodiments, the method comprises administering a loading dose of 50 mg of the compound daily for 5 days, followed by administering a maintenance dose of 8 mg of the compound three times a week. In some embodiments, the method comprises administering a loading dose of 50 mg of the compound daily for 6 days, followed by administering a maintenance dose of 8 mg of the compound three times a week. In some embodiments, the method comprises administering a loading dose of 50 mg of the compound daily for 7 days, followed by administering a maintenance dose of 8 mg of the compound three times a week. In some embodiments, the method comprises administering a loading dose of 50 mg of the compound daily for 8 days, followed by administering a maintenance dose of 8 mg of the compound three times a week. In some embodiments, the method comprises administering a loading dose of 50 mg of the compound daily for 9 days, followed by administering a maintenance dose of 8 mg of the compound three times a week. In some embodiments, the method comprises administering a loading dose of 50 mg of the compound daily for 10 days, followed by administering a maintenance dose of 8 mg of the compound three times a week. In some embodiments, the method comprises administering a loading dose of 60 mg of the compound daily for 3 days, followed by administering a maintenance dose of 8 mg of the compound three times a week. In some embodiments, the method comprises administering a loading dose of 60 mg of the compound daily for 4 days, followed by administering a maintenance dose of 8 mg of the compound three times a week. In some embodiments, the method comprises administering a loading dose of 60 mg of the compound daily for 5 days, followed by administering a maintenance dose of 8 mg of the compound three times a week. In some embodiments, the method comprises administering a loading dose of 60 mg of the compound daily for 6 days, followed by administering a maintenance dose of 8 mg of the compound three times a week. In some embodiments, the method comprises administering a loading dose of 60 mg of the compound daily for 7 days, followed by administering a maintenance dose of 8 mg of the compound three times a week. In some embodiments, the method comprises administering a loading dose of 60 mg of the compound daily for 8 days, followed by administering a maintenance dose of 8 mg of the compound three times a week. In some embodiments, the method comprises administering a loading dose of 60 mg of the compound daily for 9 days, followed by administering a maintenance dose of 8 mg of the compound three times a week. In some embodiments, the method comprises administering a loading dose of 60 mg of the compound daily for 10 days, followed by administering a maintenance dose of 8 mg of the compound three times a week. In some embodiments, the method comprises administering a loading dose of 70 mg of the compound daily for 3 days, followed by administering a maintenance dose of 8 mg of the compound three times a week. In some embodiments, the method comprises administering a loading dose of 70 mg of the compound daily for 4 days, followed by administering a maintenance dose of 8 mg of the compound three times a week. In some embodiments, the method comprises administering a loading dose of 70 mg of the compound daily for 5 days, followed by administering a maintenance dose of 8 mg of the compound three times a week. In some embodiments, the method comprises administering a loading dose of 70 mg of the compound daily for 6 days, followed by administering a maintenance dose of 8 mg of the compound three times a week. In some embodiments, the method comprises administering a loading dose of 70 mg of the compound daily for 7 days, followed by administering a maintenance dose of 8 mg of the compound three times a week. In some embodiments, the method comprises administering a loading dose of 70 mg of the compound daily for 8 days, followed by administering a maintenance dose of 8 mg of the compound three times a week. In some embodiments, the method comprises administering a loading dose of 70 mg of the compound daily for 9 days, followed by administering a maintenance dose of 8 mg of the compound three times a week. In some embodiments, the method comprises administering a loading dose of 70 mg of the compound daily for 10 days, followed by administering a maintenance dose of 8 mg of the compound three times a week.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 10 mg of the compound three times a week. In some embodiments, the method comprises administering a loading dose of 25 mg of the compound daily for 4 days, followed by administering a maintenance dose of 10 mg of the compound three times a week. In some embodiments, the method comprises administering a loading dose of 25 mg of the compound daily for 5 days, followed by administering a maintenance dose of 10 mg of the compound three times a week. In some embodiments, the method comprises administering a loading dose of 25 mg of the compound daily for 6 days, followed by administering a maintenance dose of 10 mg of the compound three times a week. In some embodiments, the method comprises administering a loading dose of 25 mg of the compound daily for 7 days, followed by administering a maintenance dose of 10 mg of the compound three times a week. In some embodiments, the method comprises administering a loading dose of 25 mg of the compound daily for 8 days, followed by administering a maintenance dose of 10 mg of the compound three times a week. In some embodiments, the method comprises administering a loading dose of 25 mg of the compound daily for 9 days, followed by administering a maintenance dose of 10 mg of the compound three times a week. In some embodiments, the method comprises administering a loading dose of 25 mg of the compound daily for 10 days, followed by administering a maintenance dose of 10 mg of the compound three times a week. In some embodiments, the method comprises administering a loading dose of 30 mg of the compound daily for 3 days, followed by administering a maintenance dose of 10 mg of the compound three times a week. In some embodiments, the method comprises administering a loading dose of 30 mg of the compound daily for 4 days, followed by administering a maintenance dose of 10 mg of the compound three times a week. In some embodiments, the method comprises administering a loading dose of 30 mg of the compound daily for 5 days, followed by administering a maintenance dose of 10 mg of the compound three times a week. In some embodiments, the method comprises administering a loading dose of 30 mg of the compound daily for 6 days, followed by administering a maintenance dose of 10 mg of the compound three times a week. In some embodiments, the method comprises administering a loading dose of 30 mg of the compound daily for 7 days, followed by administering a maintenance dose of 10 mg of the compound three times a week. In some embodiments, the method comprises administering a loading dose of 30 mg of the compound daily for 8 days, followed by administering a maintenance dose of 10 mg of the compound three times a week. In some embodiments, the method comprises administering a loading dose of 30 mg of the compound daily for 9 days, followed by administering a maintenance dose of 10 mg of the compound three times a week. In some embodiments, the method comprises administering a loading dose of 30 mg of the compound daily for 10 days, followed by administering a maintenance dose of 10 mg of the compound three times a week. In some embodiments, the method comprises administering a loading dose of 40 mg of the compound daily for 3 days, followed by administering a maintenance dose of 10 mg of the compound three times a week. In some embodiments, the method comprises administering a loading dose of 40 mg of the compound daily for 4 days, followed by administering a maintenance dose of 10 mg of the compound three times a week. In some embodiments, the method comprises administering a loading dose of 40 mg of the compound daily for 5 days, followed by administering a maintenance dose of 10 mg of the compound three times a week. In some embodiments, the method comprises administering a loading dose of 40 mg of the compound daily for 6 days, followed by administering a maintenance dose of 10 mg of the compound three times a week. In some embodiments, the method comprises administering a loading dose of 40 mg of the compound daily for 7 days, followed by administering a maintenance dose of 10 mg of the compound three times a week. In some embodiments, the method comprises administering a loading dose of 40 mg of the compound daily for 8 days, followed by administering a maintenance dose of 10 mg of the compound three times a week. In some embodiments, the method comprises administering a loading dose of 40 mg of the compound daily for 9 days, followed by administering a maintenance dose of 10 mg of the compound three times a week. In some embodiments, the method comprises administering a loading dose of 40 mg of the compound daily for 10 days, followed by administering a maintenance dose of 10 mg of the compound three times a week. In some embodiments, the method comprises administering a loading dose of 50 mg of the compound daily for 3 days, followed by administering a maintenance dose of 10 mg of the compound three times a week. In some embodiments, the method comprises administering a loading dose of 50 mg of the compound daily for 4 days, followed by administering a maintenance dose of 10 mg of the compound three times a week. In some embodiments, the method comprises administering a loading dose of 50 mg of the compound daily for 5 days, followed by administering a maintenance dose of 10 mg of the compound three times a week. In some embodiments, the method comprises administering a loading dose of 50 mg of the compound daily for 6 days, followed by administering a maintenance dose of 10 mg of the compound three times a week. In some embodiments, the method comprises administering a loading dose of 50 mg of the compound daily for 7 days, followed by administering a maintenance dose of 10 mg of the compound three times a week. In some embodiments, the method comprises administering a loading dose of 50 mg of the compound daily for 8 days, followed by administering a maintenance dose of 10 mg of the compound three times a week. In some embodiments, the method comprises administering a loading dose of 50 mg of the compound daily for 9 days, followed by administering a maintenance dose of 10 mg of the compound three times a week. In some embodiments, the method comprises administering a loading dose of 50 mg of the compound daily for 10 days, followed by administering a maintenance dose of 10 mg of the compound three times a week. In some embodiments, the method comprises administering a loading dose of 60 mg of the compound daily for 3 days, followed by administering a maintenance dose of 10 mg of the compound three times a week. In some embodiments, the method comprises administering a loading dose of 60 mg of the compound daily for 4 days, followed by administering a maintenance dose of 10 mg of the compound three times a week. In some embodiments, the method comprises administering a loading dose of 60 mg of the compound daily for 5 days, followed by administering a maintenance dose of 10 mg of the compound three times a week. In some embodiments, the method comprises administering a loading dose of 60 mg of the compound daily for 6 days, followed by administering a maintenance dose of 10 mg of the compound three times a week. In some embodiments, the method comprises administering a loading dose of 60 mg of the compound daily for 7 days, followed by administering a maintenance dose of 10 mg of the compound three times a week. In some embodiments, the method comprises administering a loading dose of 60 mg of the compound daily for 8 days, followed by administering a maintenance dose of 10 mg of the compound three times a week. In some embodiments, the method comprises administering a loading dose of 60 mg of the compound daily for 9 days, followed by administering a maintenance dose of 10 mg of the compound three times a week. In some embodiments, the method comprises administering a loading dose of 60 mg of the compound daily for 10 days, followed by administering a maintenance dose of 10 mg of the compound three times a week. In some embodiments, the method comprises administering a loading dose of 70 mg of the compound daily for 3 days, followed by administering a maintenance dose of 10 mg of the compound three times a week. In some embodiments, the method comprises administering a loading dose of 70 mg of the compound daily for 4 days, followed by administering a maintenance dose of 10 mg of the compound three times a week. In some embodiments, the method comprises administering a loading dose of 70 mg of the compound daily for 5 days, followed by administering a maintenance dose of 10 mg of the compound three times a week. In some embodiments, the method comprises administering a loading dose of 70 mg of the compound daily for 6 days, followed by administering a maintenance dose of 10 mg of the compound three times a week. In some embodiments, the method comprises administering a loading dose of 70 mg of the compound daily for 7 days, followed by administering a maintenance dose of 10 mg of the compound three times a week. In some embodiments, the method comprises administering a loading dose of 70 mg of the compound daily for 8 days, followed by administering a maintenance dose of 10 mg of the compound three times a week. In some embodiments, the method comprises administering a loading dose of 70 mg of the compound daily for 9 days, followed by administering a maintenance dose of 10 mg of the compound three times a week. In some embodiments, the method comprises administering a loading dose of 70 mg of the compound daily for 10 days, followed by administering a maintenance dose of 10 mg of the compound three times a week.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 20 mg of the compound three times a week. In some embodiments, the method comprises administering a loading dose of 25 mg of the compound daily for 4 days, followed by administering a maintenance dose of 20 mg of the compound three times a week. In some embodiments, the method comprises administering a loading dose of 25 mg of the compound daily for 5 days, followed by administering a maintenance dose of 20 mg of the compound three times a week. In some embodiments, the method comprises administering a loading dose of 25 mg of the compound daily for 6 days, followed by administering a maintenance dose of 20 mg of the compound three times a week. In some embodiments, the method comprises administering a loading dose of 25 mg of the compound daily for 7 days, followed by administering a maintenance dose of 20 mg of the compound three times a week. In some embodiments, the method comprises administering a loading dose of 25 mg of the compound daily for 8 days, followed by administering a maintenance dose of 20 mg of the compound three times a week. In some embodiments, the method comprises administering a loading dose of 25 mg of the compound daily for 9 days, followed by administering a maintenance dose of 20 mg of the compound three times a week. In some embodiments, the method comprises administering a loading dose of 25 mg of the compound daily for 10 days, followed by administering a maintenance dose of 20 mg of the compound three times a week. In some embodiments, the method comprises administering a loading dose of 30 mg of the compound daily for 3 days, followed by administering a maintenance dose of 20 mg of the compound three times a week. In some embodiments, the method comprises administering a loading dose of 30 mg of the compound daily for 4 days, followed by administering a maintenance dose of 20 mg of the compound three times a week. In some embodiments, the method comprises administering a loading dose of 30 mg of the compound daily for 5 days, followed by administering a maintenance dose of 20 mg of the compound three times a week. In some embodiments, the method comprises administering a loading dose of 30 mg of the compound daily for 6 days, followed by administering a maintenance dose of 20 mg of the compound three times a week. In some embodiments, the method comprises administering a loading dose of 30 mg of the compound daily for 7 days, followed by administering a maintenance dose of 20 mg of the compound three times a week. In some embodiments, the method comprises administering a loading dose of 30 mg of the compound daily for 8 days, followed by administering a maintenance dose of 20 mg of the compound three times a week. In some embodiments, the method comprises administering a loading dose of 30 mg of the compound daily for 9 days, followed by administering a maintenance dose of 20 mg of the compound three times a week. In some embodiments, the method comprises administering a loading dose of 30 mg of the compound daily for 10 days, followed by administering a maintenance dose of 20 mg of the compound three times a week. In some embodiments, the method comprises administering a loading dose of 40 mg of the compound daily for 3 days, followed by administering a maintenance dose of 20 mg of the compound three times a week. In some embodiments, the method comprises administering a loading dose of 40 mg of the compound daily for 4 days, followed by administering a maintenance dose of 20 mg of the compound three times a week. In some embodiments, the method comprises administering a loading dose of 40 mg of the compound daily for 5 days, followed by administering a maintenance dose of 20 mg of the compound three times a week. In some embodiments, the method comprises administering a loading dose of 40 mg of the compound daily for 6 days, followed by administering a maintenance dose of 20 mg of the compound three times a week. In some embodiments, the method comprises administering a loading dose of 40 mg of the compound daily for 7 days, followed by administering a maintenance dose of 20 mg of the compound three times a week. In some embodiments, the method comprises administering a loading dose of 40 mg of the compound daily for 8 days, followed by administering a maintenance dose of 20 mg of the compound three times a week. In some embodiments, the method comprises administering a loading dose of 40 mg of the compound daily for 9 days, followed by administering a maintenance dose of 20 mg of the compound three times a week. In some embodiments, the method comprises administering a loading dose of 40 mg of the compound daily for 10 days, followed by administering a maintenance dose of 20 mg of the compound three times a week. In some embodiments, the method comprises administering a loading dose of 50 mg of the compound daily for 3 days, followed by administering a maintenance dose of 20 mg of the compound three times a week. In some embodiments, the method comprises administering a loading dose of 50 mg of the compound daily for 4 days, followed by administering a maintenance dose of 20 mg of the compound three times a week. In some embodiments, the method comprises administering a loading dose of 50 mg of the compound daily for 5 days, followed by administering a maintenance dose of 20 mg of the compound three times a week. In some embodiments, the method comprises administering a loading dose of 50 mg of the compound daily for 6 days, followed by administering a maintenance dose of 20 mg of the compound three times a week. In some embodiments, the method comprises administering a loading dose of 50 mg of the compound daily for 7 days, followed by administering a maintenance dose of 20 mg of the compound three times a week. In some embodiments, the method comprises administering a loading dose of 50 mg of the compound daily for 8 days, followed by administering a maintenance dose of 20 mg of the compound three times a week. In some embodiments, the method comprises administering a loading dose of 50 mg of the compound daily for 9 days, followed by administering a maintenance dose of 20 mg of the compound three times a week. In some embodiments, the method comprises administering a loading dose of 50 mg of the compound daily for 10 days, followed by administering a maintenance dose of 20 mg of the compound three times a week. In some embodiments, the method comprises administering a loading dose of 60 mg of the compound daily for 3 days, followed by administering a maintenance dose of 20 mg of the compound three times a week. In some embodiments, the method comprises administering a loading dose of 60 mg of the compound daily for 4 days, followed by administering a maintenance dose of 20 mg of the compound three times a week. In some embodiments, the method comprises administering a loading dose of 60 mg of the compound daily for 5 days, followed by administering a maintenance dose of 20 mg of the compound three times a week. In some embodiments, the method comprises administering a loading dose of 60 mg of the compound daily for 6 days, followed by administering a maintenance dose of 20 mg of the compound three times a week. In some embodiments, the method comprises administering a loading dose of 60 mg of the compound daily for 7 days, followed by administering a maintenance dose of 20 mg of the compound three times a week. In some embodiments, the method comprises administering a loading dose of 60 mg of the compound daily for 8 days, followed by administering a maintenance dose of 20 mg of the compound three times a week. In some embodiments, the method comprises administering a loading dose of 60 mg of the compound daily for 9 days, followed by administering a maintenance dose of 20 mg of the compound three times a week. In some embodiments, the method comprises administering a loading dose of 60 mg of the compound daily for 10 days, followed by administering a maintenance dose of 20 mg of the compound three times a week. In some embodiments, the method comprises administering a loading dose of 70 mg of the compound daily for 3 days, followed by administering a maintenance dose of 20 mg of the compound three times a week. In some embodiments, the method comprises administering a loading dose of 70 mg of the compound daily for 4 days, followed by administering a maintenance dose of 20 mg of the compound three times a week. In some embodiments, the method comprises administering a loading dose of 70 mg of the compound daily for 5 days, followed by administering a maintenance dose of 20 mg of the compound three times a week. In some embodiments, the method comprises administering a loading dose of 70 mg of the compound daily for 6 days, followed by administering a maintenance dose of 20 mg of the compound three times a week. In some embodiments, the method comprises administering a loading dose of 70 mg of the compound daily for 7 days, followed by administering a maintenance dose of 20 mg of the compound three times a week. In some embodiments, the method comprises administering a loading dose of 70 mg of the compound daily for 8 days, followed by administering a maintenance dose of 20 mg of the compound three times a week. In some embodiments, the method comprises administering a loading dose of 70 mg of the compound daily for 9 days, followed by administering a maintenance dose of 20 mg of the compound three times a week. In some embodiments, the method comprises administering a loading dose of 70 mg of the compound daily for 10 days, followed by administering a maintenance dose of 20 mg of the compound three times a week.

In some embodiments, the loading dose is administered from 1 day to 20 days, and the maintenance dose is administered from 20 days to 37000 days. In some embodiments, the method comprises administering a loading dose of 25 mg of the compound daily for 3 days, followed by administering a maintenance dose of 30 mg of the compound three times a week. In some embodiments, the method comprises administering a loading dose of 25 mg of the compound daily for 4 days, followed by administering a maintenance dose of 30 mg of the compound three times a week. In some embodiments, the method comprises administering a loading dose of 25 mg of the compound daily for 5 days, followed by administering a maintenance dose of 30 mg of the compound three times a week. In some embodiments, the method comprises administering a loading dose of 25 mg of the compound daily for 6 days, followed by administering a maintenance dose of 30 mg of the compound three times a week. In some embodiments, the method comprises administering a loading dose of 25 mg of the compound daily for 7 days, followed by administering a maintenance dose of 30 mg of the compound three times a week. In some embodiments, the method comprises administering a loading dose of 25 mg of the compound daily for 8 days, followed by administering a maintenance dose of 30 mg of the compound three times a week. In some embodiments, the method comprises administering a loading dose of 25 mg of the compound daily for 9 days, followed by administering a maintenance dose of 30 mg of the compound three times a week. In some embodiments, the method comprises administering a loading dose of 25 mg of the compound daily for 10 days, followed by administering a maintenance dose of 30 mg of the compound three times a week. In some embodiments, the method comprises administering a loading dose of 30 mg of the compound daily for 3 days, followed by administering a maintenance dose of 30 mg of the compound three times a week. In some embodiments, the method comprises administering a loading dose of 30 mg of the compound daily for 4 days, followed by administering a maintenance dose of 30 mg of the compound three times a week. In some embodiments, the method comprises administering a loading dose of 30 mg of the compound daily for 5 days, followed by administering a maintenance dose of 30 mg of the compound three times a week. In some embodiments, the method comprises administering a loading dose of 30 mg of the compound daily for 6 days, followed by administering a maintenance dose of 30 mg of the compound three times a week. In some embodiments, the method comprises administering a loading dose of 30 mg of the compound daily for 7 days, followed by administering a maintenance dose of 30 mg of the compound three times a week. In some embodiments, the method comprises administering a loading dose of 30 mg of the compound daily for 8 days, followed by administering a maintenance dose of 30 mg of the compound three times a week. In some embodiments, the method comprises administering a loading dose of 30 mg of the compound daily for 9 days, followed by administering a maintenance dose of 30 mg of the compound three times a week. In some embodiments, the method comprises administering a loading dose of 30 mg of the compound daily for 10 days, followed by administering a maintenance dose of 30 mg of the compound three times a week. In some embodiments, the method comprises administering a loading dose of 40 mg of the compound daily for 3 days, followed by administering a maintenance dose of 30 mg of the compound three times a week. In some embodiments, the method comprises administering a loading dose of 40 mg of the compound daily for 4 days, followed by administering a maintenance dose of 30 mg of the compound three times a week. In some embodiments, the method comprises administering a loading dose of 40 mg of the compound daily for 5 days, followed by administering a maintenance dose of 30 mg of the compound three times a week. In some embodiments, the method comprises administering a loading dose of 40 mg of the compound daily for 6 days, followed by administering a maintenance dose of 30 mg of the compound three times a week. In some embodiments, the method comprises administering a loading dose of 40 mg of the compound daily for 7 days, followed by administering a maintenance dose of 30 mg of the compound three times a week. In some embodiments, the method comprises administering a loading dose of 40 mg of the compound daily for 8 days, followed by administering a maintenance dose of 30 mg of the compound three times a week. In some embodiments, the method comprises administering a loading dose of 40 mg of the compound daily for 9 days, followed by administering a maintenance dose of 30 mg of the compound three times a week. In some embodiments, the method comprises administering a loading dose of 40 mg of the compound daily for 10 days, followed by administering a maintenance dose of 30 mg of the compound three times a week. In some embodiments, the method comprises administering a loading dose of 50 mg of the compound daily for 3 days, followed by administering a maintenance dose of 30 mg of the compound three times a week. In some embodiments, the method comprises administering a loading dose of 50 mg of the compound daily for 4 days, followed by administering a maintenance dose of 30 mg of the compound three times a week. In some embodiments, the method comprises administering a loading dose of 50 mg of the compound daily for 5 days, followed by administering a maintenance dose of 30 mg of the compound three times a week. In some embodiments, the method comprises administering a loading dose of 50 mg of the compound daily for 6 days, followed by administering a maintenance dose of 30 mg of the compound three times a week. In some embodiments, the method comprises administering a loading dose of 50 mg of the compound daily for 7 days, followed by administering a maintenance dose of 30 mg of the compound three times a week. In some embodiments, the method comprises administering a loading dose of 50 mg of the compound daily for 8 days, followed by administering a maintenance dose of 30 mg of the compound three times a week. In some embodiments, the method comprises administering a loading dose of 50 mg of the compound daily for 9 days, followed by administering a maintenance dose of 30 mg of the compound three times a week. In some embodiments, the method comprises administering a loading dose of 50 mg of the compound daily for 10 days, followed by administering a maintenance dose of 30 mg of the compound three times a week. In some embodiments, the method comprises administering a loading dose of 60 mg of the compound daily for 3 days, followed by administering a maintenance dose of 30 mg of the compound three times a week. In some embodiments, the method comprises administering a loading dose of 60 mg of the compound daily for 4 days, followed by administering a maintenance dose of 30 mg of the compound v a week. In some embodiments, the method comprises administering a loading dose of 60 mg of the compound daily for 5 days, followed by administering a maintenance dose of 30 mg of the compound v a week. In some embodiments, the method comprises administering a loading dose of 60 mg of the compound daily for 6 days, followed by administering a maintenance dose of 30 mg of the compound three times a week. In some embodiments, the method comprises administering a loading dose of 60 mg of the compound daily for 7 days, followed by administering a maintenance dose of 30 mg of the compound three times a week. In some embodiments, the method comprises administering a loading dose of 60 mg of the compound daily for 8 days, followed by administering a maintenance dose of 30 mg of the compound three times a week. In some embodiments, the method comprises administering a loading dose of 60 mg of the compound daily for 9 days, followed by administering a maintenance dose of 30 mg of the compound three times a week. In some embodiments, the method comprises administering a loading dose of 60 mg of the compound daily for 10 days, followed by administering a maintenance dose of 30 mg of the compound three times a week. In some embodiments, the method comprises administering a loading dose of 70 mg of the compound daily for 3 days, followed by administering a maintenance dose of 30 mg of the compound three times a week. In some embodiments, the method comprises administering a loading dose of 70 mg of the compound daily for 4 days, followed by administering a maintenance dose of 30 mg of the compound three times a week. In some embodiments, the method comprises administering a loading dose of 70 mg of the compound daily for 5 days, followed by administering a maintenance dose of 30 mg of the compound three times a week. In some embodiments, the method comprises administering a loading dose of 70 mg of the compound daily for 6 days, followed by administering a maintenance dose of 30 mg of the compound three times a week. In some embodiments, the method comprises administering a loading dose of 70 mg of the compound daily for 7 days, followed by administering a maintenance dose of 30 mg of the compound three times a week. In some embodiments, the method comprises administering a loading dose of 70 mg of the compound daily for 8 days, followed by administering a maintenance dose of 30 mg of the compound three times a week. In some embodiments, the method comprises administering a loading dose of 70 mg of the compound daily for 9 days, followed by administering a maintenance dose of 30 mg of the compound three times a week. In some embodiments, the method comprises administering a loading dose of 70 mg of the compound daily for 10 days, followed by administering a maintenance dose of 30 mg of the compound three times a week.

In some embodiments, such a disclosed method may further comprise administering an additional loading dose during a third time period, (e.g., after an initial load and maintenance dose time period).

A disclosed method may further include administering an additional maintenance dose during a fourth time period (for example, as a part of another dose cycle after an initial load and an initial maintenance dose time). In some embodiments, a third and/or fourth time period occurs after the first and second time period.

In such disclosed methods, after 1 month or more of administration, a patient may have an improved tumor response as measured by ultrasound, CT, MRI and/or PET Scan using either RECIST 1.1 and/or volumetric assessment. In some embodiments, after 7 days, after 10 days, after 15 days, after 20 days, after 25 day, or more of administration of the compound, a patient has an improved range of motion and other symptoms disease-related such as patient-reported symptoms. In some embodiments, after 1 month, after 2 months, or more of administration of the compound, a patient has an improved range of motion and other symptoms disease-related such as patient-reported symptoms. In some embodiments, after 1 month or more of administration of the compound to the patient, the patient may have a reduced macrophage infiltration in the affected joint and/or circulating chemokine/cytokines associated with inflammation as compared to the amounts before administration. In some embodiments, the size of the tenosynovial giant cell tumor, e.g., DTGCT, decreases to 99% to 1%, e.g., 90% to 10%, e.g., 85% to 20%, e.g., 80% to 25%, e.g., 75% to 25%, e.g., 70% to 30%, e.g., 65% to 35%, e.g., 60% to 40%, e.g., 55% to 45%, e.g., 80% to 60% of its size prior to administration of the compound.

In some embodiments, the administration of Compound 1 or a pharmaceutically acceptable salt thereof is a continuous administration without a drug holiday. In some embodiments, Compound 1 or a pharmaceutically acceptable salt thereof is administered continuously over a period of time from 1 day to 100 years. In some embodiments, Compound 1 or a pharmaceutically acceptable salt thereof is administered with a drug holiday. In some embodiments, administration of Compound 1 or a pharmaceutically acceptable salt thereof is continuous for a period from 1 day to 5 years, followed by a drug holiday from 1 month to 5 years, followed by continuous administration of the Compound 1 or a pharmaceutically acceptable salt thereof for a period from 1 day to 100 years. In some embodiments, administration of Compound 1 or a pharmaceutically acceptable salt thereof is continuous for a period from 1 month to 5 years, followed by a drug holiday from 1 month to 5 years, followed by continuous administration of the Compound 1 or a pharmaceutically acceptable salt thereof for a period from 1 day to 100 years. In some embodiments, administration of Compound 1 or a pharmaceutically acceptable salt thereof is continuous for a period from 3 months to 5 years, followed by a drug holiday from 1 month to 5 years, followed by continuous administration of the Compound 1 or a pharmaceutically acceptable salt thereof for a period from 1 day to 100 years. In some embodiments, administration of Compound 1 or a pharmaceutically acceptable salt thereof is continuous for a period from 6 months to 5 years, followed by a drug holiday from 1 month to 5 years, followed by continuous administration of the Compound 1 or a pharmaceutically acceptable salt thereof for a period from 1 day to 100 years. In some embodiments, administration of Compound 1 or a pharmaceutically acceptable salt thereof is continuous for a period from 1 year to 5 years, followed by a drug holiday from 1 month to 5 years, followed by continuous administration of the Compound 1 or a pharmaceutically acceptable salt thereof for a period from 1 day to 100 years. In some embodiments, administration of Compound 1 or a pharmaceutically acceptable salt thereof is continuous for a period from 2 years to 5 years, followed by a drug holiday from 1 month to 5 years, followed by continuous administration of the Compound 1 or a pharmaceutically acceptable salt thereof for a period from 1 day to 100 years. In some embodiments, administration of Compound 1 or a pharmaceutically acceptable salt thereof is continuous for a period from 3 years to 5 years, followed by a drug holiday from 1 month to 5 years, followed by continuous administration of the Compound 1 or a pharmaceutically acceptable salt thereof for a period from 1 day to 100 years.

The disclosure contemplates administration of Compound 1 or a pharmaceutically acceptable salt to a patient in need thereof prior (neo-adjuvant) or after (adjuvant) surgery (e.g., surgical treatment of TGCT). In some embodiments, Compound 1 or a pharmaceutically acceptable salt is administered as an adjuvant. In some embodiments, Compound 1 or a pharmaceutically acceptable salt is administered as a neo-adjuvant. In some embodiments, Compound 1 or a pharmaceutically acceptable salt is administered as a neo-adjuvant and an adjuvant. In some embodiments, Compound 1 or a pharmaceutically acceptable salt is administered to a patient in need thereof as a neo-adjuvant for a period of 1 month to 6 months, followed by administration of Compound 1 or a pharmaceutically acceptable salt as an adjuvant for a period from 1 day to 100 years. In some embodiments, administration of Compound 1 or a pharmaceutically acceptable salt is administered to a patient in need thereof as a neo-adjuvant for a period of 1 month to 6 months, followed by administration of Compound 1 or a pharmaceutically acceptable salt as an adjuvant for a period from 1 day to 5 years. In some embodiments, administration of Compound 1 or a pharmaceutically acceptable salt is administered to a patient in need thereof as a neo-adjuvant for a period of 3 months to 6 months, followed by administration of Compound 1 or a pharmaceutically acceptable salt as an adjuvant for a period from 1 day to 5 years. In some embodiments, no administration of Compound 1 or a pharmaceutically acceptable salt occurs prior to surgery. In some embodiments, Compound 1 or a pharmaceutically acceptable salt is administered as an adjuvant for a period from 1 day to 100 years. In some embodiments, Compound 1 or a pharmaceutically acceptable salt is administered as an adjuvant for a period from 1 day to 5 years.

The disclosure also contemplates a method of treating tumors, e.g., GCTTS, PVNS, TGCT or DTGCT, comprising administering to the patient a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof prior to surgery. In some embodiments, administering comprises administering a loading dose of the compound daily for a first time period; and administering a maintenance dose of the compound once a week, twice a week, or three times a week for a second time period.

The disclosure also contemplates a method of treating a cancer such as those selected from the group consisting of solid tumors, acute myeloid leukemia, myelodysplastic syndrome, acute lymphocytic leukemia, and chronic lymphocytic leukemia, in a patient in need thereof (e.g., a human patient suffering from cancer), comprising administering to the patient a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof, wherein administering comprises: administering a loading dose of the compound daily for a first time period; and administering a maintenance dose of the compound daily, twice a week, or three times a week for a second time period. In some embodiments, a patient may be suffering from a solid tumor such as one of breast, cervix, pancreas, bladder, prostate, gastric, ovarian, melanoma, glioma, glioblastoma multiforme, osteosarcoma, osteolytic cancers, chondrosarcoma, histiocytosis, or lung cancer. In some embodiments, the breast cancer is ductal carcinoma in situ (DCIS). In some embodiments, the breast cancer is invasive (or infiltrating) breast cancer (ILC or IDC). In some embodiments, the breast cancer is invasive ductal carcinoma. In some embodiments, the breast cancer is invasive lobular carcinoma. In some embodiments, the pancreatic cancer is an exocrine pancreatic cancer. In some embodiments, the exocrine pancreatic cancer is pancreatic adenocarcinoma. In some embodiments, the exocrine pancreatic cancer is pancreatic ductal adenocarcinoma (PDAC). In some embodiments, the pancreatic cancer is pancreatic adenocarcinoma. In some embodiments, the pancreatic cancer is pancreatic ductal adenocarcinoma (PDAC). In some embodiments, pancreatic cancer is a pancreatic neuroendocrine tumor (PanNET).

Myeloid or white blood cells progenitor or stem cells can differentiate into blood monocytes and to tissue macrophages. Macrophages can further differentiate into liver Kupffer cells, alveolar macrophages, bone osteoclasts and histiocytes. Histiocytic disorders are a group of diseases that occur when there is an over-production of white blood cells known as histiocytes leading to organ damage and tumor formation. Histiocytic disorders comprise a wide variety of conditions that can affect both children and adults. There exist several groups of histiocytic disorders based on the types of histiocyte cells involved. In some embodiments, a histiocytic disorder is a dendritic cell disorder. In some embodiments, the dendritic cell disorder is Langerhans cell histiocytosis. In some embodiments, the dendritic cell disorder is juvenile xanthogranuloma. In some embodiments, the dendritic cell disorder is Erdheim-Chester Disease. In some embodiments, a histiocytic disorder is a macrophage cell disorder. In some embodiments, the macrophage cell disorder is hemophagocytic lymphohistiocytosis (HLH). In some embodiments, the macrophage cell disorder is Rosai-Dorfman Disease. In some embodiments, a histiocytic disorder is malignant histiocytosis. In some embodiments, malignant histiocytosis is certain kinds of leukemia or malignant tumors. Recently, recurrent disease causing (driver) activating mutations in receptor tyrosine kinase such as CSF1R (required for monocyte and macrophage development), have been characterized. CSF1R therapeutic target inhibition in histiocytosis can be possible as shown in preclinical models where CSF1R-activating alterations sensitized cells to the CSF1R-specific small-molecule inhibitors pexidartinib and BLZ945.

The expression of CSF1R and its ligand CSF1 have been demonstrated in the human chondrosarcoma cell line SW1353 (Am J Cancer Res 2017; 7(4):801-815). This cell line expresses both CSF1R receptors and the ligand CSF1, indicating an autocrine activation of this chondrosarcoma cell line. Further, silencing of CSF1R receptor kinase with shRNA in this cell line led to a significant reduction of tumor volume in a mouse in vivo xenograft model. Conversely, genetic modification that led to over-expression of CSF1R in this sarcoma cell line led to enhanced tumor growth in vivo. CSF1R overexpression significantly enhanced SW1353 cell migration, invasion, and epithelial-mesenchymal transition (EMT), whereas silencing CSF1R inhibits these processes. These results suggest that certain human chondrosarcomas expressing CSF1R could be treated with CSF1R inhibitors to inhibit tumor growth and/or inhibit invasion and metastasis.

For example, a disclosed method such as a method of treating a cancer may include administering about 10 mg to about 90 mg of a disclosed compound daily, twice a week, or three times a week to the patient in need thereof. In some embodiments, a method of treating a cancer may include administering about 5 mg to about 70 mg of a disclosed compound daily, twice a week, or three times a week to the patient in need thereof. In some embodiments, a method of treating a cancer may include administering about 5 mg to about 50 mg of a disclosed compound daily, twice a week, or three times a week to the patient in need thereof. In some embodiments, a method of treating a cancer may include administering about 5 mg to about 30 mg of a disclosed compound daily, twice a week, or three times a week to the patient in need thereof. In some embodiments, a method of treating a cancer may include administering about 6 mg to about 25 mg of a disclosed compound daily, twice a week, or three times a week to the patient in need thereof. In some embodiments, a method of treating a cancer may include administering about 6 mg to about 20 mg of a disclosed compound daily, twice a week, or three times a week to the patient in need thereof. In some embodiments, a method of treating a cancer may include administering about 20 mg to about 50 mg of a disclosed compound daily, twice a week, or three times a week to the patient in need thereof.

Such a disclosed method may include, in an embodiment, administering a loading dose of the compound daily for a first time period; and administering a maintenance dose of the compound daily, once a week, twice a week or three times a week for a second time period. For example, a loading dose may be about 10 mg/day to about 80 mg/day, or about 20 mg/day to about 60 mg/day. In some embodiments, the loading dose is about 20 mg/day, about 30 mg/day, about 40 mg/day, about 50 mg/day or about 60 mg/day. In some embodiments, the maintenance dose of the compound is about 6 mg/day, 7 mg/day, 8 mg/day, 9 mg/day, 10 mg/day, 11 mg/day, 12 mg/day, 13 mg/day, 14 mg/day, 15 mg/day, 16 mg/day, 17 mg/day, 18 mg/day, 19 mg/day, 20 mg/day, 21 mg/day, 22 mg/day, 23 mg/day, 24 mg/day, 26 mg/day, 27 mg/day, 28 mg/day, 29 mg/day, or 30 mg/day.

Administering a maintenance dose may include administering to the patient about 10 mg to about 60 mg of the compound, e.g., about 10 mg, about 20 mg, about 25 mg, about 30 mg, about 40 mg or about 50 mg, which may be each administered once, twice or three times a week.

In some embodiments, the maintenance dose may include administering to the patient about 2 mg to about 40 mg of the compound once a week. In some embodiments, the maintenance dose may include administering to the patient about 2 mg to about 30 mg of the compound once a week. In some embodiments, the maintenance dose may include administering to the patient about 2 mg to about 20 mg of the compound once a week. In some embodiments, the maintenance dose may include administering to the patient about 5 mg to about 40 mg of the compound once a week. In some embodiments, the maintenance dose may include administering to the patient about 5 mg to about 30 mg of the compound once a week. In some embodiments, the maintenance dose may include administering to the patient about 5 mg to about 20 mg of the compound once a week. In some embodiments, the maintenance dose may include administering to the patient about 6 mg to about 40 mg of the compound once a week. In some embodiments, the maintenance dose may include administering to the patient about 6 mg to about 30 mg of the compound once a week. In some embodiments, the maintenance dose may include administering to the patient about 6 mg to about 20 mg of the compound once a week. In some embodiments, the maintenance dose may include administering to the patient about 10 mg to about 40 mg of the compound once a week. In some embodiments, the maintenance dose may include administering to the patient about 10 mg to about 30 mg of the compound once a week. In some embodiments, the maintenance dose may include administering to the patient about 10 mg to about 20 mg of the compound once a week. In some embodiments, the maintenance dose may include administering to the patient about 3 mg of the compound once a week. In some embodiments, the maintenance dose may include administering to the patient about 5 mg of the compound once a week. In some embodiments, the maintenance dose may include administering to the patient about 6 mg of the compound once a week. In some embodiments, the maintenance dose may include administering to the patient about 8 mg of the compound once a week. In some embodiments, the maintenance dose may include administering to the patient about 10 mg of the compound once a week. In some embodiments, the maintenance dose may include administering to the patient about 11 mg of the compound once a week. In some embodiments, the maintenance dose may include administering to the patient about 12 mg of the compound once a week. In some embodiments, the maintenance dose may include administering to the patient about 13 mg of the compound once a week. In some embodiments, the maintenance dose may include administering to the patient about 14 mg of the compound once a week. In some embodiments, the maintenance dose may include administering to the patient about 15 mg of the compound once a week. In some embodiments, the maintenance dose may include administering to the patient about 16 mg of the compound once a week. In some embodiments, the maintenance dose may include administering to the patient about 17 mg of the compound once a week. In some embodiments, the maintenance dose may include administering to the patient about 18 mg of the compound once a week. In some embodiments, the maintenance dose may include administering to the patient about 19 mg of the compound once a week. In some embodiments, the maintenance dose may include administering to the patient about 20 mg of the compound once a week. In some embodiments, the maintenance dose may include administering to the patient about 22 mg of the compound once a week. In some embodiments, the maintenance dose may include administering to the patient about 24 mg of the compound once a week. In some embodiments, the maintenance dose may include administering to the patient about 26 mg of the compound once a week. In some embodiments, the maintenance dose may include administering to the patient about 28 mg of the compound once a week. In some embodiments, the maintenance dose may include administering to the patient about 30 mg of the compound once a week. In some embodiments, the maintenance dose may include administering to the patient about 32 mg of the compound once a week. In some embodiments, the maintenance dose may include administering to the patient about 34 mg of the compound once a week. In some embodiments, the maintenance dose may include administering to the patient about 36 mg of the compound once a week. In some embodiments, the maintenance dose may include administering to the patient about 38 mg of the compound once a week. In some embodiments, the maintenance dose may include administering to the patient about 40 mg of the compound once a week. In some embodiments, the maintenance dose may include administering to the patient about 42 mg of the compound once a week. In some embodiments, the maintenance dose may include administering to the patient about 44 mg of the compound once a week. In some embodiments, the maintenance dose may include administering to the patient about 46 mg of the compound once a week. In some embodiments, the maintenance dose may include administering to the patient about 48 mg of the compound once a week. In some embodiments, the maintenance dose may include administering to the patient about 50 mg of the compound once a week.

In some embodiments, the maintenance dose may include administering to the patient about 2 mg to about 40 mg of the compound twice a week. In some embodiments, the maintenance dose may include administering to the patient about 2 mg to about 30 mg of the compound twice a week. In some embodiments, the maintenance dose may include administering to the patient about 2 mg to about 20 mg of the compound twice a week. In some embodiments, the maintenance dose may include administering to the patient about 5 mg to about 40 mg of the compound twice a week. In some embodiments, the maintenance dose may include administering to the patient about 5 mg to about 30 mg of the compound twice a week. In some embodiments, the maintenance dose may include administering to the patient about 5 mg to about 20 mg of the compound twice a week. In some embodiments, the maintenance dose may include administering to the patient about 6 mg to about 40 mg of the compound twice a week. In some embodiments, the maintenance dose may include administering to the patient about 6 mg to about 30 mg of the compound twice a week. In some embodiments, the maintenance dose may include administering to the patient about 6 mg to about 20 mg of the compound twice a week. In some embodiments, the maintenance dose may include administering to the patient about 10 mg to about 40 mg of the compound twice a week. In some embodiments, the maintenance dose may include administering to the patient about 10 mg to about 30 mg of the compound twice a week. In some embodiments, the maintenance dose may include administering to the patient about 10 mg to about 20 mg of the compound twice a week. In some embodiments, the maintenance dose may include administering to the patient about 3 mg of the compound twice a week. In some embodiments, the maintenance dose may include administering to the patient about 5 mg of the compound twice a week. In some embodiments, the maintenance dose may include administering to the patient about 6 mg of the compound twice a week. In some embodiments, the maintenance dose may include administering to the patient about 8 mg of the compound twice a week. In some embodiments, the maintenance dose may include administering to the patient about 10 mg of the compound twice a week. In some embodiments, the maintenance dose may include administering to the patient about 11 mg of the compound twice a week. In some embodiments, the maintenance dose may include administering to the patient about 12 mg of the compound twice a week. In some embodiments, the maintenance dose may include administering to the patient about 13 mg of the compound twice a week. In some embodiments, the maintenance dose may include administering to the patient about 14 mg of the compound twice a week. In some embodiments, the maintenance dose may include administering to the patient about 15 mg of the compound twice a week. In some embodiments, the maintenance dose may include administering to the patient about 16 mg of the compound twice a week. In some embodiments, the maintenance dose may include administering to the patient about 17 mg of the compound twice a week. In some embodiments, the maintenance dose may include administering to the patient about 18 mg of the compound twice a week. In some embodiments, the maintenance dose may include administering to the patient about 19 mg of the compound twice a week. In some embodiments, the maintenance dose may include administering to the patient about 20 mg of the compound twice a week. In some embodiments, the maintenance dose may include administering to the patient about 22 mg of the compound twice a week. In some embodiments, the maintenance dose may include administering to the patient about 24 mg of the compound twice a week. In some embodiments, the maintenance dose may include administering to the patient about 26 mg of the compound twice a week. In some embodiments, the maintenance dose may include administering to the patient about 28 mg of the compound twice a week. In some embodiments, the maintenance dose may include administering to the patient about 30 mg of the compound twice a week. In some embodiments, the maintenance dose may include administering to the patient about 32 mg of the compound twice a week. In some embodiments, the maintenance dose may include administering to the patient about 34 mg of the compound twice a week. In some embodiments, the maintenance dose may include administering to the patient about 36 mg of the compound twice a week. In some embodiments, the maintenance dose may include administering to the patient about 38 mg of the compound twice a week. In some embodiments, the maintenance dose may include administering to the patient about 40 mg of the compound twice a week. In some embodiments, the maintenance dose may include administering to the patient about 42 mg of the compound twice a week. In some embodiments, the maintenance dose may include administering to the patient about 44 mg of the compound twice a week. In some embodiments, the maintenance dose may include administering to the patient about 46 mg of the compound twice a week. In some embodiments, the maintenance dose may include administering to the patient about 48 mg of the compound twice a week. In some embodiments, the maintenance dose may include administering to the patient about 50 mg of the compound twice a week.

In some embodiments, the maintenance dose may include administering to the patient about 2 mg to about 40 mg of the compound three times a week. In some embodiments, the maintenance dose may include administering to the patient about 2 mg to about 30 mg of the compound three times a week. In some embodiments, the maintenance dose may include administering to the patient about 2 mg to about 20 mg of the compound three times a week. In some embodiments, the maintenance dose may include administering to the patient about 5 mg to about 40 mg of the compound three times a week. In some embodiments, the maintenance dose may include administering to the patient about 5 mg to about 30 mg of the compound three times a week. In some embodiments, the maintenance dose may include administering to the patient about 5 mg to about 20 mg of the compound three times a week. In some embodiments, the maintenance dose may include administering to the patient about 6 mg to about 40 mg of the compound three times a week. In some embodiments, the maintenance dose may include administering to the patient about 6 mg to about 30 mg of the compound three times a week. In some embodiments, the maintenance dose may include administering to the patient about 6 mg to about 20 mg of the compound three times a week. In some embodiments, the maintenance dose may include administering to the patient about 10 mg to about 40 mg of the compound three times a week. In some embodiments, the maintenance dose may include administering to the patient about 10 mg to about 30 mg of the compound three times a week. In some embodiments, the maintenance dose may include administering to the patient about 10 mg to about 20 mg of the compound three times a week. In some embodiments, the maintenance dose may include administering to the patient about 3 mg of the compound three times a week. In some embodiments, the maintenance dose may include administering to the patient about 5 mg of the compound three times a week. In some embodiments, the maintenance dose may include administering to the patient about 6 mg of the compound three times a week. In some embodiments, the maintenance dose may include administering to the patient about 8 mg of the compound three times a week. In some embodiments, the maintenance dose may include administering to the patient about 10 mg of the compound three times a week. In some embodiments, the maintenance dose may include administering to the patient about 11 mg of the compound three times a week. In some embodiments, the maintenance dose may include administering to the patient about 12 mg of the compound three times a week. In some embodiments, the maintenance dose may include administering to the patient about 13 mg of the compound three times a week. In some embodiments, the maintenance dose may include administering to the patient about 14 mg of the compound three times a week. In some embodiments, the maintenance dose may include administering to the patient about 15 mg of the compound three times a week. In some embodiments, the maintenance dose may include administering to the patient about 16 mg of the compound three times a week. In some embodiments, the maintenance dose may include administering to the patient about 17 mg of the compound three times a week. In some embodiments, the maintenance dose may include administering to the patient about 18 mg of the compound three times a week. In some embodiments, the maintenance dose may include administering to the patient about 19 mg of the compound three times a week. In some embodiments, the maintenance dose may include administering to the patient about 20 mg of the compound three times a week. In some embodiments, the maintenance dose may include administering to the patient about 22 mg of the compound three times a week. In some embodiments, the maintenance dose may include administering to the patient about 24 mg of the compound three times a week. In some embodiments, the maintenance dose may include administering to the patient about 26 mg of the compound three times a week. In some embodiments, the maintenance dose may include administering to the patient about 28 mg of the compound three times a week. In some embodiments, the maintenance dose may include administering to the patient about 30 mg of the compound three times a week. In some embodiments, the maintenance dose may include administering to the patient about 32 mg of the compound three times a week. In some embodiments, the maintenance dose may include administering to the patient about 34 mg of the compound three times a week. In some embodiments, the maintenance dose may include administering to the patient about 36 mg of the compound three times a week. In some embodiments, the maintenance dose may include administering to the patient about 38 mg of the compound three times a week. In some embodiments, the maintenance dose may include administering to the patient about 40 mg of the compound three times a week. In some embodiments, the maintenance dose may include administering to the patient about 42 mg of the compound three times a week. In some embodiments, the maintenance dose may include administering to the patient about 44 mg of the compound three times a week. In some embodiments, the maintenance dose may include administering to the patient about 46 mg of the compound three times a week. In some embodiments, the maintenance dose may include administering to the patient about 48 mg of the compound three times a week. In some embodiments, the maintenance dose may include administering to the patient about 50 mg of the compound three times a week The maintenance dose may also be administered once daily. For example, the maintenance dose may include administering to the patient about 2 mg of the compound once a day. In some embodiments, the maintenance may include administering to the patient about 2 mg to about 40 mg of the compound once a day. In some embodiments, the maintenance may include administering to the patient about 2 mg to about 30 mg of the compound once a day. In some embodiments, the maintenance may include administering to the patient about 2 mg to about 20 mg of the compound once a day. In some embodiments, the maintenance may include administering to the patient about 5 mg to about 40 mg of the compound once a day. In some embodiments, the maintenance may include administering to the patient about 5 mg to about 30 mg of the compound once a day. In some embodiments, the maintenance may include administering to the patient about 5 mg to about 20 mg of the compound once a day. In some embodiments, the maintenance may include administering to the patient about 6 mg to about 40 mg of the compound once a day. In some embodiments, the maintenance may include administering to the patient about 6 mg to about 30 mg of the compound once a day. In some embodiments, the maintenance may include administering to the patient about 6 mg to about 20 mg of the compound once a day. In some embodiments, the maintenance may include administering to the patient about 10 mg to about 40 mg of the compound once a day. In some embodiments, the maintenance may include administering to the patient about 10 mg to about 30 mg of the compound once a day. In some embodiments, the maintenance may include administering to the patient about 10 mg to about 20 mg of the compound once a day. In some embodiments, the maintenance may include administering to the patient about 3 mg of the compound once a day. In some embodiments, the maintenance may include administering to the patient about 5 mg of the compound once a day. In some embodiments, the maintenance may include administering to the patient about 6 mg of the compound once a day. In some embodiments, the maintenance may include administering to the patient about 8 mg of the compound once a day. In some embodiments, the maintenance may include administering to the patient about 10 mg of the compound once a day. In some embodiments, the maintenance may include administering to the patient about 11 mg of the compound once a day. In some embodiments, the maintenance may include administering to the patient about 12 mg of the compound once a day. In some embodiments, the maintenance may include administering to the patient about 13 mg of the compound once a day. In some embodiments, the maintenance may include administering to the patient about 14 mg of the compound once a day. In some embodiments, the maintenance may include administering to the patient about 15 mg of the compound once a day. In some embodiments, the maintenance may include administering to the patient about 16 mg of the compound once a day. In some embodiments, the maintenance may include administering to the patient about 17 mg of the compound once a day. In some embodiments, the maintenance may include administering to the patient about 18 mg of the compound once a day. In some embodiments, the maintenance may include administering to the patient about 19 mg of the compound once a day. In some embodiments, the maintenance may include administering to the patient about 20 mg of the compound once a day. In some embodiments, the maintenance may include administering to the patient about 22 mg of the compound once a day. In some embodiments, the maintenance may include administering to the patient about 24 mg of the compound once a day. In some embodiments, the maintenance may include administering to the patient about 26 mg of the compound once a day. In some embodiments, the maintenance may include administering to the patient about 28 mg of the compound once a day. In some embodiments, the maintenance may include administering to the patient about 30 mg of the compound once a day. In some embodiments, the maintenance dose may include administering to the patient about 32 mg of the compound once a day. In some embodiments, the maintenance dose may include administering to the patient about 34 mg of the compound once a day. In some embodiments, the maintenance dose may include administering to the patient about 36 mg of the compound once a day. In some embodiments, the maintenance dose may include administering to the patient about 38 mg of the compound once a day. In some embodiments, the maintenance dose may include administering to the patient about 40 mg of the compound once a day. In some embodiments, the maintenance dose may include administering to the patient about 42 mg of the compound once a day. In some embodiments, the maintenance dose may include administering to the patient about 44 mg of the compound once a day. In some embodiments, the maintenance dose may include administering to the patient about 46 mg of the compound once a day. In some embodiments, the maintenance dose may include administering to the patient about 48 mg of the compound once a day. In some embodiments, the maintenance dose may include administering to the patient about 50 mg of the compound once a day.

In some embodiments, the maintenance dose may include administering to the patient about 2 mg to about 40 mg of the compound every other day. In some embodiments, the maintenance dose may include administering to the patient about 2 mg to about 30 mg of the compound every other day. In some embodiments, the maintenance dose may include administering to the patient about 2 mg to about 20 mg of the compound every other day. In some embodiments, the maintenance dose may include administering to the patient about 5 mg to about 40 mg of the compound every other day. In some embodiments, the maintenance dose may include administering to the patient about 5 mg to about 30 mg of the compound every other day. In some embodiments, the maintenance dose may include administering to the patient about 5 mg to about 20 mg of the compound every other day. In some embodiments, the maintenance dose may include administering to the patient about 6 mg to about 40 mg of the compound every other day. In some embodiments, the maintenance dose may include administering to the patient about 6 mg to about 30 mg of the compound every other day. In some embodiments, the maintenance dose may include administering to the patient about 6 mg to about 20 mg of the compound every other day. In some embodiments, the maintenance dose may include administering to the patient about 10 mg to about 40 mg of the compound every other day. In some embodiments, the maintenance dose may include administering to the patient about 10 mg to about 30 mg of the compound every other day. In some embodiments, the maintenance dose may include administering to the patient about 10 mg to about 20 mg of the compound every other day. In some embodiments, the maintenance dose may include administering to the patient about 3 mg of the compound every other day. In some embodiments, the maintenance dose may include administering to the patient about 5 mg of the compound every other day. In some embodiments, the maintenance dose may include administering to the patient about 6 mg of the compound every other day. In some embodiments, the maintenance dose may include administering to the patient about 8 mg of the compound every other day. In some embodiments, the maintenance dose may include administering to the patient about 10 mg of the compound every other day. In some embodiments, the maintenance dose may include administering to the patient about 11 mg of the compound every other day. In some embodiments, the maintenance dose may include administering to the patient about 12 mg of the compound every other day. In some embodiments, the maintenance dose may include administering to the patient about 13 mg of the compound every other day. In some embodiments, the maintenance dose may include administering to the patient about 14 mg of the compound every other day. In some embodiments, the maintenance dose may include administering to the patient about 15 mg of the compound every other day. In some embodiments, the maintenance dose may include administering to the patient about 16 mg of the compound every other day. In some embodiments, the maintenance dose may include administering to the patient about 17 mg of the compound every other day. In some embodiments, the maintenance dose may include administering to the patient about 18 mg of the compound every other day. In some embodiments, the maintenance dose may include administering to the patient about 19 mg of the compound every other day. In some embodiments, the maintenance dose may include administering to the patient about 20 mg of the compound every other day. In some embodiments, the maintenance dose may include administering to the patient about 22 mg of the compound every other day. In some embodiments, the maintenance dose may include administering to the patient about 24 mg of the compound every other day. In some embodiments, the maintenance dose may include administering to the patient about 26 mg of the compound every other day. In some embodiments, the maintenance dose may include administering to the patient about 28 mg of the compound every other day. In some embodiments, the maintenance dose may include administering to the patient about 30 mg of the compound every other day. In some embodiments, the maintenance dose may include administering to the patient about 32 mg of the compound every other day. In some embodiments, the maintenance dose may include administering to the patient about 34 mg of the compound every other day. In some embodiments, the maintenance dose may include administering to the patient about 36 mg of the compound every other day. In some embodiments, the maintenance dose may include administering to the patient about 38 mg of the compound every other day. In some embodiments, the maintenance dose may include administering to the patient about 40 mg of the compound every other day. In some embodiments, the maintenance dose may include administering to the patient about 42 mg of the compound every other day. In some embodiments, the maintenance dose may include administering to the patient about 44 mg of the compound every other day. In some embodiments, the maintenance dose may include administering to the patient about 46 mg of the compound every other day. In some embodiments, the maintenance dose may include administering to the patient about 48 mg of the compound every other day. In some embodiments, the maintenance dose may include administering to the patient about 50 mg of the compound every other day.

In some embodiments, the first time period, for example during which a loading dose is administered (e.g., daily or every other day, or twice daily) is about one or two weeks, or one to three weeks, e.g., such a first time period may be about 4 days, about 5 days, about 6 days, or about 10 days. In some embodiments, the first time period is about one to six days. In some embodiments, the first time period is about one to five days. In some embodiments, the first time period is about one to four days. In some embodiments, the first time period is about one to three days. In some embodiments, the first time period is about one to two days. In some embodiments, the first time period is about one to five weeks. In some embodiments, the first time period is about one to four weeks. In some embodiments, the first time period is about one to three weeks. In some embodiments, the first time period is about one to two weeks.

In some embodiments, the loading dose is about 2 mg to about 100 mg of the compound. In some embodiments, the loading dose is about 5 mg to about 90 mg of the compound. In some embodiments, the loading dose is about 10 mg to about 80 mg of the compound. In some embodiments, the loading dose is about 10 mg to about 70 mg of the compound. In some embodiments, the loading dose is about 10 mg to about 60 mg of the compound. In some embodiments, the loading dose is about 10 mg to about 50 mg of the compound. In some embodiments, the loading dose is about 10 mg to about 40 mg of the compound. In some embodiments, the loading dose is about 10 mg to about 30 mg of the compound. In some embodiments, the loading dose is about 10 mg to about 20 mg of the compound. In some embodiments, the loading dose is about 2 mg of the compound. In some embodiments, the loading dose is about 3 mg of the compound. In some embodiments, the loading dose is about 4 mg of the compound. In some embodiments, the loading dose is about 5 mg of the compound. In some embodiments, the loading dose is about 10 mg of the compound. In some embodiments, the loading dose is about 11 mg of the compound. In some embodiments, the loading dose is about 12 mg of the compound. In some embodiments, the loading dose is about 13 mg of the compound. In some embodiments, the loading dose is about 14 mg of the compound. In some embodiments, the loading dose is about 15 mg of the compound. In some embodiments, the loading dose is about 16 mg of the compound. In some embodiments, the loading dose is about 17 mg of the compound. In some embodiments, the loading dose is about 18 mg of the compound. In some embodiments, the loading dose is about 19 mg of the compound. In some embodiments, the loading dose is about 20 mg of the compound. In some embodiments, the loading dose is about 22 mg of the compound. In some embodiments, the loading dose is about 24 mg of the compound. In some embodiments, the loading dose is about 26 mg of the compound. In some embodiments, the loading dose is about 28 mg of the compound. In some embodiments, the loading dose is about 30 mg of the compound. In some embodiments, the loading dose is about 32 mg of the compound. In some embodiments, the loading dose is about 34 mg of the compound. In some embodiments, the loading dose is about 36 mg of the compound. In some embodiments, the loading dose is about 38 mg of the compound. In some embodiments, the loading dose is about 40 mg of the compound. In some embodiments, the loading dose is about 42 mg of the compound. In some embodiments, the loading dose is about 44 mg of the compound. In some embodiments, the loading dose is about 40 mg of the compound. In some embodiments, the loading dose is about 46 mg of the compound. In some embodiments, the loading dose is about 48 mg of the compound. In some embodiments, the loading dose is about 50 mg of the compound.

In some embodiments, the loading dose is about 2 mg to about 100 mg of the compound once a day. In some embodiments, the loading dose is about 2 mg to about 100 mg of the compound once a day. In some embodiments, the loading dose is about 5 mg to about 90 mg of the compound once a day. In some embodiments, the loading dose is about 10 mg to about 80 mg of the compound once a day. In some embodiments, the loading dose is about 10 mg to about 70 mg of the compound once a day. In some embodiments, the loading dose is about 10 mg to about 60 mg of the compound once a day. In some embodiments, the loading dose is about 10 mg to about 50 mg of the compound once a day. In some embodiments, the loading dose is about 10 mg to about 40 mg of the compound once a day. In some embodiments, the loading dose is about 10 mg to about 30 mg of the compound once a day. In some embodiments, the loading dose is about 10 mg to about 20 mg of the compound once a day. In some embodiments, the loading dose is about 2 mg of the compound once a day. In some embodiments, the loading dose is about 3 mg of the compound once a day. In some embodiments, the loading dose is about 4 mg of the compound once a day. In some embodiments, the loading dose is about 5 mg of the compound once a day. In some embodiments, the loading dose is about 10 mg of the compound once a day. In some embodiments, the loading dose is about 11 mg of the compound once a day. In some embodiments, the loading dose is about 12 mg of the compound once a day. In some embodiments, the loading dose is about 13 mg of the compound once a day. In some embodiments, the loading dose is about 14 mg of the compound once a day. In some embodiments, the loading dose is about 15 mg of the compound once a day. In some embodiments, the loading dose is about 16 mg of the compound once a day. In some embodiments, the loading dose is about 17 mg of the compound once a day. In some embodiments, the loading dose is about 18 mg of the compound once a day. In some embodiments, the loading dose is about 19 mg of the compound once a day. In some embodiments, the loading dose is about 20 mg of the compound once a day. In some embodiments, the loading dose is about 22 mg of the compound once a day. In some embodiments, the loading dose is about 24 mg of the compound once a day. In some embodiments, the loading dose is about 26 mg of the compound once a day. In some embodiments, the loading dose is about 28 mg of the compound once a day. In some embodiments, the loading dose is about 30 mg of the compound once a day. In some embodiments, the loading dose is about 32 mg of the compound once a day. In some embodiments, the loading dose is about 34 mg of the compound once a day. In some embodiments, the loading dose is about 36 mg of the compound once a day. In some embodiments, the loading dose is about 38 mg of the compound once a day. In some embodiments, the loading dose is about 40 mg of the compound once a day. In some embodiments, the loading dose is about 42 mg of the compound once a day. In some embodiments, the loading dose is about 44 mg of the compound once a day. In some embodiments, the loading dose is about 40 mg of the compound once a day. In some embodiments, the loading dose is about 46 mg of the compound once a day. In some embodiments, the loading dose is about 48 mg of the compound once a day. In some embodiments, the loading dose is about 50 mg of the compound once a day.

In some embodiments, the loading dose is about 2 mg to about 100 mg of the compound once a week. In some embodiments, the loading dose is about 2 mg to about 100 mg of the compound once a week. In some embodiments, the loading dose is about 5 mg to about 90 mg of the compound once a week. In some embodiments, the loading dose is about 10 mg to about 80 mg of the compound once a week. In some embodiments, the loading dose is about 10 mg to about 70 mg of the compound once a week. In some embodiments, the loading dose is about 10 mg to about 60 mg of the compound once a week. In some embodiments, the loading dose is about 10 mg to about 50 mg of the compound once a week. In some embodiments, the loading dose is about 10 mg to about 40 mg of the compound once a week. In some embodiments, the loading dose is about 10 mg to about 30 mg of the compound once a week. In some embodiments, the loading dose is about 10 mg to about 20 mg of the compound once a week. In some embodiments, the loading dose is about 2 mg of the compound once a week. In some embodiments, the loading dose is about 3 mg of the compound once a week. In some embodiments, the loading dose is about 4 mg of the compound once a week. In some embodiments, the loading dose is about 5 mg of the compound once a week. In some embodiments, the loading dose is about 10 mg of the compound once a week. In some embodiments, the loading dose is about 11 mg of the compound once a week. In some embodiments, the loading dose is about 12 mg of the compound once a week. In some embodiments, the loading dose is about 13 mg of the compound once a week. In some embodiments, the loading dose is about 14 mg of the compound once a week. In some embodiments, the loading dose is about 15 mg of the compound once a week. In some embodiments, the loading dose is about 16 mg of the compound once a week. In some embodiments, the loading dose is about 17 mg of the compound once a week. In some embodiments, the loading dose is about 18 mg of the compound once a week. In some embodiments, the loading dose is about 19 mg of the compound once a week. In some embodiments, the loading dose is about 20 mg of the compound once a week. In some embodiments, the loading dose is about 22 mg of the compound once a week. In some embodiments, the loading dose is about 24 mg of the compound once a week. In some embodiments, the loading dose is about 26 mg of the compound once a week. In some embodiments, the loading dose is about 28 mg of the compound once a week. In some embodiments, the loading dose is about 30 mg of the compound once a week. In some embodiments, the loading dose is about 32 mg of the compound once a week. In some embodiments, the loading dose is about 34 mg of the compound once a week. In some embodiments, the loading dose is about 36 mg of the compound once a week. In some embodiments, the loading dose is about 38 mg of the compound once a week. In some embodiments, the loading dose is about 40 mg of the compound once a week. In some embodiments, the loading dose is about 42 mg of the compound once a week. In some embodiments, the loading dose is about 44 mg of the compound once a week. In some embodiments, the loading dose is about 40 mg of the compound once a week. In some embodiments, the loading dose is about 46 mg of the compound once a week. In some embodiments, the loading dose is about 48 mg of the compound once a week. In some embodiments, the loading dose is about 50 mg of the compound once a week.

In some embodiments, the loading dose is about 2 mg to about 100 mg of the compound twice a week. In some embodiments, the loading dose is about 2 mg to about 100 mg of the compound twice a week. In some embodiments, the loading dose is about 5 mg to about 90 mg of the compound twice a week. In some embodiments, the loading dose is about 10 mg to about 80 mg of the compound twice a week. In some embodiments, the loading dose is about 10 mg to about 70 mg of the compound twice a week. In some embodiments, the loading dose is about 10 mg to about 60 mg of the compound twice a week. In some embodiments, the loading dose is about 10 mg to about 50 mg of the compound twice a week. In some embodiments, the loading dose is about 10 mg to about 40 mg of the compound twice a week. In some embodiments, the loading dose is about 10 mg to about 30 mg of the compound twice a week. In some embodiments, the loading dose is about 10 mg to about 20 mg of the compound twice a week. In some embodiments, the loading dose is about 2 mg of the compound twice a week. In some embodiments, the loading dose is about 3 mg of the compound twice a week. In some embodiments, the loading dose is about 4 mg of the compound twice a week. In some embodiments, the loading dose is about 5 mg of the compound twice a week. In some embodiments, the loading dose is about 10 mg of the compound twice a week. In some embodiments, the loading dose is about 11 mg of the compound twice a week. In some embodiments, the loading dose is about 12 mg of the compound twice a week. In some embodiments, the loading dose is about 13 mg of the compound twice a week. In some embodiments, the loading dose is about 14 mg of the compound twice a week. In some embodiments, the loading dose is about 15 mg of the compound twice a week. In some embodiments, the loading dose is about 16 mg of the compound twice a week. In some embodiments, the loading dose is about 17 mg of the compound twice a week. In some embodiments, the loading dose is about 18 mg of the compound twice a week. In some embodiments, the loading dose is about 19 mg of the compound twice a week. In some embodiments, the loading dose is about 20 mg of the compound twice a week. In some embodiments, the loading dose is about 22 mg of the compound twice a week. In some embodiments, the loading dose is about 24 mg of the compound twice a week. In some embodiments, the loading dose is about 26 mg of the compound twice a week. In some embodiments, the loading dose is about 28 mg of the compound twice a week. In some embodiments, the loading dose is about 30 mg of the compound twice a week. In some embodiments, the loading dose is about 32 mg of the compound twice a week. In some embodiments, the loading dose is about 34 mg of the compound twice a week. In some embodiments, the loading dose is about 36 mg of the compound twice a week. In some embodiments, the loading dose is about 38 mg of the compound twice a week. In some embodiments, the loading dose is about 40 mg of the compound twice a week. In some embodiments, the loading dose is about 42 mg of the compound twice a week. In some embodiments, the loading dose is about 44 mg of the compound twice a week. In some embodiments, the loading dose is about 40 mg of the compound twice a week. In some embodiments, the loading dose is about 46 mg of the compound twice a week. In some embodiments, the loading dose is about 48 mg of the compound twice a week. In some embodiments, the loading dose is about 50 mg of the compound twice a week.

The second time period, during which e.g. a maintenance dose is administered, may be at least about one week, or more, e.g. about one month or more (for example, about 1 month to about 6 months, to about 12 months, or more).

The method comprises administering a loading dose daily for a first time period and administering a maintenance dose daily for a second time period. In some embodiments, the first time period is from one day to 6 days, and the second period is from one to 35 days. In some embodiments, the first time period is from one day to 6 days, and the second period is from one to 30 days. In some embodiments, the first time period is from one day to 6 days, and the second period is from one to 25 days. In some embodiments, the first time period is from one day to 6 days, and the second period is from one to 22 days. In some embodiments, the first time period is from one day to 6 days, and the second period is from one to 20 days. In some embodiments, the first time period is from one day to 5 days, and the second period is from one day to 35 days. In some embodiments, the first time period is from one day to 5 days, and the second period is from one to 30 days. In some embodiments, the first time period is from one day to 5 days, and the second period is from one day to 25 days. In some embodiments, the first time period is from one day to 5 days, and the second period is from one day to 22 days. In some embodiments, the first time period is from one day to 5 days, and the second period is from one day to 20 days. In some embodiments, the first time period is from one day to 4 days, and the second period is from one day to 35 days. In some embodiments, the first time period is from one day to 4 days, and the second period is from one to 30 days. In some embodiments, the first time period is from one day to 4 days, and the second period is from one day to 25 days. In some embodiments, the first time period is from one day to 4 days, and the second period is from one day to 22 days. In some embodiments, the first time period is from one day to 4 days, and the second period is from one day to 20 days. In some embodiments, the first time period is from one day to 3 days, and the second period is from one day to 35 days. In some embodiments, the first time period is from one day to 3 days, and the second period is from one to 30 days. In some embodiments, the first time period is from one day to 3 days, and the second period is from one day to 25 days. In some embodiments, the first time period is from one day to 3 days, and the second period is from one day to 22 days. In some embodiments, the first time period is from one day to 3 days, and the second period is from one day to 20 days. In some embodiments, the first time period is from one day to 2 days, and the second period is from one day to 35 days. In some embodiments, the first time period is from one day to 2 days, and the second period is from one to 30 days. In some embodiments, the first time period is from one day to 2 days, and the second period is from one day to 25 days. In some embodiments, the first time period is from one day to 2 days, and the second period is from one day to 22 days. In some embodiments, the first time period is from one day to 2 days, and the second period is from one day to 20 days. In other embodiments, the first period of time and the second period of time combined comprise 20 days. In some embodiments, the first period of time and the second period of time combined comprise 21 days. In some embodiments, the first period of time and the second period of time combined comprise 22 days. In some embodiments, the first period of time and the second period of time combined comprise 23 days. In some embodiments, the first period of time and the second period of time combined comprise 24 days. In some embodiments, the first period of time and the second period of time combined comprise 25 days. In some embodiments, the first period of time and the second period of time combined comprise 26 days. In some embodiments, the first period of time and the second period of time combined comprise 27 days. In some embodiments, the first period of time and the second period of time combined comprise 28 days. In some embodiments, the first period of time and the second period of time combined comprise 29 days. In some embodiments, the first period of time and the second period of time combined comprise 30 days. In some embodiments, the first period of time and the second period of time combined comprise 31 days. In some embodiments, the first period of time and the second period of time combined comprise 32 days. In some embodiments, the first period of time and the second period of time combined comprise 33 days. In some embodiments, the first period of time and the second period of time combined comprise 34 days. In some embodiments, the first period of time and the second period of time combined comprise 35 days. Disclosed methods may be administered for a cycle comprising a first period of time and a second period of time. In some embodiments, the cycle comprises 20 days. In some embodiments, the cycle comprises 21 days. In some embodiments, the cycle comprises 22 days. In some embodiments, the cycle comprises 23 days. In some embodiments, the cycle comprises 24 days. In some embodiments, the cycle comprises 25 days. In some embodiments, the cycle comprises 26 days. In some embodiments, the cycle comprises 27 days. In some embodiments, the cycle comprises 28 days. In some embodiments, the cycle comprises 29 days. In some embodiments, the cycle comprises 30 days. In some embodiments, the cycle comprises 31 days. In some embodiments, the cycle comprises 32 days. In some embodiments, the cycle comprises 33 days. In some embodiments, the cycle comprises 34 days. In some embodiments, the cycle comprises 35 days. In other embodiments, the method may be administered for one to 1200 cycles. In some embodiments, the method may be administered for 10 to 1000 cycles. In some embodiments, the method may be administered for 50 to 800 cycles. In some embodiments, the method may be administered for 70 to 700 cycles. In some embodiments, the method may be administered for 100 to 500 cycles.

Contemplated methods may include treating patients suffering from solid tumors that have progressed after prior administration of another cancer therapy (e.g., an advanced tumor). For example, treatment of a solid tumor such as metastatic breast or prostate cancer with bone disease is contemplated herein. In some embodiments, the solid tumor is gastric, ovarian or non-small cell lung cancer that has malignant associated ascites or effusion(s).

Contemplated tumors that may be treated by disclosed methods includes those that expresses one or more of: CSF1R or its ligands, CSF1, and IL-34. For example, a contemplated method may further include identifying the tumor as expressing CSF1R, CSF1, and/or IL-34.

Disclosed methods may include administering a loading dose of the compound daily for a first time period; and administering a maintenance dose of the compound daily, once a week, twice a week, or three times a week for a second time period (or every other day), for example, where the maintenance dose is lower than or equal to each loading dose. A contemplated loading dose is about 10 to about 80 mg/day, or about 10 mg to about 80 mg daily. In some embodiments, the loading dose is about 20 to about 60 mg/day, e.g., about 20 mg/day, about 30 mg/day, about 40 mg/day, about 50 mg/day or about 60 mg/day. In some embodiments, the maintenance dose is about 2 mg to about 60 mg. In some embodiments, the maintenance dose is about 2 mg, about 10 mg, about 20 mg, about 25 mg, about 30 mg, about 40 mg or about 50 mg, administered daily, twice a week, or three times a week. In some embodiments, the first time period, wherein a loading dose is e.g., administered daily is about one or two weeks. Exemplary first time periods may be about 4 days, about 5 days, about 6 days, or about 10 days. In some embodiments, the second time period (e.g., where a maintenance dose is administered daily, twice a week, or three times a week), is one week, or one month to about six months or more. In some embodiments, contemplated methods further comprise administering additional loading doses during a third time period. In some embodiments, the method further comprises administering an additional maintenance dose during a fourth time period. In some embodiments, the third and/or fourth time period occurs after the first and second time period.

After 1 month, or 3 months or more of administration, a patient being treated by a disclosed method may have an improved tumor response as measured by RECIST. In some embodiments, after 1 week, or 1 month, or more of administration, the patient may have one of: reduced level of specific populations of monocytes (such as CD16+ or CSF1R+ monocytes) in blood by flow cytometry, increased levels of CSF1 in plasma, reduced levels of bone turnover markers wherein the turnover markers can include collagen fragments C-terminal fragment of collagen in serum and urine N-terminal fragment of collagen, and reduced macrophage content and/or re-polarization of pro-tumor M2 macrophages to an anti-tumoral M1 phenotype in the tumor or tumor-associated ascites/effusion fluids, as compared to the associated level before administration.

The disclosure also contemplates a method of treating a cancer such as those selected from the group consisting of solid tumors, acute myeloid leukemia, myelodysplastic syndrome, acute lymphocytic leukemia, and chronic lymphocytic leukemia, in a patient in need thereof (e.g., a human patient suffering from cancer), comprising administering to the patient a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof, and at least one other therapeutic agent. In some embodiments, a patient may be suffering from a solid tumor such as one of breast, cervix, pancreas, bladder, prostate, gastric, ovarian, melanoma, glioma, glioblastoma multiforme, osteosarcoma, osteolytic cancers, chondrosarcoma, histiocytosis, or lung cancer. In some embodiments, the breast cancer is ductal carcinoma in situ (DCIS). In some embodiments, the breast cancer is invasive (or infiltrating) breast cancer (ILC or IDC). In some embodiments, the breast cancer is invasive ductal carcinoma. In some embodiments, the breast cancer is invasive lobular carcinoma. In some embodiments, the pancreatic cancer is an exocrine pancreatic cancer. In some embodiments, the exocrine pancreatic cancer is pancreatic adenocarcinoma. In some embodiments, the exocrine pancreatic cancer is pancreatic ductal adenocarcinoma (PDAC). In some embodiments, the pancreatic cancer is pancreatic adenocarcinoma. In some embodiments, the pancreatic cancer is pancreatic ductal adenocarcinoma (PDAC). In some embodiments, pancreatic cancer is a pancreatic neuroendocrine tumor (PanNET).

The disclosure contemplates administration of Compound 1 or a pharmaceutically acceptable salt to a patient in need thereof prior (neo-adjuvant) or after (adjuvant) surgery (e.g., surgical treatment of a solid tumor). In some embodiments, Compound 1 or a pharmaceutically acceptable salt is administered as an adjuvant. In some embodiments, Compound 1 or a pharmaceutically acceptable salt is administered as a neo-adjuvant. In some embodiments, Compound 1 or a pharmaceutically acceptable salt is administered as a neo-adjuvant and an adjuvant. In some embodiments, Compound 1 or a pharmaceutically acceptable salt is administered to a patient in need thereof as a neo-adjuvant for a period of 1 month to 6 months, followed by administration of Compound 1 or a pharmaceutically acceptable salt as an adjuvant for a period from 1 day to 100 years. In some embodiments, administration of Compound 1 or a pharmaceutically acceptable salt is administered to a patient in need thereof as a neo-adjuvant for a period of 1 month to 6 months, followed by administration of Compound 1 or a pharmaceutically acceptable salt as an adjuvant for a period from 1 day to 5 years. In some embodiments, administration of Compound 1 or a pharmaceutically acceptable salt is administered to a patient in need thereof as a neo-adjuvant for a period of 3 months to 6 months, followed by administration of Compound 1 or a pharmaceutically acceptable salt as an adjuvant for a period from 1 day to 5 years. In some embodiments, no administration of Compound 1 or a pharmaceutically acceptable salt occurs prior to surgery. In some embodiments, Compound 1 or a pharmaceutically acceptable salt is administered as an adjuvant for a period from 1 day to 100 years. In some embodiments, Compound 1 or a pharmaceutically acceptable salt is administered as an adjuvant for a period from 1 day to 5 years.

Contemplated methods may further include administering another immunomodulatory therapeutic. In some embodiments, such an immunomodulatory therapeutic is an anti PD-1 therapeutic, an anti-PD-L1 therapeutic, a CD40 agonist therapeutic, an anti-CD47 therapeutic, an anti-LAG3 therapeutic, an anti-CD20 therapeutic, an anti-CD38 therapeutic, and/or an anti-TIM3 therapeutic. A disclosed method may, for example, further include administering a chemotherapeutic agent. In some embodiments, the chemotherapeutic agent is selected from the group consisting of paclitaxel, eribulin, docetaxel, gemcitabine, vemurafenib, dabrafenib, trametinib, cobimetinib, and binimetinib. In some embodiments, the method further comprises administering an immunomodulatory therapeutic and another chemotherapeutic agent.

In one aspect, described herein is a method of treating tumors known to have expression of the receptor colony-stimulating factor 1 receptor (CSF1R) and/or its ligand(s), colony stimulating factor 1 (CSF1) or interleukin (IL)-34, in a patient in need thereof, comprising administering to the patient a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof, wherein administering comprises: administering a loading dose of the compound daily for a first time period; and administering a maintenance dose of the compound daily, twice a week, or three times a week for a second time period. Such a disclosed method may comprise determining if the tumor or its microenvironment expresses CSF1R, CSF-1, or IL-34 from the patient's extracted tumor sample. In some embodiments, the disclosed method comprises determining if the tumor, its microenvironment, expresses CSF1R, CSF1, or IL-34 from the patient's extracted tumor sample, or patient's extracellular fluid, e.g., the extracellular fluid is the patient's blood plasma.

In some embodiments, a compound described herein, e.g., Compound 1, is administered at escalating doses, for example, one or both of the loading or maintenance dose may be escalated. In some embodiments, the escalating doses comprise at least a first dose level and a second dose level. In some embodiments, the escalating doses comprise at least a first dose level, a second dose level, and a third dose level. In some embodiments, the escalating doses further comprise a fourth dose level. In some embodiments, the escalating doses comprise a first dose level, a second dose level, a third dose level, a fourth dose level and a fifth dose level. In some embodiments, six, seven, eight, nine and ten dose levels are contemplated.

In some embodiments, each dose level is no more than 60% of the immediately following dose level. In some embodiments, each dose level is no more than 50% of the immediately following dose level. In some embodiments, each dose level is no more than 40% of the immediately following dose level. In some embodiments, each dose level is no more than 33% of the immediately following dose level. In some embodiments, each dose level is no more than 20% of the immediately following dose level. In some embodiments, dose levels are separated by ½ log units. In some embodiments, dose levels are separated by 1 log unit.

In some embodiments the first, second, third, and fourth dose levels are administered to the subject for from about 2 days to about 6 months in duration. In some embodiments the first, second, third, and fourth dose levels are administered to the subject for from about 7 days to about 35 days in duration. In some embodiments the first, second, third, and/or fourth dose levels are administered to the subject for from about 2 weeks to about 4 weeks in duration. In some embodiments the first, second, third, and/or fourth dose levels are administered to the subject for about 4 weeks. In some embodiments the first, second, and/or third dose levels are administered to the subject for from about 2 days to about 40 days and the fourth dose level is administered to the subject for from about 2 days to about 6 months.

In some embodiments, the first dose level is from about 5 to about 30 mg/day. In some embodiments, the second dose level is from about 20 to about 50 mg/day. In some embodiments, the third dose level is from about 30 to about 60 mg/day. In some embodiments, the fourth dose level is from about 40 to about 75 mg/day. In some embodiments, the fifth dose level is from about 50 to about 75 mg/day.

In some embodiments, the first dose level is from about 10 to about 30 mg/day (e.g., administered every day for a first time period). In some embodiments, the second dose level is from about 5 to about 30 mg/day (e.g., administered every other day; twice a week or three times a week). In some embodiments, the third dose level is from about 10 to about 50 mg/day. In some embodiments, the fourth dose level is from about 20 to about 60 mg/day. In some embodiments, the fifth dose level is from about 30 to about 75 mg/day.

In some embodiments the first dose level is about 10-80 mg/day for about 1 week or more, and the second dose level is about 10 mg to about 40 mg/day (daily, twice weekly, or three times a week, for e.g., 2 weeks or more).

In some embodiments the first dose level is about 30-60 mg/day. In some embodiments, the second dose level is about 10-30 mg/day.

In some embodiments the methods comprise the administration of five or more escalating doses to the subject. In some embodiments the first dose level is 10 mg/day, the second dose level is 20 mg/day, the third dose level is 30 mg/day, the fourth dose level is 40 mg/day, and the fifth dose level is 50 mg/day or more.

In some embodiments each dose level is administered to the subject for from 2 days to 104 weeks. In some embodiments each dose level is administered to the subject for from 2 days to 26 weeks. In some embodiments each dose level is administered to the subject for from about 1 week to about 26 weeks. In some embodiments each dose level is administered to the subject for from about 1 week to about 12 weeks. In some embodiments, each dose level is administered to the subject for 1 week to 5 weeks. In some embodiments the loading dose level is administered to the subject from 1 to 4 weeks, or about 1 to 2 weeks, or about 5-7 days. In some embodiments a maintenance dose level is administered to the subject from about 14 days to about 60 days or more. In some embodiments a loading dose level is administered to the subject for about 3 weeks, 1 month, 2 months, or more.

In some embodiments the first dose level is administered to the subject for 1 week, the second dose level is administered to the subject for 4 weeks or more.

In some embodiments the first dose level is administered to the subject for about 5-10 days, the second dose level is administered to the subject for about 2 weeks to about 1 month, 2 months or 3 months, 9 months, or more, and the optional third dose level is administered to the subject for about 5-10 days, and the optional fourth dose level is administered to the subject for about 2 weeks to about 1 month, 2 months or 3 months or more. It can be appreciated that the first and second dose may be repeated.

In some embodiments of the methods described herein, antitumor activity is assessed by an endpoint selected from the group consisting of objective response rate, disease control rate (e.g., at 12 weeks), time to best response, progression-free survival, duration of response, and a both objective response rate and disease control rate (e.g., at periods of 6 months and 1 year). In some embodiments, DTGCT is not evaluated by disease control rate.

In some embodiments of the methods described herein, tumor response in DTGCT and solid tumors is evaluated with RECIST, Version 1.1.

Combination Therapy

Compound 1 or a pharmaceutically acceptable salt thereof can be administered in combination with one or more additional therapeutic agents to treat a disorder described herein, such as cancer. For example, provided in the present disclosure is a pharmaceutical composition comprising Compound 1 or a pharmaceutically acceptable salt thereof, one or more additional therapeutic agents, and a pharmaceutically acceptable excipient. In some embodiments, Compound 1 or a pharmaceutically acceptable salt thereof and one additional therapeutic agent is administered. In some embodiments, Compound 1 or a pharmaceutically acceptable salt thereof and two additional therapeutic agents are administered. In some embodiments, Compound 1 or a pharmaceutically acceptable salt thereof and three additional therapeutic agents are administered. Combination therapy can be achieved by administering two or more therapeutic agents, each of which is formulated and administered separately. For example, Compound 1 or a pharmaceutically acceptable salt thereof and an additional therapeutic agent can be formulated and administered separately. Combination therapy can also be achieved by administering two or more therapeutic agents in a single formulation, for example a pharmaceutical composition comprising Compound 1 as one therapeutic agent and one or more additional therapeutic agents. For example, Compound 1 or a pharmaceutically acceptable salt thereof and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

Combination therapy" (or "co-therapy") includes the administration of a CSF1R inhibitor described herein and at least a second agent, e.g., an anti-PD1 therapeutic, e.g., an anti-PD1 antibody, or a chemotherapeutic agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination can be carried out over a defined time period (usually minutes, hours, days or weeks depending upon the combination selected) or until disease progression. Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single unit doses for each of the therapeutic agents. Sequential or substantially simultaneous administration of each therapeutic agent can be effected by any appropriate route including, but not limited to, oral routes, intravenous routes, intramuscular routes, subcutaneous, intratumoral injection, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally, or all therapeutic agents may be administered by intravenous injection. The sequence in which the therapeutic agents are administered is not narrowly critical.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination may be administered to a patient simultaneously, sequentially or in combination. It will be appreciated that when using a composition or method the components may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

Although not wishing to be bound by theory, it is thought that the administration of CSF1R inhibitors in accordance with the methods described herein, in combination with one or more anti-PD1 therapeutics may provide additive effects in significantly inhibiting primary tumor growth and modulating the immune system into an antitumoral state, which can be beneficial in the treatment of disorders associated with the proliferation, survival, or biological action of macrophages, including the treatment of TGCT. Examples of anti-PD1 therapeutics that may be administered in combination with CSF1R inhibitors described herein include, but are not limited to, nivolumab, pidilizumab, cemiplimab, tislelizumab, AMP-224, AMP-514, and pembrolizumab.

The CSF1R inhibitors described herein, e.g., Compound 1, can be used in combination with other immunomodulatory agents including but not limited to anti-PD-L1 therapeutics including atezolizumab, durvalumab, BMS-936559, and avelumab, anti-TIM3 therapeutics including TSR-022 and MBG453, anti-LAG3 therapeutics including relatlimab, LAG525, and TSR-033, CD40 agonist therapeutics including SGN-40, CP-870,893 and R07009789, anti-CD47 therapeutics including Hu5F9-G4, anti-CD20 therapeutics, anti-CD38 therapeutics, or other immunomodulatory therapeutics including thalidomide, lenalidomide, pomalidomide, prednisone, and dexamethasone.

Sarcomas comprise a diverse group of malignancies including more than fifty subtypes of bone and soft tissue origin. In some embodiments, a method of treating a cancer comprises administering to a patient with locally advanced and metastatic high-grade sarcoma Compound 1 in combination with avelumab. In some embodiments, a method of treating a cancer comprises administering to a patient with locally advanced sarcoma Compound 1 in combination with avelumab. In some embodiments, a method of treating a cancer comprises administering to a patient with metastatic high-grade sarcoma Compound 1 in combination with avelumab. In some embodiments, a method of treating a cancer comprises administering to a patient with advanced metastatic sarcoma Compound 1 in combination with avelumab. In some embodiments, a method of treating a cancer comprises administering to a patient with undifferentiated pleomorphic sarcoma (UPS) Compound 1 in combination with avelumab. In some embodiments, a method of treating a cancer comprises administering to a patient with myxofibrosarcoma (MFS) Compound 1 in combination with avelumab. In some embodiments, a method of treating a cancer comprises administering to a patient with leiomyosarcoma (LMS) Compound 1 in combination with avelumab. In some embodiments, a method of treating a cancer comprises administering to a patient with dedifferentiated liposarcoma (DDLPS) Compound 1 in combination with avelumab.

The CSF1R inhibitors described herein, e.g., Compound 1, can also be used in combination with one or more chemotherapeutic agents including but not limited to anti-tubulin agents (e.g., paclitaxel, paclitaxel protein-bound particles for injectable suspension, eribulin, abraxane, docetaxel, ixabepilone, taxiterem, vincristine or vinorelbine), LHRH antagonists including but not limited to leuprolide, goserelin, triptorelin, or histrelin, anti-androgen agents including but not limited to abiraterone, flutamide, bicalutamide, nilutamide, cyproterone acetate, enzalutamide, and apalutamide, anti-estrogen agents including but not limited to tamoxifen, fulvestrant, anastrozole, letrozole, and exemestane, DNA-alkylating agents (including cisplatin, carboplatin, oxaliplatin, cyclophosphamide, ifosfamide, and temozolomide), DNA intercalating agents (including doxorubicin, pegylated liposomal doxorubicin, daunorubicin, idarubicin, and epirubicin), 5-fluorouracil, capecitabine, cytarabine, decitabine, 5-aza cytadine, gemcitabine methotrexate, bortezomib, and carfilzomib.

The CSF1R inhibitors described herein, e.g., Compound 1, can also be used in combination with targeted therapeutics including kinase inhibitors erlotinib, gefitinib, lapatanib, everolimus, temsirolimus, abemaciclib, LEE011, palbociclib, crizotinib, cabozantinib, sunitinib, pazopanib, sorafenib, regorafenib, axitinib, dasatinib, imatinib, nilotinib, vemurafenib, dabrafenib, trametinib, cobimetinib, binimetinib, idelalisib, quizartinib, avapritinib, BLU-667, BLU-263, Loxo 292, larotrectinib, and quizartinib, anti-estrogen agents including but not limited to tamoxifen, fulvestrant, anastrozole, letrozole, and exemestane, anti-androgen agents including but not limited to abiraterone acetate, enzalutamide, nilutamide, bicalutamide, flutamide, cyproterone acetate, steroid agents including but not limited to prednisone and dexamethasone, PARP inhibitors including but not limited to neraparib, olaparib, and rucaparib, topoisomerase I inhibitors including but not limited to irinotecan, camptothecin, and topotecan, topoisomerase II inhibitors including but not limited to etoposide, etoposide phosphate, and mitoxantrone, Histone Deacetylase (HDAC) inhibitors including but not limited to vorinostat, romidepsin, panobinostat, valproic acid, and belinostat, DNA methylation inhibitors including but not limited to DZNep and 5-aza-2'-deoxycytidine, proteasome inhibitors including but not limited to bortezomib and carfilzomib, thalidomide, lenalidomide, pomalidomide, biological agents including but not limited to trastuzumab, ado-trastuzumab, pertuzumab, cetuximab, panitumumab, ipilimumab, tremelimumab, vaccines including but not limited to sipuleucel-T, and radiotherapy.

In some embodiments, Compound 1 or a pharmaceutically acceptable salt thereof can be used in combination with an inhibitor of the TIE2 immunokinase including rebastinib or ARRY-614. In some embodiments, Compound 1 or a pharmaceutically acceptable salt thereof can be used in combination with an anti-PD1 therapeutic. In some embodiments, Compound 1 or a pharmaceutically acceptable salt thereof can be used in combination with an inhibitor of the TIE2 immunokinase including rebastinib or ARRY-614, and an anti-PD1 therapeutic. In some embodiments, a method of treating a cancer such as those selected from the group consisting of solid tumors, acute myeloid leukemia, myelodysplastic syndrome, acute lymphocytic leukemia, and chronic lymphocytic leukemia, in a patient in need thereof (e.g., a human patient suffering from cancer), comprises administering to a patient in need thereof a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof, and an inhibitor of the TIE2 immunokinase. In some embodiments, a method of treating a cancer such as those selected from the group consisting of melanoma, solid tumors, acute myeloid leukemia, myelodysplastic syndrome, acute lymphocytic leukemia, and chronic lymphocytic leukemia, in a patient in need thereof (e.g., a human patient suffering from cancer), comprises administering to a patient in need thereof a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof, an inhibitor of the TIE2 immunokinase, and an anti-PD1 therapeutic. In some embodiments, a method of treating a cancer such as those selected from the group consisting of melanoma, solid tumors, acute myeloid leukemia, myelodysplastic syndrome, acute lymphocytic leukemia, and chronic lymphocytic leukemia, in a patient in need thereof (e.g., a human patient suffering from cancer), comprises administering to a patient in need thereof a therapeutically effective amount of the compound 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one or a pharmaceutically acceptable salt thereof, and an anti-PD1 therapeutic. In some embodiments, the cancer is breast, cervix, pancreas, bladder, prostate, gastric, ovarian, melanoma, glioma, glioblastoma multiforme, osteosarcoma, osteolytic cancers, chondrosarcoma, histiocytosis, or lung cancer. In some embodiments, the cancer is breast cancer. In some embodiments, the cancer is pancreatic cancer. In some embodiments, the breast cancer is ductal carcinoma in situ (DCIS). In some embodiments, the breast cancer is invasive (or infiltrating) breast cancer (ILC or IDC). In some embodiments, the breast cancer is invasive ductal carcinoma. In some embodiments, the breast cancer is invasive lobular carcinoma. In some embodiments, the pancreatic cancer is an exocrine pancreatic cancer. In some embodiments, the exocrine pancreatic cancer is pancreatic adenocarcinoma. In some embodiments, the exocrine pancreatic cancer is pancreatic ductal adenocarcinoma (PDAC). In some embodiments, the pancreatic cancer is pancreatic adenocarcinoma. In some embodiments, the pancreatic cancer is pancreatic ductal adenocarcinoma (PDAC). In some embodiments, pancreatic cancer is PanNET).

The CSF1R inhibitors described herein, e.g., Compound 1, can also be used in combination with anti-angiogenic agents including AMG386, bevacizumab and aflibercept, and antibody-drug-conjugates (ADCs) including brentuximab vedotin, trastuzumab emtansine, ADCs containing a payload such as a derivative of camptothecin, a pyrrolobenzodiazepine dimer (PBD), an indolinobenzodiazepine dimer (IGN), DM1, DM4, MMAE, or MMAF.

In some embodiments, the additional therapeutic agent is selected from a luteinizing hormone-releasing hormone (LHRH) analog, including goserelin and leuprolide.

In some embodiments, the additional therapeutic agent is selected from the group consisting of selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, of atumtunab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)-ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6, Azgly 10](pyro-Glu-His-Trp-Ser-Tyr-D-Ser (Bu t)-Leu-Arg-Pro-Azgly-$NH_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutanide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, ipilumumab, vemurafenib, and mixtures thereof In some embodiments, the CSF1R inhibitor described herein, e.g., Compound 1, can be used in combination with both a chemotherapeutic agent and an immunomodulatory therapeutic, e.g., a chemotherapeutic agent and an anti-PD1 therapeutic described herein.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

The following abbreviations are used in this disclosure and have the following definitions: “DCM” is dichloromethane, “DMA” is N,N-dimethylacetamide, “DMF” is N,N-dimethylformamide, “dppf” is 1,1'-bis(diphenylphosphino) ferrocene, “DMSO” is dimethylsulfoxide, “ESI” is electrospray ionization, “EtOAc” is ethyl acetate, “h” is hour or hours, “Hex” is hexane, “LiHMDS” is lithium bis(trimethylsilyl)amide, “MeOH” is methanol, “$Me_4$tBuXPhos” is di-tert-butyl(2',4',6'-triisopropyl-3,4,5,6-tetramethyl-[1,1'-biphenyl]-2-yl)phosphine, “MHz” is megahertz, “MS” is mass spectrometry, “NMR” is nuclear magnetic resonance, “$Pd(PPh_3)_4$” is tetrakis(triphenylphosphine)palladium(0), “RT” is room temperature which is also known as “ambient temp,” which will be understood to consist of a range of normal laboratory temperatures ranging from 15-25° C., and “satd.” is saturated.

Example 1. Synthetic Route to Compound 1

Compound A: 3-((2-chloropyridin-4-yl)oxy)-6-iodo-2-methylpyridine

Compound A

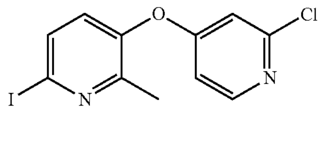

A solution of 3-hydroxy-2-methylpyridine (20.0 g, 183 mmol) and $Na_2CO_3$ (38.8 g, 367 mmol) in $H_2O$ (320 mL) and MeOH (200 mL) was treated with $I_2$ (46.5 g, 183 mmol) and stirred at RT for 1 h. The mixture was acidified with HCl (2 M), extracted with EtOAc (2×) and the combined organics were washed with brine, dried over $Na_2SO_4$ and concentrated to dryness. The material was suspended in 1:1 EtOAc/Hex, sonicated and the solid collected via filtration and dried. The filtrate was concentrated to dryness, treated with DCM, the solid collected via filtration and combined with the first solid to afford 6-iodo-2-methylpyridin-3-ol (20.5 g, 48%). MS (ESI) m/z: 236.0 ($M+H^+$).

A mixture of 6-iodo-2-methylpyridin-3-ol (6.8 g, 28.9 mmol), 2,4-dichloropyridine (8.56 g, 57.9 mmol) and $K_2CO_3$ (4.00 g, 28.9 mmol) in DMA (50 mL) was heated at 110° C. for 16 h under argon. The mixture was cooled to RT, treated with $H_2O$, extracted with EtOAc (2×) and the combined organics were washed with $H_2O$, then brine, dried over $Na_2SO_4$, concentrated to dryness and purified via silica gel chromatography (EtOAc/Hex) to afford 3-((2-chloropyridin-4-yl)oxy)-6-iodo-2-methylpyridine (7.35 g, 73%) as a white solid. MS (ESI) m/z: 346.9 ($M+H^+$).

Compound B: 3-methyl-2-(methylthio)-5-(4,4,5,5-tetramethyl-1,3,2-dioxaborolan-2-yl)pyrimidin-4 (3H)-one Compound B

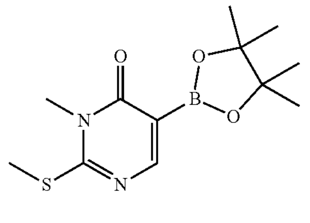

A 0° C. suspension of 2-(methylthio)pyrimidin-4(3H)-one (2.0 g, 14.1 mmol) in DMF (40 mL) was treated with solid LiHMDS (3.06 g, 18.3 mmol), followed by methyl iodide (1.14 mL, 18.3 mmol), warmed to RT and stirred overnight. The mixture was quenched with water, extracted with EtOAc (3) and the combined organics were dried over $Na_2SO_4$, concentrated to dryness and purified via silica gel chromatography (EtOAc/Hex) to afford 3-methyl-2-(methylthio)pyrimidin-4(3H)-one (1.37 g, 62%). $^1H$ NMR (400 MHz, DMSO-$d_6$): δ 7.83 (d, J=6.5 Hz, 1H), 6.17 (d, J=6.5 Hz, 1H), 3.39 (s, 3H), 2.54 (s, 3H); MS (ESI) m/z: 157.1 ($M+H^+$).

A 0° C. solution of 3-methyl-2-(methylthio)pyrimidin-4 (3H)-one (1.37 g, 8.77 mmol) in $CHCl_3$ (15 mL) was treated with bromine (0.54 mL, 10.5 mmol), stirred at 0° C. for 1 h, quenched with satd. $NaHCO_3$ (15 mL), warmed to RT slowly and stirred overnight. The mixture was extracted with DCM (3×) and the combined organics were dried over $Na_2SO_4$ and concentrated to dryness to afford 5-bromo-3-methyl-2-(methylthio)pyrimidin-4(3H)-one (2.0 g, 97% yield). $^1H$ NMR (400 MHz, DMSO-$d_6$): δ 8.24 (s, 1H), 3.45 (s, 3H), 2.55 (s, 3H); MS (ESI) m/z: 235.0 ($M+H^+$).

A mixture of 5-bromo-3-methyl-2-(methylthio)pyrimidin-4(3H)-one (1.0 g, 4.25 mmol), bis(pinacalato)diboran (1.30 g, 5.10 mmol), and KOAc (1.25 g, 12.7 mmol) in dioxane (10 mL) was sparged with Ar, treated with $PdCl_2$ (dppf)-DCM-adduct (0.17 g, 0.21 mmol), sparged again with Ar and heated at 85° C. overnight. The mixture was cooled to RT, quenched with satd. $NaHCO_3$, extracted with EtOAc (3×) and the combined organics were dried over $Na_2SO_4$ and concentrated to dryness to afford 3-methyl-2-(methylthio)-5-(4,4,5,5-tetramethyl-1,3,2-dioxaborolan-2-yl)pyrimidin-4(3H)-one (100% yield assumed). MS (ESI) m/z: 202.1 (mass of boronic acid+$H^+$).

Compound C: 3-methyl-5-(6-methyl-5-((2-(1-methyl-1H-pyrazol-4-yl)pyridin-4-yl)-oxy)pyridin-2-yl)-2-(methylthio)pyrimidin-4(3H)-one Compound C

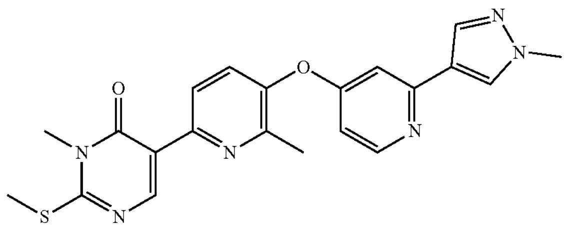

A mixture of Compound B (0.35 g, 1.73 mmol), Compound A (0.50 g, 1.44 mmol), and $K_2CO_3$ (0.60 g, 4.33 mmol) in 5:1 dioxane/water (12 mL) was sparged with Ar, treated with $Pd(PPh_3)_4$ (0.17 g, 0.14 mmol), sparged again with Ar and heated at 90° C. overnight. The mixture was quenched with satd. $NaHCO_3$, extracted with EtOAc (3×) and the combined organics were dried over $Na_2SO_4$, concentrated to dryness and purified via silica gel chromatography (EtOAc/Hex) to afford 5-(5-((2-chloropyridin-4-yl)oxy)-6-methylpyridin-2-yl)-3-methyl-2-(methyl-thio) pyrimidin-4(3H)-one (0.52 g, 67%). MS (ESI) m/z: 375.1 ($M+H^+$).

A mixture of 5-(5-((2-chloropyridin-4-yl)oxy)-6-methylpyridin-2-yl)-3-methyl-2-(methyl-thio)pyrimidin-4(3H)-one (0.52 g, 0.97 mmol), 1-methyl-4-(4,4,5,5-tetramethyl-1,3,2-dioxaborolan-2-yl)-1H-pyrazole (0.22 g, 1.07 mmol), and $K_2CO_3$ (0.40 g, 2.9 mmol) in 5:1 dioxane/water (6 mL) was sparged with Ar, treated with $Pd(PPh_3)_4$ (0.12 g, 0.10 mmol), sparged again with Ar and heated at 90° C. overnight. The solids were removed via filtration, the filtrate treated with satd. $NaHCO_3$, extracted with EtOAc (3×) and the combined organics were dried over $Na_2SO_4$, concentrated to dryness and purified via silica gel chromatography (MeOH/DCM) to afford 3-methyl-5-(6-methyl-5-((2-(1-methyl-1H-pyrazol-4-yl)pyridin-4-yl)-oxy)pyridin-2-yl)-2-(methylthio)pyrimidin-4(3H)-one (140 mg, 34%). MS (ESI) m/z: 421.1 ($M+H^+$).

Compound 1: 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one Compound 1

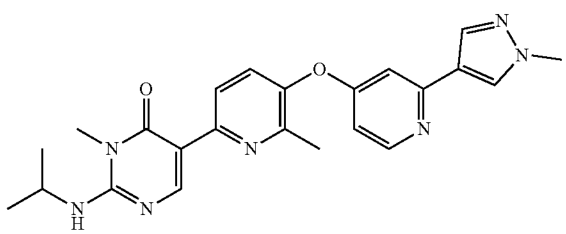 [SMILES: Cc1nc(-c2cnc(NC(C)C)n(C)c2=O)ccc1Oc1ccnc(-c2cnn(C)c2)c1]

A mixture of Compound C (0.14 g, 0.33 mmol) and isopropyl amine (3 mL, 35.0 mmol) was heated at 100° C. for 2 days in a sealed tube. The mixture was cooled to RT, the solid removed via filtration and the filtrate concentrated to dryness and purified via silica gel chromatography to obtain 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one (88 mg, 59%). $^1$H NMR (400 MHz, DMSO-$d_6$): δ 8.68 (s, 1H), 8.36 (d, J=5.7 Hz, 1H), 8.28 (d, J=8.7 Hz, 1H), 8.25 (s, 1H), 7.96 (d, J=0.7 Hz, 1H), 7.52 (d, J=8.6 Hz, 1H), 7.23 (d, J=2.4 Hz, 1H), 7.05 (d, J=7.6 Hz, 1H), 6.60 (dd, J=5.7, 2.4 Hz, 1H), 4.33 (m, 1H), 3.85 (s, 3H), 3.37 (s, 3H), 2.35 (s, 3H), 1.23 (d, J=6.6 Hz, 6H); MS (ESI) m/z: 432.2 (M+H$^+$).

Example 2. Depletion of Tumor Associated Macrophages in a Syngeneic Mouse Model of Colorectal Cancer The protocol and procedures involving the care and use of animals in the syngeneic MC38 mouse xenograft models below were reviewed and approved by the Institutional Animal Care and Use Committee (IACUC) of CrownBio (Taicang Jiangsu Province, China) prior to conduct. During the study, the care and use of animals was conducted in accordance with the regulations of the Association for Assessment and Accreditation of Laboratory Animal Care (AAALAC). All mice had food and water ad libitum. All mice were observed for clinical signs at least once daily. In the first experiment, six- to eight-week old female C57BL/6 mice were inoculated subcutaneously in the right lower flank with one million MC38 tumor cells in Phosphate Buffered Saline. When tumor burdens reached 102 mm$^3$ on average on day 12, mice were randomly assigned into groups. Groups of mice (n=10) were treated by oral gavage on days 12-18 as follows: vehicle control (0.4% hydroxypropylmethylcellulose in water) QD; Compound 1 5 mg/kg QD; Compound 1 10 mg/kg QD; or compound 1 15 mg/kg QD. Tumor volume and body weight were measured thrice weekly. Tumor burden (mg) was estimated from caliper measurements by the formula: tumor burden (mg=mm$^3$)=(length×width$^2$)/2. Tumors were collected at 2 hours post the 7th dose on day 18 and freshly processed to assess infiltrating tumor-associated macrophages by flow cytometry using antibodies to CD11b+, F4/80, and CD45+. First, tumors were washed in phosphate-buffered saline and treated with collagenase and DNase. After treatment, cells were repeatedly passed through a 70 μm cell strainer. Cells were further washed, resuspended in red blood cell lysing buffer, then washed again. Cells were adjusted to a concentration of 1×10^7 cells/mL and incubated with fluorescently-conjugated antibodies (CD45-FITC, CD11b-PE, and F4/80-APC; BioLegend). Stained cells were washed several times before analysis by flow cytometry.

In a second syngeneic MC38 xenograft experiment, seven- to nine-week old female C57BL/6 mice were inoculated with MC38 tumor cells as above. When tumor burdens reached 104 mm$^3$ on average on day 12, mice were randomly assigned into groups. Groups of mice (n=5) were treated by oral gavage on days 12-32 as follows: vehicle control (0.4% hydroxypropylmethylcellulose in water) QD; isotype control group (no oral treatments); Compound 1 5 mg/kg QD; or Compound 1 10 mg/kg QD. Vehicle mice were also treated intraperitoneally biweekly with phosphate-buffered saline, whereas all other mice were also treated intraperitoneally biweekly with a rat IgG2a isotype control antibody, that served as a control for a combination immunotherapy treatment in other cohorts not described herein. Tumors were collected on day 32, and processed for flow cytometry as described above, except cells were incubated with the fluorescently-labeled antibodies (CD45-FITC, CD11b-PE-Cy7, F4/80-APC, and CD335-PE; BioLegend).

Figure 2:
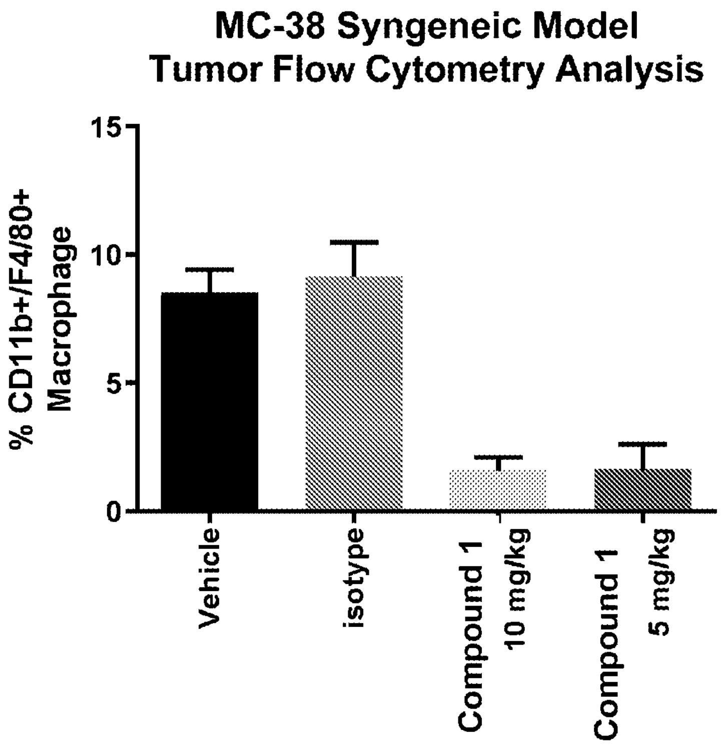
FIG. 2 depicts a change in the amount of CD11b+/F4/80+ intratumoral macrophages in mice that received treatment with Compound 1 compared to treatment with vehicle or isotype controls.

FIGS. 1 and 2 are graphical representations demonstrating depletion of tumor-associated macrophages compared to vehicle control. FIG. 1 demonstrates that after seven days of treatment with Compound 1, there is dose-dependent reduction in CD11b+/F4/80+ intratumoral macrophages (as a percent of CD45+ cells in the tumor). At the high dose, intratumoral macrophages were reduced ~67% (as a percent of CD45+ cells in the tumor). FIG. 2 demonstrates that after 21 days of treatment with Compound 1, there is a >80% reduction in intratumoral macrophages compared to vehicle or isotype controls (as a percent of all cells in the tumor). These data demonstrate that treatment of mice with Compound 1 for seven days or 21 days, leads to the depletion of intratumoral macrophages.

Example 3. Pharmacokinetic (PK) Properties and Depletion of Circulating CSF1R-Expressing Monocytes in Treated Patients Doses of Compound 1 were administered orally and assessed in seven dose-cohorts across 40 patients with advanced solid tumor malignancies and TGCT. This included one dose-cohort that received 10 mg QD, five dose-cohorts that received a schedule of weekly or twice-weekly maintenance doses dosing preceded by a five-day loading dose regimen at doses of up to 40 mg per dose, and one cohort received 50 mg QD 5-day loading dose followed by 20 mg QD. Those five cohorts were: Cohort 1, 10 mg QD (n=7); Cohort 2, 10 mg QD 5-day loading dose followed by biweekly (twice a week or "BIW") 10 mg maintenance dose (5×QD/BIW; n=3); Cohort 3, 20 mg QD 5-day loading dose followed by weekly 20 mg maintenance dose (5×QD/Q1W; n=4); Cohort 4, 20 mg QD 5-day loading dose followed by biweekly 20 mg maintenance dose (5×QD/BIW; n=4); Cohort 5, 30 mg QD 5-day loading dose followed by biweekly 30 mg maintenance dose (5×QD/BIW; n=6); Cohort 6, 40 mg QD 5-day loading dose followed by biweekly 40 mg maintenance dose (5×QD/BIW; n=5); Cohort 7, 50 mg QD 3-day loading dose followed by 20 mg maintenance dose (3×QD/QD; n=8).

PK analysis was conducted on all 38 patients. Serial blood samples were collected for PK and took place on either Day −7, Cycle 1, Day 1 (C1D1) and C2D1 at pre-dose, 0.5, 1, 2, 4, 6, 8, 10-12, and 24 hr time points or Day −7, C1D1, C1D8, and C2D1 at pre-dose, 1, 2, 4, 6, and 8 hr time points, or C1D1, C1D8, and C2D1 at pre-dose, 1, 2, 4, 6, and 8 hr time points. High fat meal was given prior to dosing of Compound 1 on Day −7. PD effects were measured by two methodologies: 1) depletion of CSF1R-expressing monocytes in peripheral blood (Cohorts 1-7) from C1D1, C1D15 and C2D1; and 2) increase of plasma levels of CSF1 and IL-34, the ligands for CSF1R (Cohorts 1-7) on C1D1, C1D15, and C2D1. For the CD16$^+$ monocyte assay, whole blood collected in an EDTA vacutainer was aliquoted into tubes and incubated with fluorescently-labeled antibodies (CD14-Alexa488 (BD Pharmingen); CD16-PE-Cy7 (BD Pharmingen); and TIE2-APC (R&D Systems). After incubation, red blood cells were lysed, and the remaining cells were washed several times before being analyzed on a flow cytometer. For the plasma CSF1 assay or IL-34, whole blood collected in an EDTA vacutainer was centrifuged, and the plasma was collected and frozen. Plasma levels of CSF1 or IL-34 were measured using a commercial ELISA kit (R&D Systems).

Mean pharmacokinetic parameters for each cohort of patients are shown in Table 1. C2D1 values for $AUC_{0\text{-}8h}$ (area under the plasma concentration-time curve at 0-8 hours); $C_{max}$ (maximum plasma concentration); and $C_{trough}$ (trough plasma concentration) are shown for all cohorts. Cohort 1 had daily dosing. Cohorts 2 onward had a 5-day loading dose, followed by once or twice weekly maintenance dose dosing. Cohort 7 had a 3-day loading dose, followed by once day maintenance dose dosing. C2D1 $AUC_{0\text{-}8h}$, $C_{max}$, and $C_{trough}$ had approximately dose-dependent increases in Cohorts 1-7.

Figure 3:
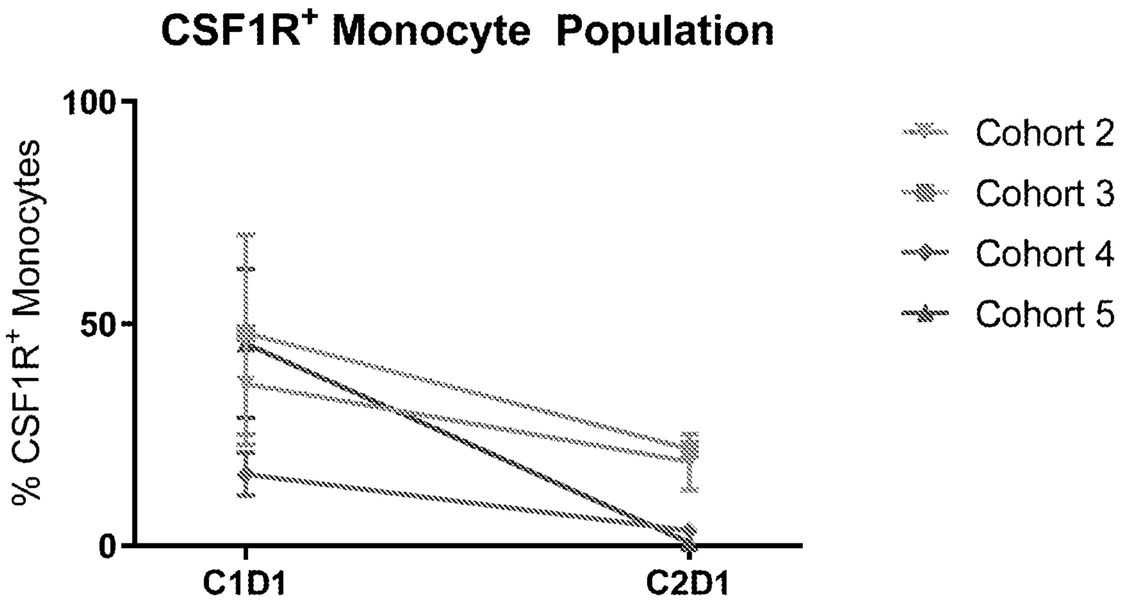
FIG. 3 depicts a graphical representation demonstrating depletion of CSF1R-expressing monocytes in peripheral blood from patients treated with Compound 1.

FIG. 3 is a graphical representation demonstrating depletion of CSF1R-expressing monocytes in peripheral blood from patients treated with Compound 1. CSF1R-expressing monocytes were reduced in Cohorts 2-5, with a greater reduction occurring in the cohorts with the highest dosage of Compound 1. Cohort 2 (n=2) had a ~48% decrease in the levels of CSF1R-expressing monocytes at C2D1 compared to the level of CSF1R-expressing monocytes on C1D1. Cohort 3 (n=1) had a ~54% decrease in the levels of CSF1R-expressing monocytes at C2D1 compared to the level of CSF1R-expressing monocytes on C1D1. Cohort 4 (n=2) had a ~79% decrease in the levels of CSF1R-expressing monocytes at C2D1 compared to the level of CSF1R-expressing monocytes on C1D1. Cohort 5 (n=2) had a ~98% decrease in the levels of CSF1R-expressing monocytes at C2D1 compared to the level of CSF1R-expressing monocytes on C1D1.

Figure 15:
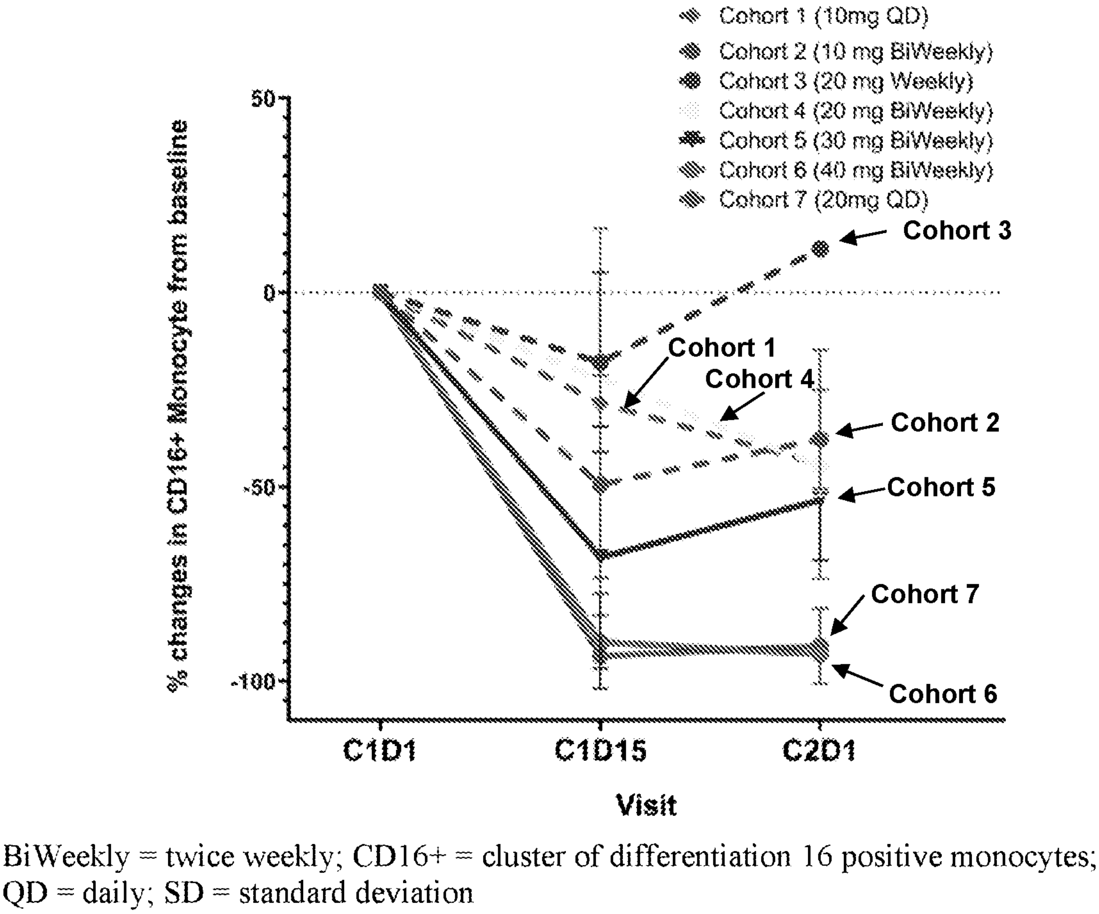
FIG. 15 depicts an exemplary graphical representation demonstrating depletion of $CD16^{+}$ monocytes in peripheral blood from patients treated with Compound 1.

FIG. 15 is a graphical representation demonstrating depletion of $CD16^+$ monocytes in peripheral blood from patients treated with Compound 1. The $CD16^+$ monocyte subset is known to be sensitive to CSF-1 treatment and, thus, serves as a pharmacodynamic marker of CSF-1R inhibition. PD data obtained from Compound 1 treated patients have shown that $CD16^+$ monocyte levels decreased with increasing Compound 1 dose and concentration, indicating blockade of CSF1R signaling. In the lower-dose cohorts (Cohorts 1-4), the percentage of $CD16^+$ monocytes of total blood monocytes at baseline decreased by 18% to 9% after 2 weeks of Compound 1 treatment. In the higher-dose cohorts (Cohorts 5-7), the percentage of $CD16^+$ monocytes of total blood monocytes at baseline decreased by 68% to 94% after 2 weeks of Compound 1 treatment.

Figure 4:
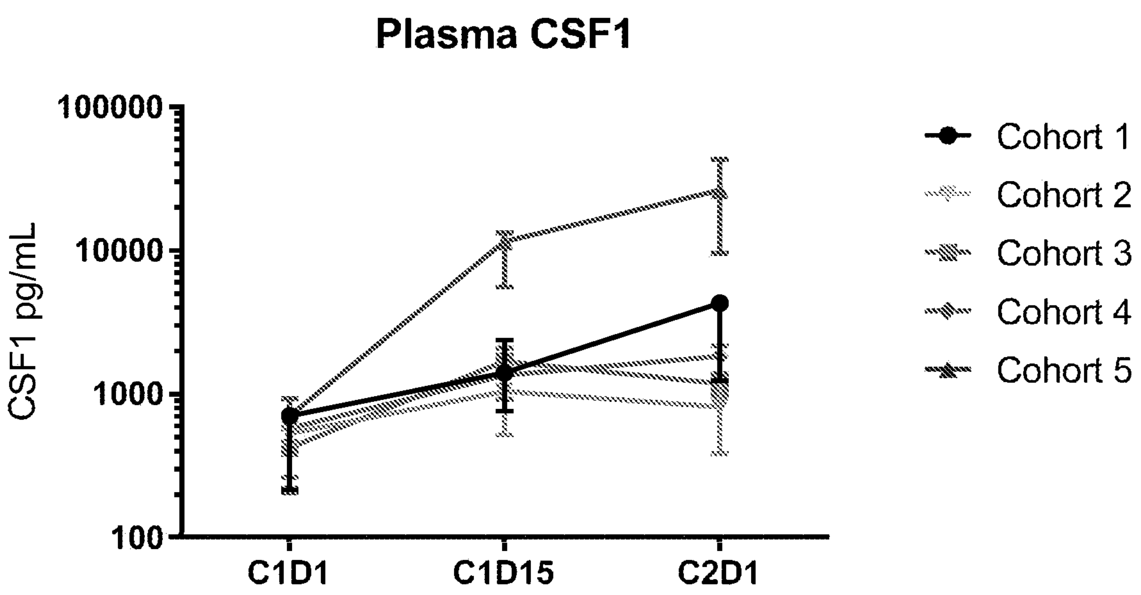
FIG. 4 depicts a graphical representation demonstrating increases in CSF1 in plasma from patients treated with Compound 1.

FIG. 4 is a graphical representation demonstrating increases in CSF1 in plasma from patients treated with Compound 1. Patients from all five cohorts had increases in levels of plasma CSF1 at C1D15 and C2D1 compared to C1D1. On average at C2D1, Cohort 1 had a 6-fold increase in plasma CSF1, Cohort 2 had a 1.5-fold increase, cohort 3 had a 2.9-fold increase, cohort 4 had a 3.2-fold increase, and cohort 5 had a 43-fold increase.

Figure 16:
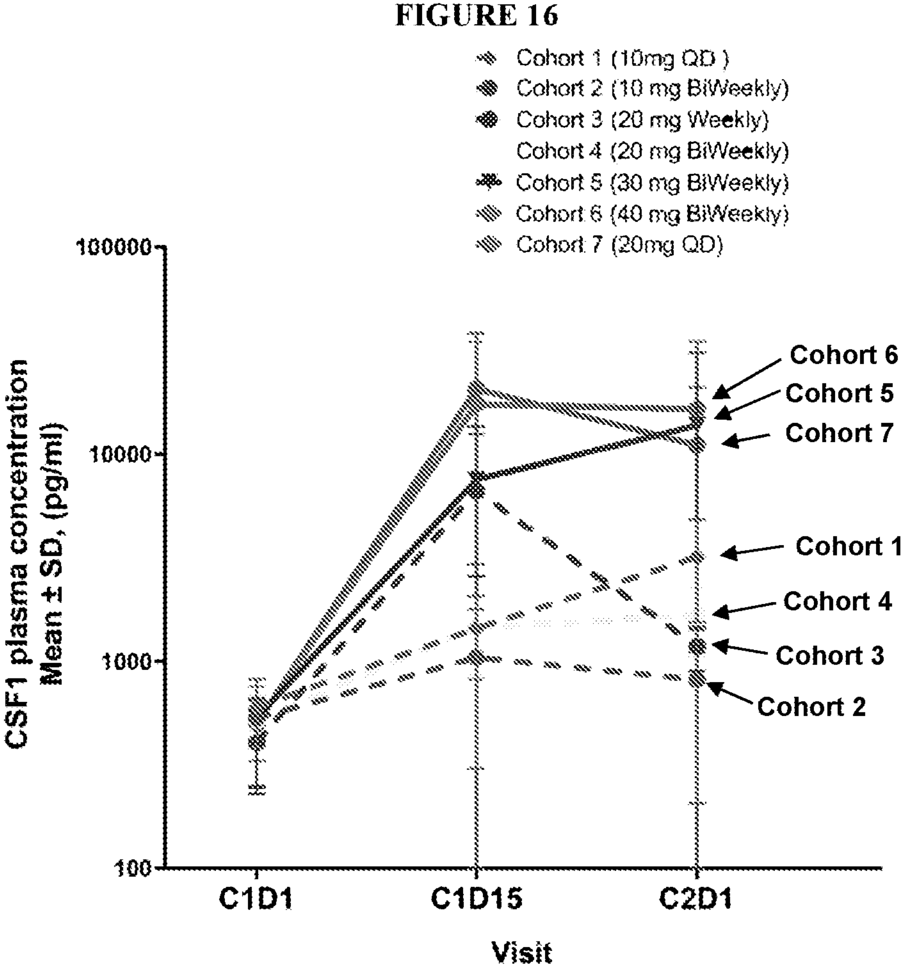
FIG. 16 depicts an exemplary graphical representation demonstrating increases in CSF1 and IL-34 in plasma from patients treated with Compound 1.

FIG. 16 is a graphical representation demonstrating increases in CSF1 and IL-34 in plasma from patients treated with Compound 1. On C1D1, all patients had detectable levels of CSF1 with a mean value of 520.7 pg/mL across all cohorts. Serum CSF1 concentrations increased with increasing Compound 1 dose and concentration. CSF1 levels in the lower-dose cohorts (Cohorts 1-4) were increased about 3- to 5-fold at C2D1 over baseline. In the higher-dose cohorts (Cohorts 5-7), patients experienced 22- to 36-fold increases in CSF1 levels at C2D1. Cohort 6 and 7 doses had similar effects on serum CSF1 levels. Compound 1 demonstrated a dose-dependent impact on circulating CSF1 concentrations. A similar trend was observed with IL-34 levels. On C1D1, all patients had detectable IL-34 levels with a mean value of 9.3 pg/mL across all cohorts. Patients enrolled in the lower-dose cohorts (Cohorts 1-4) experienced a 2- to 5-fold increase in IL-34 over baseline by C2D1. In the higher-dose cohorts (Cohorts 5-7), patients experienced 26- to 100-fold increases in IL-34 levels at C2D1. Cohort 6 and 7 doses had similar effects on serum IL-34 levels.

TABLE 1

Parameters for Day −7, Day 1 of Cycle 1, Day 8 of Cycle 1 and Day 1 of Cycle 2.

| Cohort | Visit | | N | $C_{max}$ (ng/mL) | $AUC_{0\text{-}8\ h}$ (h*ng/ml) | $C_{trough}$ (ng/mL) |
|---|---|---|---|---|---|---|
| Cohort 1 10 mg QD | −7 | Geo Mean | 7 | 75.9 | 429 | — |
| | | CV % | | 36.1 | 44.3 | — |
| | C1D1 | Geo Mean | 7 | 155 | 770 | — |
| | | CV % | | 36 | 44.3 | — |
| | C1D8 | Geo Mean | 6 | — | — | 331 |
| | | CV % | | — | — | 23.9 |
| | C2D1 | Geo Mean | 3 | 767 | 4470 | $447^c$ |
| | | CV % | | 12.3 | 17.4 | 65.2 |
| Cohort 2 10 mg QD × 5 d BIW maintenance dose | −7 | Geo Mean | 1 | 119 | 781 | — |
| | | CV % | | — | — | — |
| | C1D1 | Geo Mean | 2 | 168 | 1080 | — |
| | | CV % | | 20.8 | 24.3 | — |
| | C1D8 | Geo Mean | 3 | 248 | 1730 | 184 |
| | | CV % | | 89.9 | 89.5 | 76.5 |
| | C2D1 | Geo Mean | 3 | 149 | 1030 | 122 |
| | | CV % | | 68.7 | 63.0 | 63.3 |
| Cohort 3 20 mg QD × 5 d QW maintenance dose | −7 | Geo Mean | 4 | 242 | 1320 | — |
| | | CV % | | 31.2 | 24.9 | — |
| | C1D1 | Geo Mean | 3 | 466 | 2510 | — |
| | | CV % | | 36.7 | 24.2 | — |
| | C1D8 | Geo Mean | 3 | 1160 | $7410^b$ | 850 |
| | | CV % | | 6.2 | 15.3 | 14.2 |
| | C2D1 | Geo Mean | 2 | 530 | 3380 | 205 |
| | | CV % | | 27.9 | 20 | 10.0 |
| Cohort 4 20 mg QD × 5 d BIW maintenance dose | −7 | Geo Mean | 4 | 183 | 1090 | — |
| | | CV % | | 32.7 | 29.7 | — |
| | C1D1 | Geo Mean | 4 | 268 | 1610 | — |
| | | CV % | | 29.9 | 40.7 | — |
| | C1D8 | Geo Mean | 4 | 685 | 4660 | 483 |
| | | CV % | | 35.3 | 44.3 | 55.9 |
| | C2D1 | Geo Mean | 3 | 642 | 4300 | 441 |
| | | CV % | | 8.21 | 2.82 | 19.9 |
| Cohort 5 30 mg QD × 5 d BIW maintenance dose | −7 | Geo Mean | 6 | 278 | 1390 | — |
| | | CV % | | 42.1 | 49.8 | — |
| | C1D1 | Geo Mean | 6 | 600 | $3390^c$ | — |
| | | CV % | | 52.9 | 37.9 | — |
| | C1D8 | Geo Mean | 3 | 1400 | 8800 | 1020 |
| | | CV % | | 17.9 | 32.4 | 33.6 |
| | C2D1 | Geo Mean | 3 | 953 | 5420 | 574 |
| | | CV % | | 85.5 | 65.8 | 61.6 |
| Cohort 6 30 mg QD × 5 d BIW maintenance dose | C2D1 | Geo Mean | 3 | 1150 | 7290 | 570 |
| Cohort 7 50 mg QD × 3 d QD maintenance dose | C2D1 | Geo Mean | 3 | 1250 | 7980 | 1040 |

$AUC_{0\text{-}8\ h}$ = area under the plasma concentration-time curve at 0-8 hours; $C_{max}$ = maximum plasma concentration; $C_{trough}$ = trough plasma concentration; CV % = percent coefficient of variation; GeoMean = geometric mean; N = number of patients with observation; PK = pharmacokinetic; $T_{max}$ = time to maximum concentration.
[a] N = 6, [b] N = 2, [c] N = 5

TABLE 2

Parameters for Day −7, Day 1 of Cycle 1, Day 8 of Cycle 1 and Day 1 of Cycle 2

| Cohort | Visit | N | $T_{max}$[a] (hr) | $C_{max}$ (ng/mL) | $AUC_{0\text{-}8}$ (hr*ng/mL) |
|---|---|---|---|---|---|
| Cohort 1 | Day −7 | 7 | 6 (2, 24) | 75.9 (36.1) | 425 (44) |
| 10 mg | C1D1 | 7 | 1 (0.5, 24) | 155 (36) | 770 (44.3) |
| QD[b] | C1D8 | 6 | NA | NA | NA |

TABLE 2-continued

Parameters for Day −7, Day 1 of Cycle 1, Day 8 of Cycle 1 and Day 1 of Cycle 2

| Cohort | Visit | N | $T_{max}$[a] (hr) | $C_{max}$ (ng/mL) | $AUC_{0-8}$ (hr*ng/mL) |
|---|---|---|---|---|---|
| | C2D1 | 5 | 0.5 (0.5, 1)[c] | 767 (12.3)[c] | 4510 (15.9)[c] |
| Cohort 2 | Day −7 | 2 | 6 (4, 8) | 80.2 | 353 |
| 10 mg | C1D1 | 3 | 2 (1, 8) | 94 (134) | 467 (275) |
| Twice | C1D8 | 3 | 1 (1, 8) | 248 (89.9) | 1730 (89.5) |
| Weekly[b] | C2D1 | 3 | 1 (0.5, 4) | 149 (68.7) | 1030 (63) |
| Cohort 3 | Day −7 | 4 | 4 (1, 4) | 242 (31.2) | 1320 (24.9) |
| 20 mg | C1D1 | 3 | 1 (1, 1) | 466 (36.7) | 2510 (24.2) |
| Weekly[b] | C1D8 | 3 | 1 (0.5, 1) | 1160 (6.2) | 7290 (11.1) |
| | C2D1 | 2 | 1 (1, 1) | 530 | 3380 |
| Cohort 4 | Day −7 | 4 | 4 (2, 4) | 183 (32.7) | 1090 (29.7) |
| 20 mg | C1D1 | 4 | 0.75 (0.5, 8) | 268 (29.9) | 1610 (40.7) |
| Twice | C1D8 | 4 | 2.25 (0.5, 4) | 685 (35.3) | 4660 (44.3) |
| Weekly[b] | C2D1 | 3 | 0.5 (0.5, 2) | 642 (8.21) | 4300 (2.82) |
| Cohort 5 | Day −7 | 6 | 6 (4, 8) | 278 (42.1) | 1390 (49.8) |
| 30 mg | C1D1 | 9 | 1 (0.5, 6) | 422 (79.3) | 2250 (77.3) |
| Twice | C1D8 | 7 | 1 (1, 2)[d] | 1160 (29)[d] | 7160 (33.9)[d] |
| Weekly[b] | C2D1 | 6 | 1.5 (0.5, 2) | 822 (58) | 4750 (53.2) |
| Cohort 6 | Day −7 | 5 | 4 (4, 8) | 454 (28.3) | 2250 (28.9) |
| 40 mg | C1D1 | 5 | 2 (0.5, 6) | 830 (36.9) | 4790 (28.7) |
| Twice | C1D8 | 4 | 1 (0.5, 6) | 1860 (25.9) | 12000 (26.1) |
| Weekly[b] | C2D1 | 3 | 1 (0, 2) | 1150 (29.8) | 7290 (28.1) |
| Cohort 7 | Day −7 | 2 | 5 (2, 8) | 272 | 800 |
| 20 mg | C1D1 | 7 | 2 (0.5, 8) | 440 (84.1) | 2310 (77.4) |
| QD[e] | C1D8 | 7 | 2 (1, 4) | 1010 (42) | 6740 (33.3) |
| | C2D1 | 4 | 2 (0.5, 6) | 840 (99.8) | 5580 (86.8) |

$AUC_{0-8\ h}$ = area under the plasma concentration-time curve at 0-8 hours;
$C_{max}$ = maximum plasma concentration;
$C_{trough}$ = trough plasma concentration;
CV % = percent coefficient of variation;
GM = geometric mean;
max = maximum;
min = minimum;
N = number of patients with observation;
NA = not applicable;
PK = pharmacokinetic;
QD = daily;
$T_{max}$ = time to maximum concentration
[a]Median (Min, Max) of $T_{max}$.
[b]After 5-day QD loading dose.
[c]N = 3.
[d]N = 6.
eAfter 3-day 50 mg QD loading dose.

Figure 17:
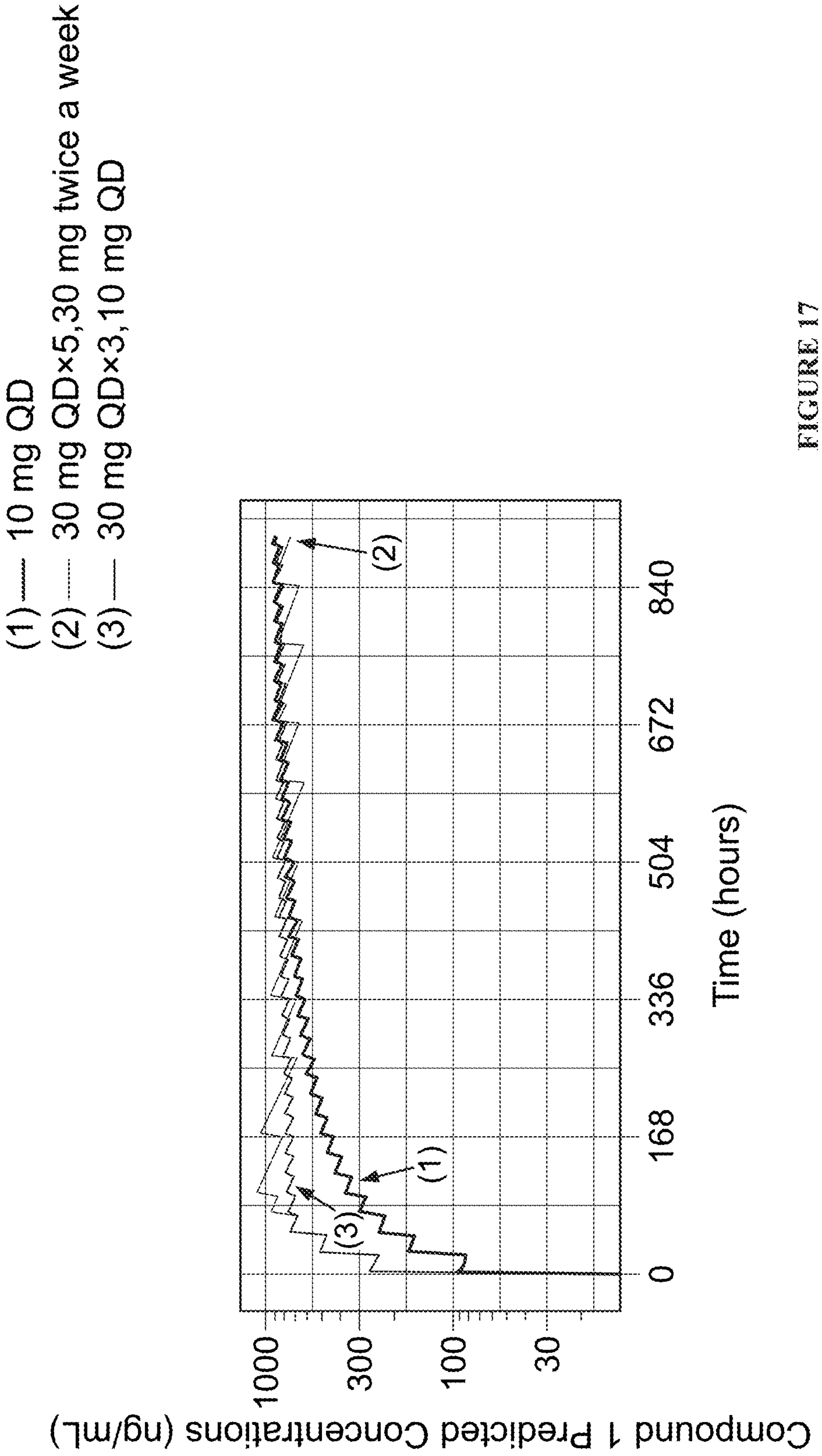
FIG. 17 depicts exemplary simulations of dosing of Compound 1. Simulated concentrations are plotted for Compound 1 when dosed at 3 different dosing regimens: (1) 10 mg QD, (2) 5-days 30 mg QD loading dose followed by 30 mg twice a week maintenance dose and (3) 3-day 30 mg QD loading dose followed by 10 mg QD maintenance dose. Pharmacokinetic simulations are based on preliminary non-parametric superposition using cohort 1-7 data from patients with evaluable pharmacokinetics at the time of analysis.

The dose escalation uses a pharmacologically guided 3+3 study design, in which Compound 1 is administered orally in repeated 28-day cycles. Based on pharmacokinetic data available from patients across dose cohorts 1 to 7, an accurate estimation of half-life is not available due to relatively short PK sampling time. Current data suggests that Compound 1 has a long half-life, with QD dosing regimens approaching stead-state levels close to C2D1. Simulations based on non-parametric superposition analysis show that steady state can be achieved faster by the use of loading doses. For example, 3-day 30 mg QD loading doses followed by a maintenance dose of 10 mg QD could achieve and maintain steady-state concentrations within approximately one week (FIG. 17). Also, simulations show that 5-day 30 mg QD loading dose followed by a biweekly (i.e. twice a week) 30 mg dose could establish steady state concentrations within approximately one week, although the peak-to-trough plasma concentration range would be wider compared to a 10 mg QD maintenance schedule due to a lower $C_{trough}$ value at steady-state (FIG. 17).

Figure 5:
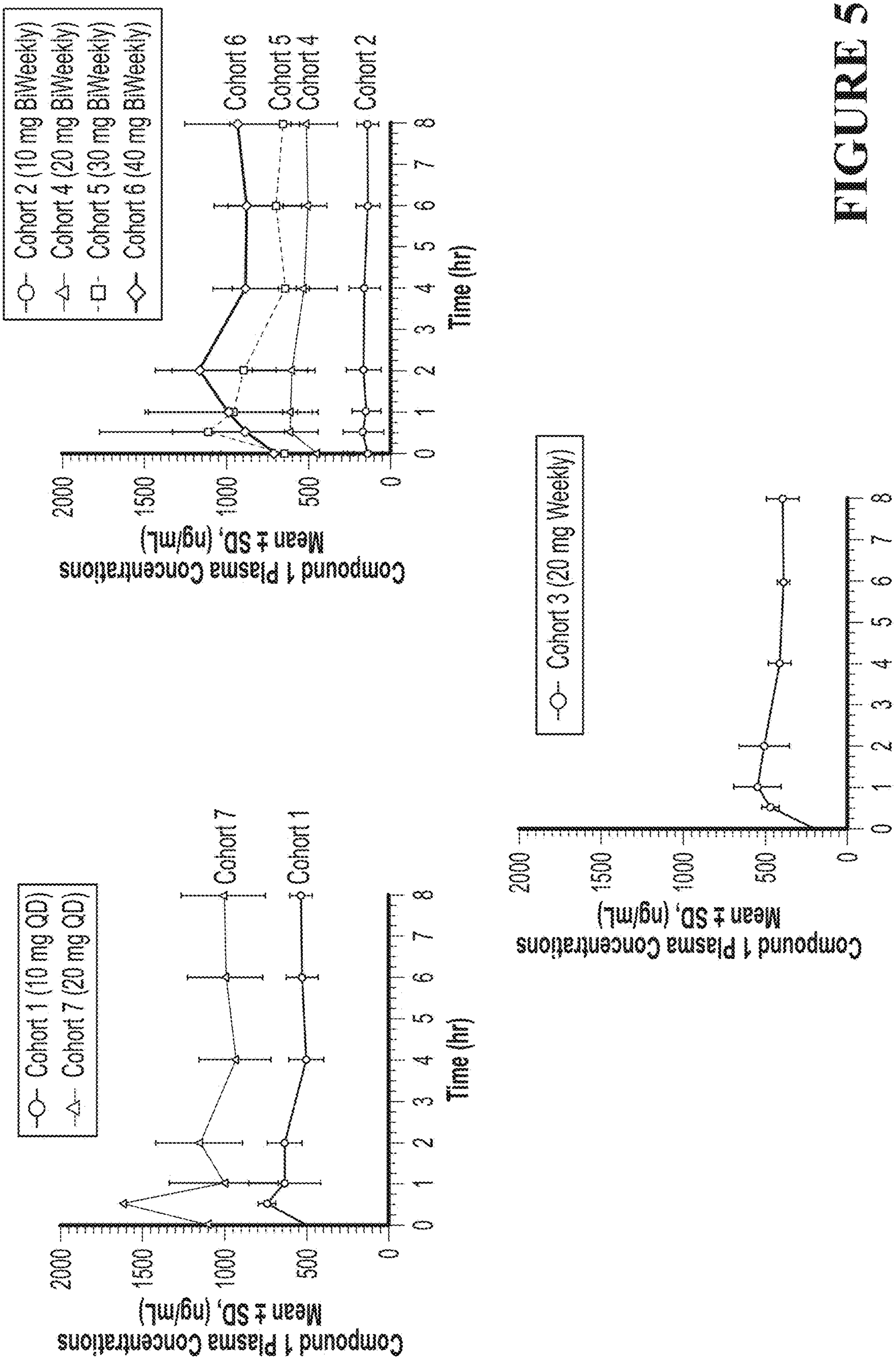
FIG. 5 depicts Compound 1 plasma concentration as a function of time at Cycle 2, Day 1 for subjects in each of Cohorts 1-7 as described in Example 3.
Figure 6:
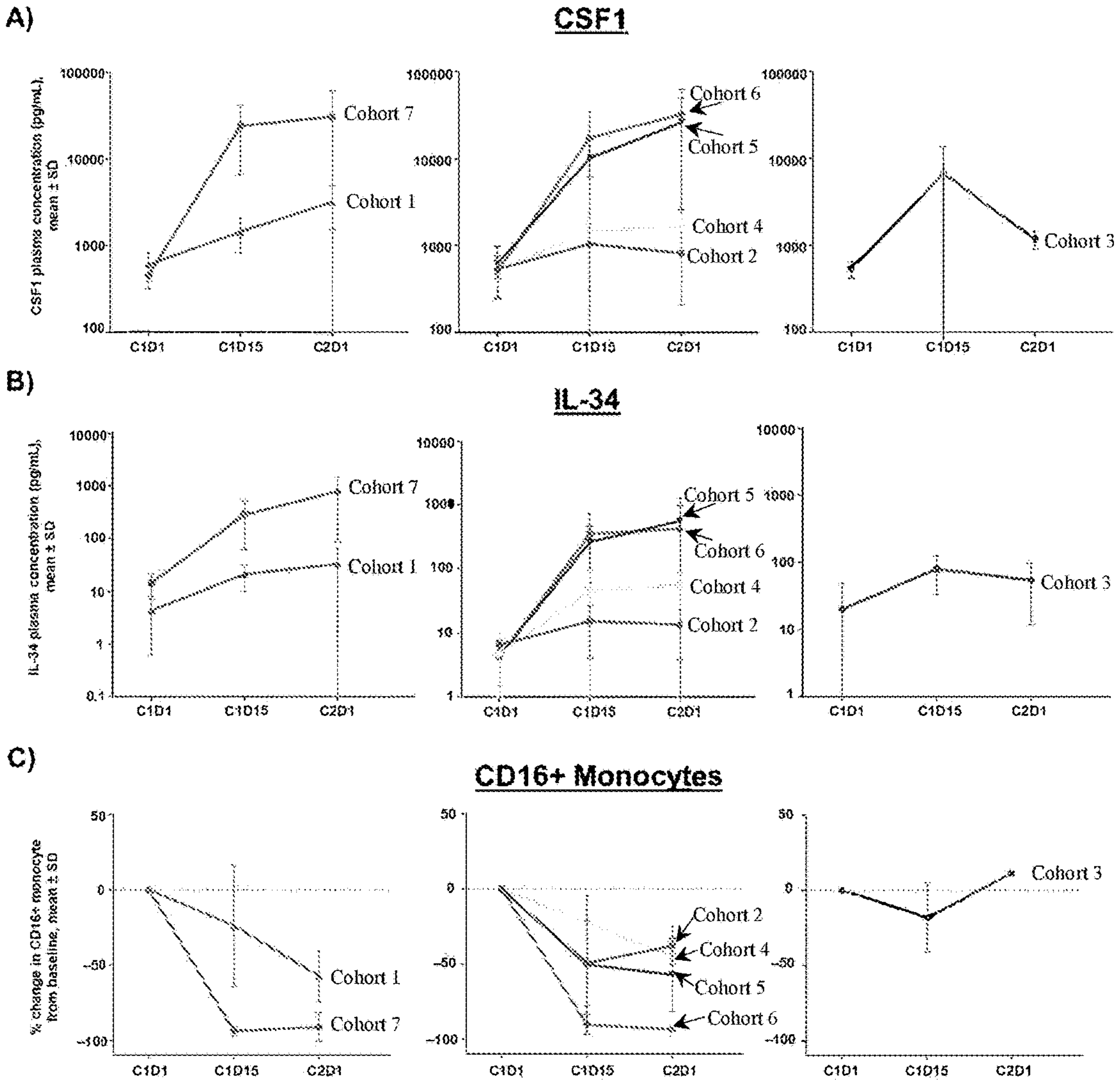
FIG. 6 depicts (A) CSF1 plasma concentration in subjects of each of Cohorts 1-7 described in Example 3 across different time periods in certain cycles (Cycle 1, Day 1; Cycle 1, Day 15; and Cycle 2, Day 1); (B) IL-34 plasma concentration in subjects of each of Cohorts 1-7 as described in Example 3 across different time periods in certain cycles (Cycle 1, Day 1; Cycle 1, Day 15; and Cycle 2, Day 1); and (C) percentage change in CD16+ monocycte population in subjects of each of Cohorts 1-7 described in Example 3 across different time periods in certain cycles (Cycle 1, Day 1; Cycle 1, Day 15; and Cycle 2, Day 1).

Compound 1 plasma concentration as a function of time for the subjects of each Cohort evaluated at C2D1 as shown in Table 1 is presented in FIG. 5. In these subjects, Compound 1 treatment causes a rise in plasma CSF1 and IL-34 that is drug concentration dependent and the rapid and sustained reduction of CD16+ monocytes that is dose dependent (FIG. 6).

Figure 7:
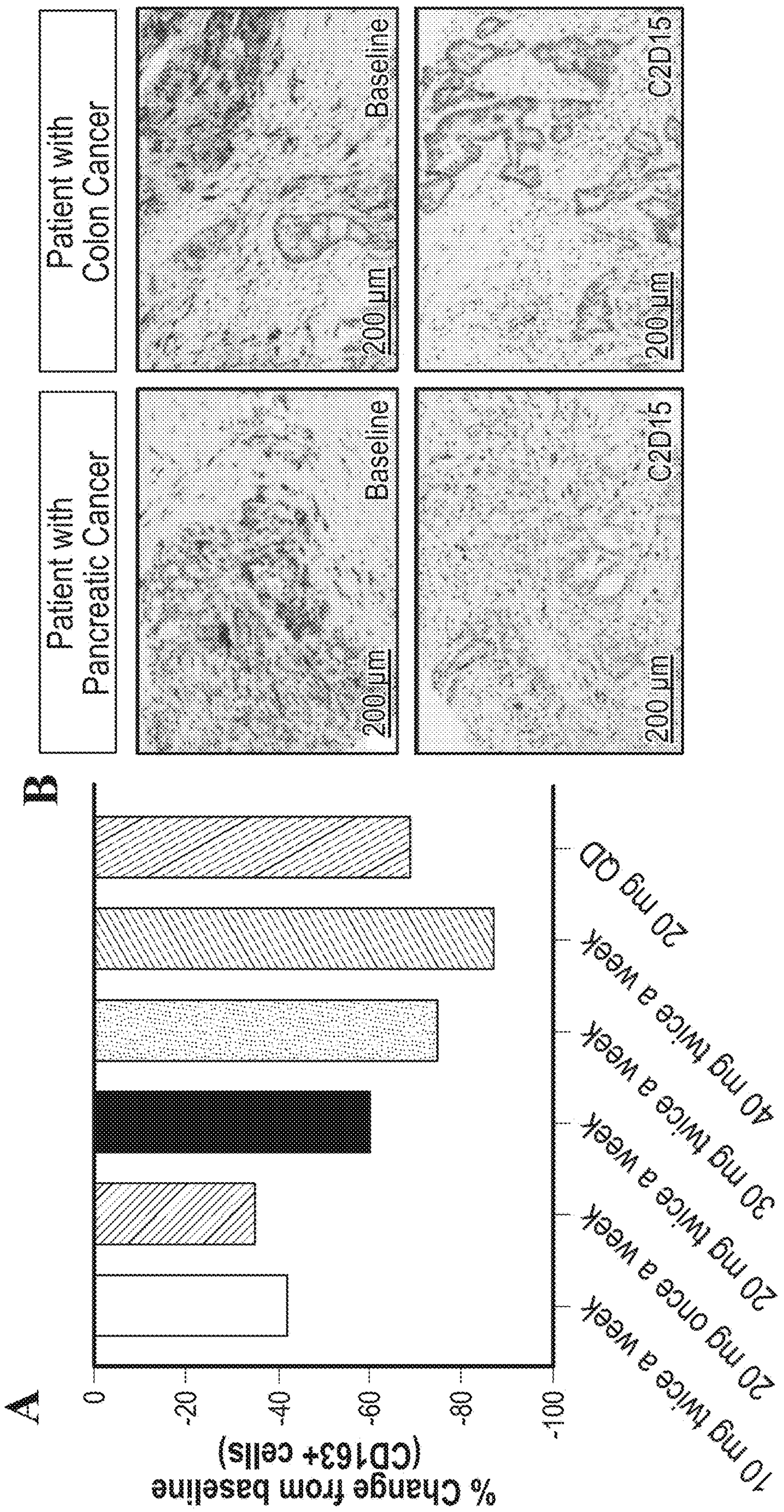
FIG. 7 depicts (A) percent changes in CD163+ macrophages in patients in selected Cohorts as defined by maintenance dose in Example 3 and (B) exemplary tumor biopsies at baseline and Cycle 2, Day 15 in patients with pancreatic cancer or colon cancer.

Changes in CD163+ macrophage populations were assessed in paired tumor biopsies taken at screening and at Cycle 2 Day 15 (C2D15) (FIG. 7). Samples were processed for IHC analysis of CD163 (10D6). Whole tissue image was analyzed by using the Flagship cTA platform to quantify CD163.

Example 4. Study with Patients Having Advanced Tumors

Antitumor activity of Compound 1 in patients with advanced tumors and dosing is evaluated in a human patient clinical trial.

The study enrolls patients with solid tumors or manifestations of cancer with known contribution of macrophages or phagocytes, i.e., tumors known to have expression of the receptor colony-stimulating factor 1 receptor (CSF1R) or its ligands, Colony stimulating factor-1 (CSF1) or interleukin (IL)-34, confirmed by the literature or prior testing. The prime example of such diseases is diffuse-type tenosynovial giant cell tumor (DTGCT), where aberrant over production of CSF1 drives recruitment of macrophages leading to local destruction of joints. anti-CSF1R therapy has demonstrated clinical efficacy in DTGCT. Patients with any common carcinomas that have high tumor-infiltrating macrophage content will be eligible for the study. In addition, tumor-associated manifestations featuring macrophage or osteoclast pathophysiology including bone metastases and ascites or effusions that typically contain high levels of macrophages will be enrolled. Lastly, as macrophages have been implicated in drug resistance or adapted response to approved therapy, Compound 1 will also be investigated in this paradigm.

The study consists of a screening period that is conducted within 28 days prior to the first dose of study drug, a treatment period of 28-day cycles, an End of Treatment visit, and Follow-up Safety visits at both 30 days and 75 days (±5 days) after the last dose of study drug. Patients will be eligible to receive study drug for up to 2 years until tumor progression, occurrence of unacceptable toxicity, or withdrawal of consent, or until commercial supply of the drug is available. This may be extended for patients who exhibit evidence of clinical benefit and tolerability to the drug, and who adhere to the study procedures. Patients may continue receiving treatment after tumor progression.

Any of the following advanced solid tumors that have progressed after treatment with all available therapies known to confer clinical benefit or for which conventional therapy is not considered effective as judged by a person of skill in the art. Any of the following advanced solid tumors that have progressed after treatment with all available therapies known to confer clinical benefit or for which conventional therapy is not considered effective can be included: solid tumors, including but not limited to, metastatic breast or prostate cancer with bone disease; solid tumors including, but not limited to, gastric, ovarian or non-small cell lung cancer that frequently have malignant associated ascites or effusion(s); tumors with known contribution of macrophages or phagocytes such as but not limited to: tumors with high tumor-infiltrating macrophage content; tumor types with high expression of the receptor CSF1R or its ligands, CSF1 or IL-34, in the tumor by previous testing; and prostate or breast cancer with bone-only disease. (Therapies for osteoporosis or management of bone metastasis with bisphosphonates or receptor activity of nuclear factor kappa-B ligand inhibitors should be stable for at least 2 months prior to initiation of Compound 1 treatment.). NSCLC patients can also be included, for those with: Histologically or cytologically confirmed metastatic, or unresectable locally advanced, recurrent NSCLC with a known EGFR mutation(s); Documented disease progression while on a previous treatment with an EGFR tyrosine kinase inhibitor (TKI); tumors, including but not limited to, metastatic breast or prostate cancer with bone disease; solid tumors including, but not limited to, gastric, ovarian or non-small cell lung cancer that frequently have malignant associated ascites or effusion(s); tumors with known contribution of macrophages or phagocytes such as but not limited to: tumors with high tumor-infiltrating macrophage content; tumor types with high expression of the receptor CSF1R or its ligands, CSF1 or IL-34, in the tumor by previous testing, or prostate or breast cancer with bone-only disease.

Patients with solid tumors received study drug orally at a starting dose of 10 mg QD, based on data from nonclinical toxicology and PK studies (Cohort 1). Following the results of Cohort 1, a transition to loading doses followed by maintenance doses occurred starting with Cohort 2 in a dose escalation scheme.

of dose escalation and the dose level of the next cohort will be determined. A patient will be evaluable in the dose escalation phase if the patient either experienced a DLT during Cycle 1 or received ≥80% of planned doses of study drug in Cycle 1. After Dose Escalation Cohort 6, a review of safety, PK and PD data will determine future escalation cohorts. No more than 50% increases in a total dose given in the first cycle will be allowed from the previous cohort.

The MTD will be defined as the highest dose level at which no more than 1 of 6 DLT-evaluable patients experiences a DLT(s) in Cycle 1 during dose escalation. An additional, lower, intermediate dose level may be explored to determine a recommended phase 2 dose (RP2D). The RP2D will be the MTD or a biologically active or maximally feasible dose lower than the MTD. Different RP2Ds may be determined for solid tumor and DTGCT patients. If none of the patients at a given dose level experience a DLT during Cycle 1, then the cohort may be expanded up 6 patients with the objective of investigating PK or if there is evidence of robust PD or antitumor activity. The determination of MTD or RP2D will require treatment of at least 6 patients at the same dose level.

TABLE 3

Loading and Maintenance Dosing Escalation Scheme

| Cohort | Loading Dose QD | Maintenance Dose (mg) | Maintenance Dosing in Cycle 1 | Total Dose in Cycle 1 (mg) | Dose Increase (%) to Cohort 2 | Dose Intensity (%) of 10 mg QD in Cycle 1 |
|---|---|---|---|---|---|---|
| 2[d] | 10 (50)[a] | 10[b] | C1D8, 12, 15, 19, 22, 26 | 110 | NA | 39 |
| 3[d] | 20 (100)[a] | 20[c] | C1D8, 15, 22 | 160 | 45 | 57 |
| 4[d] | 20 (100)[a] | 20[b] | C1D8, 12, 15, 19, 22, 26 | 220 | 38 | 79 |
| 5[d] | 30 (150)[a] | 30[b] | C1D8, 12, 15, 19, 22, 26 | 330 | 50 | 118 |
| 6[d] | 40 (200)[a] | 40[b] | C1D8, 12, 15, 19, 22, 26 | 440 | 33 | 157 |
| 7[e] | 50 (150)[a] | 20[f] | C1D4-D28 | 650 | 48 | 232 |
| 7 and above | Dose/schedule determined based on emerging data | | | | | TBD |

C = cycle; D = day; NA = not applicable; QD = once daily; TBD = to be determined.
Note:
Dosing of Cohorts 2-5 is complete.
[a]The total loading dose is shown in parenthesis
[b]Twice a week dosing.
[c]Once a week dosing.
[d]Loading dose period occurred in Cycle 1, Days 1, 2, 3, 4, and 5.
[e]Loading dose period occurred in Cycle 1, Days 1, 2, and 3.
[f]Once daily dosing.

Dose escalation of study drug is based on a pharmacologically guided 3+3 study design in patients with solid tumors (Table 3). A minimum of 3 patients is enrolled in each dose level cohort. If a patient experiences a DLT during Cycle 1, then the cohort will be expanded to 6 patients. If ≥2 patients out of 3 to 6 patients experience one or more dose-limiting toxicities (DLT(s)) during Cycle 1, dose escalation will end, and a lower dose level cohort will be expanded for determination of the maximum tolerated dose (MTD). If no additional patients experience a DLT in the expanded cohort, the dose level will be escalated. Decisions A minimum of 3 patients are enrolled in each dose level cohort, including a cohort with a loading dose followed by maintenance doses. Dose escalation of the loading and maintenance dose regimens will be conducted as follows:

Cohort 2: Compound 1 was administered orally for 5 consecutive days in the first week of Cycle 1 (C1D1-5, loading dose period) followed by biweekly (twice a week) dosing (C1D8, 12, 15, 19, 22, and 26) in subsequent weeks of Cycle 1 and beyond (D1, 5, 8, 12, 15, 19, 22, and 26 of each cycle; a maintenance dose period). The starting dose was 10 mg per day for 5-day loading and biweekly 10 mg maintenance dosing. Cohort 2 exposure of Compound 1 resulted in an $AUC_{0-8}$ at steady-state on C2D1 of 1030 hr*ng/mL (Table 1 and Table 2).

Cohort 3: Compound 1 was administered orally for 5 consecutive days in the first week of Cycle 1 (C1D1-5, loading dose period) followed by weekly dosing (C1D8, 15, 22) in subsequent weeks of Cycle 1 and beyond (D1, 8, 15, and 22 of each cycle; a maintenance dose period). The starting dose was 20 mg per day for 5-day loading and weekly 20 mg maintenance dosing. Cohort 3 exposure of Compound 1 resulted in an $AUC_{0-8}$ at steady-state on C2D1 of 3380 hr*ng/mL (Table 1 and Table 2).

Cohort 4: Compound 1 was administered orally for 5 consecutive days in the first week of Cycle 1 (C1D1-5, loading dose period) followed by biweekly (twice a week) dosing (C1D8, 12, 15, 19, 22, and 26) in subsequent weeks of Cycle 1 and beyond (D1, 5, 8, 12, 15, 19, 22, and 26 of each cycle; a maintenance dose period). The starting dose was 20 mg per day for 5-day loading and biweekly 20 mg maintenance dosing. Cohort 4 exposure of Compound 1 resulted in an $AUC_{0-8}$ at steady-state on C2D1 of 4300 hr*ng/mL (Table 1 and Table 2).

Cohort 5: Compound 1 was administered orally for 5 consecutive days in the first week of Cycle 1 (C1D1-5, loading dose period) followed by biweekly (twice a week) dosing (C1D8, 12, 15, 19, 22, and 26) in subsequent weeks of Cycle 1 and beyond (D1, 5, 8, 12, 15, 19, 22, and 26 of each cycle; a maintenance dose period). The starting dose was 30 mg per day for 5-day loading and biweekly 30 mg maintenance dosing. Cohort 5 exposure of Compound 1 resulted in an $AUC_{0-8}$ at steady-state on C2D1 of 5420 hr*ng/mL (Table 1 and Table 2).

Cohort 6: Compound 1 was administered orally for 5 consecutive days in the first week of Cycle 1 (C1D1-5, loading dose period) followed by biweekly (twice a week) dosing (C1D8, 12, 15, 19, 22, and 26) in subsequent weeks of Cycle 1 and beyond (D1, 5, 8, 12, 15, 19, 22, and 26 of each cycle; a maintenance dose period). The starting dose was 40 mg per day for 5-day loading and biweekly 40 mg maintenance dosing. Cohort 5 exposure of Compound 1 resulted in an $AUC_{0-8}$ at steady-state on C2D1 of 7290 hr*ng/mL (Table 1 and Table 2).

Cohort 7: Compound 1 was administered orally for 3 consecutive days in the first three days of Cycle 1 (C1D1-3, loading dose period) followed by daily dosing throughout Cycle 1 and beyond (D1-28 of each cycle; a maintenance dose period). The starting dose was 50 mg per day for 3-day loading and daily 20 mg maintenance dosing. Cohort 7 exposure of Compound 1 resulted in an $AUC_{0-8}$ at steady-state on C2D1 of 7980 hr*ng/mL (Table 1 and Table 2).

Above Cohort 7: Once Cohort 7 is cleared, the doses and schedules of the next and subsequent Dose Escalation Cohorts (above Cohort 7) will be determined based on analysis of PK, PD, and safety data in the previous cohorts. Dose escalation will continue by increasing a total dose given in the first cycle up to 50% from the previous cohort. Two cohorts may be run simultaneously as long as dose increases of both cohorts will not exceed the threshold of dose escalation increments (up to 50%) from the previous cohort tested and deemed safe. Additional dosing schemes (e.g., loading dosing period of 3 to 7 days or modifications to maintenance dosing schedules) may be explored based on PK, PD and safety data.

A patient may start receiving Compound 1 at a higher dose level after the completion of Cycle 2. One dose level increase will be allowed at a time. The dose level escalated to must not exceed the RP2D or MTD and needs to be deemed safe and tolerable in the dose escalation. The initiation of intra-patient dose escalation should be on the Day 1 visit of the next treatment cycle.

Patients will be dosed at the RP2D in a Cohort A. This Cohort A can enroll up to 12 solid tumor patients with high levels of CSF1, IL-34 or CSF1R expression in tumor, high tumor infiltration of macrophages, bone metastasis, ascites/effusion, or drug-resistant tumors where macrophages have been implicated as the mechanism of resistance, including but not limited to non-small-cell lung cancer (NSCLC) patients who progressed on treatment with Epidermal Growth Factor Receptor (EGFR) kinases inhibitor(s), prostate or breast cancer patients with bone metastasis, and pancreatic cancer patients. Patients in this cohort will be treated at the RP2D or MTD of Compound 1.

Pharmacokinetic (PK) samples will be collected throughout the study and PK analysis will be performed. In addition to safety and potential antitumor activity, PD effects of Compound 1 will be assessed. Pharmacodynamic (PD) biomarkers from plasma and whole blood samples will be assessed throughout the study. Pharmacodynamic (PD) evidence of treatment response will be investigated in tumors wherein paired biopsies will be obtained at screening and after study drug exposure. A single blood sample will be obtained for pharmacogenomic markers pertinent to the pharmacology of Compound 1 or its target, the CSF1R signaling pathway. As accumulation of mucin in the skin is suspected as a cause of facial and peripheral edema during treatment with anti-CSF1R therapies, pre- and post-dose skin biopsies will be performed in Cohort A. The following PK endpoints, including but not limited to, will be evaluated for both Compound 1 parent and its metabolite if detected: time to maximum observed concentration ($T_{max}$); maximum observed concentration ($C_{max}$); trough observed concentration ($C_{min}$); area under the concentration-time curve (AUC), and half-life ($t_{1/2}$).

Exploratory endpoints include Pharmacodynamics (PDs) such as levels of specific populations of monocytes (such as CD16+ or CSF1R+ monocytes; see for example, FIG. 6) in blood by flow cytometry, levels of CSF1 in plasma, levels of bone turnover markers (including collagen fragments C-terminal fragment of collagen in serum and urine N-terminal fragment of collagen), macrophage content and/or polarization in tumor or tumor-associated ascites/effusion fluids before and after treatment, the effects of Compound 1 on the immunoregulatory environment, including the number, localization, activation status (including interferon-gamma signature), of immune cell populations in tumor biopsy in cohorts, and abundance and localization of tumor-associated macrophages (TAMs) in pre-treatment vs. post-treatment tumor biopsies.

Preliminary Evidence of Antitumor Activity: The following endpoints documenting preliminary evidence of Compound 1 will be evaluated: objective response rate (ORR=confirmed complete response [CR]+partial response [PR]), disease control rate (DCR=CR+PR+stable disease [SD]) at 12 weeks, except for DTGCT, time to best response (defined as time from Cycle 1 Day 1 to PR or CR), progression-free-survival (PFS; defined as time from Cycle 1 Day 1 to disease progression or death), duration of response (DOR; time from PR or CR to disease progression or death), and objective response rate (ORR) and DCR at 6 months and 1 year.

Tumor response will be assessed by tumor type using the following criteria: for solid tumors and DTGCT: RECIST, Version 1.1; and for bone-only disease: a new lesion(s) identified by bone scan will be considered as disease progression.

In the study, the overall median treatment duration was 60.6 days. There were 5 patients with a best response of stable disease (2 with colorectal cancer and 1 each with prostate cancer, thymoma, and uveal melanoma). A patient with thymoma maintained stable disease for 6 months.

Additional descriptions of case studies of patients with DTGCT treated within this study are provided below:

Patient 1: A 24-year-old female patient diagnosed with diffuse-type TGCT in the right posterior knee in June 2016. Prior surgeries included synovectomies/mass resections in June 2016, July 2016, and December 2017. Recurrence/progression in the patient was observed on MRI by December 2018. The patient was subsequently enrolled in Cohort 5 in February 2019.

Figures 8A, 8B, 8C:
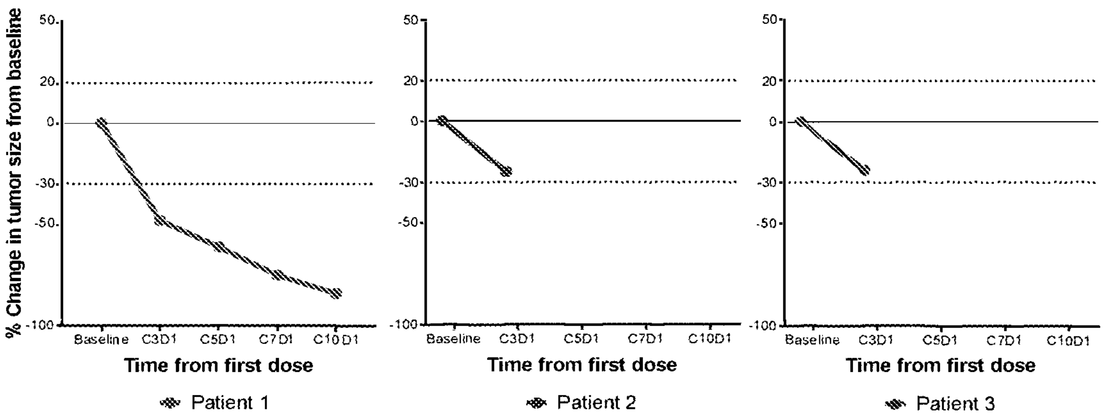
FIGS. 8A, 8B, and 8C depict percentage decreases of diffuse-type tenosynovial giant cell tumor size in Patient 1 (FIG. 8A), Patient 2 (FIG. 8B), and Patient 3 (FIG. 8C) of the additional DTGCT case studies described in Example 4 herein at certain time points in certain cycles, as determined per RECIST version 1.1.
Figure 9:
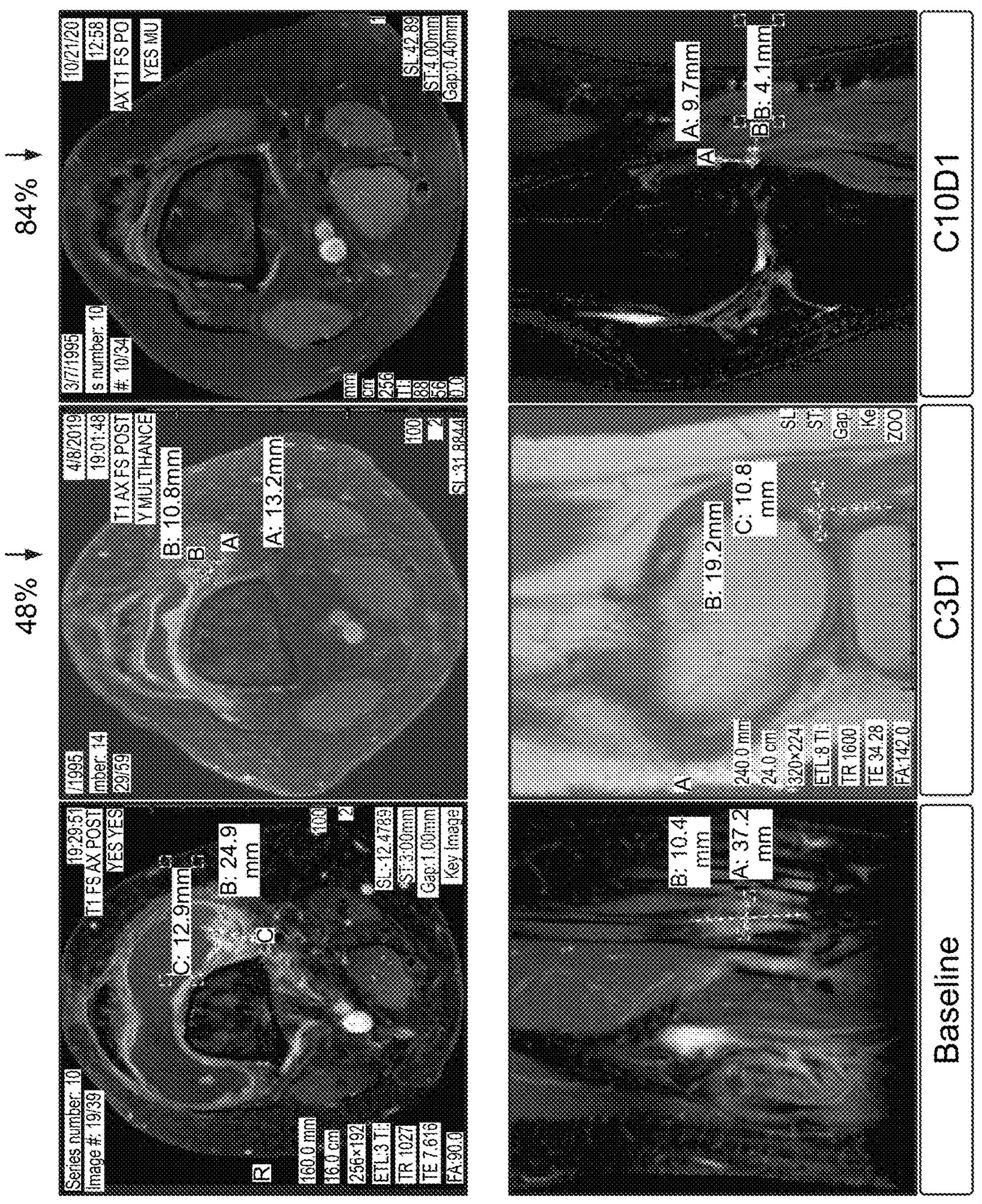
FIGS. 9 and 10 depict MRI images of tumor sites in exemplary DTGCT Patients 1 and 2, respectively, as described in Example 4 herein.

During the study, there were 48%, 61%, 75%, and 84% decreases in tumor size from baseline at C3D1, C5D1, C7D1, and C10D1, respectively, as determined per RECIST version 1.1 (FIG. 8A). MRI scans of the patient taken at certain time points during the study are shown in FIG. 9. The patient was taking Mobic and Percocet daily at baseline. On Cycle 10, Day 1, the patient was taking Percocet only as needed approximately once a week. Improved pain and swelling and effusion were nearly resolved in the first cycle.

Patient 2: A 57-year-old female patient diagnosed with diffuse-type TGCT in the right hip in 2014. Prior surgeries included resection (May 2014), synovectomy (August 2015 and August 2016), total hip replacement (August 2016), hip revision and resection (August 2018), and cryoablation (May 2019). Recurrence was observed on MRI in February 2019. The patient enrolled in July 2019 in Cohort 5.

Figure 10:
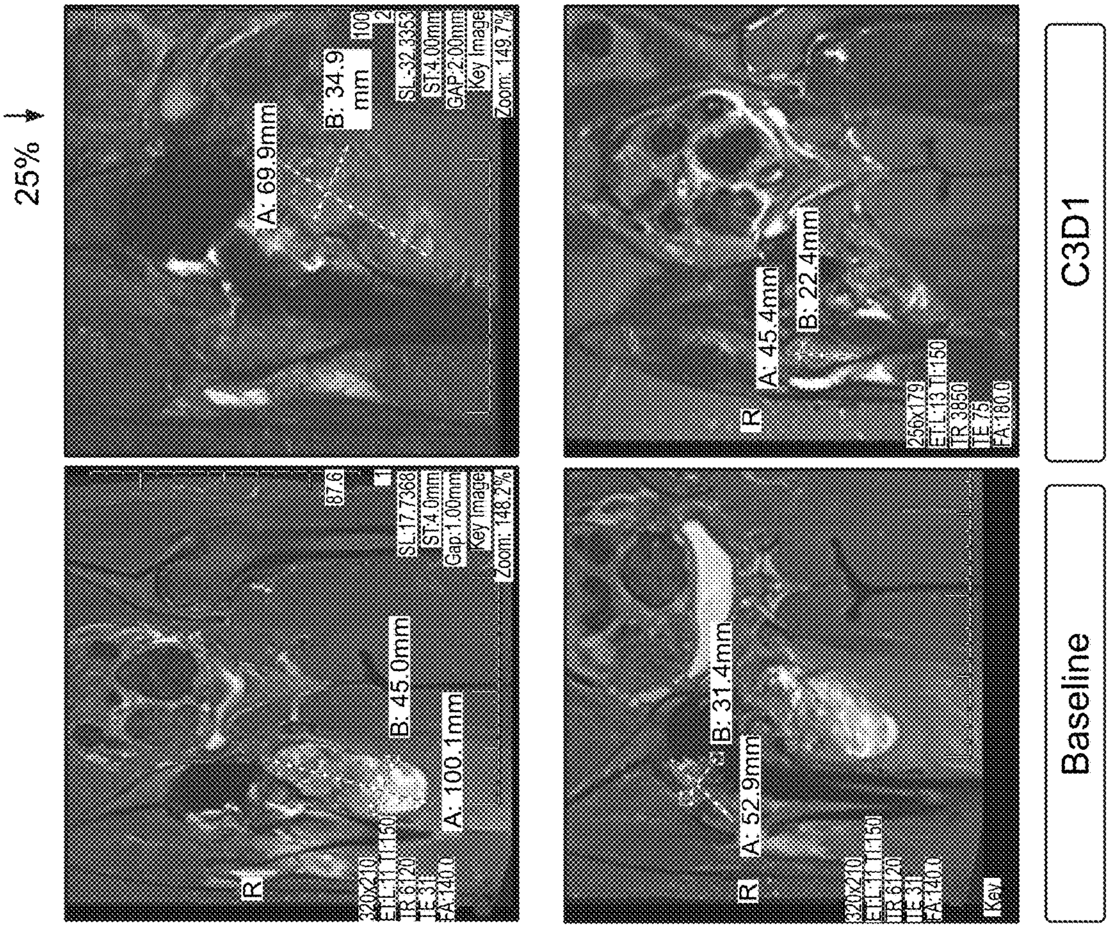

During the study, there was a 25% decrease in tumor size from baseline at C3D1 as determined per RECIST version 1.1 (FIG. 8B). MRI scans of the patient taken at certain time points during the study are shown in FIG. 10. The patient demonstrated pain improvement, increased range of motion, and less stiffness.

Patient 3: A 28-year-old male patient diagnosed with diffuse-type TGCT in the left knee in January 2016 after several years of pain. Prior surgery included resection and posterior synovectomy January 2016. Pain, swelling, and stiffness recurred due to disease progression not long after surgery. The patient was enrolled in March 2019 in Cohort 5.

During the study, there was a 24% decrease in tumor size from baseline at C3D1 as determined per RECIST version 1.1 (FIG. 8C). The patient demonstrated rapid symptom improvement, with less pain and swelling and improved range of motion after the first cycle. The patient was also able to play basketball with no pain.

Figure 11:
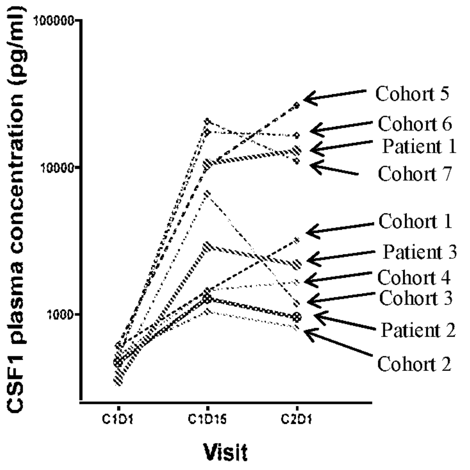
FIG. 11 depicts (A) CSF1 plasma concentration in subjects of each of Cohorts 1-7 described in Example 3 across different time periods in certain cycles (Cycle 1, Day 1; Cycle 1, Day 15; and Cycle 2, Day 1) alongside corresponding data for Patients 1, 2 and 3 of the DTGCT case studies described in Example 4; (B) IL-34 plasma concentration in subjects of each of Cohorts 1-7 as described in Example 3 across different time periods in certain cycles (Cycle 1, Day 1; Cycle 1, Day 15; and Cycle 2, Day 1) alongside corresponding data for Patients 1, 2 and 3 of the DTGCT case studies described in Example 4; and (C) percentage change in CD16+ monocycte population in subjects of each of Cohorts 1-7 described in Example 3 across different time periods in certain cycles (Cycle 1, Day 1; Cycle 1, Day 15; and Cycle 2, Day 1) alongside corresponding data for Patients 2 and 3 of the DTGCT case studies described in Example 4.
Figure 11:
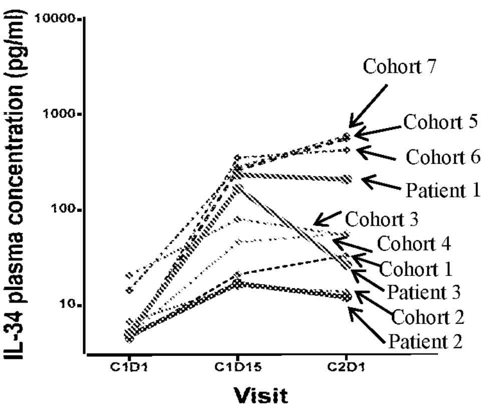
Figure 11:
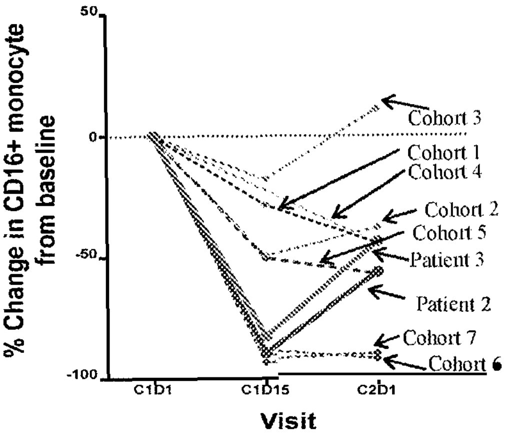

FIG. 11 additionally depicts the cohort measurements represented in FIG. 6 alongside corresponding measurements taken for Patient 1, Patient 2, and Patient 3 described above. In particular, corresponding CSF1 plasma concentration measurements are shown in FIG. 11A, corresponding IL-34 plasma concentration measurements are shown in FIG. 11B, and corresponding % change in CD16+ monocyte measurements are shown in FIG. 11C.

Example 5. Patient Study of Tenosynovial Giant Cell Tumors

Evaluation of Compound 1 in patients with diffuse-type tenosynovial giant cell tumor (DTGCT) (formerly known as pigmented villonodular synovitis or giant cell tumor of the tendon sheath) will be evaluated in a dosage Cohort B as described below. The effects of Compound 1 on range of motion and/or symptomatic relief using patient reported-symptom or outcome (PRO) measures are evaluated as well as the effects of Compound 1 on the macrophage infiltration in the affected joint and circulating chemokine/cytokines associated with inflammation.

The study will consist of a screening period that will be conducted within 28 days prior to the first dose of study drug, a treatment period of 28-day cycles, an End of Treatment visit, and Follow-up Safety visits at both 30 days and 75 days (±5 days) after the last dose of study drug. Patients will be eligible to receive study drug for up to 2 years until tumor progression, occurrence of unacceptable toxicity, or withdrawal of consent, or until commercial supply of the drug is available. This may be extended for patients who exhibit evidence of clinical benefit and tolerability to the drug, and who adhere to the study procedures. Patients may continue receiving treatment after tumor progression.

Dosage Cohort B can be initiated and enroll up to 40 patients with DTGCT to evaluate safety, PK, PD, and preliminary efficacy of Compound 1 in the patient population. Patients in Cohort B are treated with Compound 1 at a dose level at or below the RP2D or MTD as determined from the protocol of Example 4. The objectives of the study are to evaluate safety and preliminary efficacy of Compound 1. In Cohort B, evaluation of range of motion and PRO measures are conducted as additional safety and efficacy evaluations. Functional Assessment of Cohort B include assessment of range of motion of the affected joint(s) and scores generated.

For Cohort B only, patients can have a histologically confirmed diagnosis of DTGCT (formerly known as pigmented villonodular synovitis or giant cell tumor of the tendon sheath), disease for which surgical resection potentially causes worsening functional limitation or severe morbidity, symptomatic disease with at least moderate pain or stiffness (a scale of 4 or more with 10 describing the worst condition) within 1 month of the first dose, and prior treatment with anti-CSF1R therapy is allowed. Additionally, patients with DTGCT are enrolled in Dose Escalation if the eligibility criteria for Cohort B are met.

Patient reported outcomes (PROs) can be based on analysis based upon the following questionnaires: SF-36, Brief Pain Inventory (BPI), the GP5 "burden-of-side-effects" question from the FACT-G, and symptom-specific questions about "stiffness", "swelling", and "joint instability" as: Change from starting value, and Proportion of patients who report improvement relative to starting value.

TGCT or DTGCT patients treated with the FDA approved CSF1R inhibitor pexidartinib at a dose of 1000 mg daily afforded an overall response rate (ORR) of 52% in a phase 2 clinical study (*New England Journal of Medicine* 2015; 373:428). Excursions to higher dose regimens to potentially afford a higher ORR were limited by the establishment of a maximum tolerated dose (the highest dose associated with an acceptable side-effect profile) and chosen phase 2 dose of 1000 mg per day. The ENLIVEN phase 3 randomized trial of pexidartinib demonstrated an ORR of 39% at a maintenance dose of 400 mg twice daily (*The Lancet* 2019; 394: 478). Pexidartinib was reported to cause liver injury including emergence of mixed or cholestatic hepatotoxicity (*The Lancet* 2019; 394: 478). Pexidartinib also inhibits off-target kinases other than CSF1R, including FLT-3, KIT, PDGFRA, and PDGFRB.

Compound 1 of the present invention is efficacious in TGCT or DTGCT patients at much lower doses compared to that of the FDA approved CSF1R inhibitor pexidartinib. Clinical benefit has been realized with maintenance doses of 30 mg twice weekly: Patient 1, Cohort 5, with 48%, 61%, 75%, and 84% decreases in tumor size from baseline at C3D1, C5D1, C7D1, and C10D1. This response is unexpectedly superior to the 39% overall response rate observed clinically with pexidartinb dosed at 400 mg twice daily (800 mg/day).

Clinical use of the FDA approved pexidartinib in TGCT patients is limited by administration of a dose of 400 mg twice daily, i.e. the maximum tolerated dose. Furthermore, a black box warning of hepatotoxicity on the FDA label of pexidartinib evidences the potential for hepatotoxicity to limit patient treatment.

In clinical studies to-date, an MTD for Compound 1 has not been reached through Cohort 7 in which exposures provide full benefit of pharmacodynamic inhibition of CSF1R kinase as shown in FIG. 6 and ORR of up to 84% has been reached in a DGCT patient. This unexpected finding of Compound 1 compared to pexidartinib allows Compound 1 to be dosed in TGCT or DTGCT patients to maximum efficacy rather than being limited by a dose ceiling due to treatment emergent toxicities.

Example 6. Compound 1 Unexpectedly Exhibits Superior Selectivity for Inhibiting CSF1R Compared to Pexidartinib The following assays demonstrate that Compound 1 unexpectedly exhibits superior selectivity for inhibiting CSF1R compared to pexidartinib. The ability of compound 1 or pexidartinib to inhibit kinase activity of CSF1R kinase, c-KIT kinase, PDGFRα kinase, or FLT3 kinase was tested in enzymatic assays.

CSF1R Kinase (SEQ ID NO: 1) Assay

The activity of CSF1R kinase (CSF1R, SEQ ID NO: 1) was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942 Assays were conducted in 384-well plates (100 μL final volume) using 10 nM CSF1R (Eurofins), 1.5 units pyruvate kinase, 2.1 units lactate dehydrogenase, 1 mM phosphoenol pyruvate, 0.28 mM NADH, 0.7 mg/mL PolyEY and 1 mM ATP in assay buffer (100 mM Tris, pH 7.5, 15 mM $MgCl_2$, 0.5 mM DTT, 0.1% octyl-glucoside, 0.002% (w/v) BSA, and 0.002% Triton X-100). Inhibition of CSF1R was measured by adding serial diluted test compound (final assay concentration of 1% DMSO). A decrease in absorption at 340 nm was monitored continuously for 4 hours at 30° C. on a multi-mode microplate reader (BioTek). The reaction rate was calculated using the 2-3 h time frame. The reaction rate at each concentration of compound was converted to percent inhibition using controls (i.e. reaction with no test compound and reaction with a known inhibitor) and $IC_{50}$ values were calculated by fitting a four-parameter sigmoidal curve to the data using Prism (GraphPad software).

```
CSF1R Kinase sequence (Y538-end) with N-terminal
Histag
                                    (SEQ ID NO: 1)
MHHHHHHEFYKYKQKPKYQVRWKIIESYEGNSYTFIDPTQLPYNEKWEFP

RNNLQFGKTLGAGAFGKVVEATAFGLGKEDAVLKVAVKMLKSTAHADEKE

ALMSELKIMSHLGQHENIVNLLGACTHGGPVLVITEYCCYGDLLNFLRRK
```

-continued

```
AEAMLGPSLSPGQDPEGGVDYKNIHLEKKYVRRDSGFSSQGVDTYVEMRP

VSTSSNDSFSEQDLDKEDGRPLELRDLLHFSSQVAQGMAFLASKNCIHRD

VAARNVLLTNGHVAKIGDFGLARDIMNDSNYIVKGNARLPVKWMAPESIF

DCVYTVQSDVWSYGILLWEIFSLGLNPYPGILVNSKFYKLVKDGYQMAQP

AFAPKNIYSIMQACWALEPTHRPTFQQICSFLQEQAQEDRRERDYTNLPS

SSRSGGSGSSSSELEEESSSEHLTCCEQGDIAQPLLQPNNYQFC
```

c-Kit Kinase (SEQ ID NO: 2) Assay

The activity of unphosphorylated c-KIT kinase (c-KIT, SEQ ID NO: 2) was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 μL final volume) using 16 nM c-KIT (DeCode Biostructures), 1.5 units pyruvate kinase, 2.1 units lactate dehydrogenase, 1 mM phosphoenol pyruvate, 0.28 mM NADH, 0.7 mg/mL PolyEY and 1 mM ATP in assay buffer (100 mM Tris, pH 7.5, 15 mM $MgCl_2$, 0.5 mM DTT, 0.1% octyl-glucoside, 0.002% (w/v) BSA, and 0.002% Triton X-100). Inhibition of c-KIT was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 2-3 h time frame. The reaction rate at each concentration of compound was converted to percent inhibition using controls (i.e. reaction with no test compound and reaction with a known inhibitor) and $IC_{50}$ values were calculated by fitting a four-parameter sigmoidal curve to the data using Prism (GraphPad software). as implemented in the GraphPad Prism software package.

```
c-KIT Kinase sequence (T544-V976) with N-terminal
His-GST tag
                                    (SEQ ID NO: 2)
MEHHHHHHHHEYMPMEMAPILGYWKIKGLVQPTRLLLEYLEEKYEEHLYE

RDEGDKWRNKKFELGLEFPNLPYYIDGDVKLTQSMAIIRYIADKHNMLGG

CPKERAEISMLEGAVDIRYGVSRIAYSKDFETLKVDFLSKLPEMLKMFED

RLCHKTYLNGDHVTHPDFMLYDALDVVLYMDPMCLDAFPKLVCFKKRIEA

IPQIDKYLKSSKYIWPLQGWQATFGGGDHPPKSDLVPRHNQTSLYKKAGS

AAAVLEENLYFQGTYKYLQKPMYEVQWKVVEEINGNNYVYIDPTQLPYDH

KWEFPRNRLSFGKTLGAGAFGKVVEATAYGLIKSDAAMTVAVKMLKPSAH

LTEREALMSELKVLSYLGNHMNIVNLLGACTIGGPTLVITEYCCYGDLLN

FLRRKRDSFICSKQEDHAEAALYKNLLHSKESSCSDSTNEYMDMKPGVSY

VVPTKADKRRSVRIGSYIERDVTPAIMEDDELALDLEDLLSFSYQVAKGM

AFLASKNCIHRDLAARNILLTHGRITKICDFGLARDIKNDSNYVVKGNAR

LPVKWMAPESIFNCVYTFESDVWSYGIFLWELFSLGSSPYPGMPVDSKFY

KMIKEGFRMLSPEHAPAEMYDIMKTCWDADPLKRPTFKQIVQLIEKQISE

STNHIYSNLANCSPNRQKPVVDHSVRINSVGSTASSSQPLLVHDDV
```

PDGFRα Kinase (SEQ ID NO: 3) Assay

The activity of unphosphorylated PDGFRα kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 μL final volume) using 11.7 nM PDGFRα (DeCode Biostructures), 1.5 units pyruvate kinase, 2.1 units lactate dehydrogenase, 1 mM phosphoenol pyruvate, 0.28 mM NADH, 0.7 mg/mL PolyEY and 1 mM ATP in assay buffer (100 mM Tris, pH 7.5, 15 mM $MgCl_2$, 0.5 mM DTT, 0.1% octyl-glucoside, 0.002% (w/v) BSA, and 0.002% Triton X-100). Inhibition of PDGFRα was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 2-3 h time frame. The reaction rate at each concentration of compound was converted to percent inhibition using controls (i.e. reaction with no test compound and reaction with a known inhibitor) and $IC_{50}$ values were calculated by fitting a four-parameter sigmoidal curve to the data using Prism (GraphPad software).

```
PDGFRα protein sequence (residues 550-1089) with a
N-terminal GST-tag.
                                        (SEQ ID NO: 3)
MEHHHHHHHHMAPILGYWKIKGLVQPTRLLLEYLEEKYEEHLYERDEGDK

WRNKKFELGLEFPNLPYYIDGDVKLTQSMAIIRYIADKHNMLGGCPKERA

EISMLEGAVLDIRYGVSRIAYSKDFETLKVDFLSKLPEMLKMFEDRLCHK

TYLNGDHVTHPDFMLYDALDVVLYMDPMCLDAFPKLVCFKKRIEAIPQID

KYLKSSKYIAWPLQGWQATFGGGDHPPKSDLVPRHNQTSLYKKAGFEGDR

TMKQKPRYEIRWRVIESISPDGHEYIYVDPMQLPYDSRWEFPRDGLVLGR

VLGSGAFGKVVEGTAYGLSRSQPVMKVAVKMLKPTARSSEKQALMSELKI

MTHLGPHLNIVNLLGACTKSGPIYIITEYCFYGDLVNYLHKNRDSFLSHH

PEKPKKELDIFGLNPADESTRSYVILSFENNGDYMDMKQADTTQYVPMLE

RKEVSKYSDIQRSLYDRPASYKKKSMLDSEVKNLLSDDNSEGLTLLDLLS

FTYQVARGMEFLASKNCVHRDLAARNVLLAQGKIVKICDFGLARDIMHDS

NYVSKGSTFLPVKWMAPESIFDNLYTTLSDVWSYGILLWEIFSLGGTPYP

GMMVDSTFYNKIKSGYRMAKPDHATSEVYEIMVKCWNSEPEKRPSFYHLS

EIVENLLPGQYKKSYEKIHLDFLKSDHPAVARMRVDSDNAYIGVTYKNEE

DKLKDWEGGLDEQRLSADSGYIIPLPDIDPVPEEEDLGKRNRHSSQTSEE

SAIETGSSSSTFIKREDETIEDIDMMDDIGIDSSDLVEDSFL
```

FLT3 Kinase (SEQ ID NO: 4) Assay

The activity of FLT3 kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 μL final volume) using 1.6 nM FLT3 (Invitrogen), 1.5 units pyruvate kinase, 2.1 units lactate dehydrogenase, 1 mM phosphoenol pyruvate, 0.28 mM NADH, 0.7 mg/mL PolyEY and 1 mM ATP in assay buffer (100 mM Tris, pH 7.5, 15 mM $MgCl_2$, 0.5 mM DTT, 0.1% octyl-glucoside, 0.002% (w/v) BSA, and 0.002% Triton X-100). Inhibition of FLT3 was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 3-4 h time frame. The reaction rate at each concentration of compound was converted to percent inhibition using controls (i.e. reaction with no test compound and reaction with a known inhibitor) and $IC_{50}$ values were calculated by fitting a four-parameter sigmoidal curve to the data using Prism (GraphPad software).

```
FLT3 Kinase sequence (564-958) with C-terminal His
tag
                                        (SEQ ID NO: 4)
MHKYKKQFRYESQLQMVQVTGSSDNEYFYVDFREYEYDLKWEFPRENLEF

GKVLGSGAFGKVMNATAYGISKTGVSIQVAVKMLKEKADSSEREALMSEK

MMTQLGSHENIVNLLGACTLSGPIYLIFEYCCYGDLLNYLRSKREKFHRT

WTEIFKEHNFSFYPTFQSHPNSSMPGSREVQIHPDSDQISGLHGNSFHSE

DEIEYENQKRLEEEEDLNVLTFEDLLCFAYQVAKGMEFLEFKSCVHRDLA

ARNVLVTHGKVVKICDFGLARDIMSDSNYVVRGNARLPVKWMAPESLFEG

IYTIKSDVWSYGILLWEIFSLGVNPYPGIPVDANFYKLIQNGFKMDQPFY

ATEEIYIIMQSCWAFDSRKRPSFPNLTSFLGCQLADAEEAMYQNVKGVEA

CQLGTDDYDIPTTHHHHHH
```

Using the enzymatic protocols described above, Compound 1 is shown to unexpectedly have selectivity for inhibition of CSF1R kinase compared to pexidartinib in assays measuring the kinase activity of CSF1R kinase, c-KIT kinase, PDGFRα kinase, or FLT3 kinase as indicated below in Table 4.

TABLE 4

Activity of Compound 1 and Pexidartinib in Enyzmatic Assays of CSFIR kinase, c-KIT kinase, PDGFRα kinase, or FLT3 kinase.

| Example | CSF1R $IC_{50}$ (nM) | c-KIT $IC_{50}$ (nM) | PDGFRα $IC_{50}$ (nM) | FLT3 $IC_{50}$ (nM) |
|---|---|---|---|---|
| Compound 1 | 2.2 | 864 | 2,500 | 2,700 |
| Pexidartinib | 2.2 | 6.9 | 9.6 | 7.1 |

Example 7. Compound 1 Unexpectedly Retains Potency for Inhibiting Cellular CSF1R Compared to Pexidartinib when Increasing Concentrations of CSF1R Ligand CSF1 are Administered The ability of Compound 1 or pexidartinib to inhibit M-NFS-60 cellular proliferation in the presence of various concentrations of the CSF1R ligand CSF1 was tested in a cellular assay. This is relevant to the treatment of TGCT and DTGCT due to the genomic alternation of increased expression of translocated CSF1 levels that drive tumor formation.

M-NFS-60 Cell Culture

M-NFS-60 cells (catalog #CRL-1838) were obtained from the American Type Culture Collection (ATCC, Manassas, VA). Briefly, cells were grown in suspension in RPMI 1640 medium supplemented with 10% characterized fetal bovine serum (Invitrogen, Carlsbad, CA), 0.05 mM 2-mercaptoethanol, and 20 ng/mL mouse recombinant macrophage colony stimulating factor (CSF1) at 37° C., 5% $CO_2$, and 95% humidity. Cells were allowed to expand until reaching saturation at which point, they were subcultured or harvested for assay use.

M-NFS-60 Cell Proliferation Assay

A serial dilution of test compound was dispensed into a 96-well black clear bottom plate (Corning, Corning, NY).

Ten thousand cells were added per well in 200 μL complete growth medium containing various concentrations of CSF1. Plates were incubated for 67 h at 37° C., 5% $CO_2$, and 95% humidity. At the end of the incubation period 40 μL of a 440 μM solution of resazurin (Sigma, St. Louis, MO) in PBS was added to each well and incubated for an additional 5 h at 37° C., 5% $CO_2$, and 95% humidity. Plates were read on a plate reader using an excitation of 540 nM and an emission of 600 nM. $IC_{50}$ values were calculated from a series of percent inhibition values determined at a range of inhibitor concentrations using software routines as implemented in the GraphPad Prism software package.

Figure 12:
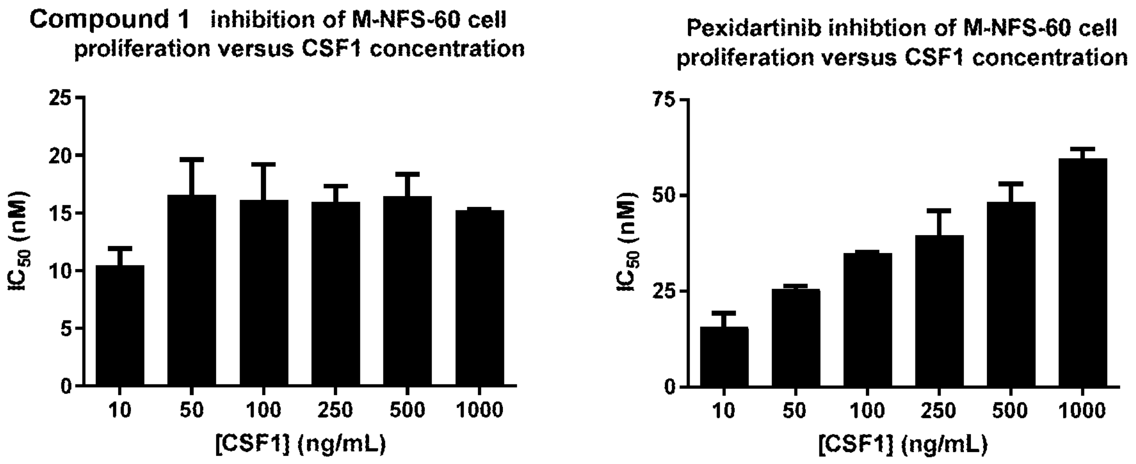
FIG. 12 depicts exemplary $IC_{50}$ values of Compound 1 or pexidartinib for inhibition of M-NFS-60 cell proliferation in the presence various levels of the CSF1R ligand, CSF1.

Compound 1 inhibited proliferation of M-NFS-60 cells, a CSF1R-dependent mouse myelogenous leukemia cell line, with an average $IC_{50}$=10.5 nM at 10 ng/mL CSF1. High concentrations of growth factor ligands for receptor tyrosine kinases can reduce the potency of kinase inhibitors due to increased ligand-induced dimerization and activation of the kinase. Unexpectedly, high levels of the CSF1R ligand, CSF1, had only small effects (<1.6-fold) on inhibition of M-NFS-60 cell proliferation by Compound 1 (FIG. 12), with an average $IC_{50}$=15.2 nM at 1,000 ng/mL CSF1. Pexidartinib had less potency at high levels of CSF1, with an average $IC_{50}$=15.7 nM at 10 ng/mL CSF1 and average $IC_{50}$=59.6 nM at 1,000 ng/mL CSF1, representing a 3.8-fold increase in $IC_{50}$ value.

Example 8. Compound 1 Unexpectedly does not Exhibit Liver Toxicity in Toxicology Studies Compared to Pexidartinib It has been previously reported that CSF1R inhibition of macrophage function promotes elevations in AST, ALT and GLDH without liver injury (Radi et al 2011 and Wang et al 2011). It may be possible that elevations in AST, ALT, and GLDH in the present study are, at least in part, a mechanistic consequence of the CSF1R inhibition.

Figure 13:
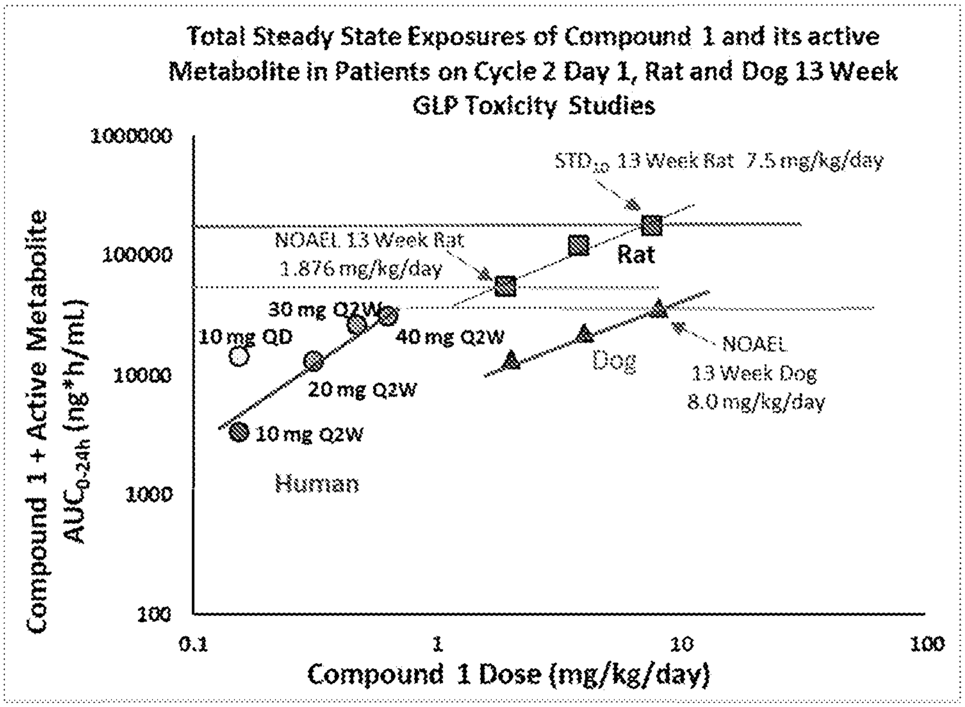
FIG. 13 depicts exemplary total steady state exposures of Compound 1 and its active metabolite in patients at Cycle 2, Day 1 of the study described in Example 8 and exemplary 13-week GLP-compliant toxicity studies in rats and dogs.

Compound 1 was evaluated for systemic toxicity in rat and dog toxicity studies. In a 4-week pivotal GLP-compliant study in Sprague-Dawley rats, Compound 1 was administered at doses of 5, 15, and 30 mg/kg/day. Minimal to mild increases in aspartate transaminase (AST), alanine transaminase (ALT), glutamate dehydrogenase (GLDH), and alkaline phosphatase (ALP) activities, with an absence of any microscopic liver changes, were noted. The NOAEL (No Observed Adverse Event Level) for the study was at a dose of 5 mg/kg/day with a safety margin of about 4.7× relative to a clinical dose exposure at 30 mg QD loading dose for 5 days followed by 30 mg twice weekly in TGCT patients, and 15 mg/kg/day as the Severely Toxic Dose in 10% of cohort animals ($STD_{10}$) with a safety margin of about 25× relative to exposure (AUC) at clinical dose of 30 mg QD loading dose for 5 days followed by 30 mg twice weekly in TGCT patients as shown in FIG. 13). Similarly, in a 13-week GLP-compliant toxicity study with 4-week recovery phase in Sprague-Dawley rats, Compound 1 was administered at doses of 1.876, 3.75, and 7.5 mg/kg/day. The clinical pathology effects were generally minimal or mild in magnitude and included elevated liver enzyme activities and findings consistent with inflammation. Increases in aspartate transaminase (AST), alanine transaminase (ALT), glutamate dehydrogenase (GLDH), and alkaline phosphatase (ALP) activities were minimal or mild, and were without corresponding microscopic liver changes. Most of the clinical observations were reversed during the recovery phase. The NOAEL for the 13-week study was at a dose of 1.875 mg/kg/day with a safety margin of about 2.3×relative to a clinical dose exposure (AUC) at 30 mg QD loading dose for 5 days followed by 30 mg twice weekly in TGCT patients (FIG. 13). The STD10 for the 13-week study was at a dose of 7.5 mg/kg/day with a safety margin of about 6.3× relative to a clinical dose exposure (AUC) at 30 mg QD loading dose for 5 days followed by 30 mg twice weekly in TGCT patients In the pivotal, 4-week GLP-compliant study in Beagle dogs, Compound 1 was administered at doses of 2.5 7.5, 15, and 25 mg/kg/day. Compound 1 related clinical observations included minimally to mildly increased AST activity in animals administered at ≥2.5 mg/kg/day. Additional findings included minimally increased ALT and GLDH activity in animals administered at ≥7.5 mg/kg/day. Hepatocellular injury was not evident in microscopic histology exams. The NOAEL and HNSTD (Highest Non-Serious Toxic Dose) for the 4-week study in dogs was at a dose of 7.5 mg/kg/day with a safety margin of about 2.1× relative to a clinical dose exposure (AUC) at 30 mg QD loading dose for 5 days followed by 30 mg twice weekly in TGCT patients.

In a 13-week GLP compliant toxicity study with 4-week recovery period in Beagle dogs, Compound 1 was administered at 2.0 mg/kg/day, 4.0 mg/kg/day, or 8.0 mg/kg/day. Compound 1 related clinical pathology effects were limited to animals administered at 8 mg/kg/day and exhibited evidence of reversibility. The clinical pathology effects were generally minimal or mild in magnitude which included elevated liver enzyme activities and findings consistent with inflammation. Increases in aspartate transaminase (AST), glutamate dehydrogenase (GLDH), and creatine kinase activities were minimal or mild, without corresponding microscopic liver changes were noted. Most of the clinical observations were reversed during the recovery phase. Increases in aspartate aminotransferase and creatine kinase activities may have resulted from CSF1R inhibition of macrophage. These clinical pathology changes did not have any microscopic correlates or effects on the overall health of the animal. Thus, the NOAEL for Compound 1 was at a dose of 8 mg/kg/day with a safety margin of about 1.6× relative to a clinical dose exposure (AUC) at 30 mg QD loading dose for 5 days followed by 30 mg twice weekly in TGCT patients. In contrast, in a pivotal 4-week study with a two week recovery period GLP toxicity study, TURALIO™ (Pexidartinib) was administered to Sprague-Dawley rats at doses of 20 mg/kg/day, 60 mg/kg/day, or 200 mg/kg/day, by oral gavage. Clinical observations for all dose groups showed increased liver enzymes, and dose-related hepatocellular centrilobular hypertrophy which correlated with corresponding higher liver enzyme levels and higher liver weights, and a higher incidence and/or severity of chronic progressive nephropathy at 200 mg/kg/day groups. A NOAEL could not be established in the pexidartinib treated rats at any of the doses tested.

Figure 14:
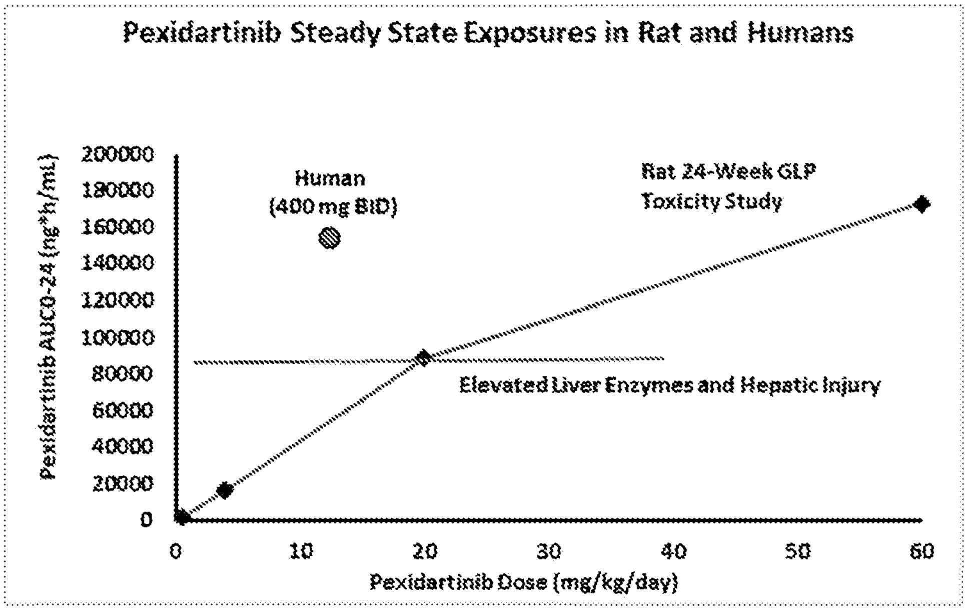
FIG. 14 depicts exemplary studies of steady state exposures of pexidartinib in rats and humans.

In the six-month GLP compliant toxicity study with 16 week recovery in rats, treatment with pexidartinib at 60 mg/kg daily (approximately 1.6 times the clinical exposure of 154930 ng·h/mL [estimated $AUC_{0-24}$ from the 77465 $AUC_{0-12}$ cited in the label] at the recommended human dose of 800 mg daily) resulted in the death of 3 main study animals due to treatment-related immunocompromise. In the liver, hemosiderin deposition and necrotizing inflammation with increased levels of aspartate aminotransferase (AST) and alanine aminotransferase (ALT) occurred at doses ≥20 mg/kg (approximately 0.6 times the clinical exposure at 800 mg) (FIG. 14). Additionally, biliary cysts and increased gamma-glutamyl transferase (GGT) levels occurred in female rats at 60 mg/kg. The liver is a major target organ clinically, with frequent elevations in transaminases, including serious liver injury.

Compound 1 and pexidartinib were compared with respect to clinical dose/exposures and the prevalence of liver enzyme and bilirubin elevations and hepatic AEs. Compound 1 dosed at 10 mg-40 mg QD or twice weekly ($AUC_{0-24}$ of about 13500-31952 ng·h/mL) exhibited the lowest clinical dose/exposure with lower magnitude of increased liver enzymes levels. No clinical indication of liver toxicity has been demonstrated with Compound 1 at any of these dose levels. Pexidartinib dosed at 800 mg per day ($AUC_{0-24}$ exposures of 154930 ng h/mL) exhibits almost a magnitude greater than Compound 1 exposures. The overall severity of all AEs (Grade 3/4 AST/ALT incidents, elevated bilirubin and serious hepatic AEs) fits into a pattern of increase in severity of liver toxicity associated with greater exposure. In comparison, Compound 1 exhibits a greater prevalence of Grade 1/2 events for AST/ALT in the absence of liver toxicity as determined in Sprague Dawley rat and Beagle dog toxicity studies, suggesting that AST/ALT elevations in the absence of hepatotoxicity is a CSF1R inhibitor class effect due to decreased clearance of AST/ALT from the circulation. Compound 1 did not exhibit Grade 3/4 elevated AST/ALT events or elevated bilirubin levels or hepatic AEs at clinically relevant and efficacious doses. The lack of demonstrated hepatotoxicity observed with Compound 1 in preclinical toxicology studies combined with the lack of observed hepatotoxicity in clinical trials provides an unexpected advantage over pexidartinib, which exhibits hepatotoxicity in preclinical toxicology studies as well as hepatoxicity in clinical trials. Thus, Compound 1 provides an unexpected profile versus pexidartinib, allowing for dosing of DTGCT patients to higher levels of efficacy without attendant liver toxicity. This favorable efficacy/adverse event profile of Compound 1 is useful in the treatment of patients with DTGCT, as these patients are anticipated to be on treatment with a CSF1R inhibitor for extended periods of time throughout their lives.

FIG. 15 is a graphical representation demonstrating depletion of $CD16^+$ monocytes in peripheral blood from patients treated with Compound 1. The $CD16^+$ monocyte subset is known to be sensitive to CSF1 treatment and, thus, serves as a pharmacodynamic marker of CSF1R inhibition. PD data obtained from Compound 1 treated patients have shown that $CD16^+$ monocyte levels decreased with increasing Compound 1 dose and concentration, indicating blockade of CSF1R signaling. In the lower-dose cohorts (Cohorts 1-4), the percentage of $CD16^+$ monocytes of total blood monocytes at baseline decreased by 18% to 9% after 2 weeks of Compound 1 treatment. In the higher-dose cohorts (Cohorts 5-7), the percentage of $CD16^+$ monocytes of total blood monocytes at baseline decreased by 68% to 94% after 2 weeks of Compound 1 treatment.

Elevation of circulating levels of the CSF1R ligands CSF1 and IL-34 are a pharmacodynamic marker for CSF1R inhibition in vivo. FIG. 16 is a graphical representation demonstrating increases in CSF1 and IL-34 in plasma from patients treated with Compound 1. On C1D1, all patients had detectable levels of CSF1 with a mean value of 520.7 pg/mL across all cohorts. Serum CSF1 concentrations increased with increasing Compound 1 dose and concentration. CSF1 levels in the lower-dose cohorts (Cohorts 1-4) were increased about 3- to 5-fold at C2D1 over baseline. In the higher-dose cohorts (Cohorts 5-7), patients experienced 22- to 36-fold increases in CSF1 levels at C2D1. Cohort 6 and 7 doses had similar effects on serum CSF1 levels. Compound 1 demonstrated a dose-dependent impact on circulating CSF1 concentrations. A similar trend was observed with IL-34 levels. On C1D1, all patients had detectable IL-34 levels with a mean value of 9.3 pg/mL across all cohorts. Patients enrolled in the lower-dose cohorts (Cohorts 1-4) experienced a 2- to 5-fold increase in IL-34 over baseline by C2D1. In the higher-dose cohorts (Cohorts 5-7), patients experienced 26- to 100-fold increases in IL-34 levels at C2D1. Cohort 6 and 7 doses had similar effects on serum IL-34 levels.

The invention claimed is:

1. A method of treating a tenosynovial giant cell tumor in a patient in need thereof, comprising administering to the patient a pharmaceutical composition comprising a compound represented by:

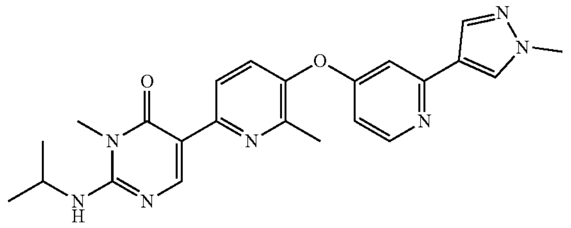

and a pharmaceutically acceptable excipient, wherein the pharmaceutical composition is administered to the patient in an amount sufficient to provide the patient about 2 mg to about 60 mg of the compound once a day, twice daily, every other day, once a week, twice weekly, or three times a week.

2. The method of claim 1, wherein the tenosynovial giant cell tumor is localized.

3. The method of claim 1, wherein the tenosynovial giant cell tumor is a diffuse-type tenosynovial giant cell tumor.

4. The method of claim 1, wherein the pharmaceutical composition is administered to the patient in an amount sufficient to provide the patient about 5 mg to about 30 mg of the compound once a day, twice daily, every other day, once a week, twice weekly, or three times a week.

5. The method of claim 1, wherein the pharmaceutical composition is administered to the patient in an amount sufficient to provide the patient about 30 mg of the compound twice weekly.

6. The method of claim 1, comprising administering to the patient the composition twice weekly for about 3 months.

7. The method of claim 1, comprising administering to the patient the composition twice weekly for about 6 months.

8. The method of claim 1, comprising administering to the patient the composition twice weekly for about 1 year.

9. The method of claim 1, comprising administering to the patient the composition twice weekly for about 2 years.

10. The method of claim 1, wherein the pharmaceutical composition is administered to the patient as a neo-adjuvant.

11. The method of claim 1, wherein the pharmaceutical composition is administered to the patient as an adjuvant.

12. A method of treating a tenosynovial giant cell tumor in a patient in need thereof, comprising administering to the patient a pharmaceutical composition comprising a compound represented by:

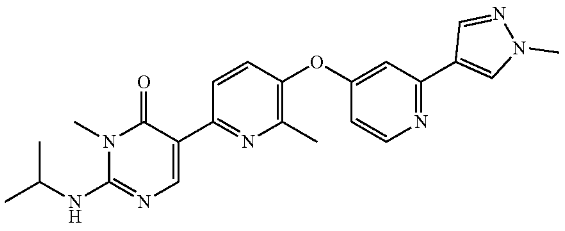 [SMILES: Cc1nc(-c2cnc(NC(C)C)n(C)c2=O)ccc1Oc1ccnc(-c2cnn(C)c2)c1]

and a pharmaceutically acceptable excipient, wherein the pharmaceutical composition is administered to the patient in an amount sufficient to provide the patient 30 mg of the compound twice weekly.

13. The method of claim 12, wherein the tenosynovial giant cell tumor is localized.

14. The method of claim 12, wherein the tenosynovial giant cell tumor is a diffuse-type tenosynovial giant cell tumor.

15. The method of claim 12, comprising administering to the patient the composition twice weekly for about 3 months.

16. The method of claim 12, comprising administering to the patient the composition twice weekly for about 6 months.

17. The method of claim 12, comprising administering to the patient the composition twice weekly for about 1 year.

18. The method of claim 12, comprising administering to the patient the composition twice weekly for about 2 years.

19. The method of claim 12, wherein the pharmaceutical composition is administered to the patient as a neo-adjuvant.

20. The method of claim 12, wherein the pharmaceutical composition is administered to the patient as an adjuvant.

21. A method of treating a tenosynovial giant cell tumor in a patient in need thereof, comprising administering to the patient a pharmaceutical composition comprising a compound represented by:

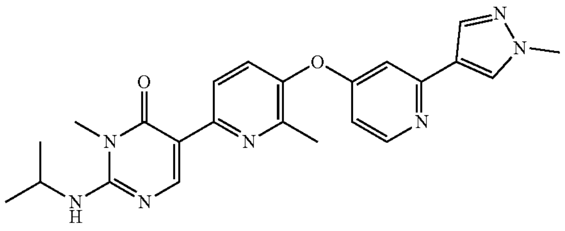 [SMILES: Cc1nc(-c2cnc(NC(C)C)n(C)c2=O)ccc1Oc1ccnc(-c2cnn(C)c2)c1]

and a pharmaceutically acceptable excipient, wherein the pharmaceutical composition is administered to the patient in an amount sufficient to provide the patient a therapeutically effective amount of the compound.

22. The method of claim 21, wherein the tenosynovial giant cell tumor is localized.

23. The method of claim 21, wherein the tenosynovial giant cell tumor is a diffuse-type tenosynovial giant cell tumor.

24. The method of claim 21, comprising administering to the patient the composition twice weekly for about 3 months.

25. The method of claim 21, comprising administering to the patient the composition twice weekly for about 6 months.

26. The method of claim 21, comprising administering to the patient the composition twice weekly for about 1 year.

27. The method of claim 21, comprising administering to the patient the composition twice weekly for about 2 years.

28. The method of claim 21, wherein the pharmaceutical composition is administered to the patient as a neo-adjuvant.

29. The method of claim 21, wherein the pharmaceutical composition is administered to the patient as an adjuvant.

* * * * *